(12) United States Patent
Mitamura et al.

(10) Patent No.: US 12,258,413 B2
(45) Date of Patent: Mar. 25, 2025

(54) BISPECIFIC ANTIBODY BINDING TO TfR

(71) Applicant: Kyowa Kirin Co., Ltd., Tokyo (JP)

(72) Inventors: Keisuke Mitamura, Tokyo (JP);
Ryosuke Nakano, Tokyo (JP);
Masayuki Kai, Tokyo (JP); Nobuaki Takahashi, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 917 days.

(21) Appl. No.: 17/418,447

(22) PCT Filed: Dec. 27, 2019

(86) PCT No.: PCT/JP2019/051594
§ 371 (c)(1),
(2) Date: Jun. 25, 2021

(87) PCT Pub. No.: WO2020/138487
PCT Pub. Date: Jul. 2, 2020

(65) Prior Publication Data
US 2022/0017635 A1   Jan. 20, 2022

(30) Foreign Application Priority Data
Dec. 28, 2018   (JP) ................... 2018-248334

(51) Int. Cl.
*C07K 16/28* (2006.01)
*A61P 35/00* (2006.01)

(52) U.S. Cl.
CPC .......... *C07K 16/2881* (2013.01); *A61P 35/00* (2018.01); *C07K 16/2863* (2013.01); *C07K 2317/31* (2013.01); *C07K 2317/34* (2013.01); *C07K 2317/55* (2013.01); *C07K 2317/92* (2013.01)

(58) Field of Classification Search
CPC ............ C07K 16/2881; C07K 16/2863; C07K 2317/31; C07K 2317/34; C07K 2317/55; C07K 2317/92; A61P 35/00
See application file for complete search history.

(56) References Cited

U.S. PATENT DOCUMENTS

| | | | |
|---|---|---|---|
| 5,705,614 A | 1/1998 | Ring | |
| 7,186,809 B2* | 3/2007 | Pluenneke | A61P 19/02 530/389.1 |
| 9,758,594 B2* | 9/2017 | Takahashi | C07K 16/468 |
| 2007/0071675 A1 | 3/2007 | Wu et al. | |
| 2011/0076722 A1 | 3/2011 | Takahashi | |
| 2012/0171120 A1 | 7/2012 | Dennis et al. | |
| 2014/0114054 A1 | 4/2014 | Kurosawa et al. | |
| 2015/0110791 A1 | 4/2015 | Zhang et al. | |
| 2015/0329636 A1 | 11/2015 | Dennis et al. | |
| 2015/0353639 A1 | 12/2015 | Watts et al. | |
| 2017/0260292 A1 | 9/2017 | Dennis et al. | |
| 2017/0335016 A1 | 11/2017 | Takahashi | |
| 2018/0002433 A1 | 1/2018 | Zhang et al. | |
| 2019/0030160 A1 | 1/2019 | Watts et al. | |
| 2019/0202936 A1 | 7/2019 | Dennis et al. | |
| 2021/0087288 A1 | 3/2021 | Zhang et al. | |

FOREIGN PATENT DOCUMENTS

| | | | |
|---|---|---|---|
| EP | 2 808 035 | 12/2014 | |
| JP | 2014-500886 | 1/2014 | |
| JP | 2015-523336 | 8/2015 | |
| JP | 2016-526878 | 9/2016 | |
| WO | 01/77342 | 10/2001 | |
| WO | 2009/131239 | 10/2009 | |
| WO | 2012/075037 | 6/2012 | |
| WO | 2012/153707 | 11/2012 | |
| WO | 2013/138400 | 9/2013 | |
| WO | 2013/177062 | 11/2013 | |
| WO | 2014/189973 | 11/2014 | |
| WO | WO-2014189973 A2 * | 11/2014 | ......... A61K 39/3955 |
| WO | 2015/152430 | 10/2015 | |

(Continued)

OTHER PUBLICATIONS

Hamilton, Thomas A. et al., "Identification of transferrin receptors on the surface of human cultured cells", Proc. Natl. Acad. Sci., Dec. 1979, vol. 76, No. 12, pp. 6406-6410.
Larson, Steven M. et al., "Common Pathway for Tumor Cell Uptake of Gallium-67 and Iron-59 via a Transferrin Receptor", J. Natl. Cancer Inst., Jan. 1980, vol. 64, No. 1, pp. 41-53.
Liu, Allen P. et al., "Local clustering of transferrin receptors promotes clathrin-coated pit initiation", The Journal of Cell Biology, 2010, vol. 191, No. 7, pp. 1381-1393.
Weissman, Allan M. et al., "Exposure of K562 Cells to Anti-receptor Monoclonal Antibody OKT9 Results in Rapid Redistribution and Enhanced Degradation of the Transferrin Receptor", The Journal of Cell Biology, Mar. 1986, vol. 102, pp. 951-958.

(Continued)

*Primary Examiner* — Brad Duffy
*Assistant Examiner* — Elizabeth A Shupe
(74) *Attorney, Agent, or Firm* — Wenderoth, Lind & Ponack, L.L.P.

(57) ABSTRACT

The present invention relates to a bispecific antibody in which an N-terminal side polypeptide is bound to an IgG portion that binds to TfR, a bispecific antibody fragment thereof, a DNA encoding the bispecific antibody or the bispecific antibody fragment thereof, a vector containing the DNA, a hybridoma and a transformant that produce the bispecific antibody or the bispecific antibody fragment thereof, a method for producing the bispecific antibody or the bispecific antibody fragment thereof, therapeutic and diagnostic agents containing the bispecific antibody or the bispecific antibody fragment thereof, therapeutic and diagnostic methods using the bispecific antibody or the bispecific antibody fragment thereof, and a reagent for detection or measurement containing the bispecific antibody or the bispecific antibody fragment thereof.

10 Claims, 18 Drawing Sheets

Specification includes a Sequence Listing.

(56) References Cited

FOREIGN PATENT DOCUMENTS

WO 2017/196874 11/2017

OTHER PUBLICATIONS

Erbitux® (cetuximab) injection, US package insert (Revised on Jun. 2018), pp. 1-20.

Libermann, T.A. et al., "Expression of Epidermal Growth Factor Receptors in Human Brain Tumors", Cancer Research, Feb. 1984, vol. 44, pp. 753-760.

Hendler, Fred J. et al., "Human Squamous Cell Lung Cancers Express Increased Epidermal Growth Factor Receptors", J. Clin. Invest., Aug. 1984, vol. 74, pp. 647-651.

International Search Report issued Feb. 25, 2020 in International (PCT) Application No. PCT/JP2019/051594, with English-language translation.

Written Opinion of the International Searching Authority issued Feb. 25, 2020 in International (PCT) Application No. PCT/JP2019/051594, with English-language translation.

Extended European Search Report issued Aug. 5, 2022 in corresponding European Patent Application No. 19901837.5.

Husain, B. et al., "Expanding the Boundaries of Biotherapeutics with Bispecific Antibodies", Biodrugs, 2018, vol. 32, No. 5, pp. 441-464.

Brinkmann, U. et al., "The making of bispecific antibodies", MABS, 2017, vol. 9, No. 2, pp. 182-212.

Van Blarcom, T. et al., "Productive common light chain libraries yield diverse panels of high affinity bispecific antibodies", MABS, 2017, vol. 10, No. 2, pp. 256-268.

\* cited by examiner (A)

(B)

SEQUENCE LISTING

```
<160> NUMBER OF SEQ ID NOS: 117

<210> SEQ ID NO 1
<211> LENGTH: 1643
<212> TYPE: DNA
<213> ORGANISM: Homo sapiens

<400> SEQUENCE: 1
tggagaatcc tgggggttat gtggcgtata gtaaggctgc aacagttact ggtaaactgg      60
tccatgctaa ttttggtact aaaaaagatt ttgaggattt atacactcct gtgaatggat     120
ctatagtgat tgtcagagca gggaaaatca cctttgcaga aaaggttgca aatgctgaaa     180
gcttaaatgc aattggtgtg ttgatataca tggaccagac taaatttccc attgttaacg     240
cagaactttc attctttgga catgctcatc tggggacagg tgacccttac acacctggat     300
tcccttcctt caatcacact cagtttccac catctcggtc atcaggattg cctaatatac     360
ctgtccagac aatctccaga gctgctgcag aaaagctgtt tggaatatg  gaaggagact     420 gtccctctga ctggaaaaca gactctacat gtaggatggt aacctcagaa agcaagaatg     480
tgaagctcac tgtgagcaat gtgctgaaag agataaaaat tcttaacatc tttggagtta     540
ttaaaggctt tgtagaacca gatcactatg ttgtagttgg ggcccagaga gatgcatggg     600
gccctggagc tgcaaaatcc ggtgtaggca cagctctcct attgaaactt gcccagatgt     660
tctcagatat ggtcttaaaa gatgggtttc agcccagcag aagcattatc tttgccagtt     720
ggagtgctgg agacttttga tcggttggtg ccactgaatg ctagaggga tacctttcgt      780 ccctgcattt aaaggctttc acttatatta atctggataa agcggttctt ggaaccagca     840
acttcaaggt ttctgccagc ccactgttgt atacgcttat tgagaaaaca atgcaaaatg     900
tgaagcatcc ggttactggg caatttctat atcaggacag caactgggcc agcaaagttg     960
agaaactcac tttagacaat gctgctttcc ctttccttgc atattctgga atcccagcag    1020
```

```
tttctttctg tttttgcgag gacacagatt atccttattt gggaaccacc atggacacct   1080
ataaggaact gattgagagg attcctgagt tgaacaaagt ggcacgagca gctgcagagg   1140
tcgctggtca gttcgtgatt aaactaaccc atgatgttga attgaacctg gactatgaga   1200
ggtacaacag ccaactgctt tcatttgtga gggatctgaa ccaatacaga gcagacataa   1260
aggaaatggg cctgagttta cagtggctgt attctgctcg tggagacttc ttccgtgcta   1320
cttccagact aacaacagat ttcgggaatg ctgagaaaac agacagattt gtcatgaaga   1380
aactcaatga tcgtgtcatg agagtggagt atcacttcct ctctccctac gtatctccaa   1440
aagagtctcc tttccgacat gtcttctggg gctccggctc tcacacgctg ccagctttac   1500
tggagaactt gaaactgcgt aaacaaaata cggtgcttt taatgaaacg ctgttcagaa    1560
accagttggc tctagctact tggactattc agggagctgc aaatgccctc tctggtgacg   1620
tttgggacat tgacaatgag ttt                                           1643
```

<210> SEQ ID NO 2
<211> LENGTH: 672
<212> TYPE: PRT
<213> ORGANISM: Homo sapiens

<400> SEQUENCE: 2

```
Cys Lys Gly Val Glu Pro Lys Thr Glu Cys Glu Arg Leu Ala Gly Thr
1               5                   10                  15

Glu Ser Pro Val Arg Glu Pro Gly Glu Asp Phe Pro Ala Ala Arg
            20                  25                  30

Arg Leu Tyr Trp Asp Asp Leu Lys Arg Lys Leu Ser Glu Lys Leu Asp
        35                  40                  45

Ser Thr Asp Phe Thr Gly Thr Ile Lys Leu Leu Asn Glu Asn Ser Tyr
    50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gly Asn Ser Val
            100                 105                 110

Ile Ile Val Asp Lys Asn Gly Arg Leu Val Tyr Leu Val Glu Asn Pro
        115                 120                 125

Gly Gly Tyr Val Ala Tyr Ser Lys Ala Ala Thr Val Thr Gly Lys Leu
    130                 135                 140

Val His Ala Asn Phe Gly Thr Lys Lys Asp Phe Glu Asp Leu Tyr Thr
145                 150                 155                 160

Pro Val Asn Gly Ser Ile Val Ile Val Arg Ala Gly Lys Ile Thr Phe
                165                 170                 175

Ala Glu Lys Val Ala Asn Ala Glu Ser Leu Asn Ala Ile Gly Val Leu
            180                 185                 190

Ile Tyr Met Asp Gln Thr Lys Phe Pro Ile Val Asn Ala Glu Leu Ser
        195                 200                 205

Phe Phe Gly His Ala His Leu Gly Thr Gly Asp Pro Tyr Thr Pro Gly
    210                 215                 220

Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Ala Glu Lys
                245                 250                 255
```

-continued

```
Leu Phe Gly Asn Met Glu Gly Asp Cys Pro Ser Asp Trp Lys Thr Asp
            260                 265                 270

Ser Thr Cys Arg Met Val Thr Ser Glu Ser Lys Asn Val Lys Leu Thr
        275                 280                 285

Val Ser Asn Val Leu Lys Glu Ile Lys Ile Leu Asn Ile Phe Gly Val
    290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                325                 330                 335

Leu Leu Leu Lys Leu Ala Gln Met Phe Ser Asp Met Val Leu Lys Asp
            340                 345                 350

Gly Phe Gln Pro Ser Arg Ser Ile Ile Phe Ala Ser Trp Ser Ala Gly
        355                 360                 365

Asp Phe Gly Ser Val Gly Ala Thr Glu Trp Leu Glu Gly Tyr Leu Ser
    370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
            405                 410                 415

Leu Ile Glu Lys Thr Met Gln Asn Val Lys His Pro Val Thr Gly Gln
        420                 425                 430

Phe Leu Tyr Gln Asp Ser Asn Trp Ala Ser Lys Val Glu Lys Leu Thr
    435                 440                 445

Leu Asp Asn Ala Ala Phe Pro Phe Leu Ala Tyr Ser Gly Ile Pro Ala
450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
            485                 490                 495

Lys Val Ala Arg Ala Ala Ala Glu Val Ala Gly Gln Phe Val Ile Lys
        500                 505                 510

Leu Thr His Asp Val Glu Leu Asn Leu Asp Tyr Glu Arg Tyr Asn Ser
    515                 520                 525

Gln Leu Leu Ser Phe Val Arg Asp Leu Asn Gln Tyr Arg Ala Asp Ile
530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
            565                 570                 575

Lys Thr Asp Arg Phe Val Met Lys Lys Leu Asn Asp Arg Val Met Arg
        580                 585                 590

Val Glu Tyr His Phe Leu Ser Pro Tyr Val Ser Pro Lys Glu Ser Pro
    595                 600                 605

Phe Arg His Val Phe Trp Gly Ser Gly Ser His Thr Leu Pro Ala Leu
610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
            645                 650                 655

Ala Ala Asn Ala Leu Ser Gly Asp Val Trp Asp Ile Asp Asn Glu Phe
        660                 665                 670
```

<210> SEQ ID NO 3
<211> LENGTH: 2016
<212> TYPE: DNA
<213> ORGANISM: Monkey

<400> SEQUENCE: 3

```
tgtaaagggg tagaaccaaa aactgagtgt gagagactgg caggcaccga gtctccagcg      60
agggaggagc cagaagagga cttccctgcg gcaccgcgct tatactggga cgacctgaag     120
agaaagttgt cagagaaact ggacaccaca gacttcacca gcaccatcaa gctgctgaat     180
gaaaatttat atgtccctcg tgaggctgga tctcaaaaag atgaaaatct tgcattgtat     240
attgaaaatc aatttcgtga atttaaacta agcaaagtct ggcgtgatca acattttgtt     300
aagattcagg tcaaggacag tgctcaaaac tcggtgatca tagttgataa gaatggtgga     360
cttgtttacc tggtgagaa tcctggggggt tatgtggcat atagtaaggc tgcaacagtt     420
actggtaaac tggtccatgc taattttggt actaaaaaag actttgagga tttagactct     480
cctgtgaatg gatctatagt gattgtcaga gcaggaaaaa tcacctttgc agaaaaggtt     540
gcaaatgctg aaagcttaaa tgcaattggt gtcttgatat atatggacca gactaaattt     600
cctattgtta aggcagacct ttcattcttt ggacatgctc atctgggaac aggtgaccct     660
tacacacctg gattcccttc cttcaatcac actcagtttc caccatctca gtcgtcagga     720
ttgcctaata tacctgtcca aacgatctcc agagctgctg cagaaaagct gtttggaaat     780
atggagggag actgtccctc tgactggaaa acagactcta cgtgtaagat ggtaacctcg     840
gaaaacaaga gtgtgaagct cacggtgagc aatgtgctga agagacaaa aattcttaac     900
atctttggag ttattaaagg cttcgtagaa ccagatcact atgttgtggt tggggcccag     960
agagatgcgt ggggcccgg agctgcaaaa tccagtgtgg ggacagctct cctgttgaaa    1020
cttgcccaga tgttctcaga tatggtctta aaagatgggt ttcagcccag cagaagcatt    1080
atctttgcca gttggagtgc tggagacttt ggatcggttg gtgccactga atggctagag    1140
ggatacctt catccttgca tttaaaggct ttcacttaca ttaatctgga taaagcggtg    1200
cttggaacca gcaacttcaa ggtttctgcc agcccgttgt tgtatacgct gattgagaaa    1260
acaatgcaag atgtgaaaca tccggttact gggcgatctc tatatcagga cagcaactgg    1320
gccagcaaag ttgagaaact cactttagac aatgctgctt tcccttttcct tgcgtattct    1380
ggaatcccag cagttttcttt ctgttttttgt gaggacacag attatcctta cttgggcacc    1440
accatggaca cctataagga actggtggag aggattcctg agctgaacaa agtggcacga    1500
gcagcggcag aagtagctgg tcagttcgtg attaaactga cccatgatac tgaattgaac    1560
ctggactatg agaggtacaa cagccagctg cttttgtttt tgagggatct gaaccagtac    1620
agagcagatg taaggaaat gggcctgagc ttgcagtggc tgtattctgc tcgtggagac    1680
ttttttccgtg ctacttccag gctaacaaca gatttcagga atgctgagaa aagggacaag    1740
tttgtcatga agaagctcaa tgatcgtgtc atgagagtcg agtattactt cctctcaccc    1800
tatgtgtctc caaaagagtc tcctttccgg cacgtcttct ggggctcggg ctcccacacg    1860
ctgtccgctt tactgagag cttgaaactg cgtagacaga ataacagtgc ttttaatgaa    1920
acgctgttca gaaccagct ggctctcgcg acttggacta ttcagggagc tgcaaatgcc    1980
ctttctggtg acgtttggga cattgacaat gagttt                             2016
```

<210> SEQ ID NO 4
<211> LENGTH: 672
<212> TYPE: PRT

<213> ORGANISM: Monkey

<400> SEQUENCE: 4

Cys Lys Gly Val Glu Pro Lys Thr Glu Cys Glu Arg Leu Ala Gly Thr
1               5                   10                  15

Glu Ser Pro Ala Arg Glu Glu Pro Glu Glu Asp Phe Pro Ala Ala Pro
            20                  25                  30

Arg Leu Tyr Trp Asp Asp Leu Lys Arg Lys Leu Ser Glu Lys Leu Asp
        35                  40                  45

Thr Thr Asp Phe Thr Ser Thr Ile Lys Leu Leu Asn Glu Asn Leu Tyr
50                  55                  60

Val Pro Arg Glu Ala Gly Ser Gln Lys Asp Glu Asn Leu Ala Leu Tyr
65                  70                  75                  80

Ile Glu Asn Gln Phe Arg Glu Phe Lys Leu Ser Lys Val Trp Arg Asp
                85                  90                  95

Gln His Phe Val Lys Ile Gln Val Lys Asp Ser Ala Gln Asn Ser Val
            100                 105                 110

Ile Ile Val Asp Lys Asn Gly Gly Leu Val Tyr Leu Val Glu Asn Pro
        115                 120                 125

Gly Gly Tyr Val Ala Tyr Ser Lys Ala Ala Thr Val Thr Gly Lys Leu
    130                 135                 140

Val His Ala Asn Phe Gly Thr Lys Lys Asp Phe Glu Asp Leu Asp Ser
145                 150                 155                 160

Pro Val Asn Gly Ser Ile Val Ile Val Arg Ala Gly Lys Ile Thr Phe
                165                 170                 175

Ala Glu Lys Val Ala Asn Ala Glu Ser Leu Asn Ala Ile Gly Val Leu
            180                 185                 190

Ile Tyr Met Asp Gln Thr Lys Phe Pro Ile Val Lys Ala Asp Leu Ser
        195                 200                 205

Phe Phe Gly His Ala His Leu Gly Thr Gly Asp Pro Tyr Thr Pro Gly
    210                 215                 220

Phe Pro Ser Phe Asn His Thr Gln Phe Pro Pro Ser Gln Ser Ser Gly
225                 230                 235                 240

Leu Pro Asn Ile Pro Val Gln Thr Ile Ser Arg Ala Ala Ala Glu Lys
                245                 250                 255

Leu Phe Gly Asn Met Glu Gly Asp Cys Pro Ser Asp Trp Lys Thr Asp
            260                 265                 270

Ser Thr Cys Lys Met Val Thr Ser Glu Asn Lys Ser Val Lys Leu Thr
        275                 280                 285

Val Ser Asn Val Leu Lys Glu Thr Lys Ile Leu Asn Ile Phe Gly Val
    290                 295                 300

Ile Lys Gly Phe Val Glu Pro Asp His Tyr Val Val Val Gly Ala Gln
305                 310                 315                 320

Arg Asp Ala Trp Gly Pro Gly Ala Ala Lys Ser Ser Val Gly Thr Ala
                325                 330                 335

Leu Leu Leu Lys Leu Ala Gln Met Phe Ser Asp Met Val Leu Lys Asp
            340                 345                 350

Gly Phe Gln Pro Ser Arg Ser Ile Ile Phe Ala Ser Trp Ser Ala Gly
        355                 360                 365

Asp Phe Gly Ser Val Gly Ala Thr Glu Trp Leu Glu Gly Tyr Leu Ser
    370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
            405                 410                 415

Leu Ile Glu Lys Thr Met Gln Asp Val Lys His Pro Val Thr Gly Arg
        420                 425                 430

Ser Leu Tyr Gln Asp Ser Asn Trp Ala Ser Lys Val Glu Lys Leu Thr
        435                 440                 445

Leu Asp Asn Ala Ala Phe Pro Phe Leu Ala Tyr Ser Gly Ile Pro Ala
    450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Val Glu Arg Ile Pro Glu Leu Asn
                485                 490                 495

Lys Val Ala Arg Ala Ala Ala Glu Val Ala Gly Gln Phe Val Ile Lys
                500                 505                 510

Leu Thr His Asp Thr Glu Leu Asn Leu Asp Tyr Glu Arg Tyr Asn Ser
        515                 520                 525

Gln Leu Leu Leu Phe Leu Arg Asp Leu Asn Gln Tyr Arg Ala Asp Val
    530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Arg Asn Ala Glu
                565                 570                 575

Lys Arg Asp Lys Phe Val Met Lys Lys Leu Asn Asp Arg Val Met Arg
                580                 585                 590

Val Glu Tyr Tyr Phe Leu Ser Pro Tyr Val Ser Pro Lys Glu Ser Pro
        595                 600                 605

Phe Arg His Val Phe Trp Gly Ser Gly Ser His Thr Leu Ser Ala Leu
    610                 615                 620

Leu Glu Ser Leu Lys Leu Arg Arg Gln Asn Asn Ser Ala Phe Asn Glu
625                 630                 635                 640

Thr Leu Phe Arg Asn Gln Leu Ala Leu Ala Thr Trp Thr Ile Gln Gly
                645                 650                 655

Ala Ala Asn Ala Leu Ser Gly Asp Val Trp Asp Ile Asp Asn Glu Phe
                660                 665                 670

<210> SEQ ID NO 5
<211> LENGTH: 2280
<212> TYPE: DNA
<213> ORGANISM: Homo sapiens

<400> SEQUENCE: 5 atggatggatc aagctagatc agcattctct aacttgtttg gtggagaacc attgtcatat    60
acccggttca gcctggctcg gcaagtagat ggcgataaca gtcatgtgga gatgaaactt   120
gctgtagatg aagaagaaaa tgctgacaat aacacaaagg ccaatgtcac aaaaccaaaa   180
aggtgtagtg gaagtatctg ctatgggact attgctgtga tcgtcttttt cttgattgga   240
tttatgattg gctacttggg ctattgtaaa ggggtagaac caaaaactga gtgtgagaga   300
ctggcaggaa ccgagtctcc agtgagggag gagccaggag aggacttccc tgcagcacgt   360
cgcttatatt gggatgacct gaagagaaag ttgtcggaga actggacag cacagacttc   420 accggcacca tcaagctgct gaatgaaaat tcatatgtcc ctcgtgaggc tggatctcaa   480
aaagatgaaa atcttgcgtt gtatgttgaa atcaatttc gtgaatttaa actcagcaaa   540
gtctggcgtg atcaacattt tgttaagatt caggtcaaag acagcgctca aaactcggtg   600

```
atcatagttg ataagaacgg tagacttgtt tacctggtgg agaatcctgg gggttatgtg    660
gcgtatagta aggctgcaac agttactggt aaactggtcc atgctaattt tggtactaaa    720
aaagattttg aggatttata cactcctgtg aatggatcta tagtgattgt cagagcaggg    780
aaaatcacct ttgcagaaaa ggttgcaaat gctgaaagct taaatgcaat tggtgtgttg    840
atatacatgg accagactaa atttcccatt gttaacgcag aactttcatt cttttggacat   900
gctcatctgg ggacaggtga cccttacaca cctggattcc cttccttcaa tcacactcag    960
tttccaccat ctcggtcatc aggattgcct aatatacctg tccagacaat ctccagagct   1020
gctgcagaaa agctgtttgg gaatatggaa ggagactgtc cctctgactg gaaaacagac   1080
tctacatgta ggatggtaac ctcagaaagc aagaatgtga agctcactgt gagcaatgtg   1140
ctgaaagaga taaaaattct taacatcttt ggagttatta aaggctttgt agaaccagat   1200
cactatgttg tagttggggc ccagagagat gcatggggcc ctggagctgc aaaatccggt   1260
gtaggcacag ctctcctatt gaaacttgcc cagatgttct cagatatggt cttaaaagat   1320
gggtttcagc ccagcagaag cattatcttt gccagttgga gtgctggaga ctttggatcg   1380
gttggtgcca ctgaatggct agagggatac cttttcgtccc tgcatttaaa ggctttcact   1440
tatattaatc tggataaagc ggttcttggt accagcaact tcaaggtttc tgccagccca   1500
ctgttgtata cgcttattga gaaacaatg caaaatgtga agcatccggt tactgggcaa   1560
tttctatatc aggacagcaa ctgggccagc aaagttgaga aactcacttt agacaatgct   1620
gctttcccctt tccttgcata ttctggaatc ccagcagttt cttttctgttt ttgcgaggac   1680
acagattatc cttatttggg taccaccatg gacacctata aggaactgat tgagaggatt   1740
cctgagttga acaaagtggc acgagcagct gcagaggtcg ctggtcagtt cgtgattaaa   1800
ctaacccatg atgttgaatt gaacctggac tatgagaggt acaacagcca actgctttca   1860
tttgtgaggg atctgaacca atacagagca gacataaagg aaatgggcct gagtttacag   1920
tggctgtatt ctgctcgtgg agacttcttc cgtgctactt ccagactaac aacagatttc   1980
gggaatgctg agaaaacaga cagatttgtc atgaagaaac tcaatgatcg tgtcatgaga   2040
gtggagtatc acttcctctc tccctacgta tctccaaaag agtctccttt ccgacatgtc   2100
ttctggggct ccggctctca cacgctgcca gctttactgg agaacttgaa actgcgtaaa   2160
caaaataacg gtgcttttaa tgaaacgctg ttcagaaacc agttggctct agctacttgg   2220
actattcagg gagctgcaaa tgccctctct ggtgacgttt gggacattga caatgagttt   2280
```

<210> SEQ ID NO 6  
<211> LENGTH: 760  
<212> TYPE: PRT  
<213> ORGANISM: Homo sapiens
<400> SEQUENCE: 6

```
Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80
```

```
Phe Met Ile Gly Tyr Leu Gly Tyr Cys Lys Gly Val Glu Pro Lys Thr
                    85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
            115                 120                 125

Arg Lys Leu Ser Glu Lys Leu Asp Ser Thr Asp Phe Thr Gly Thr Ile
            130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
                180                 185                 190

Lys Asp Ser Ala Gln Asn Ser Val Ile Val Asp Lys Asn Gly Arg
                195                 200                 205

Leu Val Tyr Leu Val Glu Asn Pro Gly Gly Tyr Val Ala Tyr Ser Lys
            210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
            275                 280                 285

Pro Ile Val Asn Ala Glu Leu Ser Phe Phe Gly His Ala His Leu Gly
290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
            370                 375                 380

Lys Ile Leu Asn Ile Phe Gly Val Ile Lys Gly Phe Val Glu Pro Asp
385                 390                 395                 400

His Tyr Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
            435                 440                 445

Ile Phe Ala Ser Trp Ser Ala Gly Asp Phe Gly Ser Val Gly Ala Thr
            450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
```

```
            500             505             510
Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
        530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
                    580                 585                 590

Val Ala Gly Gln Phe Val Ile Lys Leu Thr His Asp Val Glu Leu Asn
            595                 600                 605

Leu Asp Tyr Glu Arg Tyr Asn Ser Gln Leu Leu Ser Phe Val Arg Asp
        610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
                    660                 665                 670

Lys Leu Asn Asp Arg Val Met Arg Val Glu Tyr His Phe Leu Ser Pro
            675                 680                 685

Tyr Val Ser Pro Lys Glu Ser Pro Phe Arg His Val Phe Trp Gly Ser
        690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
                    740                 745                 750

Val Trp Asp Ile Asp Asn Glu Phe
        755                 760

<210> SEQ ID NO 7
<211> LENGTH: 2280
<212> TYPE: DNA
<213> ORGANISM: Cynomolgus monkey

<400> SEQUENCE: 7
atgatggatc aagctagatc agcattctct aacttgtttg gtggagaacc attgtcatat      60
acccggttca gcctggctcg gcaagtagac ggcgataaca gtcatgtgga gatgaaactt     120
gctgtagatg atgaagaaaa tgctgacaat aacacaaagg ccaatggcac aaaaccaaaa     180
aggtgtggtg gaaatatctg ctatgggact attgccgtga tcatcttttt cttgattggg     240
tttatgattg gctacttggg ctattgtaaa gggtagaaac caaaaactga gtgtgagaga     300
ctggcaggca ccgagtctcc agcgagggag gagccagaag aggacttccc tgcggcaccg     360
cgcttatact gggacgacct gaagagaaag ttgtcagaga aactggacac cacagacttc     420
accagcacca tcaagctgct gaatgaaaat ttatatgtcc ctcgtgaggc tggatctcaa     480
aaagatgaaa atcttgcatt gtatattgaa aatcaatttc gtgaatttaa actaagcaaa     540
gtctggcgtg atcaacattt tgttaagatt caggtcaagg acagtgctca aaactcggtg     600
atcatagttg ataagaatgg tggacttgtt tacctggtgg agaatcctgg gggttatgtg     660
```

```
gcatatagta aggctgcaac agttactggt aaactggtcc atgctaatt tggtactaaa      720
aaagactttg aggatttaga ctctcctgtg aatggatcta tagtgattgt cagagcagga      780
aaaatcacct ttgcagaaaa ggttgcaaat gctgaaagct taaatgcaat tggtgtcttg      840
atatatatgg accagactaa atttcctatt gttaaggcag acctttcatt ctttggacat      900
gctcatctgg aacaggtga cccttacaca cctggattcc cttccttcaa tcacactcag      960
tttccaccat ctcagtcgtc aggattgcct aatatacctg tccaaacgat ctccagagct     1020
gctgcagaaa agctgtttgg aaatatggag ggagactgtc cctctgactg aaaacagac     1080
tctacgtgta agatggtaac ctcggaaaac aagagtgtga agctcacggt gagcaatgtg     1140
ctgaaagaga caaaaattct taacatcttt ggagttatta aaggcttcgt agaaccagat     1200
cactatgttg tggttgggc ccagagagat gcgtgggcc ccggagctgc aaaatccagt      1260
gtggggacag ctctcctgtt gaaacttgcc cagatgttct cagatatggt cttaaaagat     1320
gggtttcagc ccagcagaag cattatcttt gccagttgga gtgctggaga ctttggatcg     1380
gttggtgcca ctgaatggct agagggatac ctttcatcct tgcatttaaa ggctttcact     1440
tacattaatc tggataaagc ggtgcttgga accagcaact tcaaggtttc tgccagcccg     1500
ttgttgtata cgctgattga gaaaacaatg caagatgtga acatccggt tactgggcga      1560
tctctatatc aggacagcaa ctgggccagc aaagttgaga aactcactt agacaatgct     1620
gctttcccctt tccttgcgta ttctggaatc ccagcagttt ctttctgttt tgtgaggac     1680
acagattatc cttacttggg caccaccatg gacacctata aggaactggt ggagaggatt     1740
cctgagctga caaagtggc acgagcagcg gcagaagtag ctggtcagtt cgtgattaaa     1800
ctgacccatg atactgaatt gaacctggac tatgagaggt acaacagcca gctgcttttg     1860
tttttgaggg atctgaacca gtacagagca gatgtaaagg aaatgggcct gagcttgcag     1920
tggctgtatt ctgctcgtgg agacttttc cgtgctactt ccaggctaac aacagatttc     1980
aggaatgctg agaaaaggga caagtttgtc atgaagaagc tcaatgatcg tgtcatgaga     2040
gtcgagtatt acttcctctc accctatgtg tctccaaaag agtctccttt ccggcacgtc     2100
ttctgggggct cgggctccca cacgctgtcc gctttactgg agagcttgaa actgcgtaga     2160
cagaataaca gtgcttttaa tgaaacgctg ttcagaaacc agctggctct cgcgacttgg     2220
actattcagg gagctgcaaa tgccctttct ggtgacgttt gggacattga caatgagttt     2280
```

<210> SEQ ID NO 8
<211> LENGTH: 760
<212> TYPE: PRT
<213> ORGANISM: Cynomolgus monkey

<400> SEQUENCE: 8

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Asp Glu Glu Asn Ala
        35                  40                  45

Asp Asn Asn Thr Lys Ala Asn Gly Thr Lys Pro Lys Arg Cys Gly Gly
    50                  55                  60

Asn Ile Cys Tyr Gly Thr Ile Ala Val Ile Ile Phe Phe Leu Ile Gly
65                  70                  75                  80

Phe Met Ile Gly Tyr Leu Gly Tyr Cys Lys Gly Val Glu Pro Lys Thr

-continued

```
                85                  90                  95
Glu Cys Glu Arg Leu Ala Gly Thr Glu Ser Pro Ala Arg Glu Glu Pro
                100                 105                 110

Glu Glu Asp Phe Pro Ala Ala Pro Arg Leu Tyr Trp Asp Asp Leu Lys
            115                 120                 125

Arg Lys Leu Ser Glu Lys Leu Asp Thr Thr Asp Phe Thr Ser Thr Ile
        130                 135                 140

Lys Leu Leu Asn Glu Asn Leu Tyr Val Pro Arg Glu Ala Gly Ser Gln
145                 150                 155                 160

Lys Asp Glu Asn Leu Ala Leu Tyr Ile Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Gly
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Asp Ser Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Lys Ala Asp Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Gln Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Lys Met Val Thr Ser
        355                 360                 365

Glu Asn Lys Ser Val Lys Leu Thr Val Ser Asn Val Leu Lys Glu Thr
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Ser Val Gly Thr Ala Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asp
            500                 505                 510
```

```
Val Lys His Pro Val Thr Gly Arg Ser Leu Tyr Gln Asp Ser Asn Trp
        515                 520                 525
Ala Ser Lys Val Glu Lys Leu Thr Leu Asp Asn Ala Ala Phe Pro Phe
        530                 535                 540
Leu Ala Tyr Ser Gly Ile Pro Ala Val Ser Phe Cys Phe Cys Glu Asp
545                 550                 555                 560
Thr Asp Tyr Pro Tyr Leu Gly Thr Thr Met Asp Thr Tyr Lys Glu Leu
                565                 570                 575
Val Glu Arg Ile Pro Glu Leu Asn Lys Val Ala Arg Ala Ala Ala Glu
                580                 585                 590
Val Ala Gly Gln Phe Val Ile Lys Leu Thr His Asp Thr Glu Leu Asn
        595                 600                 605
Leu Asp Tyr Glu Arg Tyr Asn Ser Gln Leu Leu Leu Phe Leu Arg Asp
        610                 615                 620
Leu Asn Gln Tyr Arg Ala Asp Val Lys Glu Met Gly Leu Ser Leu Gln
625                 630                 635                 640
Trp Leu Tyr Ser Ala Arg Gly Asp Phe Phe Arg Ala Thr Ser Arg Leu
                645                 650                 655
Thr Thr Asp Phe Arg Asn Ala Glu Lys Arg Asp Lys Phe Val Met Lys
                660                 665                 670
Lys Leu Asn Asp Arg Val Met Arg Val Glu Tyr Tyr Phe Leu Ser Pro
        675                 680                 685
Tyr Val Ser Pro Lys Glu Ser Pro Phe Arg His Val Phe Trp Gly Ser
        690                 695                 700
Gly Ser His Thr Leu Ser Ala Leu Leu Glu Ser Leu Lys Leu Arg Arg
705                 710                 715                 720
Gln Asn Asn Ser Ala Phe Asn Glu Thr Leu Phe Arg Asn Gln Leu Ala
                725                 730                 735
Leu Ala Thr Trp Thr Ile Gln Gly Ala Ala Asn Ala Leu Ser Gly Asp
                740                 745                 750
Val Trp Asp Ile Asp Asn Glu Phe
        755                 760

<210> SEQ ID NO 9
<211> LENGTH: 1914
<212> TYPE: DNA
<213> ORGANISM: Homo sapiens

<400> SEQUENCE: 9
atgcgaccct ccgggacggc cggggcagcg ctcctggcgc tgctggctgc gctctgcccg      60
gcgagtcggg ctctggagga aaagaaagtt tgccaaggca cgagtaacaa gctcacgcag     120
ttgggcactt ttgaagatca ttttctcagc ctccagagga tgttcaataa ctgtgaggtg     180
gtccttggga atttggaaat tacctatgtg cagaggaatt atgatctttc cttcttaaag     240
accatccagg aggtggctgg ttatgtcctc attgccctca acacagtgga gcgaattcct     300
ttggaaaacc tgcagatcat cagaggaaat atgtactacg aaaattccta tgccttagca     360
gtcttatcta actatgatgc aaataaaacc ggactgaagg agctgcccat gagaaattta     420
caggaaatcc tgcatggcgc cgtgcggttc agcaacaacc ctgccctgtg caacgtggag     480
agcatccagt ggcgggacat agtcagcagt gactttctca gcaacatgtc gatggacttc     540
cagaaccacc tggcagctg ccaaaagtgt gatccaagct gtcccaatgg agctgctgg      600 ggtgcaggag aggagaactg ccagaaactg accaaaatca tctgtgccca gcagtgctcc     660
```

```
gggcgctgcc gtggcaagtc ccccagtgac tgctgccaca accagtgtgc tgcaggctgc      720
acaggccccc gggagagcga ctgcctggtc tgccgcaaat tccgagacga agccacgtgc      780
aaggacacct gccccccact catgctctac aaccccacca cgtaccagat ggatgtgaac      840
cccgagggca aatacagctt tggtgccacc tgcgtgaaga agtgtccccg taattatgtg      900
gtgacagatc acggctcgtg cgtccgagcc tgtggggccg acagctatga gatggaggaa      960
gacggcgtcc gcaagtgtaa gaagtgcgaa gggccttgcc gcaaagtgtg taacggaata     1020
ggtattggtg aatttaaaga ctcactctcc ataaatgcta cgaatattaa acacttcaaa     1080
aactgcacct ccatcagtgg cgatctccac atcctgccgg tggcatttag gggtgactcc     1140
ttcacacata ctcctcctct ggatccacag gaactggata ttctgaaaac cgtaaaggaa     1200
atcacagggt ttttgctgat tcaggcttgg cctgaaaaca ggacggacct ccatgccttt     1260
gagaacctag aaatcatacg cggcaggacc aagcaacatg gtcagttttc tcttgcagtc     1320
gtcagcctga acataacatc cttgggatta cgctccctca aggagataag tgatggagat     1380
gtgataattt caggaaacaa aaatttgtgc tatgcaaata caataaactg gaaaaaactg     1440
tttgggacct ccggtcagaa aaccaaaatt ataagcaaca gaggtgaaaa cagctgcaag     1500
gccacaggcc aggtctgcca tgccttgtgc tcccccgagg gctgctgggg cccggagccc     1560
agggactgcg tctcttgccg gaatgtcagc cgaggcaggg aatgcgtgga caagtgcaac     1620
cttctggagg gtgagccaag ggagtttgtg gagaactctg agtgcataca gtgccaccca     1680
gagtgcctgc ctcaggccat gaacatcacc tgcacaggac ggggaccaga caactgtatc     1740
cagtgtgccc actacattga cggcccccac tgcgtcaaga cctgcccggc aggagtcatg     1800
ggagaaaaca cacccctggt ctggaagtac gcagacgccg gccatgtgtg ccacctgtgc     1860
catccaaact gcacctacgg atgcactggg ccaggtcttg aaggctgtcc aacg            1914

<210> SEQ ID NO 10
<211> LENGTH: 638
<212> TYPE: PRT
<213> ORGANISM: Homo sapiens

<400> SEQUENCE: 10

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160
```

-continued

```
Ser Ile Gln Trp Arg Asp Ile Val Ser Ser Asp Phe Leu Ser Asn Met
            165                 170                 175

Ser Met Asp Phe Gln Asn His Leu Gly Ser Cys Gln Lys Cys Asp Pro
        180                 185                 190

Ser Cys Pro Asn Gly Ser Cys Trp Gly Ala Gly Glu Asn Cys Gln
    195                 200                 205

Lys Leu Thr Lys Ile Ile Cys Ala Gln Gln Cys Ser Gly Arg Cys Arg
        210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
        260                 265                 270

Thr Thr Tyr Gln Met Asp Val Asn Pro Glu Gly Lys Tyr Ser Phe Gly
    275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
        340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
        420                 425                 430

His Gly Gln Phe Ser Leu Ala Val Val Ser Leu Asn Ile Thr Ser Leu
    435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser Cys Arg Asn
    515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575
```

```
Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr
625                 630                 635

<210> SEQ ID NO 11
<211> LENGTH: 1914
<212> TYPE: DNA
<213> ORGANISM: Monkey

<400> SEQUENCE: 11
atgcgaccct ccgggacggc cggggccgcg ctcctggcgc tgctggctgc gctctgcccc      60
gcgagtcggg ctctggagga aaagaaagtt tgccaaggca cgagtaacaa actcacgcag     120
ttgggcactt ttgaagatca tttctcagc ctccagagga tgttcaataa ctgtgaggtg     180
gtccttggga atttggaaat tacctacgtg cagaggaatt atgatctttc cttcttaaag     240
accatccagg aggtggctgg ttatgtcctc atcgccctca acacagtgga gcggattcct     300
ttggaaaacc tgcagatcat cagaggaaac atgtactatg aaaattccta tgccttagca     360
gtcttatcta actatgatgc aaataaaacc ggactgaagg agctgcccat gagaaactta     420
caggaaatcc tgcatggcgc cgtgcggttc agcaacaacc ctgccctgtg caacgtggag     480
agcatccagt ggcgggacat agtcagcagc gagtttctca gcaacatgtc gatggacttc     540
cagaaccacc tgggcagctg ccaaaagtgt gatccaagct gtcccaatgg agctgctgg     600 ggtgcaggag aggagaactg ccagaaactg accaaaatca tctgtgccca gcagtgctcc     660
gggcgctgcc gcggcaagtc ccccagtgac tgctgccaca accagtgtgc cgcgggctgc     720
acgggccccc gggagagcga ctgcctggtc tgccgcaaat tccgagacga agccacgtgc     780
aaggacacct gccccccact catgctctac aaccccacca cataccagat ggatgtgaac     840
cccgagggca atacagcttt ggtgccacc tgcgtgaaga gtgtccccg taattatgtg     900 gtgacagatc acggctcgtg cgtccgagcc tgcggggccg acagctatga gatggaggaa     960
gacggcgtcc gcaagtgtaa gaagtgcgaa gggccttgcc gcaaagtgtg taatggaata    1020
ggtattggtg aatttaaaga cacactctcc ataaatgcta caaatattaa cacttcaaa    1080 aactgcacct ccatcagtgg cgatctccac atcctgccgg tggcatttag ggtgactcc    1140 ttcacacaca ctccgcctct ggatccacag gaactggata ttctgaaaac cgtaaggaa    1200 atcacagggt ttttgctgat tcaggcttgg cctgaaaaca ggacggacct ccatgctttt    1260
gagaacctag aaatcatacg tggcaggacc aagcaacacg gtcagttttc tcttgcggtc    1320
gtcagcctga acataacatc cttgggatta cgctccctca aggagataag cgatggagat    1380
gtgataattt caggaaacaa aaatttgtgc tatgcaaata caataaactg gaaaaaactg    1440
tttgggacct ccagtcagaa aaccaaaatt ataagcaaca gaggtgaaaa cagctgcaag    1500
gccacgggcc aggtctgcca tgccttgtgc tcccccgagg ctgctgggg ccggagccc    1560 agggactgcg tctcctgtca gaatgtcagc cgaggcagag aatgcgtgga caagtgcaac    1620
atcctggagg gcgagccaag ggagtttgtg gagaactctg agtgcataca gtgccaccca    1680
gaatgcctgc cccaggtcat gaacatcacc tgcacaggac gggaccaga caactgtatc    1740 cagtgtgccc actacattga cggccccac tgcgtcaaga cctgcccagc aggagtcatg    1800
```

```
ggagaaaaca acaccctggt ctggaagtac gcagacgccg gccacgtgtg ccacttgtgc      1860
catccaaact gcacctacgg atgcactggg ccaggtcttg aaggctgtgc aagg           1914
```

<210> SEQ ID NO 12
<211> LENGTH: 638
<212> TYPE: PRT
<213> ORGANISM: Monkey

<400> SEQUENCE: 12

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Glu Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Thr Leu Ser Ile Asn
            340                 345                 350
```

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Ser Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Gln Asn
        515                 520                 525

Val Ser Arg Gly Arg Glu Cys Val Asp Lys Cys Asn Ile Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Val Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Ala Arg
625                 630                 635

<210> SEQ ID NO 13
<211> LENGTH: 3630
<212> TYPE: DNA
<213> ORGANISM: Homo sapiens

<400> SEQUENCE: 13
atgcgaccct ccgggacggc cggggcagcg ctcctggcgc tgctggctgc gctctgcccg     60
gcgagtcggg ctctggagga aaagaaagtt tgccaaggca cgagtaacaa gctcacgcag    120
ttgggcactt ttgaagatca tttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgcccat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540

```
cagaaccacc tgggcagctg ccaaaagtgt gatccaagct gtcccaatgg gagctgctgg    600
ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat tccgagacga agccacgtgc    780
aaggacacct gccccccact catgctctac aaccccacca cgtaccagat ggatgtgaac    840
cccgagggca aatacagctt tggtgccacc tgcgtgaaga gtgtccccg taattatgtg    900 gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag gggtgactcc   1140
ttcacacata ctcctcctct ggatccacag gaactggata ttctgaaaac cgtaaggaa   1200 atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga ataacatcc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaac   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca cacccctggt ctggaagtac gcagacgccg ccatgtgtg ccacctgtgc   1860 catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta aagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aaccccacg tgtgccgcct gctgggcatc   2340
tgcctcacct ccaccgtgca gctcatcacg cagctcatgc cttcggctg cctcctggac   2400 tatgtccggg aacacaaaga caatattggc tcccagtacc tgctcaactg gtgtgtgcag   2460
atcgcaaagg gcatgaacta cttggaggac gtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgactg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggtcaagtgc tggatgatag acgcagatag tcgcccaaag   2880
```

-continued

```
ttccgtgagt tgatcatcga attctccaaa atggcccgag acccccagcg ctaccttgtc    2940
attcaggggg atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg ggctgcaaag ctgtcccatc    3180
aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg gcaaccccga gtatctcaac    3420
actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca                                     3630
```

<210> SEQ ID NO 14
<211> LENGTH: 1210
<212> TYPE: PRT
<213> ORGANISM: Homo sapiens

<400> SEQUENCE: 14

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240
```

```
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
    290                 295                 300
Gly Ser Cys Val Arg Ala Cys Gly Ala Asp Ser Tyr Glu Met Glu Glu
305                 310                 315                 320
Asp Gly Val Arg Lys Cys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
        370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
```

-continued

```
                660             665             670
Ile Val Arg Lys Arg Thr Leu Arg Arg Leu Leu Gln Glu Arg Glu Leu
            675             680             685

Val Glu Pro Leu Thr Pro Ser Gly Glu Ala Pro Asn Gln Ala Leu Leu
690             695             700

Arg Ile Leu Lys Glu Thr Glu Phe Lys Lys Ile Lys Val Leu Gly Ser
705             710             715             720

Gly Ala Phe Gly Thr Val Tyr Lys Gly Leu Trp Ile Pro Glu Gly Glu
            725             730             735

Lys Val Lys Ile Pro Val Ala Ile Lys Glu Leu Arg Glu Ala Thr Ser
            740             745             750

Pro Lys Ala Asn Lys Glu Ile Leu Asp Glu Ala Tyr Val Met Ala Ser
            755             760             765

Val Asp Asn Pro His Val Cys Arg Leu Leu Gly Ile Cys Leu Thr Ser
770             775             780

Thr Val Gln Leu Ile Thr Gln Leu Met Pro Phe Gly Cys Leu Leu Asp
785             790             795             800

Tyr Val Arg Glu His Lys Asp Asn Ile Gly Ser Gln Tyr Leu Leu Asn
            805             810             815

Trp Cys Val Gln Ile Ala Lys Gly Met Asn Tyr Leu Glu Asp Arg Arg
            820             825             830

Leu Val His Arg Asp Leu Ala Ala Arg Asn Val Leu Val Lys Thr Pro
            835             840             845

Gln His Val Lys Ile Thr Asp Phe Gly Leu Ala Lys Leu Leu Gly Ala
850             855             860

Glu Glu Lys Glu Tyr His Ala Glu Gly Gly Lys Val Pro Ile Lys Trp
865             870             875             880

Met Ala Leu Glu Ser Ile Leu His Arg Ile Tyr Thr His Gln Ser Asp
            885             890             895

Val Trp Ser Tyr Gly Val Thr Val Trp Glu Leu Met Thr Phe Gly Ser
            900             905             910

Lys Pro Tyr Asp Gly Ile Pro Ala Ser Glu Ile Ser Ser Ile Leu Glu
            915             920             925

Lys Gly Glu Arg Leu Pro Gln Pro Pro Ile Cys Thr Ile Asp Val Tyr
930             935             940

Met Ile Met Val Lys Cys Trp Met Ile Asp Ala Asp Ser Arg Pro Lys
945             950             955             960

Phe Arg Glu Leu Ile Ile Glu Phe Ser Lys Met Ala Arg Asp Pro Gln
            965             970             975

Arg Tyr Leu Val Ile Gln Gly Asp Glu Arg Met His Leu Pro Ser Pro
            980             985             990

Thr Asp Ser Asn Phe Tyr Arg Ala Leu Met Asp Glu Glu Asp Met Asp
            995             1000            1005

Asp Val Val Asp Ala Asp Glu Tyr Leu Ile Pro Gln Gln Gly Phe
            1010            1015            1020

Phe Ser Ser Pro Ser Thr Ser Arg Thr Pro Leu Leu Ser Ser Leu
            1025            1030            1035

Ser Ala Thr Ser Asn Asn Ser Thr Val Ala Cys Ile Asp Arg Asn
            1040            1045            1050

Gly Leu Gln Ser Cys Pro Ile Lys Glu Asp Ser Phe Leu Gln Arg
            1055            1060            1065

Tyr Ser Ser Asp Pro Thr Gly Ala Leu Thr Glu Asp Ser Ile Asp
            1070            1075            1080
```

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 15
<211> LENGTH: 327
<212> TYPE: DNA
<213> ORGANISM: Artificial Sequence
<220> FEATURE:
<223> OTHER INFORMATION: description of the artificial sequence: the
      base sequence of A27 VL

<400> SEQUENCE: 15
gaaatagtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctcc gtggacgttc   300
ggccaaggga ccaaggtgga aatcaaa                                       327

<210> SEQ ID NO 16
<211> LENGTH: 109
<212> TYPE: PRT
<213> ORGANISM: Artificial Sequence
<220> FEATURE:
<223> OTHER INFORMATION: description of the artificial sequence: the
      amino acid sequence of A27 VL

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 17
<211> LENGTH: 12
<212> TYPE: PRT
<213> ORGANISM: Artificial Sequence
<220> FEATURE:
<223> OTHER INFORMATION: description of the artificial sequence: the
      amino acid sequence of A27 LCDR1

<400> SEQUENCE: 17

Arg Ala Ser Gln Ser Val Ser Ser Ser Tyr Leu Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: description of the artificial sequence: the
      amino acid sequence of A27 LCDR2

<400> SEQUENCE: 18

Gly Ala Ser Ser Arg Ala Thr
1               5

<210> SEQ ID NO 19
<211> LENGTH: 10
<212> TYPE: PRT
<213> ORGANISM: Artificial Sequence
<220> FEATURE:
<223> OTHER INFORMATION: description of the artificial sequence: the
      amino acid sequence of A27 LCDR3

<400> SEQUENCE: 19

Gln Gln Tyr Gly Ser Ser Pro Pro Trp Thr
1               5                   10

<210> SEQ ID NO 20
<211> LENGTH: 366
<212> TYPE: DNA
<213> ORGANISM: Artificial Sequence
<220> FEATURE:
<223> OTHER INFORMATION: description of the artificial sequence: the
      base sequence of PSM4072 VH

<400> SEQUENCE: 20
gaggtgcagc tggtggagac tgggggaggc ttggtgcaac tggggggtc cctgagactc      60 tcctgtacag cctctggatt cacctttgaa agtcatgcca tgtactgggt ccggcaagct    120
ccagggaagg gctggagtg gtctcgggt attagtaatg aggtagtag cacagagtac       180 gcagactccg tgaggggccg gttcaccatt tccagagaca attccaagaa tacggtgtat    240
ctgcaaatga acagcctgag agccgaggac acggccgtat attactgtgc gagaccaaga    300
tctccatatc tcttctacga tgctgctggt gtctggggcc aagggaccct ggtcaccgtc    360
tcctca                                                               366

<210> SEQ ID NO 21
<211> LENGTH: 122
<212> TYPE: PRT
<213> ORGANISM: Artificial Sequence
<220> FEATURE:
<223> OTHER INFORMATION: description of the artificial sequence: the
      amino acid sequence of PSM4072 VH

<400> SEQUENCE: 21

Glu Val Gln Leu Val Glu Thr Gly Gly Gly Leu Val Gln Pro Gly Gly
1               5                   10                  15

Ser Leu Arg Leu Ser Cys Thr Ala Ser Gly Phe Thr Phe Glu Ser His
            20                  25                  30

Ala Met Tyr Trp Val Arg Gln Ala Pro Gly Lys Gly Leu Glu Trp Val
        35                  40                  45

Ser Gly Ile Ser Asn Gly Gly Ser Ser Thr Glu Tyr Ala Asp Ser Val
    50                  55                  60

Arg Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Pro Arg Ser Pro Tyr Leu Phe Tyr Asp Ala Ala Gly Val Trp
            100                 105                 110

Gly Gln Gly Thr Leu Val Thr Val Ser Ser
        115                 120

<210> SEQ ID NO 22
<211> LENGTH: 5
<212> TYPE: PRT
<213> ORGANISM: Artificial Sequence
<220> FEATURE:
<223> OTHER INFORMATION: description of the artificial sequence: the
      amino acid sequence of PSM4072 HCDR1

<400> SEQUENCE: 22

Ser His Ala Met Tyr
1               5

<210> SEQ ID NO 23
<211> LENGTH: 17
<212> TYPE: PRT
<213> ORGANISM: Artificial Sequence
<220> FEATURE:
<223> OTHER INFORMATION: description of the artificial sequence: the
      amino acid sequence of PSM4072 HCDR2

<400> SEQUENCE: 23

Gly Ile Ser Asn Gly Gly Ser Ser Thr Glu Tyr Ala Asp Ser Val Arg
1               5                   10                  15

Gly

<210> SEQ ID NO 24
<211> LENGTH: 13
<212> TYPE: PRT
<213> ORGANISM: Artificial Sequence
<220> FEATURE:
<223> OTHER INFORMATION: description of the artificial sequence: the
      amino acid sequence of PSM4072 HCDR3

<400> SEQUENCE: 24

Pro Arg Ser Pro Tyr Leu Phe Tyr Asp Ala Ala Gly Val
1               5                   10

<210> SEQ ID NO 25
<211> LENGTH: 366
<212> TYPE: DNA
<213> ORGANISM: Artificial Sequence
<220> FEATURE:
<223> OTHER INFORMATION: description of the artificial sequence: the
      base sequence of R327 VH

<400> SEQUENCE: 25

```
gaggtgcagc tggtggagac cggggggaggc ttggtacagc ctgggggggtc cctgagactc    60
tcctgtgcag cctctggatt cagctttgac aagtatacca tgaactgggt ccgccaggct    120
ccagggaagg gctgagagtg gtctcagtt atttctaatg ggggagtttc tacagactac    180
gcagactccg ttaagggccg gttcaccgtc tccagagaca attccaagaa cacactgtac    240
ctgcaaatga acagcctgag agccgaggat atggccacat attactgtgc gcgtgcgagc    300
cagccgtggc tctataggac cggtgcggat gtgtggggcc aggggacaat ggtcaccgtc    360
tcttca                                                                366
```

<210> SEQ ID NO 26
<211> LENGTH: 122
<212> TYPE: PRT
<213> ORGANISM: Artificial Sequence
<220> FEATURE:
<223> OTHER INFORMATION: description of the artificial sequence: the amino acid sequence of R327 VH

<400> SEQUENCE: 26

```
Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Ser Phe Asp Lys Tyr
            20                  25                  30

Thr Met Asn Trp Val Arg Gln Ala Pro Gly Lys Gly Leu Glu Trp Val
        35                  40                  45

Ser Val Ile Ser Asn Gly Gly Val Ser Thr Asp Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Met Ala Thr Tyr Tyr Cys
                85                  90                  95

Ala Arg Ala Ser Gln Pro Trp Leu Tyr Arg Thr Gly Ala Asp Val Trp
            100                 105                 110

Gly Gln Gly Thr Met Val Thr Val Ser Ser
        115                 120
```

<210> SEQ ID NO 27
<211> LENGTH: 5
<212> TYPE: PRT
<213> ORGANISM: Artificial Sequence
<220> FEATURE:
<223> OTHER INFORMATION: description of the artificial sequence: the amino acid sequence of R327 HCDR1

<400> SEQUENCE: 27

```
Lys Tyr Thr Met Asn
1               5
```

<210> SEQ ID NO 28
<211> LENGTH: 17
<212> TYPE: PRT
<213> ORGANISM: Artificial Sequence
<220> FEATURE:
<223> OTHER INFORMATION: description of the artificial sequence: the amino acid sequence of R327 HCDR2

<400> SEQUENCE: 28

```
Val Ile Ser Asn Gly Gly Val Ser Thr Asp Tyr Ala Asp Ser Val Lys
1               5                   10                  15
```

```
<210> SEQ ID NO 29
<211> LENGTH: 13
<212> TYPE: PRT
<213> ORGANISM: Artificial Sequence
<220> FEATURE:
<223> OTHER INFORMATION: description of the artificial sequence: the
      amino acid sequence of R327 HCDR3

<400> SEQUENCE: 29

Ala Ser Gln Pro Trp Leu Tyr Arg Thr Gly Ala Asp Val
1               5                   10

<210> SEQ ID NO 30
<211> LENGTH: 366
<212> TYPE: DNA
<213> ORGANISM: Artificial Sequence
<220> FEATURE:
<223> OTHER INFORMATION: description of the artificial sequence: the
      base sequence of TfR1071 VH

<400> SEQUENCE: 30
tacgtgcagc tggtggagtc tgggggaggc ttggtacagc ctgggggggtc cctgagactc      60 tcctgtgcag cctctggatt cagctttgac aagtatacca tgaactgggt ccgccaggct     120
ccagggaagg ggctggagtg ggtctcagtt atttctaatg gggagttttc tacagactac     180
gcagactccg ttaagggccg gttcaccgtc tccagagaca attccaagaa cacactgtac     240
ctgcaaatga acagcctgag agccgaggat atggccacat attactgtgc gcgtgcgagc     300
cagccgtggc tctataggac cggtgcggat gtgtggggcc aggggaccct ggtcaccgtc     360
tcctca                                                                366

<210> SEQ ID NO 31
<211> LENGTH: 122
<212> TYPE: PRT
<213> ORGANISM: Artificial Sequence
<220> FEATURE:
<223> OTHER INFORMATION: description of the artificial sequence: the
      amino acid sequence of TfR1071 VH

<400> SEQUENCE: 31

Tyr Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Asp Lys Tyr
            20                  25                  30

Thr Met Asn Trp Val Arg Gln Ala Pro Gly Lys Gly Leu Glu Trp Val
        35                  40                  45

Ser Val Ile Ser Asn Gly Gly Val Ser Thr Asp Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Met Ala Thr Tyr Tyr Cys
                85                  90                  95

Ala Arg Ala Ser Gln Pro Trp Leu Tyr Arg Thr Gly Ala Asp Val Trp
            100                 105                 110

Gly Gln Gly Thr Leu Val Thr Val Ser Ser
        115                 120

<210> SEQ ID NO 32
```

<210> SEQ ID NO 32
<211> LENGTH: 5
<212> TYPE: PRT
<213> ORGANISM: Artificial Sequence
<220> FEATURE:
<223> OTHER INFORMATION: description of the artificial sequence: the
      amino acid sequence of TfR1071 HCDR1

<400> SEQUENCE: 32

Lys Tyr Thr Met Asn
1               5

<210> SEQ ID NO 33
<211> LENGTH: 17
<212> TYPE: PRT
<213> ORGANISM: Artificial Sequence
<220> FEATURE:
<223> OTHER INFORMATION: description of the artificial sequence: the
      amino acid sequence of TfR1071 HCDR2

<400> SEQUENCE: 33

Val Ile Ser Asn Gly Gly Val Ser Thr Asp Tyr Ala Asp Ser Val Lys
1               5                   10                  15

Gly

<210> SEQ ID NO 34
<211> LENGTH: 13
<212> TYPE: PRT
<213> ORGANISM: Artificial Sequence
<220> FEATURE:
<223> OTHER INFORMATION: description of the artificial sequence: the
      amino acid sequence of TfR1071 HCDR3

<400> SEQUENCE: 34

Ala Ser Gln Pro Trp Leu Tyr Arg Thr Gly Ala Asp Val
1               5                   10

<210> SEQ ID NO 35
<211> LENGTH: 366
<212> TYPE: DNA
<213> ORGANISM: Artificial Sequence
<220> FEATURE:
<223> OTHER INFORMATION: description of the artificial sequence: the
      base sequence of TfR4016 VH

<400> SEQUENCE: 35
tacgtgcagc tggtggagtc tgggggaggc ttggtacagc ctggggggtc cctgagactc      60
tcctgtgcag cctctggatt cagctttgac aagtatacca tgaactgggt ccgccaggct     120
ccagggaagg ggctggagtg gtctcagtt atttctaatg ggggagtttc tacagactac     180
gcagactccg ttaagggccg gttcaccgtc tccagagaca attccaagaa cacactgtac     240
ctgcaaatga acagcctgag agccgaggat atggccacat attactgtgc gcgtgcgagc     300
cagccgtggc tctataggac cggtgcggat gtgtggggcc aggggaccac ggtcaccgtc     360
tcctca                                                                366

<210> SEQ ID NO 36
<211> LENGTH: 122
<212> TYPE: PRT
<213> ORGANISM: Artificial Sequence
<220> FEATURE:
<223> OTHER INFORMATION: description of the artificial sequence: the
      amino acid sequence of TfR4016 VH

<400> SEQUENCE: 36

Tyr Val Gln Leu Val Glu Ser Gly Gly Gly Leu Val Gln Pro Gly Gly

```
            1               5                  10                  15
        Ser Leu Arg Leu Ser Cys Ala Ala Ser Gly Phe Ser Phe Asp Lys Tyr
                        20                  25                  30

Thr Met Asn Trp Val Arg Gln Ala Pro Gly Lys Gly Leu Glu Trp Val
                        35                  40                  45

Ser Val Ile Ser Asn Gly Gly Val Ser Thr Asp Tyr Ala Asp Ser Val
                        50                  55                  60

Lys Gly Arg Phe Thr Val Ser Arg Asp Asn Ser Lys Asn Thr Leu Tyr
        65                      70                  75                  80

Leu Gln Met Asn Ser Leu Arg Ala Glu Asp Met Ala Thr Tyr Tyr Cys
                        85                  90                  95

Ala Arg Ala Ser Gln Pro Trp Leu Tyr Arg Thr Gly Ala Asp Val Trp
                        100                 105                 110

Gly Gln Gly Thr Thr Val Thr Val Ser Ser
                        115                 120

<210> SEQ ID NO 37
<211> LENGTH: 5
<212> TYPE: PRT
<213> ORGANISM: Artificial Sequence
<220> FEATURE:
<223> OTHER INFORMATION: description of the artificial sequence: the
      amino acid sequence of TfR4016 HCDR1

<400> SEQUENCE: 37

Lys Tyr Thr Met Asn
1               5

<210> SEQ ID NO 38
<211> LENGTH: 17
<212> TYPE: PRT
<213> ORGANISM: Artificial Sequence
<220> FEATURE:
<223> OTHER INFORMATION: description of the artificial sequence: the
      amino acid sequence of TfR4016 HCDR2

<400> SEQUENCE: 38

Val Ile Ser Asn Gly Gly Val Ser Thr Asp Tyr Ala Asp Ser Val Lys
1               5                   10                  15

Gly

<210> SEQ ID NO 39
<211> LENGTH: 13
<212> TYPE: PRT
<213> ORGANISM: Artificial Sequence
<220> FEATURE:
<223> OTHER INFORMATION: description of the artificial sequence: the
      amino acid sequence of TfR4016 HCDR3

<400> SEQUENCE: 39

Ala Ser Gln Pro Trp Leu Tyr Arg Thr Gly Ala Asp Val
1               5                   10

<210> SEQ ID NO 40
<211> LENGTH: 366
<212> TYPE: DNA
<213> ORGANISM: Artificial Sequence
<220> FEATURE:
<223> OTHER INFORMATION: description of the artificial sequence: the
      base sequence of cyno186 VH

<400> SEQUENCE: 40
caggtgcagc tggtggagtc tgggggagaa ttcgtacagc ctgggggtc cctgagactc       60
```

-continued

```
tcctgtgcag cctctggatt ccccttttaaa ggctatgcca tgaattgggt ccgccaggct    120
ccagggaagg gattggagtg ggtctcaaga ataagtaatg gtggtagcta catagactac    180
gcagactccg taaagggccg gttcaccatc tccagagaca attccaagaa cacgctgtat    240
ttgcaaatag acagcctgag aaccgaggac acggccgtat attactgtgc gaaagcgaag    300
gacgcctata ggtggaacaa cgctatagac gaatggggcc aagggaccct ggtcaccgtc    360
tcctca    366
```

<210> SEQ ID NO 41
<211> LENGTH: 122
<212> TYPE: PRT
<213> ORGANISM: Artificial Sequence
<220> FEATURE:
<223> OTHER INFORMATION: description of the artificial sequence: the amino acid sequence of cyno186 VH

<400> SEQUENCE: 41

Gln Val Gln Leu Val Glu Ser Gly Gly Glu Phe Val Gln Pro Gly Gly
1               5                   10                  15

Ser Leu Arg Leu Ser Cys Ala Ala Ser Gly Phe Pro Phe Lys Gly Tyr
            20                  25                  30

Ala Met Asn Trp Val Arg Gln Ala Pro Gly Lys Gly Leu Glu Trp Val
        35                  40                  45

Ser Arg Ile Ser Asn Gly Gly Ser Tyr Ile Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asp Ser Leu Arg Thr Glu Asp Thr Ala Val Tyr Tyr Cys
                85                  90                  95

Ala Lys Ala Lys Asp Ala Tyr Arg Trp Asn Asn Ala Ile Asp Glu Trp
            100                 105                 110

Gly Gln Gly Thr Leu Val Thr Val Ser Ser
        115                 120

<210> SEQ ID NO 42
<211> LENGTH: 5
<212> TYPE: PRT
<213> ORGANISM: Artificial Sequence
<220> FEATURE:
<223> OTHER INFORMATION: description of the artificial sequence: the amino acid sequence of cyno186 HCDR1

<400> SEQUENCE: 42

Gly Tyr Ala Met Asn
1               5

<210> SEQ ID NO 43
<211> LENGTH: 17
<212> TYPE: PRT
<213> ORGANISM: Artificial Sequence
<220> FEATURE:
<223> OTHER INFORMATION: description of the artificial sequence: the amino acid sequence of cyno186 HCDR2

<400> SEQUENCE: 43

Arg Ile Ser Asn Gly Gly Ser Tyr Ile Asp Tyr Ala Asp Ser Val Lys
1               5                   10                  15

Gly

```
<210> SEQ ID NO 44
<211> LENGTH: 13
<212> TYPE: PRT
<213> ORGANISM: Artificial Sequence
<220> FEATURE:
<223> OTHER INFORMATION: description of the artificial sequence: the
      amino acid sequence of cyno186 HCDR3

<400> SEQUENCE: 44

Ala Lys Asp Ala Tyr Arg Trp Asn Asn Ala Ile Asp Glu
1               5                   10

<210> SEQ ID NO 45
<211> LENGTH: 366
<212> TYPE: DNA
<213> ORGANISM: Artificial Sequence
<220> FEATURE:
<223> OTHER INFORMATION: description of the artificial sequence: the
      base sequence of cyno292 VH

<400> SEQUENCE: 45
caggtgcagc tggtgcaatc tggggggaggc ctggtcaagc ctgggggggtc cctgagaatc      60 tcctgtacaa cctctggatt cccctttgat ggctatacca tgacctgggt ccgccaggct     120
ccagggaagg gctggagtg gtctcaagt attagtaatg gtggtagcac cattttcgtc      180
tcagactcag tgagaggccg attcaccatc tccagagaca cgccaagaa ttcactgtat      240 ctccaaatga acaacgtggg agccgaggac acggctgtgt attactgtgc gagagctcga      300
gatgcgtatg gctggacgct tccttctgac atctggggcc aagggacaat ggtcaccgtc      360
tcttca                                                                  366

<210> SEQ ID NO 46
<211> LENGTH: 122
<212> TYPE: PRT
<213> ORGANISM: Artificial Sequence
<220> FEATURE:
<223> OTHER INFORMATION: description of the artificial sequence: the
      amino acid sequence of cyno292 VH

<400> SEQUENCE: 46

Gln Val Gln Leu Val Gln Ser Gly Gly Gly Leu Val Lys Pro Gly Gly
1               5                   10                  15

Ser Leu Arg Ile Ser Cys Thr Thr Ser Gly Phe Pro Phe Asp Gly Tyr
            20                  25                  30

Thr Met Thr Trp Val Arg Gln Ala Pro Gly Lys Gly Leu Glu Trp Val
        35                  40                  45

Ser Ser Ile Ser Asn Gly Gly Ser Thr Ile Phe Val Ser Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Asn Val Gly Ala Glu Asp Thr Ala Val Tyr Tyr Cys
                85                  90                  95

Ala Arg Ala Arg Asp Ala Tyr Gly Trp Thr Leu Pro Ser Asp Ile Trp
            100                 105                 110

Gly Gln Gly Thr Met Val Thr Val Ser Ser
        115                 120

<210> SEQ ID NO 47
<211> LENGTH: 5
<212> TYPE: PRT
<213> ORGANISM: Artificial Sequence
<220> FEATURE:
```

<223> OTHER INFORMATION: description of the artificial sequence: the
      amino acid sequence of cyno292 HCDR1

<400> SEQUENCE: 47

Gly Tyr Thr Met Thr
1               5

<210> SEQ ID NO 48
<211> LENGTH: 17
<212> TYPE: PRT
<213> ORGANISM: Artificial Sequence
<220> FEATURE:
<223> OTHER INFORMATION: description of the artificial sequence: the
      amino acid sequence of cyno292 HCDR2

<400> SEQUENCE: 48

Ser Ile Ser Asn Gly Gly Ser Thr Ile Phe Val Ser Asp Ser Val Arg
1               5                   10                  15

Gly

<210> SEQ ID NO 49
<211> LENGTH: 13
<212> TYPE: PRT
<213> ORGANISM: Artificial Sequence
<220> FEATURE:
<223> OTHER INFORMATION: description of the artificial sequence: the
      amino acid sequence of cyno292 HCDR3

<400> SEQUENCE: 49

Ala Arg Asp Ala Tyr Gly Trp Thr Leu Pro Ser Asp Ile
1               5                   10

<210> SEQ ID NO 50
<211> LENGTH: 122
<212> TYPE: PRT
<213> ORGANISM: Artificial Sequence
<220> FEATURE:
<223> OTHER INFORMATION: description of the artificial sequence: the
      amino acid sequence of TfR1007 VH

<400> SEQUENCE: 50

Glu Val Gln Leu Val Glu Ser Gly Gly Gly Leu Val Gln Pro Gly Gly
1               5                   10                  15

Ser Leu Ser Leu Ser Cys Ala Ala Ser Gly Phe Ser Phe Lys Gly Tyr
            20                  25                  30

Ser Met Ser Trp Val Arg Gln Ala Pro Gly Lys Gly Leu Glu Trp Val
        35                  40                  45

Ser Ser Leu Ser Asn Gly Gly Gly Ser Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Leu Gly Ala Tyr Tyr Ile Lys Ser Ala Met Asp Val Trp
            100                 105                 110

Gly Gln Gly Thr Thr Val Thr Val Ser Ser
        115                 120

<210> SEQ ID NO 51
<211> LENGTH: 122
<212> TYPE: PRT
<213> ORGANISM: Artificial Sequence
<220> FEATURE:

<223> OTHER INFORMATION: description of the artificial sequence: the
      amino acid sequence of cyno163 VH

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Gly Ile Ser Asn Gly Gly Ser Ser Thr Glu Tyr Ala Asp Ser Val
    50                  55                  60

Arg Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Pro Arg Ser Pro Tyr Leu Phe Tyr Asp Ala Ala Gly Val Trp
            100                 105                 110

Gly Gln Gly Thr Met Val Thr Val Ser Ser
        115                 120

<210> SEQ ID NO 52
<211> LENGTH: 123
<212> TYPE: PRT
<213> ORGANISM: Artificial Sequence
<220> FEATURE:
<223> OTHER INFORMATION: description of the artificial sequence: the
      amino acid sequence of 22-30 VH

<400> SEQUENCE: 52

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Leu Asp Thr Ser Lys Asn Gln Phe Ser Leu
65                  70                  75                  80

Arg Leu Ser Ser Val Thr Thr Ala Asp Thr Ala Leu Tyr Tyr Cys Thr
                85                  90                  95

Arg Glu Ala Gly Tyr Tyr Asp Ser Ser Gly Tyr Tyr Gly Phe Asp Tyr
            100                 105                 110

Trp Gly Gln Gly Thr Leu Val Thr Val Ser Ser
        115                 120

<210> SEQ ID NO 53
<211> LENGTH: 107
<212> TYPE: PRT
<213> ORGANISM: Artificial Sequence
<220> FEATURE:
<223> OTHER INFORMATION: description of the artificial sequence: the
      amino acid sequence of 22-30 VL

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp

```
                20                  25                  30
Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Tyr Asn Tyr Pro Tyr
                85                  90                  95

Thr Phe Gly Gln Gly Thr Lys Leu Glu Ile Lys
            100                 105

<210> SEQ ID NO 54
<211> LENGTH: 114
<212> TYPE: PRT
<213> ORGANISM: Artificial Sequence
<220> FEATURE:
<223> OTHER INFORMATION: description of the artificial sequence: the
      amino acid sequence of T14 VH

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Val Val Ser Gly Thr Phe Ser Asn Phe
            20                  25                  30

Asn Met Asn Trp Val Arg Gln Ala Pro Gly Lys Gly Leu Glu Trp Val
            35                  40                  45

Ser Tyr Ile Ser Gly Ser Ser Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Val Ser Ser Ser Trp Tyr Tyr Trp Gly Gln Gly Thr Leu Val Thr Val
            100                 105                 110

Ser Ser

<210> SEQ ID NO 55
<211> LENGTH: 123
<212> TYPE: PRT
<213> ORGANISM: Artificial Sequence
<220> FEATURE:
<223> OTHER INFORMATION: description of the artificial sequence: the
      amino acid sequence of TfR434 VH

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Pro Phe Lys Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Ser Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95
```

Ala Arg Asp Ser Asn Phe Trp Ser Gly Tyr Tyr Ser Pro Val Asp Val
            100                 105                 110

Trp Gly Gln Gly Thr Thr Val Thr Val Ser Ser
        115                 120

<210> SEQ ID NO 56
<211> LENGTH: 123
<212> TYPE: PRT
<213> ORGANISM: Artificial Sequence
<220> FEATURE:
<223> OTHER INFORMATION: description of the artificial sequence: the
      amino acid sequence of TfR435 VH

<400> SEQUENCE: 56

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Pro Phe Lys Ser Tyr
            20                  25                  30

Gly Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Asp Ser Asn Phe Trp Ser Gly Tyr Tyr Ser Pro Val Asp Val
            100                 105                 110

Trp Gly Gln Gly Thr Thr Val Thr Val Ser Ser
        115                 120

<210> SEQ ID NO 57
<211> LENGTH: 111
<212> TYPE: PRT
<213> ORGANISM: Artificial Sequence
<220> FEATURE:
<223> OTHER INFORMATION: description of the artificial sequence: the
      amino acid sequence of TfR434,435 VL

<400> SEQUENCE: 57

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Ser Val Gln Trp Tyr Gln Gln Arg Pro Gly Ser Ala Pro Ile Thr Val
        35                  40                  45

Ile Tyr Glu Asp Thr Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Gln Thr Glu Asp Glu Ala Asp Tyr Tyr Cys Gln Ser Tyr Asp Ser
                85                  90                  95

Ala Tyr His Trp Val Phe Gly Gly Gly Thr Lys Leu Ala Val Leu
            100                 105                 110

<210> SEQ ID NO 58
<211> LENGTH: 366
<212> TYPE: DNA
<213> ORGANISM: Artificial Sequence
<220> FEATURE:
<223> OTHER INFORMATION: description of the artificial sequence: the
      base sequence of E08 VH

<400> SEQUENCE: 58
gaggtgcagc tggtggagtc tgggggaggc ttggtacagc ctgggggtc cctgagactc    60 tcctgtgcag cctctggatt cagctttaac aacaatgcca tgaactgggt ccgtcaggct   120
ccagggaagg ggctggagtg ggtctcaggt attcgtgccg atggcggtac gacatactac   180
gcagactccg tgaagggccg gttcaccatc tccagagaca attccaagaa cacactgtat   240
ctgcaaatga acagcctgag agccgaggac acggccgtat atttctgtgg aaagacgcct   300
gactgggaaa tcttctacta cgctatggac gcctggggcc aagggaccac ggtcaccgtc   360
tcctca                                                              366

<210> SEQ ID NO 59
<211> LENGTH: 122
<212> TYPE: PRT
<213> ORGANISM: Artificial Sequence
<220> FEATURE:
<223> OTHER INFORMATION: description of the artificial sequence: the
      amino acid sequence of E08 VH

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Asn Asn Asn
            20                  25                  30

Ala Met Asn Trp Val Arg Gln Ala Pro Gly Lys Gly Leu Glu Trp Val
        35                  40                  45

Ser Gly Ile Arg Ala Asp Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Gly Lys Thr Pro Asp Trp Glu Ile Phe Tyr Tyr Ala Met Asp Ala Trp
            100                 105                 110

Gly Gln Gly Thr Thr Val Thr Val Ser Ser
        115                 120

<210> SEQ ID NO 60
<211> LENGTH: 5
<212> TYPE: PRT
<213> ORGANISM: Artificial Sequence
<220> FEATURE:
<223> OTHER INFORMATION: description of the artificial sequence: the
      amino acid sequence of E08 HCDR1

<400> SEQUENCE: 60

Asn Asn Ala Met Asn
1               5

<210> SEQ ID NO 61
<211> LENGTH: 17
<212> TYPE: PRT
<213> ORGANISM: Artificial Sequence
<220> FEATURE:
<223> OTHER INFORMATION: description of the artificial sequence: the
      amino acid sequence of E08 HCDR2

<400> SEQUENCE: 61

```
Gly Ile Arg Ala Asp Gly Gly Thr Thr Tyr Tyr Ala Asp Ser Val Lys
1               5                   10                  15
Gly

<210> SEQ ID NO 62
<211> LENGTH: 13
<212> TYPE: PRT
<213> ORGANISM: Artificial Sequence
<220> FEATURE:
<223> OTHER INFORMATION: description of the artificial sequence: the
      amino acid sequence of E08 HCDR3

<400> SEQUENCE: 62

Thr Pro Asp Trp Glu Ile Phe Tyr Tyr Ala Met Asp Ala
1               5                   10

<210> SEQ ID NO 63
<211> LENGTH: 363
<212> TYPE: DNA
<213> ORGANISM: Artificial Sequence
<220> FEATURE:
<223> OTHER INFORMATION: description of the artificial sequence: the
      base sequence of E12 VH

<400> SEQUENCE: 63
caggtgcagc tggtggagtc tggggggaggc ttggtacagc ctggggggtc cctgagactc      60
tcctgtgcag cctctagatt cacctttagc gcctatgcca tgggctgggt cgccaggct      120 ccagggaagg gctggagtg gtctcaatt attgatagtg gtggtgtgta cacatactac       180
gcagactcca tgaagggccg cttcaccatc tccagagaca attccaagaa cacgctgtat     240
ctgcaaatga acagcctgag agccgaggac acggccgtat attactgtgc gagagatcat    300
tatggtgttg tttggggact tggagattac tggggccagg gaaccctggt cactgtctcc    360
tca                                                                  363

<210> SEQ ID NO 64
<211> LENGTH: 121
<212> TYPE: PRT
<213> ORGANISM: Artificial Sequence
<220> FEATURE:
<223> OTHER INFORMATION: description of the artificial sequence: the
      amino acid sequence of E12 VH

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Ala Ser Arg Phe Thr Phe Ser Ala Tyr
                20                  25                  30

Ala Met Gly Trp Val Arg Gln Ala Pro Gly Lys Gly Leu Glu Trp Val
            35                  40                  45

Ser Ile Ile Asp Ser Gly Gly Val Tyr Thr Tyr Tyr Ala Asp Ser Met
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Tyr Gly Val Val Trp Gly Leu Gly Asp Tyr Trp Gly
            100                 105                 110

Gln Gly Thr Leu Val Thr Val Ser Ser
            115                 120
```

<210> SEQ ID NO 65
<211> LENGTH: 5
<212> TYPE: PRT
<213> ORGANISM: Artificial Sequence
<220> FEATURE:
<223> OTHER INFORMATION: description of the artificial sequence: the
      amino acid sequence of E12 HCDR1

<400> SEQUENCE: 65

Ala Tyr Ala Met Gly
1               5

<210> SEQ ID NO 66
<211> LENGTH: 17
<212> TYPE: PRT
<213> ORGANISM: Artificial Sequence
<220> FEATURE:
<223> OTHER INFORMATION: description of the artificial sequence: the
      amino acid sequence of E12 HCDR2

<400> SEQUENCE: 66

Ile Ile Asp Ser Gly Gly Val Tyr Thr Tyr Tyr Ala Asp Ser Met Lys
1               5                   10                  15

Gly

<210> SEQ ID NO 67
<211> LENGTH: 12
<212> TYPE: PRT
<213> ORGANISM: Artificial Sequence
<220> FEATURE:
<223> OTHER INFORMATION: description of the artificial sequence: the
      amino acid sequence of E12 HCDR3

<400> SEQUENCE: 67

Asp His Tyr Gly Val Val Trp Gly Leu Gly Asp Tyr
1               5                   10

<210> SEQ ID NO 68
<211> LENGTH: 354
<212> TYPE: DNA
<213> ORGANISM: Artificial Sequence
<220> FEATURE:
<223> OTHER INFORMATION: description of the artificial sequence: the
      base sequence of E17 VH

<400> SEQUENCE: 68
caggtgcagc tacagcagtg gggcgcagga ctgttgaagc cttcggagac tctgtccctc      60
acctgcgcac tgtacagtgg gtccttcagt gctcaggact ggagctggat ccgccagtcc    120
ccagagaagg ggctggagtg gattggggaa atctggcaag ggggaaaaac caactacaac    180
ccgtccctca agagtcgagt tagtatatca agagacaact ccaagaacca gttgtccctg    240
cagctgagct ctgtgaccgc cgcggacacg gctgtgtatt actgtgcgag gtggactgg    300 tcttatcgtg tttttgaaat ctggggccaa gggacaatgg tcaccgtctc ttca         354

<210> SEQ ID NO 69
<211> LENGTH: 118
<212> TYPE: PRT
<213> ORGANISM: Artificial Sequence
<220> FEATURE:
<223> OTHER INFORMATION: description of the artificial sequence: the
      amino acid sequence of E17 VH

<400> SEQUENCE: 69

Gln Val Gln Leu Gln Gln Trp Gly Ala Gly Leu Leu Lys Pro Ser Glu
1               5                   10                  15

Thr Leu Ser Leu Thr Cys Ala Leu Tyr Ser Gly Ser Phe Ser Ala Gln
            20                  25                  30

Asp Trp Ser Trp Ile Arg Gln Ser Pro Glu Lys Gly Leu Glu Trp Ile
        35                  40                  45

Gly Glu Ile Trp Gln Gly Gly Lys Thr Asn Tyr Asn Pro Ser Leu Lys
    50                  55                  60

Ser Arg Val Ser Ile Ser Arg Asp Asn Ser Lys Asn Gln Leu Ser Leu
65                  70                  75                  80

Gln Leu Ser Ser Val Thr Ala Ala Asp Thr Ala Val Tyr Tyr Cys Ala
                85                  90                  95

Arg Val Asp Trp Ser Tyr Arg Val Phe Glu Ile Trp Gly Gln Gly Thr
            100                 105                 110

Met Val Thr Val Ser Ser
            115

<210> SEQ ID NO 70
<211> LENGTH: 5
<212> TYPE: PRT
<213> ORGANISM: Artificial Sequence
<220> FEATURE:
<223> OTHER INFORMATION: description of the artificial sequence: the
      amino acid sequence of E17 HCDR1

<400> SEQUENCE: 70

Ala Gln Asp Trp Ser
1               5

<210> SEQ ID NO 71
<211> LENGTH: 16
<212> TYPE: PRT
<213> ORGANISM: Artificial Sequence
<220> FEATURE:
<223> OTHER INFORMATION: description of the artificial sequence: the
      amino acid sequence of E17 HCDR2

<400> SEQUENCE: 71

Glu Ile Trp Gln Gly Gly Lys Thr Asn Tyr Asn Pro Ser Leu Lys Ser
1               5                   10                  15

<210> SEQ ID NO 72
<211> LENGTH: 10
<212> TYPE: PRT
<213> ORGANISM: Artificial Sequence
<220> FEATURE:
<223> OTHER INFORMATION: description of the artificial sequence: the
      amino acid sequence of E17 HCDR3

<400> SEQUENCE: 72

Val Asp Trp Ser Tyr Arg Val Phe Glu Ile
1               5                   10

<210> SEQ ID NO 73
<211> LENGTH: 123
<212> TYPE: PRT
<213> ORGANISM: Artificial Sequence
<220> FEATURE:
<223> OTHER INFORMATION: description of the artificial sequence: the
      amino acid sequence of KME07 VH

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Phe
            20                  25                  30

Ala Phe Gly Trp Val Arg Gln Ala Pro Gly Gln Gly Leu Glu Trp Met
        35                  40                  45

Gly Glu Val Arg Pro Gly Phe Gly Thr Glu Ile Leu Thr Gln Asn Phe
50                      55                  60

Gln Asp Arg Val Thr Ile Thr Ala Asp Glu Ser Thr Ser Thr Thr Tyr
65                      70                  75                  80

Met Glu Leu Arg Ser Leu Lys Ser Glu Asp Thr Ala Val Tyr Tyr Cys
            85                  90                  95

Ala Arg Gly Leu Leu Arg Gly Gly Tyr Ile Glu Asn Pro Phe Glu Ile
            100                 105                 110

Trp Gly Gln Gly Thr Leu Val Thr Val Ser Ser
            115                 120

<210> SEQ ID NO 74
<211> LENGTH: 123
<212> TYPE: PRT
<213> ORGANISM: Artificial Sequence
<220> FEATURE:
<223> OTHER INFORMATION: description of the artificial sequence: the
      amino acid sequence of KME09 VH

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Phe
            20                  25                  30

Ala Trp Gly Trp Val Arg Gln Ala Pro Gly Gln Gly Leu Glu Trp Met
        35                  40                  45

Gly Glu Ile Arg Pro Gly Phe Gly Thr Glu Ile Tyr Ala Gln Asn Phe
50                      55                  60

Gln Asp Arg Val Thr Phe Ile Thr Asp Glu Ala Thr Ser Thr Thr Tyr
65                      70                  75                  80

Met Glu Leu Ser Ser Leu Lys Ser Glu Asp Thr Ala Val Tyr Tyr Cys
            85                  90                  95

Ala Arg Gly Leu Leu Arg Ser Gly Tyr Ile Asp Asn Pro Cys Asp Ile
            100                 105                 110

Trp Gly Gln Gly Thr Met Val Thr Val Ser Ser
            115                 120

<210> SEQ ID NO 75
<211> LENGTH: 125
<212> TYPE: PRT
<213> ORGANISM: Artificial Sequence
<220> FEATURE:
<223> OTHER INFORMATION: description of the artificial sequence: the
      amino acid sequence of KME11 VH

<400> SEQUENCE: 75

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Thr Tyr
            20                  25                  30

Gly Ile Thr Trp Val Arg Gln Ala Pro Gly Gln Gly Phe Ala Trp Met
        35                  40                  45

Gly Glu Ile Ile Pro Ser Leu Gly Ile Val Asn Tyr Ala Gln Lys Phe
50                      55                  60

Gln Gly Arg Val Thr Ile Thr Ala Asp Glu Ser Thr Ser Thr Val Tyr
65                  70                  75                  80

Met Glu Leu Ser Ser Val Thr Tyr Glu Asp Thr Ala Val Tyr Tyr Cys
                85                  90                  95

Ala Gly Asp Glu Leu Ser Glu Gly His Ser Gly Tyr Tyr His Gly Met
            100                 105                 110

Asp Val Trp Gly Gln Gly Thr Thr Val Thr Val Ser Ser
        115                 120                 125

<210> SEQ ID NO 76
<211> LENGTH: 119
<212> TYPE: PRT
<213> ORGANISM: Artificial Sequence
<220> FEATURE:
<223> OTHER INFORMATION: description of the artificial sequence: the
      amino acid sequence of Cetuximab VH

<400> SEQUENCE: 76

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 77
<211> LENGTH: 107
<212> TYPE: PRT
<213> ORGANISM: Artificial Sequence
<220> FEATURE:
<223> OTHER INFORMATION: description of the artificial sequence: the
      amino acid sequence of Cetuximab VL

<400> SEQUENCE: 77

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 78
<211> LENGTH: 117
<212> TYPE: PRT
<213> ORGANISM: Artificial Sequence
<220> FEATURE:
<223> OTHER INFORMATION: description of the artificial sequence: the
      amino acid sequence of HN3 VH

<400> SEQUENCE: 78

Gln Val Gln Leu Val Gln Ser Gly Gly Gly Leu Val Gln Pro Gly Gly
1               5                  10                  15

Ser Leu Arg Leu Ser Cys Ala Ala Ser Tyr Phe Asp Phe Asp Ser Tyr
            20                  25                  30

Glu Met Ser Trp Val Arg Gln Ala Pro Gly Lys Gly Leu Glu Trp Ile
        35                  40                  45

Gly Ser Ile Tyr His Ser Gly Ser Thr Tyr Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Thr Tyr Tyr Cys Ala
                85                  90                  95

Arg Val Asn Met Asp Arg Phe Asp Tyr Trp Gly Gln Gly Thr Leu Val
            100                 105                 110

Thr Val Ser Ser Ser
        115

<210> SEQ ID NO 79
<211> LENGTH: 2
<212> TYPE: PRT
<213> ORGANISM: Artificial Sequence
<220> FEATURE:
<223> OTHER INFORMATION: description of the artificial sequence: the
      amino acid of sequence of linker

<400> SEQUENCE: 79

Glu Ser
1

<210> SEQ ID NO 80
<211> LENGTH: 5
<212> TYPE: PRT
<213> ORGANISM: Artificial Sequence
<220> FEATURE:
<223> OTHER INFORMATION: description of the artificial sequence: the
      amino acid of sequence of linker

<400> SEQUENCE: 80

Glu Ser Lys Tyr Gly
1               5

<210> SEQ ID NO 81
<211> LENGTH: 7
<212> TYPE: PRT
<213> ORGANISM: Artificial Sequence
<220> FEATURE:
<223> OTHER INFORMATION: description of the artificial sequence: the
      amino acid of sequence of linker

<400> SEQUENCE: 81

Glu Ser Lys Tyr Gly Pro Pro
1               5

```
<210> SEQ ID NO 82
<211> LENGTH: 5
<212> TYPE: PRT
<213> ORGANISM: Artificial Sequence
<220> FEATURE:
<223> OTHER INFORMATION: description of the artificial sequence: the
      amino acid of sequence of linker

<400> SEQUENCE: 82

Gly Gly Gly Gly Ser
1               5

<210> SEQ ID NO 83
<211> LENGTH: 981
<212> TYPE: DNA
<213> ORGANISM: Artificial Sequence
<220> FEATURE:
<223> OTHER INFORMATION: description of the artificial sequence: the
      base sequence of IgG4PE R409K constant region

<400> SEQUENCE: 83
gctagcacca agggccatc cgtcttcccc ctggcgccct gctccaggag cacctccgag      60
agcacagccg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc cccatgccc accatgccca gcacctgagt tcgaggggg accatcagtc      360 ttcctgttcc cccaaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaagcta accgtggaca agagcaggtg gcaggagggg    900
aatgtcttct catgctccgt gatgcatgag gctctgcaca accactacac acagaagagc    960
ctctccctgt ctctgggtaa a                                              981

<210> SEQ ID NO 84
<211> LENGTH: 327
<212> TYPE: PRT
<213> ORGANISM: Artificial Sequence
<220> FEATURE:
<223> OTHER INFORMATION: description of the artificial sequence: the
      amino acid sequence of IgG4PE R409K constant region

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
            50                  55                  60
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 85
<211> LENGTH: 294
<212> TYPE: DNA
<213> ORGANISM: Artificial Sequence
<220> FEATURE:
<223> OTHER INFORMATION: description of the artificial sequence: the
      base sequence of modified codons of IgG4 CH1

<400> SEQUENCE: 85
gctagcacca aaggaccttc tgtatttcct cttgcgccat gctctcgctc tacgtcagaa      60
tcaactgccg ctctggggtg cctggttaaa gactacttcc cggagcctgt gacagtgagt     120
tggaactccg gcgccctgac atcaggagtg catacatttc ccgccgtgct tcagagcagc     180
ggactttata gcctcagcag tgtggtgacc gtgccatctt ccagcctggg gaccaagacc     240
tacacctgta acgtggacca caaacccagc aacaccaagg ttgataagag ggtc          294

<210> SEQ ID NO 86
<211> LENGTH: 327
<212> TYPE: PRT
<213> ORGANISM: Artificial Sequence
```

```
<220> FEATURE:
<223> OTHER INFORMATION: description of the artificial sequence: the
      amino acid sequence of IgG4PE constant region

<400> SEQUENCE: 86

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 87
<211> LENGTH: 763
<212> TYPE: PRT
<213> ORGANISM: Mus musculus

<400> SEQUENCE: 87

Met Met Asp Gln Ala Arg Ser Ala Phe Ser Asn Leu Phe Gly Gly Glu
1               5                   10                  15
```

```
Pro Leu Ser Tyr Thr Arg Phe Ser Leu Ala Arg Gln Val Asp Gly Asp
            20                  25                  30

Asn Ser His Val Glu Met Lys Leu Ala Ala Asp Glu Glu Asn Ala
        35                  40                  45

Asp Asn Asn Met Lys Ala Ser Val Arg Lys Pro Lys Arg Phe Asn Gly
50                  55                  60

Arg Leu Cys Phe Ala Ala Ile Ala Leu Val Ile Phe Phe Leu Ile Gly
65                  70                  75                  80

Phe Met Ser Gly Tyr Leu Gly Tyr Cys Lys Arg Val Glu Gln Lys Glu
                85                  90                  95

Glu Cys Val Lys Leu Ala Glu Thr Glu Thr Asp Lys Ser Glu Thr
            100                 105                 110

Met Glu Thr Glu Asp Val Pro Thr Ser Ser Arg Leu Tyr Trp Ala Asp
            115                 120                 125

Leu Lys Thr Leu Leu Ser Glu Lys Leu Asn Ser Ile Glu Phe Ala Asp
    130                 135                 140

Thr Ile Lys Gln Leu Ser Gln Asn Thr Tyr Thr Pro Arg Glu Ala Gly
145                 150                 155                 160

Ser Gln Lys Asp Glu Ser Leu Ala Tyr Tyr Ile Glu Asn Gln Phe His
                165                 170                 175

Glu Phe Lys Phe Ser Lys Val Trp Arg Asp Glu His Tyr Val Lys Ile
            180                 185                 190

Gln Val Lys Ser Ser Ile Gly Gln Asn Met Val Thr Ile Val Gln Ser
            195                 200                 205

Asn Gly Asn Leu Asp Pro Val Glu Ser Pro Glu Gly Tyr Val Ala Phe
    210                 215                 220

Ser Lys Pro Thr Glu Val Ser Gly Lys Leu Val His Ala Asn Phe Gly
225                 230                 235                 240

Thr Lys Lys Asp Phe Glu Glu Leu Ser Tyr Ser Val Asn Gly Ser Leu
                245                 250                 255

Val Ile Val Arg Ala Gly Glu Ile Thr Phe Ala Glu Lys Val Ala Asn
            260                 265                 270

Ala Gln Ser Phe Asn Ala Ile Gly Val Leu Ile Tyr Met Asp Lys Asn
            275                 280                 285

Lys Phe Pro Val Val Glu Ala Asp Leu Ala Leu Phe Gly His Ala His
    290                 295                 300

Leu Gly Thr Gly Asp Pro Tyr Thr Pro Gly Phe Pro Ser Phe Asn His
305                 310                 315                 320

Thr Gln Phe Pro Pro Ser Gln Ser Ser Gly Leu Pro Asn Ile Pro Val
                325                 330                 335

Gln Thr Ile Ser Arg Ala Ala Glu Lys Leu Phe Gly Lys Met Glu
            340                 345                 350

Gly Ser Cys Pro Ala Arg Trp Asn Ile Asp Ser Ser Cys Lys Leu Glu
            355                 360                 365

Leu Ser Gln Asn Gln Asn Val Lys Leu Ile Val Lys Asn Val Leu Lys
    370                 375                 380

Glu Arg Arg Ile Leu Asn Ile Phe Gly Val Ile Lys Gly Tyr Glu Glu
385                 390                 395                 400

Pro Asp Arg Tyr Val Val Val Gly Ala Gln Arg Asp Ala Leu Gly Ala
                405                 410                 415

Gly Val Ala Ala Lys Ser Ser Val Gly Thr Gly Leu Leu Leu Lys Leu
            420                 425                 430
```

-continued

```
Ala Gln Val Phe Ser Asp Met Ile Ser Lys Asp Gly Phe Arg Pro Ser
            435                 440                 445

Arg Ser Ile Ile Phe Ala Ser Trp Thr Ala Gly Asp Phe Gly Ala Val
450                 455                 460

Gly Ala Thr Glu Trp Leu Glu Gly Tyr Leu Ser Ser Leu His Leu Lys
465                 470                 475                 480

Ala Phe Thr Tyr Ile Asn Leu Asp Lys Val Val Leu Gly Thr Ser Asn
                485                 490                 495

Phe Lys Val Ser Ala Ser Pro Leu Leu Tyr Thr Leu Met Gly Lys Ile
            500                 505                 510

Met Gln Asp Val Lys His Pro Val Asp Gly Lys Ser Leu Tyr Arg Asp
            515                 520                 525

Ser Asn Trp Ile Ser Lys Val Glu Lys Leu Ser Phe Asp Asn Ala Ala
530                 535                 540

Tyr Pro Phe Leu Ala Tyr Ser Gly Ile Pro Ala Val Ser Phe Cys Phe
545                 550                 555                 560

Cys Glu Asp Ala Asp Tyr Pro Tyr Leu Gly Thr Arg Leu Asp Thr Tyr
                565                 570                 575

Glu Ala Leu Thr Gln Lys Val Pro Gln Leu Asn Gln Met Val Arg Thr
            580                 585                 590

Ala Ala Glu Val Ala Gly Gln Leu Ile Ile Lys Leu Thr His Asp Val
            595                 600                 605

Glu Leu Asn Leu Asp Tyr Glu Met Tyr Asn Ser Lys Leu Leu Ser Phe
            610                 615                 620

Met Lys Asp Leu Asn Gln Phe Lys Thr Asp Ile Arg Asp Met Gly Leu
625                 630                 635                 640

Ser Leu Gln Trp Leu Tyr Ser Ala Arg Gly Asp Tyr Phe Arg Ala Thr
                645                 650                 655

Ser Arg Leu Thr Thr Asp Phe His Asn Ala Glu Lys Thr Asn Arg Phe
            660                 665                 670

Val Met Arg Glu Ile Asn Asp Arg Ile Met Lys Val Glu Tyr His Phe
            675                 680                 685

Leu Ser Pro Tyr Val Ser Pro Arg Glu Ser Pro Phe Arg His Ile Phe
690                 695                 700

Trp Gly Ser Gly Ser His Thr Leu Ser Ala Leu Val Glu Asn Leu Lys
705                 710                 715                 720

Leu Arg Gln Lys Asn Ile Thr Ala Phe Asn Glu Thr Leu Phe Arg Asn
                725                 730                 735

Gln Leu Ala Leu Ala Thr Trp Thr Ile Gln Gly Val Ala Asn Ala Leu
            740                 745                 750

Ser Gly Asp Ile Trp Asn Ile Asp Asn Glu Phe
            755                 760
```

<210> SEQ ID NO 88
<211> LENGTH: 672
<212> TYPE: PRT
<213> ORGANISM: Artificial Sequence
<220> FEATURE:
<223> OTHER INFORMATION: description of the artificial sequence: the amino acid sequence of Apical domain mouse chimera of human TfR extracellular domain

<400> SEQUENCE: 88

```
Cys Lys Gly Val Glu Pro Lys Thr Glu Cys Glu Arg Leu Ala Gly Thr
1               5                   10                  15

Glu Ser Pro Val Arg Glu Glu Pro Gly Glu Asp Phe Pro Ala

```
                20                  25                  30
Arg Leu Tyr Trp Asp Leu Lys Arg Lys Leu Ser Glu Lys Leu Asp
            35                  40                  45
Ser Thr Asp Phe Thr Gly Thr Ile Lys Leu Leu Asn Glu Asn Ser Tyr
    50                  55                  60
Val Pro Arg Glu Ala Gly Ser Gln Lys Asp Glu Asn Leu Ala Leu Tyr
65                  70                  75                  80
Val Glu Asn Gln Phe Arg Glu Phe Lys Leu Ser Lys Val Trp Arg Asp
                85                  90                  95
Gln His Phe Val Lys Ile Gln Val Lys Ser Ser Ile Gly Gln Asn Met
            100                 105                 110
Val Thr Ile Val Gln Ser Asn Gly Asn Leu Asp Pro Val Glu Ser Pro
            115                 120                 125
Glu Gly Tyr Val Ala Phe Ser Lys Pro Thr Glu Val Ser Gly Lys Leu
            130                 135                 140
Val His Ala Asn Phe Gly Thr Lys Lys Asp Phe Glu Glu Leu Ser Tyr
145                 150                 155                 160
Ser Val Asn Gly Ser Leu Val Ile Val Arg Ala Gly Glu Ile Thr Phe
                165                 170                 175
Ala Glu Lys Val Ala Asn Ala Gln Ser Phe Asn Ala Ile Gly Val Leu
            180                 185                 190
Ile Tyr Met Asp Lys Asn Lys Phe Pro Val Val Glu Ala Asp Leu Ala
            195                 200                 205
Leu Phe Gly His Ala His Leu Gly Thr Gly Asp Pro Tyr Thr Pro Gly
            210                 215                 220
Phe Pro Ser Phe Asn His Thr Gln Phe Pro Pro Ser Gln Ser Ser Gly
225                 230                 235                 240
Leu Pro Asn Ile Pro Val Gln Thr Ile Ser Arg Ala Ala Ala Glu Lys
                245                 250                 255
Leu Phe Gly Lys Met Glu Gly Ser Cys Pro Ala Arg Trp Asn Ile Asp
            260                 265                 270
Ser Ser Cys Lys Leu Glu Leu Ser Gln Asn Gln Asn Val Lys Leu Ile
            275                 280                 285
Val Lys Asn Val Leu Lys Glu Ile Lys Ile Leu Asn Ile Phe Gly Val
            290                 295                 300
Ile Lys Gly Phe Val Glu Pro Asp His Tyr Val Val Gly Ala Gln
305                 310                 315                 320
Arg Asp Ala Trp Gly Pro Gly Ala Ala Lys Ser Gly Val Gly Thr Ala
                325                 330                 335
Leu Leu Leu Lys Leu Ala Gln Met Phe Ser Asp Met Val Leu Lys Asp
            340                 345                 350
Gly Phe Gln Pro Ser Arg Ser Ile Ile Phe Ala Ser Trp Ser Ala Gly
            355                 360                 365
Asp Phe Gly Ser Val Gly Ala Thr Glu Trp Leu Glu Gly Tyr Leu Ser
            370                 375                 380
Ser Leu His Leu Lys Ala Phe Thr Tyr Ile Asn Leu Asp Lys Ala Val
385                 390                 395                 400
Leu Gly Thr Ser Asn Phe Lys Val Ser Ala Ser Pro Leu Leu Tyr Thr
                405                 410                 415
Leu Ile Glu Lys Thr Met Gln Asn Val Lys His Pro Val Thr Gly Gln
            420                 425                 430
Phe Leu Tyr Gln Asp Ser Asn Trp Ala Ser Lys Val Glu Lys Leu Thr
            435                 440                 445
```

Leu Asp Asn Ala Ala Phe Pro Phe Leu Ala Tyr Ser Gly Ile Pro Ala
         450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
                485                 490                 495

Lys Val Ala Arg Ala Ala Ala Glu Val Ala Gly Gln Phe Val Ile Lys
                500                 505                 510

Leu Thr His Asp Val Glu Leu Asn Leu Asp Tyr Glu Arg Tyr Asn Ser
        515                 520                 525

Gln Leu Leu Ser Phe Val Arg Asp Leu Asn Gln Tyr Arg Ala Asp Ile
530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
                565                 570                 575

Lys Thr Asp Arg Phe Val Met Lys Lys Leu Asn Asp Arg Val Met Arg
                580                 585                 590

Val Glu Tyr His Phe Leu Ser Pro Tyr Val Ser Pro Lys Glu Ser Pro
        595                 600                 605

Phe Arg His Val Phe Trp Gly Ser Gly Ser His Thr Leu Pro Ala Leu
610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
                645                 650                 655

Ala Ala Asn Ala Leu Ser Gly Asp Val Trp Asp Ile Asp Asn Glu Phe
                660                 665                 670

<210> SEQ ID NO 89
<211> LENGTH: 675
<212> TYPE: PRT
<213> ORGANISM: Artificial Sequence
<220> FEATURE:
<223> OTHER INFORMATION: description of the artificial sequence: the
      amino acid sequence of Protease-like domain mouse chimera of human
      TfR extracellular domain

<400> SEQUENCE: 89

Cys Lys Arg Val Glu Gln Lys Glu Glu Cys Val Lys Leu Ala Glu Thr
1               5                   10                  15

Glu Glu Thr Asp Lys Ser Glu Thr Met Glu Thr Glu Asp Val Pro Thr
            20                  25                  30

Ser Ser Arg Leu Tyr Trp Ala Asp Leu Lys Thr Leu Leu Ser Glu Lys
        35                  40                  45

Leu Asn Ser Ile Glu Phe Ala Asp Thr Ile Lys Gln Leu Ser Gln Asn
    50                  55                  60

Thr Tyr Thr Pro Arg Glu Ala Gly Ser Gln Lys Asp Glu Ser Leu Ala
65                  70                  75                  80

Tyr Tyr Ile Glu Asn Gln Phe His Glu Phe Lys Phe Ser Lys Val Trp
                85                  90                  95

Arg Asp Glu His Tyr Val Lys Ile Gln Val Lys Asp Ser Ala Gln Asn
            100                 105                 110

Ser Val Ile Ile Val Asp Lys Asn Gly Arg Leu Val Tyr Leu Val Glu
        115                 120                 125

```
Asn Pro Gly Gly Tyr Val Ala Tyr Ser Lys Ala Ala Thr Val Thr Gly
    130                 135                 140

Lys Leu Val His Ala Asn Phe Gly Thr Lys Lys Asp Phe Glu Asp Leu
145                 150                 155                 160

Tyr Thr Pro Val Asn Gly Ser Ile Val Ile Val Arg Ala Gly Lys Ile
                165                 170                 175

Thr Phe Ala Glu Lys Val Ala Asn Ala Glu Ser Leu Asn Ala Ile Gly
                180                 185                 190

Val Leu Ile Tyr Met Asp Gln Thr Lys Phe Pro Ile Val Asn Ala Glu
            195                 200                 205

Leu Ser Phe Phe Gly His Ala His Leu Gly Thr Gly Asp Pro Tyr Thr
    210                 215                 220

Pro Gly Phe Pro Ser Phe Asn His Thr Gln Phe Pro Pro Ser Arg Ser
225                 230                 235                 240

Ser Gly Leu Pro Asn Ile Pro Val Gln Thr Ile Ser Arg Ala Ala Ala
                245                 250                 255

Glu Lys Leu Phe Gly Asn Met Glu Gly Asp Cys Pro Ser Asp Trp Lys
                260                 265                 270

Thr Asp Ser Thr Cys Arg Met Val Thr Ser Glu Ser Lys Asn Val Lys
            275                 280                 285

Leu Thr Val Ser Asn Val Leu Lys Glu Arg Arg Ile Leu Asn Ile Phe
    290                 295                 300

Gly Val Ile Lys Gly Tyr Glu Glu Pro Asp Arg Tyr Val Val Val Gly
305                 310                 315                 320

Ala Gln Arg Asp Ala Leu Gly Ala Gly Val Ala Ala Lys Ser Ser Val
                325                 330                 335

Gly Thr Gly Leu Leu Leu Lys Leu Ala Gln Val Phe Ser Asp Met Ile
            340                 345                 350

Ser Lys Asp Gly Phe Arg Pro Ser Arg Ser Ile Ile Phe Ala Ser Trp
    355                 360                 365

Thr Ala Gly Asp Phe Gly Ala Val Gly Ala Thr Glu Trp Leu Glu Gly
    370                 375                 380

Tyr Leu Ser Ser Leu His Leu Lys Ala Phe Thr Tyr Ile Asn Leu Asp
385                 390                 395                 400

Lys Val Val Leu Gly Thr Ser Asn Phe Lys Val Ser Ala Ser Pro Leu
                405                 410                 415

Leu Tyr Thr Leu Met Gly Lys Ile Met Gln Asp Val Lys His Pro Val
            420                 425                 430

Asp Gly Lys Ser Leu Tyr Arg Asp Ser Asn Trp Ile Ser Lys Val Glu
    435                 440                 445

Lys Leu Ser Phe Asp Asn Ala Ala Tyr Pro Phe Leu Ala Tyr Ser Gly
    450                 455                 460

Ile Pro Ala Val Ser Phe Cys Phe Cys Glu Asp Ala Asp Tyr Pro Tyr
465                 470                 475                 480

Leu Gly Thr Arg Leu Asp Thr Tyr Glu Ala Leu Thr Gln Lys Val Pro
                485                 490                 495

Gln Leu Asn Gln Met Val Arg Thr Ala Ala Glu Val Ala Gly Gln Leu
            500                 505                 510

Ile Ile Lys Leu Thr His Asp Val Glu Leu Asn Leu Asp Tyr Glu Arg
    515                 520                 525

Tyr Asn Ser Gln Leu Leu Ser Phe Val Arg Asp Leu Asn Gln Tyr Arg
    530                 535                 540

Ala Asp Ile Lys Glu Met Gly Leu Ser Leu Gln Trp Leu Tyr Ser Ala
```

```
                545                 550                 555                 560
Arg Gly Asp Phe Phe Arg Ala Thr Ser Arg Leu Thr Thr Asp Phe Gly
                565                 570                 575

Asn Ala Glu Lys Thr Asp Arg Phe Val Met Lys Lys Leu Asn Asp Arg
                580                 585                 590

Val Met Arg Val Glu Tyr His Phe Leu Ser Pro Tyr Val Ser Pro Lys
                595                 600                 605

Glu Ser Pro Phe Arg His Val Phe Trp Gly Ser Gly Ser His Thr Leu
                610                 615                 620

Pro Ala Leu Leu Glu Asn Leu Lys Leu Arg Lys Gln Asn Asn Gly Ala
625                 630                 635                 640

Phe Asn Glu Thr Leu Phe Arg Asn Gln Leu Ala Leu Ala Thr Trp Thr
                645                 650                 655

Ile Gln Gly Ala Ala Asn Ala Leu Ser Gly Asp Val Trp Asp Ile Asp
                660                 665                 670

Asn Glu Phe
        675
```

<210> SEQ ID NO 90
<211> LENGTH: 672
<212> TYPE: PRT
<213> ORGANISM: Artificial Sequence
<220> FEATURE:
<223> OTHER INFORMATION: description of the artificial sequence: the
      amino acid sequence of A01

<400> SEQUENCE: 90

```
Cys Lys Gly Val Glu Pro Lys Thr Glu Cys Glu Arg Leu Ala Gly Thr
1               5                   10                  15

Glu Ser Pro Val Arg Glu Pro Gly Glu Asp Phe Pro Ala Ala Arg
                20                  25                  30

Arg Leu Tyr Trp Asp Asp Leu Lys Arg Lys Leu Ser Glu Lys Leu Asp
                35                  40                  45

Ser Thr Asp Phe Thr Gly Thr Ile Lys Leu Leu Asn Glu Asn Ser Tyr
        50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gln Asn Ser Val
                100                 105                 110

Ile Ile Val Asp Lys Asn Gly Arg Leu Val Tyr Leu Val Glu Asn Pro
            115                 120                 125

Gly Gly Tyr Val Ala Tyr Ser Lys Ala Ala Thr Val Thr Gly Lys Leu
        130                 135                 140

Val His Ala Asn Phe Gly Thr Lys Lys Asp Phe Glu Asp Leu Tyr Thr
145                 150                 155                 160

Pro Val Asn Gly Ser Ile Val Ile Val Arg Ala Gly Lys Ile Thr Phe
                165                 170                 175

Ala Glu Lys Val Ala Asn Ala Glu Ser Leu Asn Ala Ile Gly Val Leu
            180                 185                 190

Ile Tyr Met Asp Lys Asn Lys Phe Pro Ile Val Asn Ala Glu Leu Ser
        195                 200                 205

Phe Phe Gly His Ala His Leu Gly Thr Gly Asp Pro Tyr Thr Pro Gly
        210                 215                 220
```

```
Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Ala Glu Lys
            245                 250                 255

Leu Phe Gly Asn Met Glu Gly Asp Cys Pro Ser Asp Trp Lys Thr Asp
        260                 265                 270

Ser Ser Cys Arg Met Val Thr Ser Glu Ser Lys Asn Val Lys Leu Thr
    275                 280                 285

Val Ser Asn Val Leu Lys Glu Ile Lys Ile Leu Asn Ile Phe Gly Val
290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                325                 330                 335

Leu Leu Leu Lys Leu Ala Gln Met Phe Ser Asp Met Val Leu Lys Asp
            340                 345                 350

Gly Phe Gln Pro Ser Arg Ser Ile Ile Phe Ala Ser Trp Ser Ala Gly
        355                 360                 365

Asp Phe Gly Ser Val Gly Ala Thr Glu Trp Leu Glu Gly Tyr Leu Ser
    370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
                405                 410                 415

Leu Ile Glu Lys Thr Met Gln Asn Val Lys His Pro Val Thr Gly Gln
            420                 425                 430

Phe Leu Tyr Gln Asp Ser Asn Trp Ala Ser Lys Val Glu Lys Leu Thr
        435                 440                 445

Leu Asp Asn Ala Ala Phe Pro Phe Leu Ala Tyr Ser Gly Ile Pro Ala
    450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
                485                 490                 495

Lys Val Ala Arg Ala Ala Ala Glu Val Ala Gly Gln Phe Val Ile Lys
            500                 505                 510

Leu Thr His Asp Val Glu Leu Asn Leu Asp Tyr Glu Arg Tyr Asn Ser
        515                 520                 525

Gln Leu Leu Ser Phe Val Arg Asp Leu Asn Gln Tyr Arg Ala Asp Ile
    530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
                565                 570                 575

Lys Thr Asp Arg Phe Val Met Lys Lys Leu Asn Asp Arg Val Met Arg
            580                 585                 590

Val Glu Tyr His Phe Leu Ser Pro Tyr Val Ser Pro Lys Glu Ser Pro
        595                 600                 605

Phe Arg His Val Phe Trp Gly Ser Gly Ser His Thr Leu Pro Ala Leu
    610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
```

```
                    645                 650                 655
Ala Ala Asn Ala Leu Ser Gly Asp Val Trp Asp Ile Asp Asn Glu Phe
                660                 665                 670

<210> SEQ ID NO 91
<211> LENGTH: 672
<212> TYPE: PRT
<213> ORGANISM: Artificial Sequence
<220> FEATURE:
<223> OTHER INFORMATION: description of the artificial sequence: the
      amino acid sequence of A02

<400> SEQUENCE: 91

Cys Lys Gly Val Glu Pro Lys Thr Glu Cys Glu Arg Leu Ala Gly Thr
1               5                   10                  15

Glu Ser Pro Val Arg Glu Pro Gly Glu Asp Phe Pro Ala Ala Arg
            20                  25                  30

Arg Leu Tyr Trp Asp Asp Leu Lys Arg Lys Leu Ser Glu Lys Leu Asp
        35                  40                  45

Ser Thr Asp Phe Thr Gly Thr Ile Lys Leu Leu Asn Glu Asn Ser Tyr
    50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gln Asn Ser Val
            100                 105                 110

Ile Ile Val Asp Lys Asn Gly Arg Leu Val Tyr Leu Val Glu Asn Pro
        115                 120                 125

Gly Gly Tyr Val Ala Tyr Ser Lys Ala Ala Thr Val Thr Gly Lys Leu
    130                 135                 140

Val His Ala Asn Phe Gly Thr Lys Lys Asp Phe Glu Asp Leu Tyr Thr
145                 150                 155                 160

Pro Val Asn Gly Ser Ile Val Ile Val Arg Ala Gly Lys Ile Thr Phe
                165                 170                 175

Ala Glu Lys Val Ala Asn Ala Glu Ser Leu Asn Ala Ile Gly Val Leu
            180                 185                 190

Ile Tyr Met Asp Gln Thr Lys Phe Pro Ile Val Asn Ala Glu Leu Ser
        195                 200                 205

Phe Phe Gly His Ala His Leu Gly Thr Gly Asp Pro Tyr Thr Pro Gly
    210                 215                 220

Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Ala Glu Lys
                245                 250                 255

Leu Phe Gly Asn Met Glu Gly Ser Cys Pro Ala Arg Trp Asn Thr Asp
            260                 265                 270

Ser Thr Cys Arg Met Val Thr Ser Glu Ser Lys Asn Val Lys Leu Thr
        275                 280                 285

Val Ser Asn Val Leu Lys Glu Ile Lys Ile Leu Asn Ile Phe Gly Val
    290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                325                 330                 335
```

```
Leu Leu Leu Lys Leu Ala Gln Met Phe Ser Asp Met Val Leu Lys Asp
            340                 345                 350

Gly Phe Gln Pro Ser Arg Ser Ile Ile Phe Ala Ser Trp Ser Ala Gly
        355                 360                 365

Asp Phe Gly Ser Val Gly Ala Thr Glu Trp Leu Glu Gly Tyr Leu Ser
370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
                405                 410                 415

Leu Ile Glu Lys Thr Met Gln Asn Val Lys His Pro Val Thr Gly Gln
            420                 425                 430

Phe Leu Tyr Gln Asp Ser Asn Trp Ala Ser Lys Val Glu Lys Leu Thr
        435                 440                 445

Leu Asp Asn Ala Ala Phe Pro Phe Leu Ala Tyr Ser Gly Ile Pro Ala
450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
                485                 490                 495

Lys Val Ala Arg Ala Ala Ala Glu Val Ala Gly Gln Phe Val Ile Lys
            500                 505                 510

Leu Thr His Asp Val Glu Leu Asn Leu Asp Tyr Glu Arg Tyr Asn Ser
        515                 520                 525

Gln Leu Leu Ser Phe Val Arg Asp Leu Asn Gln Tyr Arg Ala Asp Ile
530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
                565                 570                 575

Lys Thr Asp Arg Phe Val Met Lys Lys Leu Asn Asp Arg Val Met Arg
            580                 585                 590

Val Glu Tyr His Phe Leu Ser Pro Tyr Val Ser Pro Lys Glu Ser Pro
        595                 600                 605

Phe Arg His Val Phe Trp Gly Ser Gly Ser His Thr Leu Pro Ala Leu
610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
                645                 650                 655

Ala Ala Asn Ala Leu Ser Gly Asp Val Trp Asp Ile Asp Asn Glu Phe
            660                 665                 670

<210> SEQ ID NO 92
<211> LENGTH: 672
<212> TYPE: PRT
<213> ORGANISM: Artificial Sequence
<220> FEATURE:
<223> OTHER INFORMATION: description of the artificial sequence: the
      amino acid sequence of A03

<400> SEQUENCE: 92

Cys Lys Gly Val Glu Pro Lys Thr Glu Cys Glu Arg Leu Ala Gly Thr
1               5                   10                  15

Glu Ser Pro Val Arg Glu Glu Pro Gly Glu Asp Phe Pro Ala Ala Arg
            20                  25                  30
```

-continued

```
Arg Leu Tyr Trp Asp Asp Leu Lys Arg Lys Leu Ser Glu Lys Leu Asp
        35                  40                  45

Ser Thr Asp Phe Thr Gly Thr Ile Lys Leu Leu Asn Glu Asn Ser Tyr
 50                  55                  60

Val Pro Arg Glu Ala Gly Ser Gln Lys Asp Glu Asn Leu Ala Leu Tyr
 65                  70                  75                  80

Val Glu Asn Gln Phe Arg Glu Phe Lys Leu Ser Lys Val Trp Arg Asp
                 85                  90                  95

Gln His Phe Val Lys Ile Gln Val Lys Asp Ser Ala Gln Asn Ser Val
                100                 105                 110

Ile Ile Val Asp Lys Asn Gly Arg Leu Val Tyr Leu Val Glu Asn Pro
                115                 120                 125

Gly Gly Tyr Val Ala Tyr Ser Lys Ala Ala Thr Val Thr Gly Lys Leu
        130                 135                 140

Val His Ala Asn Phe Gly Thr Lys Lys Asp Phe Glu Glu Leu Tyr Thr
145                 150                 155                 160

Pro Val Asn Gly Ser Ile Val Ile Val Arg Ala Gly Glu Ile Thr Phe
                165                 170                 175

Ala Glu Lys Val Ala Asn Ala Glu Ser Leu Asn Ala Ile Gly Val Leu
                180                 185                 190

Ile Tyr Met Asp Gln Thr Lys Phe Pro Ile Val Asn Ala Glu Leu Ser
        195                 200                 205

Phe Phe Gly His Ala His Leu Gly Thr Gly Asp Pro Tyr Thr Pro Gly
        210                 215                 220

Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Ala Glu Lys
                245                 250                 255

Leu Phe Gly Asn Met Glu Gly Asp Cys Pro Ser Asp Trp Lys Thr Asp
                260                 265                 270

Ser Thr Cys Arg Met Val Thr Ser Glu Ser Lys Asn Val Lys Leu Thr
        275                 280                 285

Val Ser Asn Val Leu Lys Glu Ile Lys Ile Leu Asn Ile Phe Gly Val
        290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                325                 330                 335

Leu Leu Leu Lys Leu Ala Gln Met Phe Ser Asp Met Val Leu Lys Asp
        340                 345                 350

Gly Phe Gln Pro Ser Arg Ser Ile Ile Phe Ala Ser Trp Ser Ala Gly
        355                 360                 365

Asp Phe Gly Ser Val Gly Ala Thr Glu Trp Leu Glu Gly Tyr Leu Ser
370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
                405                 410                 415

Leu Ile Glu Lys Thr Met Gln Asn Val Lys His Pro Val Thr Gly Gln
                420                 425                 430

Phe Leu Tyr Gln Asp Ser Asn Trp Ala Ser Lys Val Glu Lys Leu Thr
        435                 440                 445
```

```
Leu Asp Asn Ala Ala Phe Pro Phe Leu Ala Tyr Ser Gly Ile Pro Ala
    450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
                485                 490                 495

Lys Val Ala Arg Ala Ala Ala Glu Val Ala Gly Gln Phe Val Ile Lys
                500                 505                 510

Leu Thr His Asp Val Glu Leu Asn Leu Asp Tyr Glu Arg Tyr Asn Ser
            515                 520                 525

Gln Leu Leu Ser Phe Val Arg Asp Leu Asn Gln Tyr Arg Ala Asp Ile
            530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
                565                 570                 575

Lys Thr Asp Arg Phe Val Met Lys Lys Leu Asn Asp Arg Val Met Arg
                580                 585                 590

Val Glu Tyr His Phe Leu Ser Pro Tyr Val Ser Pro Lys Glu Ser Pro
            595                 600                 605

Phe Arg His Val Phe Trp Gly Ser Gly Ser His Thr Leu Pro Ala Leu
            610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
                645                 650                 655

Ala Ala Asn Ala Leu Ser Gly Asp Val Trp Asp Ile Asp Asn Glu Phe
                660                 665                 670

<210> SEQ ID NO 93
<211> LENGTH: 672
<212> TYPE: PRT
<213> ORGANISM: Artificial Sequence
<220> FEATURE:
<223> OTHER INFORMATION: description of the artificial sequence: the
      amino acid sequence of A04

<400> SEQUENCE: 93

Cys Lys Gly Val Glu Pro Lys Thr Glu Cys Glu Arg Leu Ala Gly Thr
1               5                   10                  15

Glu Ser Pro Val Arg Glu Glu Pro Gly Glu Asp Phe Pro Ala Ala Arg
                20                  25                  30

Arg Leu Tyr Trp Asp Asp Leu Lys Arg Lys Leu Ser Glu Lys Leu Asp
            35                  40                  45

Ser Thr Asp Phe Thr Gly Thr Ile Lys Leu Leu Asn Glu Asn Ser Tyr
        50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gln Asn Ser Val
            100                 105                 110

Ile Ile Val Asp Lys Asn Gly Arg Leu Val Tyr Leu Val Glu Asn Pro
        115                 120                 125

Gly Gly Tyr Val Ala Tyr Ser Lys Ala Ala Thr Val Thr Gly Lys Leu
    130                 135                 140
```

-continued

```
Val His Ala Asn Phe Gly Thr Lys Lys Asp Phe Glu Glu Leu Tyr Thr
145                 150                 155                 160

Pro Val Asn Gly Ser Ile Val Ile Val Arg Ala Gly Glu Ile Thr Phe
                165                 170                 175

Ala Glu Lys Val Ala Asn Ala Glu Ser Leu Asn Ala Ile Gly Val Leu
            180                 185                 190

Ile Tyr Met Asp Gln Thr Lys Phe Pro Ile Val Asn Ala Glu Leu Ser
        195                 200                 205

Phe Phe Gly His Ala His Leu Gly Thr Gly Asp Pro Tyr Thr Pro Gly
    210                 215                 220

Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Glu Lys
                245                 250                 255

Leu Phe Gly Asn Met Glu Gly Asp Cys Pro Ser Arg Trp Lys Thr Asp
            260                 265                 270

Ser Thr Cys Arg Met Val Thr Ser Glu Ser Lys Asn Val Lys Leu Thr
        275                 280                 285

Val Ser Asn Val Leu Lys Glu Ile Lys Ile Leu Asn Ile Phe Gly Val
    290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                325                 330                 335

Leu Leu Leu Lys Leu Ala Gln Met Phe Ser Asp Met Val Leu Lys Asp
            340                 345                 350

Gly Phe Gln Pro Ser Arg Ser Ile Ile Phe Ala Ser Trp Ser Ala Gly
        355                 360                 365

Asp Phe Gly Ser Val Gly Ala Thr Glu Trp Leu Glu Gly Tyr Leu Ser
    370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
                405                 410                 415

Leu Ile Glu Lys Thr Met Gln Asn Val Lys His Pro Val Thr Gly Gln
            420                 425                 430

Phe Leu Tyr Gln Asp Ser Asn Trp Ala Ser Lys Val Glu Lys Leu Thr
        435                 440                 445

Leu Asp Asn Ala Ala Phe Pro Phe Leu Ala Tyr Ser Gly Ile Pro Ala
    450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
                485                 490                 495

Lys Val Ala Arg Ala Ala Ala Glu Val Ala Gly Gln Phe Val Ile Lys
            500                 505                 510

Leu Thr His Asp Val Glu Leu Asn Leu Asp Tyr Glu Arg Tyr Asn Ser
        515                 520                 525

Gln Leu Leu Ser Phe Val Arg Asp Leu Asn Gln Tyr Arg Ala Asp Ile
    530                 535                 540

Lys Glu Met Gly Leu Ser Leu Gln Trp Leu Tyr Ser Ala Arg Gly Asp
545                 550                 555                 560
```

-continued

```
Phe Phe Arg Ala Thr Ser Arg Leu Thr Thr Asp Phe Gly Asn Ala Glu
                565                 570                 575

Lys Thr Asp Arg Phe Val Met Lys Lys Leu Asn Asp Arg Val Met Arg
            580                 585                 590

Val Glu Tyr His Phe Leu Ser Pro Tyr Val Ser Pro Lys Glu Ser Pro
        595                 600                 605

Phe Arg His Val Phe Trp Gly Ser Gly Ser His Thr Leu Pro Ala Leu
    610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
                645                 650                 655

Ala Ala Asn Ala Leu Ser Gly Asp Val Trp Asp Ile Asp Asn Glu Phe
            660                 665                 670
```

<210> SEQ ID NO 94
<211> LENGTH: 672
<212> TYPE: PRT
<213> ORGANISM: Artificial Sequence
<220> FEATURE:
<223> OTHER INFORMATION: description of the artificial sequence: the amino acid sequence of A05

<400> SEQUENCE: 94

```
Cys Lys Gly Val Glu Pro Lys Thr Glu Cys Glu Arg Leu Ala Gly Thr
1               5                   10                  15

Glu Ser Pro Val Arg Glu Pro Gly Glu Asp Phe Pro Ala Ala Arg
            20                  25                  30

Arg Leu Tyr Trp Asp Asp Leu Lys Arg Lys Leu Ser Glu Lys Leu Asp
            35                  40                  45

Ser Thr Asp Phe Thr Gly Thr Ile Lys Leu Leu Asn Glu Asn Ser Tyr
        50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gln Asn Ser Val
            100                 105                 110

Ile Ile Val Asp Lys Asn Gly Arg Leu Val Tyr Leu Val Glu Asn Pro
        115                 120                 125

Gly Gly Tyr Val Ala Tyr Ser Lys Ala Ala Thr Val Thr Gly Lys Leu
    130                 135                 140

Val His Ala Asn Phe Gly Thr Lys Lys Asp Phe Glu Asp Leu Tyr Thr
145                 150                 155                 160

Ser Val Asn Gly Ser Ile Val Ile Val Arg Ala Gly Lys Ile Thr Phe
                165                 170                 175

Ala Glu Lys Val Ala Asn Ala Glu Ser Phe Asn Ala Ile Gly Val Leu
            180                 185                 190

Ile Tyr Met Asp Gln Thr Lys Phe Pro Ile Val Asn Ala Glu Leu Ser
        195                 200                 205

Phe Phe Gly His Ala His Leu Gly Thr Gly Asp Pro Tyr Thr Pro Gly
    210                 215                 220

Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Ala Glu Lys
                245                 250                 255
```

```
Leu Phe Gly Asn Met Glu Gly Asp Cys Pro Ser Asp Trp Lys Thr Asp
            260                 265                 270

Ser Thr Cys Arg Met Val Thr Ser Glu Ser Lys Asn Val Lys Leu Thr
            275                 280                 285

Val Ser Asn Val Leu Lys Glu Ile Lys Ile Leu Asn Ile Phe Gly Val
290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
            325                 330                 335

Leu Leu Leu Lys Leu Ala Gln Met Phe Ser Asp Met Val Leu Lys Asp
            340                 345                 350

Gly Phe Gln Pro Ser Arg Ser Ile Ile Phe Ala Ser Trp Ser Ala Gly
            355                 360                 365

Asp Phe Gly Ser Val Gly Ala Thr Glu Trp Leu Glu Gly Tyr Leu Ser
            370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
            405                 410                 415

Leu Ile Glu Lys Thr Met Gln Asn Val Lys His Pro Val Thr Gly Gln
            420                 425                 430

Phe Leu Tyr Gln Asp Ser Asn Trp Ala Ser Lys Val Glu Lys Leu Thr
            435                 440                 445

Leu Asp Asn Ala Ala Phe Pro Phe Leu Ala Tyr Ser Gly Ile Pro Ala
450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
            485                 490                 495

Lys Val Ala Arg Ala Ala Ala Glu Val Ala Gly Gln Phe Val Ile Lys
            500                 505                 510

Leu Thr His Asp Val Glu Leu Asn Leu Asp Tyr Glu Arg Tyr Asn Ser
            515                 520                 525

Gln Leu Leu Ser Phe Val Arg Asp Leu Asn Gln Tyr Arg Ala Asp Ile
            530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
            565                 570                 575

Lys Thr Asp Arg Phe Val Met Lys Lys Leu Asn Asp Arg Val Met Arg
            580                 585                 590

Val Glu Tyr His Phe Leu Ser Pro Tyr Val Ser Pro Lys Glu Ser Pro
            595                 600                 605

Phe Arg His Val Phe Trp Gly Ser Gly Ser His Thr Leu Pro Ala Leu
            610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
            645                 650                 655

Ala Ala Asn Ala Leu Ser Gly Asp Val Trp Asp Ile Asp Asn Glu Phe
            660                 665                 670
```

<210> SEQ ID NO 95
<211> LENGTH: 672
<212> TYPE: PRT
<213> ORGANISM: Artificial Sequence
<220> FEATURE:
<223> OTHER INFORMATION: description of the artificial sequence: the amino acid sequence of A06

<400> SEQUENCE: 95

```
Cys Lys Gly Val Glu Pro Lys Thr Glu Cys Glu Arg Leu Ala Gly Thr
1               5                   10                  15

Glu Ser Pro Val Arg Glu Pro Gly Glu Asp Phe Pro Ala Ala Arg
            20                  25                  30

Arg Leu Tyr Trp Asp Asp Leu Lys Arg Lys Leu Ser Glu Lys Leu Asp
        35                  40                  45

Ser Thr Asp Phe Thr Gly Thr Ile Lys Leu Leu Asn Glu Asn Ser Tyr
    50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gln Asn Ser Val
            100                 105                 110

Ile Ile Val Asp Lys Asn Gly Arg Leu Val Tyr Leu Val Glu Asn Pro
        115                 120                 125

Gly Gly Tyr Val Ala Tyr Ser Lys Ala Ala Thr Val Thr Gly Lys Leu
    130                 135                 140

Val His Ala Asn Phe Gly Thr Lys Lys Asp Phe Glu Asp Leu Tyr Thr
145                 150                 155                 160

Pro Val Asn Gly Ser Ile Val Ile Val Arg Ala Gly Lys Ile Thr Phe
                165                 170                 175

Ala Glu Lys Val Ala Asn Ala Gln Ser Leu Asn Ala Ile Gly Val Leu
            180                 185                 190

Ile Tyr Met Asp Gln Thr Lys Phe Pro Ile Val Asn Ala Glu Leu Ser
        195                 200                 205

Phe Phe Gly His Ala His Leu Gly Thr Gly Asp Pro Tyr Thr Pro Gly
    210                 215                 220

Phe Pro Ser Phe Asn His Thr Gln Phe Pro Ser Arg Ser Ser Gly
225                 230                 235                 240

Leu Pro Asn Ile Pro Val Gln Thr Ile Ser Arg Ala Ala Ala Glu Lys
                245                 250                 255

Leu Phe Gly Asn Met Glu Gly Asp Cys Pro Ser Asp Trp Lys Thr Asp
            260                 265                 270

Ser Thr Cys Arg Met Val Thr Ser Glu Ser Lys Asn Val Lys Leu Thr
        275                 280                 285

Val Ser Asn Val Leu Lys Glu Ile Lys Ile Leu Asn Ile Phe Gly Val
    290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                325                 330                 335

Leu Leu Leu Lys Leu Ala Gln Met Phe Ser Asp Met Val Leu Lys Asp
            340                 345                 350

Gly Phe Gln Pro Ser Arg Ser Ile Ile Phe Ala Ser Trp Ser Ala Gly
        355                 360                 365
```

Asp Phe Gly Ser Val Gly Ala Thr Glu Trp Leu Glu Gly Tyr Leu Ser
              370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
                405                 410                 415

Leu Ile Glu Lys Thr Met Gln Asn Val Lys His Pro Val Thr Gly Gln
              420                 425                 430

Phe Leu Tyr Gln Asp Ser Asn Trp Ala Ser Lys Val Glu Lys Leu Thr
              435                 440                 445

Leu Asp Asn Ala Ala Phe Pro Phe Leu Ala Tyr Ser Gly Ile Pro Ala
450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
                485                 490                 495

Lys Val Ala Arg Ala Ala Ala Glu Val Ala Gly Gln Phe Val Ile Lys
              500                 505                 510

Leu Thr His Asp Val Glu Leu Asn Leu Asp Tyr Glu Arg Tyr Asn Ser
              515                 520                 525

Gln Leu Leu Ser Phe Val Arg Asp Leu Asn Gln Tyr Arg Ala Asp Ile
530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
                565                 570                 575

Lys Thr Asp Arg Phe Val Met Lys Lys Leu Asn Asp Arg Val Met Arg
              580                 585                 590

Val Glu Tyr His Phe Leu Ser Pro Tyr Val Ser Pro Lys Glu Ser Pro
              595                 600                 605

Phe Arg His Val Phe Trp Gly Ser Gly Ser His Thr Leu Pro Ala Leu
610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
                645                 650                 655

Ala Ala Asn Ala Leu Ser Gly Asp Val Trp Asp Ile Asp Asn Glu Phe
              660                 665                 670

<210> SEQ ID NO 96
<211> LENGTH: 672
<212> TYPE: PRT
<213> ORGANISM: Artificial Sequence
<220> FEATURE:
<223> OTHER INFORMATION: description of the artificial sequence: the
      amino acid sequence of A07

<400> SEQUENCE: 96

Cys Lys Gly Val Glu Pro Lys Thr Glu Cys Glu Arg Leu Ala Gly Thr
1               5                   10                  15

Glu Ser Pro Val Arg Glu Pro Gly Glu Asp Phe Pro Ala Ala Arg
                20                  25                  30

Arg Leu Tyr Trp Asp Asp Leu Lys Arg Lys Leu Ser Glu Lys Leu Asp
              35                  40                  45

Ser Thr Asp Phe Thr Gly Thr Ile Lys Leu Leu Asn Glu Asn Ser Tyr

```
            50                  55                  60
Val Pro Arg Glu Ala Gly Ser Gln Lys Asp Glu Asn Leu Ala Leu Tyr
 65                  70                  75                  80

Val Glu Asn Gln Phe Arg Glu Phe Lys Leu Ser Lys Val Trp Arg Asp
                     85                  90                  95

Gln His Phe Val Lys Ile Gln Val Lys Asp Ser Ala Gln Asn Ser Val
                    100                 105                 110

Ile Ile Val Asp Lys Asn Gly Arg Leu Val Tyr Leu Val Glu Asn Pro
                    115                 120                 125

Gly Gly Tyr Val Ala Tyr Ser Lys Ala Ala Thr Val Thr Gly Lys Leu
                    130                 135                 140

Val His Ala Asn Phe Gly Thr Lys Lys Asp Phe Glu Asp Leu Tyr Thr
145                 150                 155                 160

Pro Val Asn Gly Ser Ile Val Ile Val Arg Ala Gly Lys Ile Thr Phe
                    165                 170                 175

Ala Glu Lys Val Ala Asn Ala Glu Ser Leu Asn Ala Ile Gly Val Leu
                    180                 185                 190

Ile Tyr Met Asp Gln Thr Lys Phe Pro Ile Val Asn Ala Glu Leu Ser
                    195                 200                 205

Phe Phe Gly His Ala His Leu Gly Thr Gly Asp Pro Tyr Thr Pro Gly
                    210                 215                 220

Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Ala Glu Lys
                    245                 250                 255

Leu Phe Gly Asn Met Glu Gly Asp Cys Pro Ser Asp Trp Lys Thr Asp
                    260                 265                 270

Ser Thr Cys Arg Leu Glu Thr Ser Gln Ser Lys Asn Val Lys Leu Thr
                    275                 280                 285

Val Ser Asn Val Leu Lys Glu Ile Lys Ile Leu Asn Ile Phe Gly Val
                    290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                    325                 330                 335

Leu Leu Leu Lys Leu Ala Gln Met Phe Ser Asp Met Val Leu Lys Asp
                    340                 345                 350

Gly Phe Gln Pro Ser Arg Ser Ile Ile Phe Ala Ser Trp Ser Ala Gly
                    355                 360                 365

Asp Phe Gly Ser Val Gly Ala Thr Glu Trp Leu Glu Gly Tyr Leu Ser
                    370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
                    405                 410                 415

Leu Ile Glu Lys Thr Met Gln Asn Val Lys His Pro Val Thr Gly Gln
                    420                 425                 430

Phe Leu Tyr Gln Asp Ser Asn Trp Ala Ser Lys Val Glu Lys Leu Thr
                    435                 440                 445

Leu Asp Asn Ala Ala Phe Pro Phe Leu Ala Tyr Ser Gly Ile Pro Ala
                    450                 455                 460

Val Ser Phe Cys Phe Cys Glu Asp Thr Asp Tyr Pro Tyr Leu Gly Thr
465                 470                 475                 480
```

```
Thr Met Asp Thr Tyr Lys Glu Leu Ile Glu Arg Ile Pro Glu Leu Asn
                485                 490                 495

Lys Val Ala Arg Ala Ala Glu Val Ala Gly Gln Phe Val Ile Lys
            500                 505                 510

Leu Thr His Asp Val Glu Leu Asn Leu Asp Tyr Glu Arg Tyr Asn Ser
            515                 520                 525

Gln Leu Leu Ser Phe Val Arg Asp Leu Asn Gln Tyr Arg Ala Asp Ile
            530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
            565                 570                 575

Lys Thr Asp Arg Phe Val Met Lys Lys Leu Asn Asp Arg Val Met Arg
            580                 585                 590

Val Glu Tyr His Phe Leu Ser Pro Tyr Val Ser Pro Lys Glu Ser Pro
            595                 600                 605

Phe Arg His Val Phe Trp Gly Ser Gly Ser His Thr Leu Pro Ala Leu
            610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
            645                 650                 655

Ala Ala Asn Ala Leu Ser Gly Asp Val Trp Asp Ile Asp Asn Glu Phe
            660                 665                 670

<210> SEQ ID NO 97
<211> LENGTH: 671
<212> TYPE: PRT
<213> ORGANISM: Artificial Sequence
<220> FEATURE:
<223> OTHER INFORMATION: description of the artificial sequence: the
      amino acid sequence of A08

<400> SEQUENCE: 97

Cys Lys Gly Val Glu Pro Lys Thr Glu Cys Glu Arg Leu Ala Gly Thr
1               5                   10                  15

Glu Ser Pro Val Arg Glu Glu Pro Gly Glu Asp Phe Pro Ala Ala Arg
            20                  25                  30

Arg Leu Tyr Trp Asp Asp Leu Lys Arg Lys Leu Ser Glu Lys Leu Asp
            35                  40                  45

Ser Thr Asp Phe Thr Gly Thr Ile Lys Leu Leu Asn Glu Asn Ser Tyr
            50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gln Asn Ser Val
            100                 105                 110

Ile Ile Val Gln Lys Asn Gly Arg Leu Asp Leu Val Glu Asn Pro Gly
            115                 120                 125

Gly Tyr Val Ala Tyr Ser Lys Ala Ala Thr Val Thr Gly Lys Leu Val
            130                 135                 140

His Ala Asn Phe Gly Thr Lys Lys Asp Phe Glu Asp Leu Tyr Thr Pro
145                 150                 155                 160

Val Asn Gly Ser Ile Val Ile Val Arg Ala Gly Lys Ile Thr Phe Ala
```

```
              165                 170                 175
Glu Lys Val Ala Asn Ala Glu Ser Leu Asn Ala Ile Gly Val Leu Ile
            180                 185                 190

Tyr Met Asp Gln Thr Lys Phe Pro Ile Val Asn Ala Glu Leu Ser Phe
            195                 200                 205

Phe Gly His Ala His Leu Gly Thr Gly Asp Pro Tyr Thr Pro Gly Phe
            210                 215                 220

Pro Ser Phe Asn His Thr Gln Phe Pro Pro Ser Arg Ser Ser Gly Leu
225                 230                 235                 240

Pro Asn Ile Pro Val Gln Thr Ile Ser Arg Ala Ala Glu Lys Leu
                    245                 250                 255

Phe Gly Lys Met Glu Gly Asp Cys Pro Ser Asp Trp Lys Thr Asp Ser
                    260                 265                 270

Thr Cys Arg Met Val Thr Ser Glu Ser Gln Asn Val Lys Leu Thr Val
                    275                 280                 285

Ser Asn Val Leu Lys Glu Ile Lys Ile Leu Asn Ile Phe Gly Val Ile
            290                 295                 300

Lys Gly Phe Val Glu Pro Asp His Tyr Val Val Gly Ala Gln Arg
305                 310                 315                 320

Asp Ala Trp Gly Pro Gly Ala Ala Lys Ser Gly Val Gly Thr Ala Leu
                    325                 330                 335

Leu Leu Lys Leu Ala Gln Met Phe Ser Asp Met Val Leu Lys Asp Gly
                    340                 345                 350

Phe Gln Pro Ser Arg Ser Ile Ile Phe Ala Ser Trp Ser Ala Gly Asp
                    355                 360                 365

Phe Gly Ser Val Gly Ala Thr Glu Trp Leu Glu Gly Tyr Leu Ser Ser
            370                 375                 380

Leu His Leu Lys Ala Phe Thr Tyr Ile Asn Leu Asp Lys Ala Val Leu
385                 390                 395                 400

Gly Thr Ser Asn Phe Lys Val Ser Ala Ser Pro Leu Leu Tyr Thr Leu
                    405                 410                 415

Ile Glu Lys Thr Met Gln Asn Val Lys His Pro Val Thr Gly Gln Phe
                    420                 425                 430

Leu Tyr Gln Asp Ser Asn Trp Ala Ser Lys Val Glu Lys Leu Thr Leu
            435                 440                 445

Asp Asn Ala Ala Phe Pro Phe Leu Ala Tyr Ser Gly Ile Pro Ala Val
450                 455                 460

Ser Phe Cys Phe Cys Glu Asp Thr Asp Tyr Pro Tyr Leu Gly Thr Thr
465                 470                 475                 480

Met Asp Thr Tyr Lys Glu Leu Ile Glu Arg Ile Pro Glu Leu Asn Lys
                    485                 490                 495

Val Ala Arg Ala Ala Ala Glu Val Ala Gly Gln Phe Val Ile Lys Leu
                    500                 505                 510

Thr His Asp Val Glu Leu Asn Leu Asp Tyr Glu Arg Tyr Asn Ser Gln
            515                 520                 525

Leu Leu Ser Phe Val Arg Asp Leu Asn Gln Tyr Arg Ala Asp Ile Lys
            530                 535                 540

Glu Met Gly Leu Ser Leu Gln Trp Leu Tyr Ser Ala Arg Gly Asp Phe
545                 550                 555                 560

Phe Arg Ala Thr Ser Arg Leu Thr Thr Asp Phe Gly Asn Ala Glu Lys
                    565                 570                 575

Thr Asp Arg Phe Val Met Lys Lys Leu Asn Asp Arg Val Met Arg Val
                    580                 585                 590
```

```
Glu Tyr His Phe Leu Ser Pro Tyr Val Ser Pro Lys Glu Ser Pro Phe
            595                 600                 605

Arg His Val Phe Trp Gly Ser Gly Ser His Thr Leu Pro Ala Leu Leu
            610                 615                 620

Glu Asn Leu Lys Leu Arg Lys Gln Asn Asn Gly Ala Phe Asn Glu Thr
625                 630                 635                 640

Leu Phe Arg Asn Gln Leu Ala Leu Ala Thr Trp Thr Ile Gln Gly Ala
            645                 650                 655

Ala Asn Ala Leu Ser Gly Asp Val Trp Asp Ile Asp Asn Glu Phe
            660                 665                 670

<210> SEQ ID NO 98
<211> LENGTH: 672
<212> TYPE: PRT
<213> ORGANISM: Artificial Sequence
<220> FEATURE:
<223> OTHER INFORMATION: description of the artificial sequence: the
      amino acid sequence of A09

<400> SEQUENCE: 98

Cys Lys Gly Val Glu Pro Lys Thr Glu Cys Glu Arg Leu Ala Gly Thr
1               5                   10                  15

Glu Ser Pro Val Arg Glu Pro Gly Glu Asp Phe Pro Ala Ala Arg
            20                  25                  30

Arg Leu Tyr Trp Asp Asp Leu Lys Arg Lys Leu Ser Glu Lys Leu Asp
            35                  40                  45

Ser Thr Asp Phe Thr Gly Thr Ile Lys Leu Leu Asn Glu Asn Ser Tyr
50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gln Asn Ser Val
            100                 105                 110

Ile Ile Val Asp Lys Asn Gly Arg Leu Val Tyr Leu Val Glu Asn Pro
        115                 120                 125

Gly Gly Tyr Val Ala Tyr Ser Lys Pro Thr Glu Val Ser Gly Lys Leu
    130                 135                 140

Val His Ala Asn Phe Gly Thr Lys Lys Asp Phe Glu Asp Leu Tyr Thr
145                 150                 155                 160

Pro Val Asn Gly Ser Ile Val Ile Val Arg Ala Gly Lys Ile Thr Phe
                165                 170                 175

Ala Glu Lys Val Ala Asn Ala Glu Ser Leu Asn Ala Ile Gly Val Leu
            180                 185                 190

Ile Tyr Met Asp Gln Thr Lys Phe Pro Ile Val Asn Ala Glu Leu Ser
        195                 200                 205

Phe Phe Gly His Ala His Leu Gly Thr Gly Asp Pro Tyr Thr Pro Gly
    210                 215                 220

Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Ala Glu Lys
                245                 250                 255

Leu Phe Gly Asn Met Glu Gly Asp Cys Pro Ser Asp Trp Lys Thr Asp
            260                 265                 270

Ser Thr Cys Arg Met Val Thr Ser Glu Ser Lys Asn Val Lys Leu Thr
```

|   |   |   | 275 |   |   |   | 280 |   |   |   | 285 |   |   |
|---|---|---|---|---|---|---|---|---|---|---|---|---|---|

Val Ser Asn Val Leu Lys Glu Ile Lys Ile Leu Asn Ile Phe Gly Val
290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                325                 330                 335

Leu Leu Leu Lys Leu Ala Gln Met Phe Ser Asp Met Val Leu Lys Asp
                340                 345                 350

Gly Phe Gln Pro Ser Arg Ser Ile Ile Phe Ala Ser Trp Ser Ala Gly
                355                 360                 365

Asp Phe Gly Ser Val Gly Ala Thr Glu Trp Leu Glu Gly Tyr Leu Ser
370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
                405                 410                 415

Leu Ile Glu Lys Thr Met Gln Asn Val Lys His Pro Val Thr Gly Gln
                420                 425                 430

Phe Leu Tyr Gln Asp Ser Asn Trp Ala Ser Lys Val Glu Lys Leu Thr
                435                 440                 445

Leu Asp Asn Ala Ala Phe Pro Phe Leu Ala Tyr Ser Gly Ile Pro Ala
                450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
                485                 490                 495

Lys Val Ala Arg Ala Ala Ala Glu Val Ala Gly Gln Phe Val Ile Lys
                500                 505                 510

Leu Thr His Asp Val Glu Leu Asn Leu Asp Tyr Glu Arg Tyr Asn Ser
                515                 520                 525

Gln Leu Leu Ser Phe Val Arg Asp Leu Asn Gln Tyr Arg Ala Asp Ile
530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
                565                 570                 575

Lys Thr Asp Arg Phe Val Met Lys Lys Leu Asn Asp Arg Val Met Arg
                580                 585                 590

Val Glu Tyr His Phe Leu Ser Pro Tyr Val Ser Pro Lys Glu Ser Pro
                595                 600                 605

Phe Arg His Val Phe Trp Gly Ser Gly Ser His Thr Leu Pro Ala Leu
610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
                645                 650                 655

Ala Ala Asn Ala Leu Ser Gly Asp Val Trp Asp Ile Asn Glu Phe
                660                 665                 670

<210> SEQ ID NO 99
<211> LENGTH: 672
<212> TYPE: PRT
<213> ORGANISM: Artificial Sequence -continued
<220> FEATURE:
<223> OTHER INFORMATION: description of the artificial sequence: the amino acid sequence of A10

<400> SEQUENCE: 99

```
Cys Lys Gly Val Glu Pro Lys Thr Glu Cys Glu Arg Leu Ala Gly Thr
1               5                   10                  15

Glu Ser Pro Val Arg Glu Pro Gly Glu Asp Phe Pro Ala Ala Arg
            20                  25                  30

Arg Leu Tyr Trp Asp Asp Leu Arg Lys Leu Ser Glu Lys Leu Asp
        35                  40                  45

Ser Thr Asp Phe Thr Gly Thr Ile Lys Leu Leu Asn Glu Asn Ser Tyr
    50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gly Asn Ser Val
            100                 105                 110

Ile Ile Val Asp Lys Asn Gly Arg Leu Val Tyr Leu Val Glu Asn Pro
        115                 120                 125

Gly Gly Tyr Val Ala Tyr Ser Lys Pro Thr Glu Val Thr Gly Lys Leu
    130                 135                 140

Val His Ala Asn Phe Gly Thr Lys Lys Asp Phe Glu Asp Leu Tyr Thr
145                 150                 155                 160

Pro Val Asn Gly Ser Ile Val Ile Val Arg Ala Gly Lys Ile Thr Phe
                165                 170                 175

Ala Glu Lys Val Ala Asn Ala Glu Ser Leu Asn Ala Ile Gly Val Leu
            180                 185                 190

Ile Tyr Met Asp Gln Thr Lys Phe Pro Ile Val Asn Ala Glu Leu Ser
        195                 200                 205

Phe Phe Gly His Ala His Leu Gly Thr Gly Asp Pro Tyr Thr Pro Gly
    210                 215                 220

Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Glu Lys
                245                 250                 255

Leu Phe Gly Asn Met Glu Gly Asp Cys Pro Ser Asp Trp Lys Thr Asp
            260                 265                 270

Ser Thr Cys Arg Met Val Thr Ser Glu Ser Lys Asn Val Lys Leu Thr
        275                 280                 285

Val Ser Asn Val Leu Lys Glu Ile Lys Ile Leu Asn Ile Phe Gly Val
    290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                325                 330                 335

Leu Leu Leu Lys Leu Ala Gln Met Phe Ser Asp Met Val Leu Lys Asp
            340                 345                 350

Gly Phe Gln Pro Ser Arg Ser Ile Ile Phe Ala Ser Trp Ser Ala Gly
        355                 360                 365

Asp Phe Gly Ser Val Gly Ala Thr Glu Trp Leu Glu Gly Tyr Leu Ser
    370                 375                 380

Ser Leu His Leu Lys Ala Phe Thr Tyr Ile Asn Leu Asp Lys Ala Val
```

```
                385                 390                 395                 400
Leu Gly Thr Ser Asn Phe Lys Val Ser Ala Ser Pro Leu Leu Tyr Thr
                405                 410                 415
Leu Ile Glu Lys Thr Met Gln Asn Val Lys His Pro Val Thr Gly Gln
                420                 425                 430
Phe Leu Tyr Gln Asp Ser Asn Trp Ala Ser Lys Val Glu Lys Leu Thr
                435                 440                 445
Leu Asp Asn Ala Ala Phe Pro Phe Leu Ala Tyr Ser Gly Ile Pro Ala
                450                 455                 460
Val Ser Phe Cys Phe Cys Glu Asp Thr Asp Tyr Pro Tyr Leu Gly Thr
465                 470                 475                 480
Thr Met Asp Thr Tyr Lys Glu Leu Ile Glu Arg Ile Pro Glu Leu Asn
                485                 490                 495
Lys Val Ala Arg Ala Ala Ala Glu Val Ala Gly Gln Phe Val Ile Lys
                500                 505                 510
Leu Thr His Asp Val Glu Leu Asn Leu Asp Tyr Glu Arg Tyr Asn Ser
                515                 520                 525
Gln Leu Leu Ser Phe Val Arg Asp Leu Asn Gln Tyr Arg Ala Asp Ile
                530                 535                 540
Lys Glu Met Gly Leu Ser Leu Gln Trp Leu Tyr Ser Ala Arg Gly Asp
545                 550                 555                 560
Phe Phe Arg Ala Thr Ser Arg Leu Thr Thr Asp Phe Gly Asn Ala Glu
                565                 570                 575
Lys Thr Asp Arg Phe Val Met Lys Lys Leu Asn Asp Arg Val Met Arg
                580                 585                 590
Val Glu Tyr His Phe Leu Ser Pro Tyr Val Ser Pro Lys Glu Ser Pro
                595                 600                 605
Phe Arg His Val Phe Trp Gly Ser Gly Ser His Thr Leu Pro Ala Leu
                610                 615                 620
Leu Glu Asn Leu Lys Leu Arg Lys Gln Asn Asn Gly Ala Phe Asn Glu
625                 630                 635                 640
Thr Leu Phe Arg Asn Gln Leu Ala Leu Ala Thr Trp Thr Ile Gln Gly
                645                 650                 655
Ala Ala Asn Ala Leu Ser Gly Asp Val Trp Asp Ile Asp Asn Glu Phe
                660                 665                 670

<210> SEQ ID NO 100
<211> LENGTH: 673
<212> TYPE: PRT
<213> ORGANISM: Artificial Sequence
<220> FEATURE:
<223> OTHER INFORMATION: description of the artificial sequence: the
      amino acid sequence of A11

<400> SEQUENCE: 100

Cys Lys Gly Val Glu Pro Lys Thr Glu Cys Glu Arg Leu Ala Gly Thr
1               5                   10                  15
Glu Ser Pro Val Arg Glu Glu Pro Gly Glu Asp Phe Pro Ala Ala Arg
                20                  25                  30
Arg Leu Tyr Trp Asp Asp Leu Lys Arg Lys Leu Ser Glu Lys Leu Asp
                35                  40                  45
Ser Thr Asp Phe Thr Gly Thr Ile Lys Leu Leu Asn Glu Asn Ser Tyr
                50                  55                  60
Val Pro Arg Glu Ala Gly Ser Gln Lys Asp Glu Asn Leu Ala Leu Tyr
65                  70                  75                  80
```

```
Val Glu Asn Gln Phe Arg Glu Phe Lys Leu Ser Lys Val Trp Arg Asp
                85                  90                  95

Gln His Phe Val Lys Ile Gln Val Lys Ser Ser Ile Gly Gln Asn Ser
            100                 105                 110

Val Ile Ile Val Asp Lys Asn Gly Arg Leu Val Tyr Leu Val Glu Asn
        115                 120                 125

Pro Gly Gly Tyr Val Ala Tyr Ser Lys Ala Ala Thr Val Thr Gly Lys
    130                 135                 140

Leu Val His Ala Asn Phe Gly Thr Lys Lys Asp Phe Glu Asp Leu Tyr
145                 150                 155                 160

Thr Pro Val Asn Gly Ser Ile Val Ile Val Arg Ala Gly Lys Ile Thr
                165                 170                 175

Phe Ala Glu Lys Val Ala Asn Ala Glu Ser Leu Asn Ala Ile Gly Val
            180                 185                 190

Leu Ile Tyr Met Asp Gln Thr Lys Phe Pro Ile Val Asn Ala Glu Leu
        195                 200                 205

Ser Phe Phe Gly His Ala His Leu Gly Thr Gly Asp Pro Tyr Thr Pro
    210                 215                 220

Gly Phe Pro Ser Phe Asn His Thr Gln Phe Pro Pro Ser Arg Ser Ser
225                 230                 235                 240

Gly Leu Pro Asn Ile Pro Val Gln Thr Ile Ser Arg Ala Ala Ala Glu
                245                 250                 255

Lys Leu Phe Gly Asn Met Glu Gly Asp Cys Pro Ser Asp Trp Lys Thr
            260                 265                 270

Asp Ser Thr Cys Arg Met Val Thr Ser Glu Ser Lys Asn Val Lys Leu
        275                 280                 285

Thr Val Lys Asn Val Leu Lys Glu Ile Lys Ile Leu Asn Ile Phe Gly
    290                 295                 300

Val Ile Lys Gly Phe Val Glu Pro Asp His Tyr Val Val Gly Ala
305                 310                 315                 320

Gln Arg Asp Ala Trp Gly Pro Gly Ala Ala Lys Ser Gly Val Gly Thr
                325                 330                 335

Ala Leu Leu Leu Lys Leu Ala Gln Met Phe Ser Asp Met Val Leu Lys
            340                 345                 350

Asp Gly Phe Gln Pro Ser Arg Ser Ile Ile Phe Ala Ser Trp Ser Ala
        355                 360                 365

Gly Asp Phe Gly Ser Val Gly Ala Thr Glu Trp Leu Glu Gly Tyr Leu
    370                 375                 380

Ser Ser Leu His Leu Lys Ala Phe Thr Tyr Ile Asn Leu Asp Lys Ala
385                 390                 395                 400

Val Leu Gly Thr Ser Asn Phe Lys Val Ser Ala Ser Pro Leu Leu Tyr
                405                 410                 415

Thr Leu Ile Glu Lys Thr Met Gln Asn Val Lys His Pro Val Thr Gly
            420                 425                 430

Gln Phe Leu Tyr Gln Asp Ser Asn Trp Ala Ser Lys Val Glu Lys Leu
        435                 440                 445

Thr Leu Asp Asn Ala Ala Phe Pro Phe Leu Ala Tyr Ser Gly Ile Pro
    450                 455                 460

Ala Val Ser Phe Cys Phe Cys Glu Asp Thr Asp Tyr Pro Tyr Leu Gly
465                 470                 475                 480

Thr Thr Met Asp Thr Tyr Lys Glu Leu Ile Glu Arg Ile Pro Glu Leu
                485                 490                 495

Asn Lys Val Ala Arg Ala Ala Ala Glu Val Ala Gly Gln Phe Val Ile
```

-continued

```
                500              505              510
Lys Leu Thr His Asp Val Glu Leu Asn Leu Asp Tyr Glu Arg Tyr Asn
            515              520              525

Ser Gln Leu Leu Ser Phe Val Arg Asp Leu Asn Gln Tyr Arg Ala Asp
            530              535              540

Ile Lys Glu Met Gly Leu Ser Leu Gln Trp Leu Tyr Ser Ala Arg Gly
545              550              555              560

Asp Phe Phe Arg Ala Thr Ser Arg Leu Thr Thr Asp Phe Gly Asn Ala
            565              570              575

Glu Lys Thr Asp Arg Phe Val Met Lys Lys Leu Asn Asp Arg Val Met
            580              585              590

Arg Val Glu Tyr His Phe Leu Ser Pro Tyr Val Ser Pro Lys Glu Ser
            595              600              605

Pro Phe Arg His Val Phe Trp Gly Ser Gly Ser His Thr Leu Pro Ala
            610              615              620

Leu Leu Glu Asn Leu Lys Leu Arg Lys Gln Asn Asn Gly Ala Phe Asn
625              630              635              640

Glu Thr Leu Phe Arg Asn Gln Leu Ala Leu Ala Thr Trp Thr Ile Gln
            645              650              655

Gly Ala Ala Asn Ala Leu Ser Gly Asp Val Trp Asp Ile Asp Asn Glu
            660              665              670

Phe
```

<210> SEQ ID NO 101
<211> LENGTH: 672
<212> TYPE: PRT
<213> ORGANISM: Artificial Sequence
<220> FEATURE:
<223> OTHER INFORMATION: description of the artificial sequence: the amino acid sequence of A12

<400> SEQUENCE: 101

```
Cys Lys Gly Val Glu Pro Lys Thr Glu Cys Glu Arg Leu Ala Gly Thr
1                5               10               15

Glu Ser Pro Val Arg Glu Glu Pro Gly Glu Asp Phe Pro Ala Ala Arg
            20               25               30

Arg Leu Tyr Trp Asp Asp Leu Lys Arg Lys Leu Ser Glu Lys Leu Asp
            35               40               45

Ser Thr Asp Phe Thr Gly Thr Ile Lys Leu Leu Asn Glu Asn Ser Tyr
            50               55               60

Val Pro Arg Glu Ala Gly Ser Gln Lys Asp Glu Asn Leu Ala Leu Tyr
65               70               75               80

Val Glu Asn Gln Phe Arg Glu Phe Lys Leu Ser Lys Val Trp Arg Asp
            85               90               95

Gln His Phe Val Lys Ile Gln Val Lys Asp Ser Ala Gln Asn Ser Val
            100              105              110

Ile Ile Val Asp Lys Asn Gly Arg Leu Val Tyr Leu Val Glu Asn Pro
            115              120              125

Glu Gly Tyr Val Ala Tyr Ser Lys Ala Ala Thr Val Thr Gly Lys Leu
            130              135              140

Val His Ala Asn Phe Gly Thr Lys Lys Asp Phe Glu Asp Leu Tyr Thr
145              150              155              160

Pro Val Asn Gly Ser Ile Val Ile Val Arg Ala Gly Lys Ile Thr Phe
            165              170              175

Ala Glu Lys Val Ala Asn Ala Glu Ser Leu Asn Ala Ile Gly Val Leu
```

```
            180                 185                 190
Ile Tyr Met Asp Gln Thr Lys Phe Pro Ile Val Asn Ala Glu Leu Ala
        195                 200                 205
Phe Phe Gly His Ala His Leu Gly Thr Gly Asp Pro Tyr Thr Pro Gly
        210                 215                 220
Phe Pro Ser Phe Asn His Thr Gln Phe Pro Pro Ser Arg Ser Ser Gly
225                 230                 235                 240
Leu Pro Asn Ile Pro Val Gln Thr Ile Ser Arg Ala Ala Glu Lys
            245                 250                 255
Leu Phe Gly Asn Met Glu Gly Asp Cys Pro Ser Asp Trp Lys Thr Asp
            260                 265                 270
Ser Thr Cys Arg Met Val Thr Ser Glu Ser Lys Asn Val Lys Leu Thr
        275                 280                 285
Val Ser Asn Val Leu Lys Glu Ile Lys Ile Leu Asn Ile Phe Gly Val
        290                 295                 300
Ile Lys Gly Phe Val Glu Pro Asp His Tyr Val Val Gly Ala Gln
305                 310                 315                 320
Arg Asp Ala Trp Gly Pro Gly Ala Ala Lys Ser Gly Val Gly Thr Ala
            325                 330                 335
Leu Leu Leu Lys Leu Ala Gln Met Phe Ser Asp Met Val Leu Lys Asp
            340                 345                 350
Gly Phe Gln Pro Ser Arg Ser Ile Ile Phe Ala Ser Trp Ser Ala Gly
            355                 360                 365
Asp Phe Gly Ser Val Gly Ala Thr Glu Trp Leu Glu Gly Tyr Leu Ser
        370                 375                 380
Ser Leu His Leu Lys Ala Phe Thr Tyr Ile Asn Leu Asp Lys Ala Val
385                 390                 395                 400
Leu Gly Thr Ser Asn Phe Lys Val Ser Ala Ser Pro Leu Leu Tyr Thr
            405                 410                 415
Leu Ile Glu Lys Thr Met Gln Asn Val Lys His Pro Val Thr Gly Gln
            420                 425                 430
Phe Leu Tyr Gln Asp Ser Asn Trp Ala Ser Lys Val Glu Lys Leu Thr
            435                 440                 445
Leu Asp Asn Ala Ala Phe Pro Phe Leu Ala Tyr Ser Gly Ile Pro Ala
        450                 455                 460
Val Ser Phe Cys Phe Cys Glu Asp Thr Asp Tyr Pro Tyr Leu Gly Thr
465                 470                 475                 480
Thr Met Asp Thr Tyr Lys Glu Leu Ile Glu Arg Ile Pro Glu Leu Asn
            485                 490                 495
Lys Val Ala Arg Ala Ala Ala Glu Val Ala Gly Gln Phe Val Ile Lys
            500                 505                 510
Leu Thr His Asp Val Glu Leu Asn Leu Asp Tyr Glu Arg Tyr Asn Ser
            515                 520                 525
Gln Leu Leu Ser Phe Val Arg Asp Leu Asn Gln Tyr Arg Ala Asp Ile
        530                 535                 540
Lys Glu Met Gly Leu Ser Leu Gln Trp Leu Tyr Ser Ala Arg Gly Asp
545                 550                 555                 560
Phe Phe Arg Ala Thr Ser Arg Leu Thr Thr Asp Phe Gly Asn Ala Glu
            565                 570                 575
Lys Thr Asp Arg Phe Val Met Lys Lys Leu Asn Asp Arg Val Met Arg
            580                 585                 590
Val Glu Tyr His Phe Leu Ser Pro Tyr Val Ser Pro Lys Glu Ser Pro
        595                 600                 605
```

Phe Arg His Val Phe Trp Gly Ser Gly Ser His Thr Leu Pro Ala Leu
            610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
            645                 650                 655

Ala Ala Asn Ala Leu Ser Gly Asp Val Trp Asp Ile Asp Asn Glu Phe
            660                 665                 670

<210> SEQ ID NO 102
<211> LENGTH: 672
<212> TYPE: PRT
<213> ORGANISM: Artificial Sequence
<220> FEATURE:
<223> OTHER INFORMATION: description of the artificial sequence: the
      amino acid sequence of A13

<400> SEQUENCE: 102

Cys Lys Gly Val Glu Pro Lys Thr Glu Cys Glu Arg Leu Ala Gly Thr
1               5                   10                  15

Glu Ser Pro Val Arg Glu Pro Gly Glu Asp Phe Pro Ala Ala Arg
            20                  25                  30

Arg Leu Tyr Trp Asp Asp Leu Lys Arg Lys Leu Ser Glu Lys Leu Asp
            35                  40                  45

Ser Thr Asp Phe Thr Gly Thr Ile Lys Leu Leu Asn Glu Asn Ser Tyr
            50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gln Asn Ser Val
            100                 105                 110

Ile Ile Val Gln Ser Asn Gly Arg Leu Val Tyr Leu Val Glu Asn Pro
            115                 120                 125

Gly Gly Tyr Val Ala Tyr Ser Lys Ala Ala Thr Val Thr Gly Lys Leu
130                 135                 140

Val His Ala Asn Phe Gly Thr Lys Lys Asp Phe Glu Asp Leu Tyr Thr
145                 150                 155                 160

Pro Val Asn Gly Ser Ile Val Ile Val Arg Ala Gly Lys Ile Thr Phe
                165                 170                 175

Ala Glu Lys Val Ala Asn Ala Glu Ser Leu Asn Ala Ile Gly Val Leu
            180                 185                 190

Ile Tyr Met Asp Gln Thr Lys Phe Pro Ile Val Asn Ala Glu Leu Ser
            195                 200                 205

Phe Phe Gly His Ala His Leu Gly Thr Gly Asp Pro Tyr Thr Pro Gly
210                 215                 220

Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Ala Glu Lys
                245                 250                 255

Leu Phe Gly Asn Met Glu Gly Asp Cys Pro Ser Asp Trp Lys Thr Asp
            260                 265                 270

Ser Thr Cys Arg Met Val Thr Ser Glu Ser Lys Asn Val Lys Leu Thr
            275                 280                 285

Val Ser Asn Val Leu Lys Glu Ile Lys Ile Leu Asn Ile Phe Gly Val

```
            290                 295                 300
Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                325                 330                 335

Leu Leu Leu Lys Leu Ala Gln Met Phe Ser Asp Met Val Leu Lys Asp
                340                 345                 350

Gly Phe Gln Pro Ser Arg Ser Ile Ile Phe Ala Ser Trp Ser Ala Gly
                355                 360                 365

Asp Phe Gly Ser Val Gly Ala Thr Glu Trp Leu Glu Gly Tyr Leu Ser
                370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
                405                 410                 415

Leu Ile Glu Lys Thr Met Gln Asn Val Lys His Pro Val Thr Gly Gln
                420                 425                 430

Phe Leu Tyr Gln Asp Ser Asn Trp Ala Ser Lys Val Glu Lys Leu Thr
                435                 440                 445

Leu Asp Asn Ala Ala Phe Pro Phe Leu Ala Tyr Ser Gly Ile Pro Ala
450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
                485                 490                 495

Lys Val Ala Arg Ala Ala Ala Glu Val Ala Gly Gln Phe Val Ile Lys
                500                 505                 510

Leu Thr His Asp Val Glu Leu Asn Leu Asp Tyr Glu Arg Tyr Asn Ser
                515                 520                 525

Gln Leu Leu Ser Phe Val Arg Asp Leu Asn Gln Tyr Arg Ala Asp Ile
                530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
                565                 570                 575

Lys Thr Asp Arg Phe Val Met Lys Lys Leu Asn Asp Arg Val Met Arg
                580                 585                 590

Val Glu Tyr His Phe Leu Ser Pro Tyr Val Ser Pro Lys Glu Ser Pro
                595                 600                 605

Phe Arg His Val Phe Trp Gly Ser Gly Ser His Thr Leu Pro Ala Leu
                610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
                645                 650                 655

Ala Ala Asn Ala Leu Ser Gly Asp Val Trp Asp Ile Asp Asn Glu Phe
                660                 665                 670

<210> SEQ ID NO 103
<211> LENGTH: 672
<212> TYPE: PRT
<213> ORGANISM: Artificial Sequence
<220> FEATURE:
<223> OTHER INFORMATION: description of the artificial sequence: the
      amino acid sequence of A14
```

<400> SEQUENCE: 103

```
Cys Lys Gly Val Glu Pro Lys Thr Glu Cys Glu Arg Leu Ala Gly Thr
1               5                   10                  15

Glu Ser Pro Val Arg Glu Pro Gly Glu Asp Phe Pro Ala Ala Arg
            20                  25                  30

Arg Leu Tyr Trp Asp Asp Leu Lys Arg Lys Leu Ser Glu Lys Leu Asp
        35                  40                  45

Ser Thr Asp Phe Thr Gly Thr Ile Lys Leu Leu Asn Glu Asn Ser Tyr
    50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95

Gln His Phe Val Lys Ile Gln Val Lys Asp Ser Ala Gln Asn Ser Val
            100                 105                 110

Ile Ile Val Gln Ser Asn Gly Arg Leu Val Tyr Leu Val Glu Asn Pro
        115                 120                 125

Gly Gly Tyr Val Ala Tyr Ser Lys Ala Ala Thr Val Thr Gly Lys Leu
    130                 135                 140

Val His Ala Asn Phe Gly Thr Lys Lys Asp Phe Glu Asp Leu Tyr Thr
145                 150                 155                 160

Pro Val Asn Gly Ser Ile Val Ile Val Arg Ala Gly Lys Ile Thr Phe
                165                 170                 175

Ala Glu Lys Val Ala Asn Ala Glu Ser Leu Asn Ala Ile Gly Val Leu
            180                 185                 190

Ile Tyr Met Asp Gln Thr Lys Phe Pro Ile Val Asn Ala Glu Leu Ser
        195                 200                 205

Phe Phe Gly His Ala His Leu Gly Thr Gly Asp Pro Tyr Thr Pro Gly
    210                 215                 220

Phe Pro Ser Phe Asn His Thr Gln Phe Pro Pro Ser Arg Ser Ser Gly
225                 230                 235                 240

Leu Pro Asn Ile Pro Val Gln Thr Ile Ser Arg Ala Ala Ala Glu Lys
                245                 250                 255

Leu Phe Gly Asn Met Glu Gly Asp Cys Pro Ser Asp Trp Lys Thr Asp
            260                 265                 270

Ser Thr Cys Arg Met Val Thr Ser Gln Ser Lys Asn Val Lys Leu Thr
        275                 280                 285

Val Ser Asn Val Leu Lys Glu Ile Lys Ile Leu Asn Ile Phe Gly Val
    290                 295                 300

Ile Lys Gly Phe Val Glu Pro Asp His Tyr Val Val Val Gly Ala Gln
305                 310                 315                 320

Arg Asp Ala Trp Gly Pro Gly Ala Ala Lys Ser Gly Val Gly Thr Ala
                325                 330                 335

Leu Leu Leu Lys Leu Ala Gln Met Phe Ser Asp Met Val Leu Lys Asp
            340                 345                 350

Gly Phe Gln Pro Ser Arg Ser Ile Ile Phe Ala Ser Trp Ser Ala Gly
        355                 360                 365

Asp Phe Gly Ser Val Gly Ala Thr Glu Trp Leu Glu Gly Tyr Leu Ser
    370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
```

```
                405                 410                 415
Leu Ile Glu Lys Thr Met Gln Asn Val Lys His Pro Val Thr Gly Gln
            420                 425                 430

Phe Leu Tyr Gln Asp Ser Asn Trp Ala Ser Lys Val Glu Lys Leu Thr
            435                 440                 445

Leu Asp Asn Ala Ala Phe Pro Phe Leu Ala Tyr Ser Gly Ile Pro Ala
450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
            485                 490                 495

Lys Val Ala Arg Ala Ala Ala Glu Val Ala Gly Gln Phe Val Ile Lys
            500                 505                 510

Leu Thr His Asp Val Glu Leu Asn Leu Asp Tyr Glu Arg Tyr Asn Ser
            515                 520                 525

Gln Leu Leu Ser Phe Val Arg Asp Leu Asn Gln Tyr Arg Ala Asp Ile
            530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
                565                 570                 575

Lys Thr Asp Arg Phe Val Met Lys Lys Leu Asn Asp Arg Val Met Arg
            580                 585                 590

Val Glu Tyr His Phe Leu Ser Pro Tyr Val Ser Pro Lys Glu Ser Pro
            595                 600                 605

Phe Arg His Val Phe Trp Gly Ser Gly Ser His Thr Leu Pro Ala Leu
610                 615                 620

Leu Glu Asn Leu Lys Leu Arg Lys Gln Asn Asn Gly Ala Phe Asn Glu
625                 630                 635                 640

Thr Leu Phe Arg Asn Gln Leu Ala Leu Ala Thr Trp Thr Ile Gln Gly
                645                 650                 655

Ala Ala Asn Ala Leu Ser Gly Asp Val Trp Asp Ile Asp Asn Glu Phe
            660                 665                 670

<210> SEQ ID NO 104
<211> LENGTH: 672
<212> TYPE: PRT
<213> ORGANISM: Artificial Sequence
<220> FEATURE:
<223> OTHER INFORMATION: description of the artificial sequence: the
      amino acid sequence of A15

<400> SEQUENCE: 104

Cys Lys Gly Val Glu Pro Lys Thr Glu Cys Glu Arg Leu Ala Gly Thr
1               5                   10                  15

Glu Ser Pro Val Arg Glu Glu Pro Gly Glu Asp Phe Pro Ala Ala Arg
            20                  25                  30

Arg Leu Tyr Trp Asp Asp Leu Lys Arg Lys Leu Ser Glu Lys Leu Asp
            35                  40                  45

Ser Thr Asp Phe Thr Gly Thr Ile Lys Leu Leu Asn Glu Asn Ser Tyr
50                  55                  60

Val Pro Arg Glu Ala Gly Ser Gln Lys Asp Glu Asn Leu Ala Leu Tyr
65                  70                  75                  80

Val Glu Asn Gln Phe Arg Glu Phe Lys Leu Ser Lys Val Trp Arg Asp
                85                  90                  95
```

```
Gln His Phe Val Lys Ile Gln Val Lys Asp Ser Ala Gln Asn Met Val
                100                 105                 110
Thr Ile Val Asp Lys Asn Gly Arg Leu Val Tyr Pro Val Glu Ser Pro
            115                 120                 125
Gly Gly Tyr Val Ala Tyr Ser Lys Ala Ala Thr Val Thr Gly Lys Leu
        130                 135                 140
Val His Ala Asn Phe Gly Thr Lys Lys Asp Phe Glu Asp Leu Tyr Thr
145                 150                 155                 160
Pro Val Asn Gly Ser Ile Val Ile Val Arg Ala Gly Lys Ile Thr Phe
                165                 170                 175
Ala Glu Lys Val Ala Asn Ala Glu Ser Leu Asn Ala Ile Gly Val Leu
            180                 185                 190
Ile Tyr Met Asp Gln Thr Lys Phe Pro Ile Val Asn Ala Glu Leu Ser
        195                 200                 205
Phe Phe Gly His Ala His Leu Gly Thr Gly Asp Pro Tyr Thr Pro Gly
210                 215                 220
Phe Pro Ser Phe Asn His Thr Gln Phe Pro Pro Ser Arg Ser Ser Gly
225                 230                 235                 240
Leu Pro Asn Ile Pro Val Gln Thr Ile Ser Arg Ala Ala Ala Glu Lys
                245                 250                 255
Leu Phe Gly Asn Met Glu Gly Asp Cys Pro Ser Asp Trp Lys Thr Asp
            260                 265                 270
Ser Thr Cys Arg Met Val Thr Ser Glu Ser Lys Asn Val Lys Leu Thr
        275                 280                 285
Val Ser Asn Val Leu Lys Glu Ile Lys Ile Leu Asn Ile Phe Gly Val
290                 295                 300
Ile Lys Gly Phe Val Glu Pro Asp His Tyr Val Val Gly Ala Gln
305                 310                 315                 320
Arg Asp Ala Trp Gly Pro Gly Ala Ala Lys Ser Gly Val Gly Thr Ala
                325                 330                 335
Leu Leu Leu Lys Leu Ala Gln Met Phe Ser Asp Met Val Leu Lys Asp
            340                 345                 350
Gly Phe Gln Pro Ser Arg Ser Ile Ile Phe Ala Ser Trp Ser Ala Gly
        355                 360                 365
Asp Phe Gly Ser Val Gly Ala Thr Glu Trp Leu Glu Gly Tyr Leu Ser
370                 375                 380
Ser Leu His Leu Lys Ala Phe Thr Tyr Ile Asn Leu Asp Lys Ala Val
385                 390                 395                 400
Leu Gly Thr Ser Asn Phe Lys Val Ser Ala Ser Pro Leu Leu Tyr Thr
                405                 410                 415
Leu Ile Glu Lys Thr Met Gln Asn Val Lys His Pro Val Thr Gly Gln
            420                 425                 430
Phe Leu Tyr Gln Asp Ser Asn Trp Ala Ser Lys Val Glu Lys Leu Thr
        435                 440                 445
Leu Asp Asn Ala Ala Phe Pro Phe Leu Ala Tyr Ser Gly Ile Pro Ala
450                 455                 460
Val Ser Phe Cys Phe Cys Glu Asp Thr Asp Tyr Pro Tyr Leu Gly Thr
465                 470                 475                 480
Thr Met Asp Thr Tyr Lys Glu Leu Ile Glu Arg Ile Pro Glu Leu Asn
                485                 490                 495
Lys Val Ala Arg Ala Ala Ala Glu Val Ala Gly Gln Phe Val Ile Lys
            500                 505                 510
Leu Thr His Asp Val Glu Leu Asn Leu Asp Tyr Glu Arg Tyr Asn Ser
```

```
                  515                 520                 525
    Gln Leu Leu Ser Phe Val Arg Asp Leu Asn Gln Tyr Arg Ala Asp Ile
                  530                 535                 540

Lys Glu Met Gly Leu Ser Leu Gln Trp Leu Tyr Ser Ala Arg Gly Asp
    545                 550                 555                 560

Phe Phe Arg Ala Thr Ser Arg Leu Thr Thr Asp Phe Gly Asn Ala Glu
                        565                 570                 575

Lys Thr Asp Arg Phe Val Met Lys Lys Leu Asn Asp Arg Val Met Arg
                    580                 585                 590

Val Glu Tyr His Phe Leu Ser Pro Tyr Val Ser Pro Lys Glu Ser Pro
                    595                 600                 605

Phe Arg His Val Phe Trp Gly Ser Gly Ser His Thr Leu Pro Ala Leu
                    610                 615                 620

Leu Glu Asn Leu Lys Leu Arg Lys Gln Asn Asn Gly Ala Phe Asn Glu
    625                 630                 635                 640

Thr Leu Phe Arg Asn Gln Leu Ala Leu Ala Thr Trp Thr Ile Gln Gly
                        645                 650                 655

Ala Ala Asn Ala Leu Ser Gly Asp Val Trp Asp Ile Asp Asn Glu Phe
                    660                 665                 670

<210> SEQ ID NO 105
<211> LENGTH: 672
<212> TYPE: PRT
<213> ORGANISM: Artificial Sequence
<220> FEATURE:
<223> OTHER INFORMATION: description of the artificial sequence: the
      amino acid sequence of A16

<400> SEQUENCE: 105

Cys Lys Gly Val Glu Pro Lys Thr Glu Cys Glu Arg Leu Ala Gly Thr
    1               5                   10                  15

Glu Ser Pro Val Arg Glu Glu Pro Gly Glu Asp Phe Pro Ala Ala Arg
                    20                  25                  30

Arg Leu Tyr Trp Asp Asp Leu Lys Arg Lys Leu Ser Glu Lys Leu Asp
                35                  40                  45

Ser Thr Asp Phe Thr Gly Thr Ile Lys Leu Leu Asn Glu Asn Ser Tyr
            50                  55                  60

Val Pro Arg Glu Ala Gly Ser Gln Lys Asp Glu Asn Leu Ala Leu Tyr
    65                  70                  75                  80

Val Glu Asn Gln Phe Arg Glu Phe Lys Leu Ser Lys Val Trp Arg Asp
                        85                  90                  95

Gln His Phe Val Lys Ile Gln Val Lys Asp Ser Ala Gln Asn Met Val
                    100                 105                 110

Ile Ile Val Asp Lys Asn Gly Arg Leu Val Tyr Leu Val Glu Asn Pro
                115                 120                 125

Gly Gly Tyr Val Ala Tyr Ser Lys Ala Ala Glu Val Thr Gly Lys Leu
            130                 135                 140

Val His Ala Asn Phe Gly Thr Lys Lys Asp Phe Glu Asp Leu Tyr Thr
    145                 150                 155                 160

Pro Val Asn Gly Ser Ile Val Ile Val Arg Ala Gly Lys Ile Thr Phe
                        165                 170                 175

Ala Glu Lys Val Ala Asn Ala Glu Ser Leu Asn Ala Ile Gly Val Leu
                    180                 185                 190

Ile Tyr Met Asp Gln Thr Lys Phe Pro Ile Val Asn Ala Glu Leu Ser
                195                 200                 205
```

```
Phe Phe Gly His Ala His Leu Gly Thr Gly Asp Pro Tyr Thr Pro Gly
    210                 215                 220

Phe Pro Ser Phe Asn His Thr Gln Phe Pro Ser Arg Ser Ser Gly
225                 230                 235                 240

Leu Pro Asn Ile Pro Val Gln Thr Ile Ser Arg Ala Ala Glu Lys
                245                 250                 255

Leu Phe Gly Asn Met Glu Gly Asp Cys Pro Ser Asp Trp Lys Thr Asp
            260                 265                 270

Ser Thr Cys Arg Met Val Thr Ser Glu Ser Lys Asn Val Lys Leu Ile
                275                 280                 285

Val Ser Asn Val Leu Lys Glu Ile Lys Ile Leu Asn Ile Phe Gly Val
    290                 295                 300

Ile Lys Gly Phe Val Glu Pro Asp His Tyr Val Val Gly Ala Gln
305                 310                 315                 320

Arg Asp Ala Trp Gly Pro Gly Ala Ala Lys Ser Gly Val Gly Thr Ala
                325                 330                 335

Leu Leu Leu Lys Leu Ala Gln Met Phe Ser Asp Met Val Leu Lys Asp
            340                 345                 350

Gly Phe Gln Pro Ser Arg Ser Ile Ile Phe Ala Ser Trp Ser Ala Gly
            355                 360                 365

Asp Phe Gly Ser Val Gly Ala Thr Glu Trp Leu Glu Gly Tyr Leu Ser
370                 375                 380

Ser Leu His Leu Lys Ala Phe Thr Tyr Ile Asn Leu Asp Lys Ala Val
385                 390                 395                 400

Leu Gly Thr Ser Asn Phe Lys Val Ser Ala Ser Pro Leu Leu Tyr Thr
                405                 410                 415

Leu Ile Glu Lys Thr Met Gln Asn Val Lys His Pro Val Thr Gly Gln
            420                 425                 430

Phe Leu Tyr Gln Asp Ser Asn Trp Ala Ser Lys Val Glu Lys Leu Thr
            435                 440                 445

Leu Asp Asn Ala Ala Phe Pro Phe Leu Ala Tyr Ser Gly Ile Pro Ala
    450                 455                 460

Val Ser Phe Cys Phe Cys Glu Asp Thr Asp Tyr Pro Tyr Leu Gly Thr
465                 470                 475                 480

Thr Met Asp Thr Tyr Lys Glu Leu Ile Glu Arg Ile Pro Glu Leu Asn
                485                 490                 495

Lys Val Ala Arg Ala Ala Ala Glu Val Ala Gly Gln Phe Val Ile Lys
                500                 505                 510

Leu Thr His Asp Val Glu Leu Asn Leu Asp Tyr Glu Arg Tyr Asn Ser
            515                 520                 525

Gln Leu Leu Ser Phe Val Arg Asp Leu Asn Gln Tyr Arg Ala Asp Ile
    530                 535                 540

Lys Glu Met Gly Leu Ser Leu Gln Trp Leu Tyr Ser Ala Arg Gly Asp
545                 550                 555                 560

Phe Phe Arg Ala Thr Ser Arg Leu Thr Thr Asp Phe Gly Asn Ala Glu
                565                 570                 575

Lys Thr Asp Arg Phe Val Met Lys Lys Leu Asn Asp Arg Val Met Arg
                580                 585                 590

Val Glu Tyr His Phe Leu Ser Pro Tyr Val Ser Pro Lys Glu Ser Pro
            595                 600                 605

Phe Arg His Val Phe Trp Gly Ser Gly Ser His Thr Leu Pro Ala Leu
    610                 615                 620

Leu Glu Asn Leu Lys Leu Arg Lys Gln Asn Asn Gly Ala Phe Asn Glu
```

```
                625                 630                 635                 640
Thr Leu Phe Arg Asn Gln Leu Ala Leu Ala Thr Trp Thr Ile Gln Gly
                    645                 650                 655

Ala Ala Asn Ala Leu Ser Gly Asp Val Trp Asp Ile Asp Asn Glu Phe
                    660                 665                 670

<210> SEQ ID NO 106
<211> LENGTH: 122
<212> TYPE: PRT
<213> ORGANISM: Artificial Sequence
<220> FEATURE:
<223> OTHER INFORMATION: description of the artificial sequence: the
      amino acid sequence of VH starting with TfR1071 EVQL

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Asp Lys Tyr
            20                  25                  30

Thr Met Asn Trp Val Arg Gln Ala Pro Gly Lys Gly Leu Glu Trp Val
        35                  40                  45

Ser Val Ile Ser Asn Gly Gly Val Ser Thr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Met Ala Thr Tyr Tyr Cys
                85                  90                  95

Ala Arg Ala Ser Gln Pro Trp Leu Tyr Arg Thr Gly Ala Asp Val Trp
            100                 105                 110

Gly Gln Gly Thr Leu Val Thr Val Ser Ser
        115                 120

<210> SEQ ID NO 107
<211> LENGTH: 5
<212> TYPE: PRT
<213> ORGANISM: Artificial Sequence
<220> FEATURE:
<223> OTHER INFORMATION: description of the artificial sequence: the
      amino acid sequence of TfR1007 HCDR1

<400> SEQUENCE: 107

Gly Tyr Ser Met Ser
1               5

<210> SEQ ID NO 108
<211> LENGTH: 17
<212> TYPE: PRT
<213> ORGANISM: Artificial Sequence
<220> FEATURE:
<223> OTHER INFORMATION: description of the artificial sequence: the
      amino acid sequence of TfR1007 HCDR2

<400> SEQUENCE: 108

Ser Leu Ser Asn Gly Gly Gly Ser Ser Tyr Tyr Ala Asp Ser Val Lys
1               5                   10                  15

Gly

<210> SEQ ID NO 109
<211> LENGTH: 13
<212> TYPE: PRT
<213> ORGANISM: Artificial Sequence
<220> FEATURE:
```

<223> OTHER INFORMATION: description of the artificial sequence: the
      amino acid sequence of TfR1007 HCDR3

<400> SEQUENCE: 109

Thr Leu Gly Ala Tyr Tyr Ile Lys Ser Ala Met Asp Val
1               5                   10

<210> SEQ ID NO 110
<211> LENGTH: 119
<212> TYPE: PRT
<213> ORGANISM: Artificial Sequence
<220> FEATURE:
<223> OTHER INFORMATION: description of the artificial sequence: the
      amino acid sequence of Cetuximab VH

<400> SEQUENCE: 110

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 111
<211> LENGTH: 107
<212> TYPE: PRT
<213> ORGANISM: Artificial Sequence
<220> FEATURE:
<223> OTHER INFORMATION: description of the artificial sequence: the
      amino acid sequence of Cetuximab VL

<400> SEQUENCE: 111

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 112
<211> LENGTH: 119
<212> TYPE: PRT

```
<213> ORGANISM: Artificial Sequence
<220> FEATURE:
<223> OTHER INFORMATION: description of the artificial sequence: the
      amino acid sequence of Panitumumab VH

<400> SEQUENCE: 112

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
            115

<210> SEQ ID NO 113
<211> LENGTH: 107
<212> TYPE: PRT
<213> ORGANISM: Artificial Sequence
<220> FEATURE:
<223> OTHER INFORMATION: description of the artificial sequence: the
      amino acid sequence of Panitumumab VL

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 114
<211> LENGTH: 121
<212> TYPE: PRT
<213> ORGANISM: Artificial Sequence
<220> FEATURE:
<223> OTHER INFORMATION: description of the artificial sequence: the
      amino acid sequence of Necitumumab VH

<400> SEQUENCE: 114

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30
```

```
Asp Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asp Tyr Asn Pro Ser
 50                  55                  60

Leu Lys Ser Arg Val Thr Met Ser Val Asp Thr Ser Lys Asn Gln Phe
 65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser
            115                 120

<210> SEQ ID NO 115
<211> LENGTH: 107
<212> TYPE: PRT
<213> ORGANISM: Artificial Sequence
<220> FEATURE:
<223> OTHER INFORMATION: description of the artificial sequence: the
      amino acid sequence of Necitumumab VL

<400> SEQUENCE: 115

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys His Gln Tyr Gly Ser Thr Pro Leu
                 85                  90                  95

Thr Phe Gly Gly Gly Thr Lys Ala Glu Ile Lys
            100                 105

<210> SEQ ID NO 116
<211> LENGTH: 123
<212> TYPE: PRT
<213> ORGANISM: Artificial Sequence
<220> FEATURE:
<223> OTHER INFORMATION: description of the artificial sequence: the
      amino acid sequence of Nimotuzumab VH

<400> SEQUENCE: 116

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Asn Tyr
             20                  25                  30

Tyr Ile Tyr Trp Val Lys Gln Arg Pro Gly Gln Gly Leu Glu Trp Ile
         35                  40                  45

Gly Gly Ile Asn Pro Thr Ser Gly Gly Ser Asn Phe Asn Glu Lys Phe
 50                  55                  60

Lys Thr Lys Ala Thr Leu Thr Val Asp Glu Ser Ser Thr Thr Ala Tyr
 65                  70                  75                  80

Met Gln Leu Ser Ser Leu Thr Ser Glu Asp Ser Ala Val Tyr Tyr Cys
                 85                  90                  95
```

```
Thr Arg Gln Gly Leu Trp Phe Asp Ser Asp Gly Arg Gly Phe Asp Phe
            100                 105                 110

Trp Gly Gln Gly Thr Thr Leu Thr Val Ser Ser
        115                 120

<210> SEQ ID NO 117
<211> LENGTH: 112
<212> TYPE: PRT
<213> ORGANISM: Artificial Sequence
<220> FEATURE:
<223> OTHER INFORMATION: description of the artificial sequence: the
      amino acid sequence of Nimotuzumab VL

<400> SEQUENCE: 117

Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Asp Trp Tyr Leu Gln Lys Pro Gly Gln Ser
        35                  40                  45

Pro Asn Leu Leu Ile Tyr Lys Val Ser Asn Arg Glu Ser Gly Val Pro
    50                  55                  60

Asp Arg Phe Arg Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Tyr
                85                  90                  95

Ser His Val Pro Trp Thr Phe Gly Gly Gly Thr Lys Leu Glu Ile Lys
            100                 105                 110
```

BISPECIFIC ANTIBODY BINDING TO TfR

TECHNICAL FIELD

The present invention relates to a bispecific antibody including an antigen-binding domain that binds to a transferrin receptor (TfR) and an antigen-binding domain that binds to a cell surface antigen, a bispecific antibody fragment thereof, a DNA encoding the bispecific antibody or the bispecific antibody fragment thereof, a vector containing the DNA, a hybridoma and a transformant that produce the bispecific antibody or the bispecific antibody fragment thereof, a method for producing the bispecific antibody or the bispecific antibody fragment thereof, therapeutic and diagnostic agents containing the bispecific antibody or the bispecific antibody fragment thereof, therapeutic and diagnostic methods using the bispecific antibody or the bispecific antibody fragment thereof, and a reagent for detection or measurement containing the bispecific antibody or the bispecific antibody fragment thereof.

BACKGROUND ART

An antibody is a glycoprotein present in serum or tissue fluid of all mammals, and recognizes a foreign antigen in the body. The antibody is involved in the body's defense by activating a complement system or activating effector functions of FcR-expressing cells such as phagocytic capacity, antibody-dependent cellular cytotoxicity capacity, mediator liberation capacity, and antigen presenting capability through binding to a receptor (FcR) present on a cell surface.

One molecule of antibody is composed of two homologous light chains (L chains) and two homologous heavy chains (H chains) and includes two antigen-binding domains. The classes and subclasses of the antibody are determined by the H chain, and each class and subclass have a different unique function. There are five different classes of human antibodies; IgG, IgA, IgM, IgD, and IgE. IgG is further classified into subclasses of IgG1, IgG2, IgG3, and IgG4, and IgA is further classified into subclasses of IgA1 and IgA2 (Charles A. J. et. al., Immunobiology, 1997, Current Biology Ltd/Garland Publishing, Inc.).

A multivalent antibody is an antibody including a plurality of antigen-binding domains in one molecule. As an example of the multivalent antibody, first, it has been reported that a divalent antibody that monovalently binds to each of different two types of antigens was produced by expressing H chains and L chains derived from two different types of antibodies by one cell using a hybrid hybridoma (NPL 1). However, in this method, about 10 combinations of the H chains and the L chains of the antibodies occur. Therefore, the production amount of the multivalent antibody with a desired combination of the H chains and the L chains is low, and further, it is difficult to selectively isolate and purify such a multivalent antibody, and thus, the yield of a desired antibody decreases.

In order to overcome this problem, an attempt to produce an antibody with a desired combination by linking a plurality of antigen-binding domains and expressing them as a single polypeptide chain so as to reduce the variation of combinations between subunits has been reported.

As one example, an antibody including a single chain Fv (scFv) in which antigen-binding domains of an H chain and an L chain are linked with one polypeptide (NPL 2) is known. Further, an antibody in which two antigen-binding domains are linked using a CH1 domain of an H chain constant region of IgG1 or a partial fragment of the domain, and an L chain constant region or a flexible linker (Gly-Gly-Gly-Gly-Ser; SEQ ID NO: 82), and the like have been reported (PTLs 1 and 2).

These conventional multivalent antibodies had drawbacks that aggregation is likely to occur, and the stability and productivity are low. On the other hand, however, it has been found that a multivalent antibody, which includes a plurality of antigen-binding domains in a single H chain polypeptide, and in which an antibody heavy chain variable region is bound through a linker having an amino acid sequence of an immunoglobulin domain or a fragment thereof has high stability and also has high productivity (PTL 3).

A transferrin receptor (hereinafter also referred to as TfR) was identified as a cell membrane structure expressed on the surface of reticulocytes. TfR has a function of taking up iron bound to transferrin (hereinafter also referred to as Tf) into cells. Since iron is an essential metal for maintaining cell homeostasis and cell proliferation, TfR for taking up iron is expressed at a high level in trophoblastic cells of the placenta, reticulocytes, activated lymphocytes, and normal tissues with high iron uptake. Further, it is also known that TfR is expressed at a high level in various tumor cells that actively proliferate (NPLs 3 and 4). It is known that when TfR is crosslinked on a cell membrane, internalization by clathrin-dependent endocytosis is promoted and TfR is degraded (NPLs 5 and 6).

Since the expression level of TfR in normal cells other than bone marrow cells is low and the expression level in cancer cells that actively proliferate is high, TfR has long been recognized as a molecular target for cancer therapy. As a molecule targeting TfR, for example, a TfR neutralizing antibody that exhibits strong drug efficacy in a mouse cancer-bearing model is known (PTL 4).

It is known that the expression of a specific membrane protein is enhanced in cancer cells as compared with normal cells. A pharmaceutical having a function of killing only cancer cells by an antibody that selectively recognizes such a membrane protein has been developed. For example, an antibody pharmaceutical targeting an epidermal growth factor receptor (hereinafter referred to as EGFR) for large intestine cancer or head and neck cancer has been clinically confirmed to be effective (NPL 7).

EGFR is a tyrosine kinase-type receptor discovered as a receptor for an epidermal growth factor (hereinafter referred to as EGF). EGFR is a transmembrane glycoprotein with a molecular weight of 170 kDa, and forms a dimer when a ligand binds thereto and activates a downstream intracellular signal transduction pathway, thereby promoting cell proliferation, differentiation, invasion, metastasis, etc.

EGFR is expressed in various cells such as epithelial, mesenchymal, and neural cells, but is expressed at a high level in many cancer cells such as a brain tumor or squamous cell carcinoma (NPLs 8 and 9), and therefore is known as a cancer antigen.

It is known that by using a molecule that can bind to two types of membrane proteins, one antigen molecule can be used as a scaffold and the other antigen molecule can be internalized and degraded (PTLs 5 and 6). Further, it has been reported that when a peptide that recognizes a cancer cell-specific membrane protein and a peptide that recognizes TfR are chemically bound or linked by a hybridoma fusion method, a growth inhibitory activity is exhibited against cells that express both antigens under the condition of adding an iron chelating agent (PTL 7).

CITATION LIST

Patent Literature

PTL 1: US Patent Application Publication No. 2007/0071675
PTL 2: WO 2001/077342
PTL 3: WO 2009/131239
PTL 4: WO 2012/153707
PTL 5: WO 2013/138400
PTL 6: European Patent Application Publication No. 2808035
PTL 7: U.S. Pat. No. 570,561

Non Patent Literature

NPL 1: Suresh et. al., Methods Enzymol. 121, 210-228, 1986
NPL 2: Kranz et. al., J. Hematother. 5, 403-408, 1995
NPL 3: Hamilton T A et al., PNAS USA 76 6406-10, 1979
NPL 4: Larson S M et al., J Natl Cancer Inst. 64 41-53, 1980
NPL 5: Liu A P et al., J Cell Biol. 191 1381-93, 2010
NPL 6: Weissman A M et. al., J Cell Biol. 102 951-8, 1986
NPL 7: Erbitux U S package insert (revised on June 2018)
NPL 8: Libermann T A et al., Cancer Res. 44 753-60, 1984
NPL 9: Hendler F J et al., J Clin Invest. 74 647-51, 1984

SUMMARY OF INVENTION

Technical Problem

An object of the present invention is to provide a novel bispecific antibody that binds to TfR and a cell surface antigen, a bispecific antibody fragment thereof, a DNA encoding the bispecific antibody or the bispecific antibody fragment thereof, a vector containing the DNA, a hybridoma and a transformant that produce the bispecific antibody or the bispecific antibody fragment thereof, a method for producing the bispecific antibody or the bispecific antibody fragment thereof, therapeutic and diagnostic agents containing the bispecific antibody or the bispecific antibody fragment thereof, therapeutic and diagnostic methods using the bispecific antibody or the bispecific antibody fragment thereof, and a reagent for detection or measurement containing the bispecific antibody or the bispecific antibody fragment thereof.

Solution to Problem

As means for solving the above problems, the present invention provides a bispecific antibody or a bispecific antibody fragment thereof, which binds to TfR and a cell surface antigen, and in which a polypeptide having an antigen-binding domain to a cell surface antigen (also referred to as N-terminal side polypeptide) binds directly or through a linker to the N-terminal side of an IgG portion that binds to TfR.

That is, the present invention relates to the following.

1. A bispecific antibody or a bispecific antibody fragment thereof, which binds to a transferrin receptor (TfR) and a cell surface antigen, including an IgG portion that binds to TfR and an N-terminal side polypeptide that binds to the cell surface antigen, wherein the polypeptide binds directly or through a linker to the N terminus of a heavy chain of the IgG portion.

2. The bispecific antibody or the bispecific antibody fragment thereof according to the above 1, wherein the IgG portion includes a heavy chain variable region (VH) having complementarity determining region (CDR) 1 containing the amino acid sequence represented by SEQ ID NO: 32 or an amino acid sequence modified from the amino acid sequence represented by SEQ ID NO: 32 by at least one substitution selected from a substitution of tyrosine at position 2 with alanine or phenylalanine and a substitution of threonine at position 3 with alanine or glycine, CDR2 containing the amino acid sequence represented by SEQ ID NO: 33 or an amino acid sequence modified from the amino acid sequence represented by SEQ ID NO: 33 by at least one substitution selected from a substitution of valine at position 1 with alanine, a substitution of isoleucine at position 2 with alanine or leucine, a substitution of valine at position 7 with glutamic acid, a substitution of aspartic acid at position 10 with alanine, and a substitution of aspartic acid at position 13 with proline, and CDR3 containing the amino acid sequence represented by SEQ ID NO: 34 or an amino acid sequence modified from the amino acid sequence represented by SEQ ID NO: 34 by at least one substitution selected from a substitution of glutamine at position 3 with alanine or aspartic acid, a substitution of proline at position 4 with an arbitrary natural amino acid, a substitution of tryptophan at position 5 with alanine, phenylalanine, histidine, or tyrosine, a substitution of tyrosine at position 7 with alanine or phenylalanine, and a substitution of valine at position 13 with leucine, and a light chain variable region (VL) having CDRs 1 to 3 containing the amino acid sequences represented by SEQ ID NOS: 17 to 19, respectively.

3. The bispecific antibody or the bispecific antibody fragment thereof according to the above 1, wherein the IgG portion includes one VH selected from the following (ai) to (ci), and VL having CDRs 1 to 3 containing the amino acid sequences represented by SEQ ID NOS: 17 to 19, respectively:

(ai) VH having CDRs 1 to 3 containing the amino acid sequences represented by SEQ ID NOS: 32 to 34, respectively;
(bi) VH having CDRs 1 to 3 containing the amino acid sequences represented by SEQ ID NOS: 42 to 44, respectively; and
(ci) VH having CDRs 1 to 3 containing the amino acid sequences represented by SEQ ID NOS: 47 to 49, respectively.

4. The bispecific antibody or the bispecific antibody fragment thereof according to the above 1 or 2, wherein the IgG portion includes VH containing the amino acid sequence represented by any one of SEQ ID NOS: 26, 31, 36, 41, and 46, and VL containing the amino acid sequence represented by SEQ ID NO: 16.

5. The bispecific antibody or the bispecific antibody fragment thereof according to the above 1, wherein the IgG portion includes VL having CDRs 1 to 3 containing the amino acid sequences represented by SEQ ID NOS: 17 to 19, respectively, and one VH selected from the following (a) to (m):

(a) VH having CDRs 2 and 3 containing the amino acid sequences represented by SEQ ID NOS: 33 and 34, respectively, and CDR1 containing an amino acid sequence modified from the amino acid sequence represented by SEQ ID NO: 32 by a substitution of tyrosine at position 2 with alanine or phenylalanine;

(b) VH having CDRs 2 and 3 containing the amino acid sequences represented by SEQ ID NOS: 33 and 34, respectively, and CDR1 containing an amino acid sequence modified from the amino acid sequence represented by SEQ ID NO: 32 by a substitution of threonine at position 3 with alanine or glycine;

(c) VH having CDRs 1 and 3 containing the amino acid sequences represented by SEQ ID NOS: 32 and 34, respectively, and CDR2 containing an amino acid sequence modified from the amino acid sequence represented by SEQ ID NO: 33 by a substitution of valine at position 1 with alanine;

(d) VH having CDRs 1 and 3 containing the amino acid sequences represented by SEQ ID NOS: 32 and 34, respectively, and CDR2 containing an amino acid sequence modified from the amino acid sequence represented by SEQ ID NO: 33 by a substitution of isoleucine at position 2 with alanine or leucine;

(e) VH having CDRs 1 and 3 containing the amino acid sequences represented by SEQ ID NOS: 32 and 34, respectively, and CDR2 containing an amino acid sequence modified from the amino acid sequence represented by SEQ ID NO: 33 by a substitution of valine at position 7 with glutamic acid;

(f) VH having CDRs 1 and 3 containing the amino acid sequences represented by SEQ ID NOS: 32 and 34, respectively, and CDR2 containing an amino acid sequence modified from the amino acid sequence represented by SEQ ID NO: 33 by a substitution of aspartic acid at position 10 with alanine;

(g) VH having CDRs 1 and 3 containing the amino acid sequences represented by SEQ ID NOS: 32 and 34, respectively, and CDR2 containing an amino acid sequence modified from the amino acid sequence represented by SEQ ID NO: 33 by a substitution of aspartic acid at position 13 with proline;

(h) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of glutamine at position 3 with alanine or aspartic acid;

(i) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of proline at position 4 with an arbitrary natural amino acid;

(j) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of proline at position 4 with alanine, tyrosine, serine, aspartic acid, glutamine, glutamic acid, threonine, arginine, glycine, lysine, methionine, valine, leucine, isoleucine, tryptophan, phenylalanine, or histidine;

(k) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of tryptophan at position 5 with alanine, phenylalanine, histidine, or tyrosine;

(l) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of tyrosine at position 7 with alanine or phenylalanine; and (m) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of valine with leucine.

6. The bispecific antibody or the bispecific antibody fragment thereof according to the above 1, wherein the IgG portion includes VL containing the amino acid sequence represented by SEQ ID NO: 16 and VH containing an amino acid sequence modified from the amino acid sequence represented by SEQ ID NO: 31 by at least one substitution selected from Y32A, Y32F, T33A, T33G, L45A, V48A, V50A, I51A, I51L, V55E, D58A, D61P, Q97A, Q97D, W99A, W99F, W99H, W99Y, Y100AA, Y100AF, V102L, and a substitution of P98 with an arbitrary amino acid indicated in the EU index as in Kabat et al. (hereinafter EU index).

7. The bispecific antibody or the bispecific antibody fragment thereof according to the above 1, wherein the IgG portion includes VL containing the amino acid sequence represented by SEQ ID NO: 16 and VH containing an amino acid sequence modified from the amino acid sequence represented by SEQ ID NO: 31 by any one substitution selected from Y32A, Y32F, T33A, T33G, L45A, V48A, V50A, I51A, I51L, V55E, D58A, D61P, Q97A, Q97D, W99A, W99F, W99H, W99Y, Y100AA, Y100AF, V102L, P98A, P98Y, P98S, P98D, P98Q, P98E, P98T, P98R, P98G, P98K, P98M, P98V, P98L, P98I, P98W, P98F, and P98H indicated in the EU index.

8. The bispecific antibody or the bispecific antibody fragment thereof according to the above 1, wherein the IgG portion recognizes at least one amino acid residue selected from Asp at position 352, Ser at position 355, Asp at position 356, and Lys at position 358, and at least one amino acid residue selected from Met at position 365, Val at position 366, and Glu at position 369 in the amino acid sequence of TfR represented by SEQ ID NO: 6.

9. The bispecific antibody or the bispecific antibody fragment thereof according to any one of the above 1 to 8, wherein a heavy chain constant region of the IgG portion contains the amino acid sequence represented by SEQ ID NO: 84 or SEQ ID NO: 86.

10. The bispecific antibody or the bispecific antibody fragment thereof according to any one of the above 1 to 9, wherein the cell surface antigen is EGFR or GPC3.

11. The bispecific antibody or the bispecific antibody fragment thereof according to any one of the above 1 to 10, wherein the cell surface antigen is EGFR.

12. The bispecific antibody or the bispecific antibody fragment thereof according to any one of the above 1 to 11, wherein the N-terminal side polypeptide is any one of Fab, Fab', scFv, dsFv, and VHH of an antibody against the cell surface antigen.

13. The bispecific antibody or the bispecific antibody fragment thereof according to any one of the above 1 to 12, wherein the N-terminal side polypeptide is Fab of an antibody against the cell surface antigen.

14. The bispecific antibody or the bispecific antibody fragment thereof according to any one of the above 1 to 9, wherein the N-terminal side polypeptide is Fab of an antibody against EGFR, and the antibody is an antibody including VH having CDRs 1 to 3 containing the amino acid sequences represented by SEQ ID NOS: 60 to 62, respectively, or SEQ ID NOS: 65 to 67, respectively, and VL having CDRs 1 to 3 containing the amino acid sequences represented by SEQ ID NOS: 17 to 19, respectively.

15. The bispecific antibody or the bispecific antibody fragment thereof according to the above 14, wherein the antibody against EGFR is an antibody selected from the following (a) to (e):
   (a) an antibody including VH containing the amino acid sequence represented by SEQ ID NO: 59 or SEQ ID NO: 64 and VL containing the amino acid sequence represented by SEQ ID NO: 16;
   (b) an antibody including VH containing the amino acid sequence represented by SEQ ID NO: 110 and VL containing the amino acid sequence represented by SEQ ID NO: 111;
   (c) an antibody including VH containing the amino acid sequence represented by SEQ ID NO: 112 and VL containing the amino acid sequence represented by SEQ ID NO: 113;
   (d) an antibody including VH containing the amino acid sequence represented by SEQ ID NO: 114 and VL containing the amino acid sequence represented by SEQ ID NO: 115; and
   (e) an antibody including VH containing the amino acid sequence represented by SEQ ID NO: 116 and VL containing the amino acid sequence represented by SEQ ID NO: 117.

16. The bispecific antibody or the bispecific antibody fragment thereof according to any one of the above 13 to 15, wherein the heavy chain C terminus of the Fab directly binds to the heavy chain N terminus of the IgG portion.

17. The bispecific antibody or the bispecific antibody fragment thereof according to any one of the above 13 to 15, wherein the heavy chain C terminus of the Fab binds to the heavy chain N terminus of the IgG portion through a linker.

18. The bispecific antibody or the bispecific antibody fragment thereof according to the above 17, wherein the amino acid sequence of the linker is composed of part or all of the amino acid sequence of a hinge region of IgG.

19. The bispecific antibody or the bispecific antibody fragment thereof according to any one of the above 13 to 18, wherein the Fab and the IgG portion each include a light chain composed of the same amino acid sequence.

20. A DNA encoding the bispecific antibody or the bispecific antibody fragment thereof according to any one of the above 1 to 19.

21. A recombinant vector containing the DNA according to the above 20.

22. A transformant, obtainable by introducing the recombinant vector according to the above 21 into a host cell.

23. A method for producing the bispecific antibody or the bispecific antibody fragment thereof according to any one of the above 1 to 19, including culturing the transformant according to the above 22 in a culture medium, allowing the transformant to produce and accumulate the bispecific antibody or the bispecific antibody fragment thereof according to any one of the above 1 to 19 in a culture, and collecting the bispecific antibody or the bispecific antibody fragment thereof from the culture.

24. A therapeutic and/or diagnostic agent for a disease associated with at least one of human TfR and a cell surface antigen, containing the bispecific antibody or the bispecific antibody fragment thereof according to any one of the above 1 to 19 as an active ingredient.

25. The therapeutic agent and/or diagnostic agent according to the above 24, wherein the disease associated with at least one of human TfR and a cell surface antigen is cancer.

26. A therapeutic and/or diagnostic method for a disease associated with at least one of human TfR and a cell surface antigen, using the bispecific antibody or the bispecific antibody fragment thereof according to any one of the above 1 to 19.

27. The method according to the above 26, wherein the disease associated with at least one of human TfR and a cell surface antigen is cancer.

28. The bispecific antibody or the bispecific antibody fragment thereof according to any one of the above 1 to 19 for use in therapy and/or diagnosis for a disease associated with at least one of human TfR and a cell surface antigen.

29. The bispecific antibody or the bispecific antibody fragment thereof according to the above 28, wherein the disease associated with at least one of human TfR and a cell surface antigen is cancer.

30. Use of the bispecific antibody or the bispecific antibody fragment thereof according to any one of the above 1 to 19 for producing a therapeutic and/or diagnostic agent for a disease associated with at least one of human TfR and a cell surface antigen.

31. The use according to the above 30, wherein the disease associated with at least one of human TfR and a cell surface antigen is cancer.

32. A reagent for detecting or measuring at least one of human TfR and a cell surface antigen, containing the bispecific antibody or the bispecific antibody fragment thereof according to any one of the above 1 to 19.

Advantageous Effects of Invention

According to the present invention, a novel bispecific antibody that binds to TfR and a cell surface antigen, a bispecific antibody fragment thereof, a DNA encoding the bispecific antibody or the bispecific antibody fragment thereof, a vector containing the DNA, a hybridoma and a transformant that produce the bispecific antibody or the bispecific antibody fragment thereof, a method for producing the bispecific antibody or the bispecific antibody fragment thereof, therapeutic and diagnostic agents containing the bispecific antibody or the bispecific antibody fragment thereof, therapeutic and diagnostic methods using the bispecific antibody or the bispecific antibody fragment thereof, and a reagent for detection or measurement containing the bispecific antibody or the bispecific antibody fragment thereof can be provided.

BRIEF DESCRIPTION OF DRAWINGS

FIG. 1(A) shows a bispecific antibody in which an N-terminal side polypeptide is Fab, and a polypeptide including VH of Fab is bound to the N terminus of an IgG portion. FIG. 1(B) shows a bispecific antibody in which an N-terminal side polypeptide is VHH. FIG. 1(C) shows a bispecific antibody in which an N-terminal side polypeptide is Fab, and a polypeptide including VL of Fab is bound to the N terminus of an IgG portion.

FIGS. 2(A) to 2(C) show the results of evaluating the expression level of EGFR in OE21 cells, T.Tn cells, and U-937 cells, respectively, by a flow cytometer. FIGS. 2(D) to 2(F) show the results of evaluating the expression level of TfR in OE21 cells, T.Tn cells, and U-937 cells, respectively, by a flow cytometer. The vertical axis represents the cell count, and the horizontal axis represents the fluorescence intensity. The solid line indicates the binding affinity of an anti-TfR antibody or an anti-EGFR antibody, and the histogram filled with gray indicates the binding affinity of an isotype antibody that is a negative control.

FIGS. 3(A) to 3(C) show the results of evaluating the expression level of GPC3 in HepG2 cells, HuH-7 cells, and HLE cells, respectively, by a flow cytometer. FIGS. 3(D) to 3(F) show the results of evaluating the expression level of TfR in HepG2 cells, HuH-7 cells, and HLE cells, respectively, by a flow cytometer. FIGS. 3(G) to 3(I) show the results of evaluating the expression level of EGFR in HepG2 cells, HuH-7 cells, and HLE cells, respectively, by a flow cytometer. The vertical axis represents the cell count, and the horizontal axis represents the fluorescence intensity. The solid line indicates the binding affinity of an anti-GPC3 antibody, an anti-TfR antibody, or an anti-EGFR antibody, and the histogram filled with gray indicates the binding affinity of an isotype antibody or an anti-DNP antibody that is a negative control.

DESCRIPTION OF EMBODIMENTS

Figure 1:
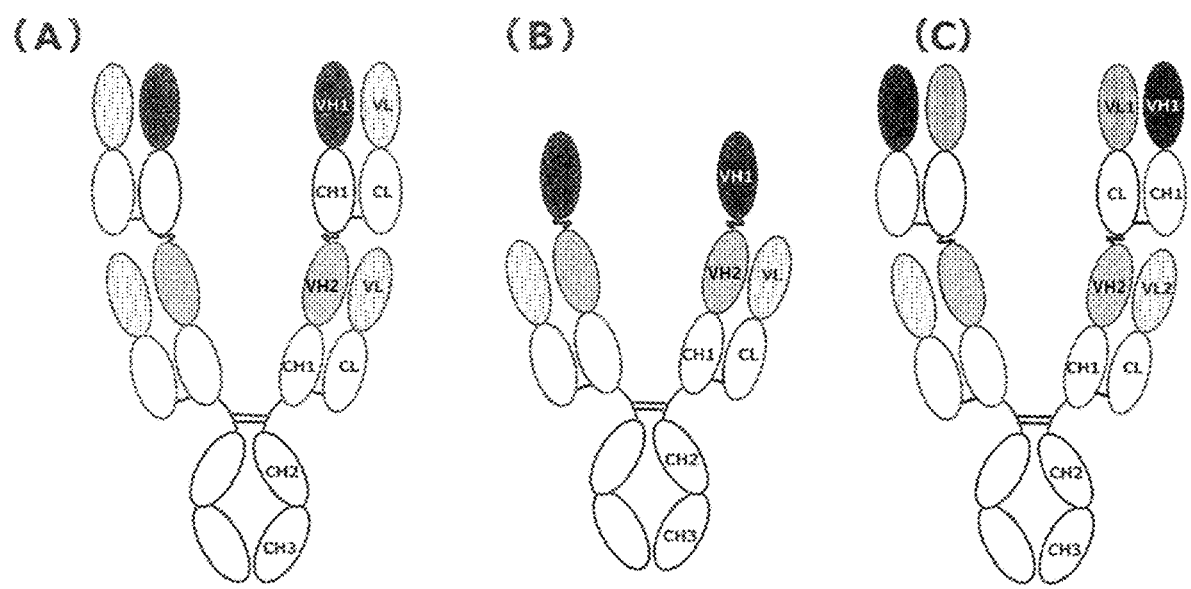
FIG. 1 shows an example of a structure of a bispecific antibody of the present invention.

The present invention relates to a bispecific antibody or a bispecific antibody fragment thereof, which binds to TfR and a cell surface antigen, and in which a polypeptide having an antigen-binding domain to the cell surface antigen (also referred to as N-terminal side polypeptide) binds directly or through a linker to the N-terminal side of an IgG portion that binds to TfR (hereinafter referred to as the bispecific antibody or the bispecific antibody fragment thereof of the present invention).

The TfR in the present invention is used synonymously with CD71, TFR1, TR, T9, p90, and IMD46. As the TfR, for example, human TfR containing the amino acid sequence represented by GenBank accession No. NP_003225 in NCBI (ncbi.nlm.nih.gov) or SEQ ID NO: 6, monkey TfR containing the amino acid sequence represented by SEQ ID NO: 8, and the like are exemplified. Further, for example, a polypeptide that is composed of an amino acid sequence in which one or more amino acids are deleted, substituted, or added in the amino acid sequence represented by SEQ ID NO: 6, GenBank accession No. NP_003225, or SEQ ID NO: 8, and that has the function of TfR is exemplified.

A polypeptide containing an amino acid sequence having generally 70% or more, preferably 80% or more, and more preferably 90% or more homology with the amino acid sequence represented by SEQ ID NO: 6, GenBank accession No. NP_003225, or SEQ ID NO: 8, and most preferably, a polypeptide that is composed of an amino acid sequence having 95%, 96%, 97%, 98%, and 99% or more homology and that has the function of TfR are also included in the TfR of the present invention.

The polypeptide having an amino acid sequence in which one or more amino acid residues are deleted, substituted, or added in the amino acid sequence represented by SEQ ID NO: 6, GenBank accession No. NP_003225, or SEQ ID NO: 8 can be obtained by, for example, introducing a site-specific mutation into a DNA encoding the amino acid sequence represented by SEQ ID NO: 6, GenBank accession No. NP_003225, or SEQ ID NO: 8 using a site-specific mutagenesis method [Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proceeding of the National Academy of Sciences in USA, 82, 488 (1985)], or the like. The number of amino acids to be deleted, substituted, or added is not particularly limited, but is preferably one to several tens, for example, 1 to 20, and more preferably one to several, for example, 1 to 5 amino acids.

As a gene encoding the TfR, for example, the nucleotide sequence of human TfR represented by SEQ ID NO: 5 or GenBank accession No. NM_003234, the nucleotide sequence of monkey TfR represented by SEQ ID NO: 7, and the like are exemplified. Further, for example, a gene that is composed of a nucleotide sequence in which one or more nucleotides are deleted, substituted, or added in the nucleotide sequence represented by SEQ ID NO: 5, GenBank accession No. NM_003234, or SEQ ID NO: 7 and that contains a DNA encoding a polypeptide having the function of TfR, a gene that is composed of preferably a nucleotide sequence having 60% or more homology, more preferably a nucleotide sequence having 80% or more homology, and further more preferably a nucleotide sequence having 95% or more homology with the nucleotide sequence represented by SEQ ID NO: 5, GenBank accession No. NM_003234, or SEQ ID NO: 7, and that contains a DNA encoding a polypeptide having the function of TfR, a gene that is composed of a DNA which hybridizes with a DNA composed of the nucleotide sequence represented by SEQ ID NO: 5, GenBank accession No. NM_003234, or SEQ ID NO: 7 under stringent conditions, and that contains a DNA encoding a polypeptide having the function of TfR, and the like are also included in the gene encoding the TfR of the present invention.

The DNA which hybridizes under stringent conditions means, for example, a hybridizable DNA obtained by a colony hybridization method, a plaque hybridization method, a southern blot hybridization method, a DNA microarray method, or the like using a DNA having the nucleotide sequence represented by SEQ ID NO: 5 or GenBank accession No. NM_003234 as a probe. Specifically, a DNA that can be identified by washing a filter or a microscope slide under the condition of 65° C. using an SSC solution at a 0.1 to 2× concentration (a composition of the SSC solution at a 1× concentration is composed of 150 mmol/L sodium chloride and 15 mmol/L sodium citrate), after performing hybridization [Molecular Cloning, A Laboratory Manual, Second Edition, Cold Spring Harbor Laboratory Press (1989), Current Protocols in Molecular Biology, John Wiley & Sons (1987-1997), DNA Cloning 1: Core Techniques, A Practical Approach, Second Edition, Oxford University (1995)] at 65° C. in the presence of 0.7 to 1.0 mol/L sodium chloride using a filter or a microscope slide on which a DNA derived from a hybridized colony or plaque, or a PCR product or an oligo DNA having the sequence is immobilized can be exemplified. As the hybridizable DNA, for example, a DNA preferably having 60% or more homology, more preferably a DNA having 80% or more homology, and further more preferably a DNA having 95% or more homology with the nucleotide sequence represented by SEQ ID NO: 5 or GenBank accession No. NM_003234 can be exemplified.

A gene polymorphism is often observed in a nucleotide sequence of a gene encoding a protein of a eukaryote. A gene in which a small-scale mutation has occurred in a nucleotide sequence due to such a polymorphism among genes used in the present invention is also included in the gene encoding the TfR of the present invention.

The numerical value of homology in the present invention may be a numerical value calculated using a homology search program known to those skilled in the art unless otherwise particularly specified, however, with respect to a nucleotide sequence, a numerical value calculated using a default parameter in BLAST [J. Mol. Biol., 215, 403 (1990)], and the like are exemplified, and with respect to an amino acid sequence, a numerical value calculated using a default parameter in BLAST 2 [Nucleic Acids Research, 25, 3389 (1997), Genome Research, 7, 649 (1997), ncbi.nlm.nih.gov], and the like are exemplified.

As for the default parameters, G (Cost to open gap) is 5 in the case of a nucleotide sequence and 11 in the case of an amino acid sequence, -E (Cost to extend gap) is 2 in the case of a nucleotide sequence and 1 in the case of an amino acid sequence, -q (Penalty for nucleotide mismatch) is -3, -r (reward for nucleotide match) is 1, -e (expect value) is 10, -W (wordsize) is 11 residues in the case of a nucleotide sequence and 3 residues in the case of an amino acid sequence, -y [Dropoff (X) for blast extensions in bits] is 20 in the case of blastn and 7 in the case of programs other than blastn, -X (X dropoff value for gapped alignment in bits) is 15, and -Z (final X dropoff value for gapped alignment in bits) is 50 in the case of blastn and 25 in the case of programs other than blastn (ncbi.nlm.nih.gov).

A polypeptide composed of a partial sequence of the amino acid sequence of TfR can be produced by a method known to those skilled in the art, and can be produced by, for example, deleting part of the DNA encoding the amino acid sequence represented by SEQ ID NO: 6, GenBank accession No. NP_003225, or SEQ ID NO: 8 and culturing a transformant transfected with an expression vector containing the resulting DNA. In addition, for example, a polypeptide having an amino acid sequence in which one or more amino acids are deleted, substituted, or added in the partial sequence of the amino acid sequence represented by SEQ ID NO: 6, GenBank accession No. NP_003225, or SEQ ID NO: 8 can be obtained by the same method as described above based on the polypeptide or the DNA produced by the above method. Further, a polypeptide composed of the partial sequence of the amino acid sequence of TfR, or a polypeptide having an amino acid sequence in which one or more amino acids are deleted, substituted, or added in the partial sequence of the amino acid sequence of TfR can also be produced using a chemical synthesis method such as a fluorenylmethyloxycarbonyl (Fmoc) method or a t-butyloxycarbonyl (tBoc) method.

As an extracellular domain of TfR in the present invention, for example, a region in which an amino acid sequence of human TfR represented by GenBank accession No. NP_003225 is predicted using a known transmembrane region prediction program SOSUI (sosui.proteome.bio.tu-at.ac.jp), TMHMM ver. 2 (cbs.dtu.dk), ExPASy Proteomics Server (Ca.expasy.org), or the like is exemplified. Specifically, an amino acid sequence shown at positions 89 to 760 of SEQ ID NO: 2 or GenBank accession No. NP_003225 is exemplified.

As the function of TfR, uptake of iron essential for cell survival and proliferation is exemplified. When a complex of iron and transferrin binds to TfR, the complex is incorporated into a cell by endocytosis. When the pH in the endosome decreases, iron is released from transferrin and migrates into the cytoplasm through DMT1 and is utilized in cell proliferation or energy production. It is known that a complex of TfR and transferrin from which iron has been released is generally not degraded and moves again to the cell surface (document: Yamashiro D J et al., Cell 37 789-800, 1984).

Examples of cells that express TfR include many normal tissue cells including bone marrow and placenta cells, many types of cancer cells including large intestine cancer, head and neck cancer, a brain tumor, a hematopoietic tumor, liver cancer, and esophageal cancer, and many cancer cell lines such as HT29, HSC-2, RAMOS, K562, HepG2, OE21, T.Tn, U-937, HuH-7, and HLE.

The cell surface antigen of the present invention refers to an antigen other than TfR among antigens such as proteins and peptide chains expressed on the cell membrane of cancer cells or the like. The cell surface antigen of the present invention may be any as long as a protein or a polypeptide such as an antibody can bind thereto, but is preferably a cell surface antigen that is internalized and/or degraded by binding of a protein or a polypeptide such as an antibody. Further, as the cell surface antigen of the present invention, a protein expressed at a high level in cancer cells or a cell population involved in a specific disease is preferred. Preferred examples of such a cell surface antigen include EGFR, GPC3, and the like.

The EGFR in the present invention is used synonymously with ERBB, ERBB1, HER1, PIG61, MENA, NISBD2, SA7, and c-Erb-1.

As the EGFR, for example, human EGFR containing the amino acid sequence represented by GenBank accession No. NP005219 or SEQ ID NO: 14; and monkey EGFR containing the amino acid sequence represented by GenBank accession No. XP_005549616.1 are exemplified. Further, for example, a polypeptide that is composed of an amino acid sequence in which one or more amino acids are deleted, substituted, or added in the amino acid sequence represented by SEQ ID NO: 14, NP005219, or GenBank accession No. XP_005549616.1, and that has the function of EGFR is exemplified.

A polypeptide containing an amino acid sequence having preferably 70% or more, more preferably 80% or more, and further more preferably 90% or more homology with the amino acid sequence represented by SEQ ID NO: 14, NP005219, or GenBank accession No. XP_005549616.1, and most preferably, a polypeptide that is composed of an amino acid sequence having 95%, 96%, 97%, 98%, and 99% or more homology and that has the function of EGFR are also included in the EGFR of the present invention.

The polypeptide having an amino acid sequence in which one or more amino acid residues are deleted, substituted, or added in the amino acid sequence represented by SEQ ID NO: 14, NP005219, or GenBank accession No. XP_005549616.1 can be obtained by, for example, introducing a site-specific mutation into a DNA encoding the amino acid sequence represented by SEQ ID NO: 14, NP005219, or GenBank accession No. XP_005549616.1 using the above-mentioned site-specific mutagenesis method, or the like. The number of amino acids to be deleted, substituted, or added is not particularly limited, but is preferably one to several tens, for example, 1 to 20, and more preferably one to several, for example, 1 to 5 amino acids.

As a gene encoding EGFR in the present invention, for example, a gene of human EGFR containing a nucleotide sequence represented by GenBank accession No. NM_005228 or SEQ ID NO: 13 is exemplified.

Further, for example, a gene that is composed of a nucleotide sequence in which one or more nucleotides are deleted, substituted, or added in the nucleotide sequence represented by SEQ ID NO: 13 or GenBank accession No. NM_005228, and that contains a DNA encoding a polypeptide having the function of EGFR, a gene that is composed of a nucleotide sequence having 60% or more homology, preferably a nucleotide sequence having 80% or more homology, and more preferably a nucleotide sequence having 95% or more homology with the nucleotide sequence represented by SEQ ID NO: 13 or GenBank accession No. NM_005228, and that contains a DNA encoding a polypeptide having the function of EGFR, a gene that is composed of a DNA which hybridizes with a DNA containing the nucleotide sequence represented by SEQ ID NO: 13 or GenBank accession No. NM_005228 under stringent conditions, and that contains a DNA encoding a polypeptide having the function of EGFR, and the like are also included in the gene encoding the EGFR of the present invention.

As an extracellular domain of EGFR in the present invention, for example, a region in which the amino acid sequence of human EGFR represented by GenBank accession No. NP005219 is predicted using a known transmembrane region prediction program SOSUI (sosui.proteome.bio.tuat.ac.jp), TMHMM ver. 2 (cbs.dtu.dk), ExPASy Proteomics Server (Ca.expasy.org), or the like is exemplified. Specifically, an amino acid sequence shown at positions 25 to 645 of SEQ ID NO: 10 or GenBank accession No. NP005219 is exemplified.

As the function of EGFR, for example, a function as a receptor for EGF, a function in which a dimer is formed after binding to EGF, and cell proliferation, survival, invasion, migration, or the like is promoted through signaling such as Ras/Raf/MAPK pathway, PI3K/Akt pathway, or Jak/STAT pathway. It is known that EGFR on a cell membrane is internalized when EGF binds thereto, and migrates to the lysosome by endocytosis and is degraded (Ebner R et al., Cell Regul. 2 599-612, 1991).

Examples of cells that express EGFR include epithelial cells of normal tissues including skin, large intestine, and lung, epithelial cancer cells including large intestine cancer, head and neck cancer, lung cancer, and esophageal cancer, and cancer cell lines such as HT29, HSC-2, NCI-H1975, OE21, T.Tn, and A431.

The GPC3 in the present invention is used synonymously with DGSX, GTR2-2, MXR7, OCI-5, SDYS, SGB, SGBS, and SGBS1.

As the function of GPC3, for example, a function of being involved in cell division or proliferation of cancer cells such as liver cancer by binding to a protein associated with Wnt pathway or Frizzled pathway is exemplified.

As the GPC3, for example, human GPC3 containing the amino acid sequence represented by GenBank accession No. P51654 is exemplified.

As an extracellular domain of the GPC3 in the present invention, for example, a region in which the amino acid sequence of human GPC3 represented by GenBank accession No. P51654 is predicted using a known transmembrane region prediction program SOSUI (sosui.proteome.bio.tuat.ac.jp), TMHMM ver. 2 (cbs.dtu.dk), ExPASy Proteomics Server (Ca.expasy.org), or the like is exemplified. Specifically, an amino acid sequence shown at positions 1 to 559 of GenBank accession No. P51654 is exemplified.

Examples of cells that express GPC3 include fetal liver cells, cancer cells such as liver cancer cells, and cancer cell lines such as HepG2 and HuH-7

An antibody is a protein derived from a gene (referred to as "antibody gene") encoding all or part of a heavy chain variable region, a heavy chain constant region, a light chain variable region, and a light chain constant region constituting an immunoglobulin. The antibody of the present invention also includes an antibody or an antibody fragment having any immunoglobulin class and subclass.

The heavy chain (H chain) refers to a polypeptide having a higher molecular weight of the two types of polypeptides constituting an immunoglobulin molecule. The heavy chain determines the antibody class and subclass. IgA, IgD, IgE, IgG, and IgM include an α chain, a δ chain, an ε chain, a γ chain, and a μ chain as the heavy chain, respectively, and the heavy chain constant region is characterized by a different amino acid sequence. The light chain (L chain) refers to a polypeptide having a lower molecular weight of the two types of polypeptides constituting an immunoglobulin molecule. In the case of a human antibody, there are two types of light chains: a κ chain and a λ chain.

The variable region (V region) generally refers to a region rich in diversity present in the amino acid sequence at the N-terminal side of an immunoglobulin. Because a part other than the variable region has a structure with less diversity, it is called a constant region (C region). The respective variable regions of the heavy chain and the light chain are associated to form an antigen-binding domain and determine the binding property of the antibody to the antigen.

In the heavy chain of a human antibody, a variable region corresponds to the amino acid sequence at positions 1 to 117 in the EU index of Kabat et al. (Kabat et al., Sequences of proteins of immunological interest, 1991 Fifth edition), and a constant region corresponds to the amino acid sequence downstream of position 118. In the light chain of a human antibody, the amino acid sequence at positions 1 to 107 numbered according to Kabat et al. (Kabat numbering) corresponds to a variable region, and the amino acid sequence downstream of position 108 corresponds to a constant region. Hereinafter, the heavy chain variable region or the light chain variable region is abbreviated as VH or VL.

The antigen-binding domain is a domain that recognizes and binds to an antigen in an antibody, and refers to a domain that forms a complementary conformation with an antigenic determinant (epitope). The antigen-binding domain causes a strong intermolecular interaction with an antigenic determinant. The antigen-binding domain is constituted by VH and VL having at least three complementarity determining regions (CDRs). In the case of a human antibody, VH and VL each have three CDRs. These CDRs are referred to as CDR1, CDR2, and CDR3, respectively, in order from the N-terminal side.

In the constant region, the heavy chain constant region and the light chain constant region are referred to as CH and CL, respectively. The CH is classified into an a. chain, a δ chain, an ε chain, a γ chain, and a μ chain which are subclasses of the heavy chain. The CH is constituted by a CH1 domain, a hinge domain, a CH2 domain, and a CH3 domain arranged in order from the N-terminal side, and the CH2 domain and the CH3 domain together are called an Fc region. On the other hand, the CL is classified into two subclasses called a Cλ chain and a Cκ chain.

A monoclonal antibody is an antibody secreted by an antibody-producing cell maintaining monoclonality, and recognizes a single epitope (also referred to as antigenic determinant). The monoclonal antibody molecules have the same amino acid sequence (primary structure) and have a single structure. A polyclonal antibody refers to a population of antibody molecules secreted by antibody-producing cells of different clones. An oligoclonal antibody refers to a population of antibody molecules in which a plurality of different monoclonal antibodies are mixed.

The epitope is a structural domain of an antigen that an antibody recognizes and binds to. Examples of the epitope include a single amino acid sequence, a conformation composed of an amino acid sequence, an amino acid sequence to which a sugar chain is bound, a conformation composed of an amino acid sequence to which a sugar chain is bound, and the like, each of which a monoclonal antibody recognizes and binds to.

Examples of the monoclonal antibody in the present invention include an antibody produced by a hybridoma, and a genetically recombinant antibody produced by a transformant transformed with an expression vector containing an antibody gene.

The hybridoma can be prepared by, for example, preparing an antigen, obtaining an antibody-producing cell having antigen specificity from an animal immunized with the antigen, and then fusing the antibody-producing cell with a myeloma cell. A desired monoclonal antibody can be obtained by culturing the hybridoma or by administering the hybridoma to an animal to convert the hybridoma into an ascites tumor, separating the culture solution or the ascites, followed by purification. As the animal to be immunized with the antigen, any animal can be used as long as it can produce a hybridoma, however, a mouse, a rat, a hamster, a rabbit, or the like is preferably used. In addition, the hybridoma can also be produced by obtaining a cell having an antibody-producing ability from such an immunized animal, subjecting the cell to in vitro immunization, and then fusing the cell with a myeloma cell.

Examples of the genetically recombinant antibody in the present invention include antibodies produced using a gene recombinant technique such as a recombinant mouse antibody, a recombinant rat antibody, a recombinant hamster antibody, a recombinant rabbit antibody, a human chimeric antibody (also referred to as chimeric antibody), a humanized antibody (also referred to as CDR-grafted antibody), and a human antibody. In the genetically recombinant antibody, it is possible to determine which animal species the heavy chain and the light chain variable regions and constant regions derived from are applied according to the animal species to be used as a target and the purpose. For example, when the animal species to be used as a target is a human, as the variable region, one derived from a human or a non-human animal such as a mouse can be adopted, and as the constant region and the linker, those derived from a human can be adopted.

The chimeric antibody refers to an antibody composed of VH and VL of an antibody of an animal other than a human (non-human animal) and CH and CL of a human antibody. As the non-human animal, any animal such as a mouse, a rat, a hamster, or a rabbit can be used as long as it can produce a hybridoma. The chimeric antibody can be produced by obtaining cDNAs encoding VH and VL from a hybridoma derived from a non-human animal that produces a monoclonal antibody, inserting each of the cDNAs into an expression vector for an animal cell having DNAs encoding CH and CL of a human antibody, thereby constructing a chimeric antibody expression vector, and then introducing the vector into an animal cell to cause expression.

The humanized antibody refers to an antibody in which CDRs of VH and VL of a non-human animal antibody is grafted in the corresponding CDRs of VH and VL of a human antibody. A region other than the CDRs of VH and VL is referred to as a framework region (hereinafter referred to as FR). The humanized antibody can be produced by constructing a cDNA encoding the amino acid sequence of VH composed of the amino acid sequence of CDRs of VH of a non-human animal antibody and the amino acid sequence of FR of VH of an arbitrary human antibody, and a cDNA encoding the amino acid sequence of VL composed of the amino acid sequence of CDRs of VL of a non-human animal antibody and the amino acid sequence of FR of VL of an arbitrary human antibody, inserting each of the cDNAs into an expression vector for an animal cell having DNAs encoding CH and CL of a human antibody, thereby constructing a humanized antibody expression vector, and then introducing the vector into an animal cell to cause expression.

The human antibody originally refers to an antibody that is naturally present in the human body, but also includes antibodies that are obtained from a human antibody phage library and a human antibody-producing transgenic animal, each of which is produced by recent advancement of genetic engineering, cellular engineering, or developmental engineering technology, and the like.

The antibody that is naturally present in the human body can be obtained by, for example, infecting human peripheral blood lymphocytes with an EB virus or the like so as to immortalize the lymphocytes, followed by cloning to culture a lymphocyte that produces the antibody, and then purifying the antibody from the culture supernatant.

The human antibody phage library is a library in which an antibody fragment such as Fab or scFv is expressed on phage surfaces by inserting an antibody gene prepared from a human B cell into a phage gene. It is possible to collect a phage that has expressed an antibody fragment having a desired antigen-binding activity on the surface from the library using a binding activity to a substrate on which an antigen is immobilized as an index. The antibody fragment can be further converted into a human antibody molecule composed of two complete H chains and two complete L chains using a genetic engineering technique.

The human antibody-producing transgenic animal means an animal in which a human antibody gene is incorporated into a cell. Specifically, for example, a human antibody-producing transgenic mouse can be produced by introducing a human antibody gene into a mouse ES cell, implanting the ES cell to a mouse early embryo and then allowing the embryo to develop into an individual. A human antibody derived from the human antibody-producing transgenic animal can be prepared by obtaining a hybridoma using a conventional hybridoma production method that is performed for a non-human animal, and culturing the hybridoma, thereby producing and accumulating the antibody in the culture supernatant.

The CH of the genetically recombinant antibody may be any as long as it belongs to a human immunoglobulin, but is preferably CH of human immunoglobulin G (hIgG) class. Further, it is possible to use CH of any subclass such as hIgG1, hIgG2, hIgG3, and hIgG4 which belong to the hIgG class. In addition, the CL of the genetically recombinant antibody may be any as long as it belongs to a human immunoglobulin, and CL of the K class or the k class can be used.

In the present invention, the bispecific antibody refers to a polypeptide or a protein that specifically binds to each of two different types of epitopes. Each of the antigen-binding domains of the bispecific antibody may bind to different epitopes of a single antigen or may bind to different antigens.

In the present invention, the binding of a polypeptide, an antibody or an antibody fragment thereof, or a bispecific antibody or a bispecific antibody fragment thereof to any one of a cell surface antigen such as EGFR or GPC3 and TfR can be confirmed by a method in which the binding affinity of the antibody to a cell that has expressed a cell surface antigen or TfR desired to be evaluated is confirmed using, for example, a known immunological detection method, preferably a fluorescent cell staining method, or the like. Further, it is also possible to use known immunological detection methods [Monoclonal Antibodies—Principles and Practice, Third Edition, Academic Press (1996), Antibodies—A Laboratory Manual, Cold Spring Harbor Laboratory (1988), Monoclonal Antibody Experimental Manual, Kodansha scientific books (1987)], and the like in combination.

In the present invention, an antigen-binding domain that binds to a cell surface antigen such as EGFR or GPC3 or TfR may be any as long as it specifically recognizes and binds to a cell surface antigen such as EGFR or GPC3 or TfR. For example, the domain may be in any form of a polypeptide, a protein molecule and a fragment thereof, a conjugate body with the a low-molecular weight molecule or a natural product of the protein molecule, and the like that can be produced by a gene recombination technique such as an antibody, a ligand, a receptor, or a naturally occurring interacting molecule.

Further, the antigen-binding domain may be a binding protein recombined by utilizing a binding domain of a known binding molecule such as an antibody, a ligand, or a receptor, and specific examples include a recombinant protein having CDR of an antibody that binds to each antigen, an antibody variable region having CDR, a recombinant protein including an antibody variable region and a binding domain of a ligand that binds to each antigen, and the like. Among these, the antigen-binding domain is preferably an antibody variable region in the present invention.

As the bispecific antibody or the bispecific antibody fragment thereof of the present invention, for example, a bispecific antibody or a bispecific antibody fragment thereof having a TfR internalization and/or degradation activity is exemplified. The bispecific antibody or the bispecific antibody fragment thereof of the present invention is preferably a bispecific antibody or a bispecific antibody fragment thereof that does not exhibit the TfR internalization and/or degradation activity against a cell that does not express a cell surface antigen such as EGFR or GPC3 but exhibits the TfR internalization and/or degradation activity only against a cell that has expressed a cell surface antigen such as EGFR or GPC3. Such a bispecific antibody or a bispecific antibody fragment thereof selectively exhibits the TfR internalization and/or degradation activity against a pathogenic cell such as a cancer cell that expresses a cell surface antigen such as EGFR or GPC3, and therefore is preferred from the viewpoint that a side effect accompanying nonspecific internalization and/or degradation of TfR is not caused.

The TfR internalization and/or degradation activity possessed by the bispecific antibody or the bispecific antibody fragment thereof of the present invention refers to an activity that pulls TfR into the internalization and/or degradation pathway of a cell surface antigen when the bispecific antibody or the bispecific antibody fragment thereof binds to both a cell surface antigen such as EGFR or GPC3 on a cell and TfR so as to induce internalization and/or degradation, or the like.

The bispecific antibody or the bispecific antibody fragment thereof of the present invention may bind to a cell surface antigen such as EGFR or GPC3 and TfR expressed on the same cell or may bind to a cell surface antigen such as EGFR or GPC3 and TfR expressed on different cells, but is preferably one that binds to a cell surface antigen such as EGFR or GPC3 and TfR expressed on the same cell.

The bispecific antibody or the bispecific antibody fragment thereof of the present invention is preferably one that induces cell death of a cell that has expressed a target cell surface antigen such as EGFR or GPC3 by inducing internalization and/or degradation of TfR.

The TfR internalization and/or degradation activity possessed by the bispecific antibody or the bispecific antibody fragment thereof of the present invention can be confirmed by, for example, evaluating the TfR protein level on a cell surface of a cell or in a cell that expresses TfR such as OE21, T.Tn, TE-8, U-937, HepG2, HuH-7, or HLE, a viable cell count, a cell proliferation rate, a cell viability, cell iron uptake, or the like.

That is, as the bispecific antibody or the bispecific antibody fragment thereof of the present invention, specifically, a bispecific antibody or a bispecific antibody fragment thereof that induces degradation of TfR when binding to both a cell surface antigen such as EGFR or GPC3 and TfR, and the like are exemplified.

The number of binding domains to a certain antigen possessed by a single molecule of a bispecific antibody refers to a binding valence. For example, in the present invention, when a single molecule of a bispecific antibody has two antigen-binding domains that bind to EGFR and two antigen-binding domains that bind to TfR, the bispecific antibody divalently binds to each of EGFR and TfR.

In addition, an antibody including a plurality of antigen-binding domains that are bound through an appropriate linker such as a linker including an immunoglobulin domain or a fragment thereof is also included in the bispecific antibody of the present invention.

The bispecific antibody of the present invention can be produced using a known production technique ([Nature Protocols, 9, 2450-2463 (2014)], WO 1998/050431, WO 2001/7734, WO 2002/002773, and WO 2009/131239) or the like.

The bispecific antibody of the present invention has a structure in which a polypeptide (also referred to as N-terminal side polypeptide) having a binding ability to a cell surface antigen binds directly or through a linker to the heavy chain N terminus of an IgG portion that binds to TfR.

In the present invention, the immunoglobulin domain includes a peptide that has an amino acid sequence similar to an immunoglobulin and is composed of about 100 amino acid residues in which at least two cysteine residues are present as a smallest unit. In the present invention, the immunoglobulin domain also includes a polypeptide including a plurality of immunoglobulin domains as the smallest unit described above. Examples of the immunoglobulin domain include VH, CH1, CH2, and CH3 of an immunoglobulin heavy chain, and VL and CL of an immunoglobulin light chain, and the like.

The animal species of the immunoglobulin is not particularly limited, but is preferably a human. In addition, the subclass of the constant region of the immunoglobulin heavy chain may be any of IgD, IgM, IgG1, IgG2, IgG3, IgG4, IgA1, IgA2, and IgE, and preferably, IgG-derived and IgM-derived subclasses are exemplified. In addition, the subclass of the constant region of the immunoglobulin light chain may be either of κ and λ.

Further, the immunoglobulin domain is also present in proteins other than the immunoglobulin, and for example, immunoglobulin domains included in proteins belonging to the immunoglobulin superfamily such as a major histocompatibility antigen (MHC), CD1, B7, and a T cell receptor (TCR) are exemplified. As the immunoglobulin domain used for the bispecific antibody of the present invention, any immunoglobulin domain can be applied.

In the case of human IgG, CH1 refers to a region having the amino acid sequence at positions 118 to 215 indicated in the EU index. Similarly, CH2 refers to a region having the amino acid sequence at positions 231 to 340 indicated in the EU index of Kabat et al., and CH3 refers to a region having the amino acid sequence at positions 341 to 447 indicated in the EU index of Kabat et al. Between CH1 and CH2, an amino acid region rich in flexibility called a hinge region (hereinafter sometimes referred to as hinge) is present. The hinge region refers to a region having the amino acid sequence at positions 216 to 230 indicated in the EU index of Kabat et al.

The CL refers to a region having the amino acid sequence at positions 108 to 214 indicated by Kabat numbering in the case of the K chain of a human antibody, and refers to a region having the amino acid sequence at positions 108 to 215 in the case of the λ chain.

An IgG-type antibody of the present invention is also referred to as an IgG portion and refers to a partial structure of IgG that constitutes the bispecific antibody of the present invention or IgG in which an Fc portion is modified, and has a heterotetramer structure obtained by assembling two heterodimers composed of one light chain and one heavy chain. The IgG portion that binds to TfR of the present invention refers to an IgG portion that recognizes TfR, that is, an IgG portion having a function of specifically recognizing and binding to the extracellular domain of TfR.

The heavy chain constant region of the IgG may be in any subclass such as IgG1, IgG2, IgG3, or IgG4. Further, part of the amino acid sequence thereof may be deleted, added, substituted, and/or inserted. In addition, all or part of the fragments of the amino acid sequence composed of CH1, a hinge, CH2, and CH3 of the heavy chain of IgG can be appropriately combined and used. Further, the amino acid sequences thereof can also be used by partially deleting or changing the order. In addition, the subclass of IgG used for the IgG portion is not particularly limited, but is preferably IgG4, or an IgG4 mutant obtained by substituting a Ser residue at position 228 in the heavy chain constant region of IgG4 with Pro, and a Leu residue at position 235 therein with Asn (hereinafter referred to as IgG4PE), or an IgG4 mutant obtained by substituting a Ser residue at position 228 in the heavy chain constant region of IgG4 with Pro, a Leu residue at position 235 therein with Asn, and an Arg residue at position 409 therein with Lys (hereinafter referred to as IgG4PE R409K).

For example, an IgG portion in which the heavy chain constant region (CH1-hinge-CH2-CH3 in this order from the N-terminal side) is composed of IgG4PE containing the amino acid sequence represented by SEQ ID NO: 86 or an IgG portion in which the heavy chain constant region is composed of IgG4PE R409K containing the amino acid sequence represented by SEQ ID NO: 84 is preferred.

Two variable regions included in the IgG portion of the present invention preferably recognize the same antigen. Further, they preferably have the same structure and the same amino acid sequence.

In the present invention, the N-terminal side polypeptide that binds to a cell surface antigen is a partial structure constituting the bispecific antibody of the present invention, and refers to a polypeptide that is present on the N-terminal side of the heavy chain or the light chain of the IgG portion, and specifically recognizes and binds to the extracellular region of each cell surface antigen.

The bispecific antibody of the present invention may have N-terminal side polypeptides, one each at the N terminus of the heavy chain or the light chain of both two heterodimers constituting the IgG portion or may have one N-terminal side polypeptide only at the N terminus of one of the heterodimers, but preferably has N-terminal side polypeptides one each at the N terminus of the heavy chain or the light chain of both. When the bispecific antibody has N-terminal side polypeptides one each at the N terminus of the heavy chain or the light chain of both, these polypeptides may be the same or different, but are preferably the same N-terminal side polypeptide.

The N-terminal side polypeptide of the present invention may be a single chain or a multimer composed of a plurality of polypeptide chains as long as it has an antigen-binding ability to a cell surface antigen. As the N-terminal side polypeptide, for example, Fab, Fab', scFv, dsFv, and VHH of an antibody against a cell surface antigen are exemplified, but Fab or VHH is preferred. Further, a ligand molecule or a receptor molecule against a cell surface antigen can also be used similarly.

The antibodies against a cell surface antigen each refer to a monoclonal antibody that specifically recognizes and binds to the extracellular domain of the corresponding cell surface antigen. For example, an anti-EGFR antibody and an anti-GPC3 antibody refer to monoclonal antibodies that specifically recognize and bind to the extracellular domain of EGFR and GPC3, respectively.

The linker in the present invention may be any as long as it is a molecular structure for binding the IgG portion to the N-terminal side polypeptide, but is preferably a peptide chain. As the amino acid sequence of the peptide chain, for example, ES (SEQ ID NO: 79), ESKYG (SEQ ID NO: 80), ESKYGPP (SEQ ID NO: 81), GGGGS (SEQ ID NO: 82), or one composed of a repetitive sequence of GGGGS (SEQ ID NO: 82), or one composed of the sequence of part or all of a hinge region and a constant region of a CH1 domain or the like of an antibody, or the like is exemplified.

When the bispecific antibody of the present invention has Fab of an antibody against a cell surface antigen as the N-terminal side polypeptide, a light chain included in the Fab and the light chain of the IgG portion may be the same or different, but are preferably the same. Further, the light chain may be either a λ chain or a κ chain, but is preferably a κ chain.

An antibody or an antibody fragment thereof, in which one or more of amino acid residues are deleted, added, substituted, or inserted in the amino acid sequence constituting the bispecific antibody or the bispecific antibody fragment thereof of the present invention, and which has the same activity as the antibody or the antibody fragment thereof is also included in the bispecific antibody or the antibody fragment thereof of the present invention.

The number of amino acids to be deleted, substituted, inserted, and/or added is one or more, and is not particularly limited, and is a number such that deletion, substitution, insertion, or addition can be carried out using a well-known technique such as a site-specific mutagenesis method described in Molecular Cloning, The Second Edition, Cold Spring Harbor Laboratory Press (1989), Current Protocols in Molecular Biology, John Willy & Sons (1987-1997), Nucleic Acids Research, 10, 6487 (1982), Proc. Natl. Acad. Sci., USA, 79, 6409 (1982), Gene, 34, 315 (1985), Nucleic Acids Research, 13, 4431 (1985), Proc. Natl. Acad. Sci USA, 82, 488 (1985), or the like. For example, it is generally one to several tens, preferably 1 to 20, more preferably 1 to 10, and further more preferably 1 to 5.

The above description that one or more of amino acid residues in the amino acid sequence of the bispecific antibody of the present invention are deleted, substituted, inserted, or added indicates as follows. The description means that there is a deletion, substitution, insertion, or addition of one or a plurality of amino acid residues in arbitrary one or a plurality of amino acid sequences in the same sequence. Further, such a deletion, substitution, insertion, or addition may sometimes occur simultaneously, and the amino acid residues to be substituted, inserted, or added may be either a natural type or an unnatural type.

Examples of the natural amino acid residue include L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, L-cysteine, and the like.

Hereinafter, preferred examples of mutually substitutable amino acid residues are shown. Amino acid residues included in the same group can be mutually substituted.

group A: leucine, isoleucine, norleucine, valine, norvaline, alanine, 2-aminobutanoic acid, methionine, O-methylserine, t-butyl glycine, t-butyl alanine, and cyclohexylalanine group B: aspartic acid, glutamic acid, isoaspartic acid, isoglutamic acid, 2-aminoadipic acid, and 2-aminosuberic acid group C: asparagine and glutamine group D: lysine, arginine, ornithine, 2,4-diaminobutanoic acid, and 2,3-diaminopropionic acid group E: proline, 3-hydroxyproline, and 4-hydroxyproline group F: serine, threonine, and homoserine group G: phenylalanine and tyrosine The bispecific antibody or the bispecific antibody fragment thereof of the present invention also includes an antibody containing any amino acid residue subjected to a post-translational modification. Examples of the post-translational modification include a deletion of a lysine residue at the C terminus of the H chain (lysine clipping), a substitution of a glutamine residue at the N terminus of a polypeptide with pyroglutamate (pyroGlu), and the like [Beck et al, Analytical Chemistry, 85, 715-736 (2013)].

Specific examples of the bispecific antibody of the present invention include any one bispecific antibody selected from the group consisting of the following (1) to (4), and the like:

(1) a bispecific antibody including Fab containing a variable region of an antibody against a cell surface antigen and an IgG portion that binds to TfR, wherein the Fab directly binds to the N terminus of the heavy chain of the IgG portion;

(2) a bispecific antibody including Fab containing VH having CDRs 1 to 3 of VH and VL having CDRs 1 to 3 of VL of an antibody against a cell surface antigen and an IgG portion that binds to TfR, wherein the Fab directly binds to the N terminus of the heavy chain of the IgG portion;

(3) a bispecific antibody including Fab containing VH and VL of an antibody against a cell surface antigen and an IgG portion that binds to TfR, wherein the Fab directly binds to the N terminus of the heavy chain of the IgG portion; and (4) a bispecific antibody including VHH that binds to a cell surface antigen and an IgG portion that binds to TfR, wherein the VHH directly binds to the N terminus of the heavy chain of the IgG portion.

In the bispecific antibodies described in the above (1) to (3), the VL of the IgG portion that binds to TfR and the VL of the Fab may be the same or different, but are preferably the same.

As an example of the IgG portion that binds to TfR of the present invention, an IgG portion that binds to TfR and includes VL having CDRs 1, 2, and 3 containing the amino acid sequences represented by SEQ ID NOS: 17, 18, and 19, respectively, and VH having CDRs 1 to 3 shown in the following 1) to 3) is exemplified.

1) CDR1 containing the amino acid sequence represented by SEQ ID NO: 32 or an amino acid sequence modified from the amino acid sequence represented by SEQ ID NO: 32 by at least one substitution selected from a substitution of tyrosine at position 2 with alanine or phenylalanine and a substitution of threonine at position 3 with alanine or glycine.

2) CDR2 containing the amino acid sequence represented by SEQ ID NO: 33 or an amino acid sequence modified from the amino acid sequence represented by SEQ ID NO: 33 by at least one substitution selected from a substitution of valine at position 1 with alanine, a substitution of isoleucine at position 2 with alanine or leucine, a substitution of valine at position 7 with glutamic acid, a substitution of aspartic acid at position 10 with alanine, and a substitution of aspartic acid at position 13 with proline.

3) CDR3 containing the amino acid sequence represented by SEQ ID NO: 34 or an amino acid sequence modified from the amino acid sequence represented by SEQ ID NO: 34 by at least one substitution selected from a substitution of glutamine at position 3 with alanine or aspartic acid, a substitution of proline at position 4 with an arbitrary natural amino acid, a substitution of tryptophan at position 5 with alanine, phenylalanine, histidine, or tyrosine, a substitution of tyrosine at position 7 with alanine or phenylalanine, and a substitution of valine at position 13 with leucine. As the substitution of proline at position 4 with an arbitrary natural amino acid, for example, a substitution thereof with alanine, tyrosine, serine, aspartic acid, glutamine, glutamic acid, threonine, arginine, glycine, lysine, methionine, valine, leucine, isoleucine, tryptophan, phenylalanine, or histidine is exemplified.

The IgG portion that binds to TfR of the present invention also includes an IgG portion that binds to TfR and contains the amino acid sequences of CDRs 1 to 3 of VH and VL having at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% homology with the corresponding amino acid sequences of CDRs 1 to 3 of VH represented by SEQ ID NOS: 32, 33, and 34, respectively, and amino acid sequences of CDRs 1 to 3 of VL represented by SEQ ID NOS: 17 to 19, respectively.

The IgG portion that binds to TfR of the present invention also includes an antibody described in the following (ai) or (aii):
- (ai) an IgG portion that binds to TfR and binds to TfR competitively with an anti-TfR antibody including VL having CDRs 1, 2, and 3 containing the amino acid sequences represented by SEQ ID NOS: 17, 18, and 19, respectively, and VH having CDRs 1, 2, and 3 containing the amino acid sequences represented by SEQ ID NOS: 32, 33, and 34, respectively; or
- (aii) an IgG portion that binds to TfR and binds to the same epitope as an anti-TfR antibody including VL having CDRs 1, 2, and 3 containing the amino acid sequences represented by SEQ ID NOS: 17, 18, and 19, respectively, and VH having CDRs 1, 2, and 3 containing the amino acid sequences represented by SEQ ID NOS: 32, 33, and 34, respectively.

The IgG portion that binds to TfR of the present invention also includes an antibody described in the following (bi) or (bii):
- (bi) an IgG portion that binds to TfR competitively with an anti-TfR antibody including VL having CDRs 1, 2, and 3 containing the amino acid sequences represented by SEQ ID NOS: 17, 18, and 19, respectively, and VH having CDRs 1, 2, and 3 containing the amino acid sequences represented by SEQ ID NOS: 42, 43, and 44, respectively; or
- (bii) an IgG portion that binds to TfR and binds to the same epitope as an anti-TfR antibody including VL having CDRs 1, 2, and 3 containing the amino acid sequences represented by SEQ ID NOS: 17, 18, and 19, respectively, and VH having CDRs 1, 2, and 3 containing the amino acid sequences represented by SEQ ID NOS: 42, 43, and 44, respectively.

The IgG portion that binds to TfR of the present invention also includes an antibody described in the following (ci) or (cii):
- (ci) an IgG portion that binds to TfR competitively with an anti-TfR antibody including VL having CDRs 1, 2, and 3 containing the amino acid sequences represented by SEQ ID NOS: 17, 18, and 19, respectively, and VH having CDRs 1, 2, and 3 containing the amino acid sequences represented by SEQ ID NOS: 47, 48, and 49, respectively; or
- (cii) an IgG portion that binds to TfR and binds to the same epitope as an anti-TfR antibody including VL having CDRs 1, 2, and 3 containing the amino acid sequences represented by SEQ ID NOS: 17, 18, and 19, respectively, and VH having CDRs 1, 2, and 3 containing the amino acid sequences represented by SEQ ID NOS: 47, 48, and 49, respectively.

As another example of the IgG portion that binds to TfR of the present invention, an IgG portion that binds to TfR and includes VL containing the amino acid sequence represented by SEQ ID NO: 16, and VH containing the amino acid sequence represented by SEQ ID NO: 26, 31, 36, 41, 46, or 106 is exemplified.

As one example of the IgG portion that binds to TfR of the present invention, an IgG portion that binds to TfR and includes VL having CDRs 1 to 3 containing the amino acid sequences represented by SEQ ID NOS: 17 to 19, respectively, and one VH selected from the following is exemplified:
- (a) VH having CDRs 2 and 3 containing the amino acid sequences represented by SEQ ID NOS: 33 and 34, respectively, and CDR1 containing an amino acid sequence modified from the amino acid sequence represented by SEQ ID NO: 32 by a substitution of tyrosine at position 2 with alanine or phenylalanine;
- (b) VH having CDRs 2 and 3 containing the amino acid sequences represented by SEQ ID NOS: 33 and 34, respectively, and CDR1 containing an amino acid sequence modified from the amino acid sequence represented by SEQ ID NO: 32 by a substitution of threonine at position 3 with alanine or glycine;
- (c) VH having CDRs 1 and 3 containing the amino acid sequences represented by SEQ ID NOS: 32 and 34, respectively, and CDR2 containing an amino acid sequence modified from the amino acid sequence represented by SEQ ID NO: 33 by a substitution of valine at position 1 with alanine;
- (d) VH having CDRs 1 and 3 containing the amino acid sequences represented by SEQ ID NOS: 32 and 34, respectively, and CDR2 containing an amino acid sequence modified from the amino acid sequence represented by SEQ ID NO: 33 by a substitution of isoleucine at position 2 with alanine or leucine;
- (e) VH having CDRs 1 and 3 containing the amino acid sequences represented by SEQ ID NOS: 32 and 34, respectively, and CDR2 containing an amino acid sequence modified from the amino acid sequence represented by SEQ ID NO: 33 by a substitution of valine at position 7 with glutamic acid;
- (f) VH having CDRs 1 and 3 containing the amino acid sequences represented by SEQ ID NOS: 32 and 34, respectively, and CDR2 containing an amino acid sequence modified from the amino acid sequence represented by SEQ ID NO: 33 by a substitution of aspartic acid at position 10 with alanine;
- (g) VH having CDRs 1 and 3 containing the amino acid sequences represented by SEQ ID NOS: 32 and 34, respectively, and CDR2 containing an amino acid sequence modified from the amino acid sequence represented by SEQ ID NO: 33 by a substitution of aspartic acid at position 13 with proline;
- (h) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of glutamine at position 3 with alanine or aspartic acid;
- (i) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of proline at position 4 with an arbitrary natural amino acid;

(j) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of proline at position 4 with alanine, tyrosine, serine, aspartic acid, glutamine, glutamic acid, threonine, arginine, glycine, lysine, methionine, valine, leucine, isoleucine, tryptophan, phenylalanine, or histidine;

(k) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of tryptophan at position 5 with alanine, phenylalanine, histidine, or tyrosine;

(l) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of tyrosine at position 7 with alanine or phenylalanine; and (m) VH having CDRs 1 and 2 containing the amino acid sequences represented by SEQ ID NOS: 32 and 33, respectively, and CDR3 containing an amino acid sequence modified from the amino acid sequence represented by SEQ ID NO: 34 by a substitution of valine with leucine.

As one example of the IgG portion that binds to TfR of the present invention, an IgG portion that binds to TfR and includes VL containing the amino acid sequence represented by SEQ ID NO: 16 and VH containing an amino acid sequence modified from the amino acid sequence represented by SEQ ID NO: 31 by at least one substitution selected from Y32A, Y32F, T33A, T33G, L45A, V48A, V50A, I51A, I51L, V55E, D58A, D61P, Q97A, Q97D, W99A, W99F, W99H, W99Y, Y100AA, Y100AF, V102L, and a substitution of P98 with an arbitrary amino acid indicated in the EU index as in Kabat et al. (hereinafter EU index) is exemplified.

As one example of the IgG portion that binds to TfR of the present invention, an IgG portion that binds to TfR and includes VL containing the amino acid sequence represented by SEQ ID NO: 16 and VH containing an amino acid sequence modified from the amino acid sequence represented by SEQ ID NO: 31 by any one substitution selected from Y32A, Y32F, T33A, T33G, L45A, V48A, V50A, I51A, I51L, V55E, D58A, D61P, Q97A, Q97D, W99A, W99F, W99H, W99Y, Y100AA, Y100AF, V102L, P98A, P98Y, P98S, P98D, P98Q, P98E, P98T, P98R, P98G, P98K, P98M, P98V, P98L, P98I, P98W, P98F, and P98H indicated in the EU index is exemplified.

As one example of the IgG portion that binds to TfR of the present invention, an IgG portion that binds to TfR and recognizes at least one amino acid residue selected from Asp at position 352, Ser at position 355, Asp at position 356, and Lys at position 358, and at least one amino acid residue selected from Met at position 365, Val at position 366, and Glu at position 369 in the amino acid sequence of TfR represented by SEQ ID NO: 6 is exemplified. As one embodiment of the IgG portion that binds to TfR, for example, an IgG portion that binds to TfR and recognizes at least two amino acid residues selected from Asp at position 352, Ser at position 355, Asp at position 356, and Lys at position 358, and at least two amino acid residues selected from Met at position 365, Val at position 366, and Glu at position 369; an IgG portion that binds to TfR and recognizes at least three amino acid residues selected from Asp at position 352, Ser at position 355, Asp at position 356, and Lys at position 358, and all the following amino acid residues: Met at position 365, Val at position 366, and Glu at position 369; and an IgG portion that binds to TfR and recognizes all the following amino acid residues: Asp at position 352, Ser at position 355, Asp at position 356, and Lys at position 358, and all the following amino acid residues: Met at position 365, Val at position 366, and Glu at position 369 are exemplified.

As one example of the anti-EGFR antibody of the present invention, an anti-EGFR antibody including VL having CDRs 1, 2, and 3 containing the amino acid sequences represented by SEQ ID NOS: 17, 18, and 19, respectively, and any one VH selected from the following (2a) to (2b) is exemplified:

(2a) VH having CDRs 1, 2, and 3 containing the amino acid sequences represented by SEQ ID NOS: 60, 61, and 62, respectively; and (2b) VH having CDRs 1, 2, and 3 containing the amino acid sequences represented by SEQ ID NOS: 65, 66, and 67, respectively.

The anti-EGFR antibody of the present invention also includes an anti-EGFR antibody that contains the amino acid sequences of CDRs 1 to 3 of VH and VL having at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% homology respectively with the corresponding amino acid sequences of CDRs 1 to 3 of VH shown in any one of the above (2a) to (2b) and amino acid sequences of CDRs 1 to 3 of VL represented by SEQ ID NOS: 17 to 19, respectively.

The anti-EGFR antibody of the present invention also includes an antibody described in the following (i) or (ii):

(i) an antibody that binds to EGFR competitively with an anti-EGFR antibody including VL having CDRs 1, 2, and 3 containing the amino acid sequences represented by SEQ ID NOS: 17, 18, and 19, respectively, and VH shown in any one of the above (2a) to (2b); or (ii) an antibody that binds to the same epitope as an anti-EGFR antibody including VL having CDRs 1, 2, and 3 containing the amino acid sequences represented by SEQ ID NOS: 17, 18, and 19, respectively, and VH shown in any one of the above (2a) to (2b).

As another example of the anti-EGFR antibody of the present invention, one bispecific antibody selected from the following (a) to (e) is exemplified:

(a) an antibody including VH containing the amino acid sequence represented by SEQ ID NO: 59 or SEQ ID NO: 64, and VL containing the amino acid sequence represented by SEQ ID NO: 16;

(b) an antibody including VH containing the amino acid sequence represented by SEQ ID NO: 110, and VL containing the amino acid sequence represented by SEQ ID NO: 111;

(c) an antibody including VH containing the amino acid sequence represented by SEQ ID NO: 112, and VL containing the amino acid sequence represented by SEQ ID NO: 113;

(d) an antibody including VH containing the amino acid sequence represented by SEQ ID NO: 114, and VL containing the amino acid sequence represented by SEQ ID NO: 115; and (e) an antibody including VH containing the amino acid sequence represented by SEQ ID NO: 116, and VL containing the amino acid sequence represented by SEQ ID NO: 117.

As one embodiment of the present invention, a bispecific antibody, which includes an N-terminal side polypeptide and an IgG portion that binds to TfR, and in which the N-terminal side polypeptide is Fab, and the C terminus of VH-CH1 of the Fab binds directly or through a linker to the heavy chain N terminus of the IgG portion that binds to TfR is also exemplified.

Further, as one embodiment of the present invention, a bispecific antibody, which includes an N-terminal side polypeptide and an IgG portion that binds to TfR, and in which the N-terminal side polypeptide is Fab, and the C terminus of VL-CL of the Fab binds directly or through a linker to the heavy chain N terminus of the IgG portion that binds to TfR is also exemplified.

As one embodiment of the present invention, a bispecific antibody which includes an IgG portion that binds to TfR and an N-terminal side polypeptide that binds to EGFR is exemplified.

More specific examples of the bispecific antibody of the present invention include bispecific antibodies represented by the following (i) to (iv).

(i) A bispecific antibody, which includes Fab of an anti-EGFR antibody including VL having CDRs 1, 2, and 3 containing the amino acid sequences represented by SEQ ID NOS: 17, 18, and 19, respectively, and VH having CDRs 1, 2, and 3 containing the amino acid sequences represented by SEQ ID NOS: 60, 61, and 62, respectively, and an IgG portion that binds to TfR and includes VL having CDRs 1, 2, and 3 containing the amino acid sequences represented by SEQ ID NOS: 17, 18, and 19, respectively, and any one VH selected from the following (a) to (f), and
in which the Fab binds directly or through a linker to the heavy chain N terminus of the IgG portion that binds to TfR:
(a) VH having CDRs 1, 2, and 3 containing the amino acid sequences represented by SEQ ID NOS: 22, 23, and 24, respectively;
(b) VH having CDRs 1, 2, and 3 containing the amino acid sequences represented by SEQ ID NOS: 27, 28, and 29, respectively;
(c) VH having CDRs 1, 2, and 3 containing the amino acid sequences represented by SEQ ID NOS: 32, 33, and 34, respectively;
(d) VH having CDRs 1, 2, and 3 containing the amino acid sequences represented by SEQ ID NOS: 37, 38, and 39, respectively;
(e) VH having CDRs 1, 2, and 3 containing the amino acid sequences represented by SEQ ID NOS: 42, 43, and 44, respectively; and
(f) VH having CDRs 1, 2, and 3 containing the amino acid sequences represented by SEQ ID NOS: 47, 48, and 49, respectively.

(ii) A bispecific antibody, which includes Fab of an anti-EGFR antibody including VL having CDRs 1, 2, and 3 containing the amino acid sequences represented by SEQ ID NOS: 17, 18, and 19, respectively, and VH having CDRs 1, 2, and 3 containing the amino acid sequences represented by SEQ ID NOS: 65, 66, and 67, respectively, and an IgG portion that binds to TfR and includes VL having CDRs 1, 2, and 3 containing the amino acid sequences represented by SEQ ID NOS: 17, 18, and 19, respectively, and any one VH selected from the following (a) to (f), and
in which the Fab binds directly or through a linker to the heavy chain N terminus of the IgG portion that binds to TfR:
(a) VH having CDRs 1, 2, and 3 containing the amino acid sequences represented by SEQ ID NOS: 22, 23, and 24, respectively;
(b) VH having CDRs 1, 2, and 3 containing the amino acid sequences represented by SEQ ID NOS: 27, 28, and 29, respectively;
(c) VH having CDRs 1, 2, and 3 containing the amino acid sequences represented by SEQ ID NOS: 32, 33, and 34, respectively;
(d) VH having CDRs 1, 2, and 3 containing the amino acid sequences represented by SEQ ID NOS: 37, 38, and 39, respectively;
(e) VH having CDRs 1, 2, and 3 containing the amino acid sequences represented by SEQ ID NOS: 42, 43, and 44, respectively; and
(f) VH having CDRs 1, 2, and 3 containing the amino acid sequences represented by SEQ ID NOS: 47, 48, and 49, respectively.

(iii) A bispecific antibody, which includes Fab of an anti-EGFR antibody including VL having CDRs 1, 2, and 3 containing the amino acid sequences represented by SEQ ID NOS: 17, 18, and 19, respectively, and VH having CDRs 1, 2, and 3 containing the amino acid sequences represented by SEQ ID NOS: 70, 71, and 72, respectively, and an IgG portion that binds to TfR and includes VL having CDRs 1, 2, and 3 containing the amino acid sequences represented by SEQ ID NOS: 17, 18, and 19, respectively, and any one VH selected from the following (a) to (f), and
in which the Fab binds directly or through a linker to the heavy chain N terminus of the IgG portion that binds to TfR:
(a) VH having CDRs 1, 2, and 3 containing the amino acid sequences represented by SEQ ID NOS: 22, 23, and 24, respectively;
(b) VH having CDRs 1, 2, and 3 containing the amino acid sequences represented by SEQ ID NOS: 27, 28, and 29, respectively;
(c) VH having CDRs 1, 2, and 3 containing the amino acid sequences represented by SEQ ID NOS: 32, 33, and 34, respectively;
(d) VH having CDRs 1, 2, and 3 containing the amino acid sequences represented by SEQ ID NOS: 37, 38, and 39, respectively;
(e) VH having CDRs 1, 2, and 3 containing the amino acid sequences represented by SEQ ID NOS: 42, 43, and 44, respectively; and
(f) VH having CDRs 1, 2, and 3 containing the amino acid sequences represented by SEQ ID NOS: 47, 48, and 49, respectively.

(iv) A bispecific antibody, which includes Fab of an anti-EGFR antibody including VL containing the amino acid sequence represented by SEQ ID NO: 16 and VH containing the amino acid sequence represented by SEQ ID NO: 59, and an IgG portion that binds to TfR and includes VL containing the amino acid sequence represented by SEQ ID NO: 16 and VH containing the amino acid sequence represented by SEQ ID NO: 21, 26, 31, 36, 41, or 46, and
in which the Fab binds directly or through a linker to the heavy chain N terminus of the IgG portion that binds to TfR.

(v) A bispecific antibody, which includes Fab of an anti-EGFR antibody including VL containing the amino acid sequence represented by SEQ ID NO: 16 and VH containing the amino acid sequence represented by SEQ ID NO: 64, and an IgG portion that binds to TfR and includes VL containing the amino acid sequence represented by SEQ ID NO: 16 and VH containing the amino acid sequence represented by SEQ ID NO: 21, 26, 31, 36, 41, or 46, and in which the Fab binds directly or through a linker to the heavy chain N terminus of the IgG portion that binds to TfR.

(vi) A bispecific antibody, which includes Fab of an anti-EGFR antibody including VL containing the amino acid sequence represented by SEQ ID NO: 16 and VH containing the amino acid sequence represented by SEQ ID NO: 69, and an IgG portion that binds to TfR and includes VL containing the amino acid sequence represented by SEQ ID NO: 16 and VH containing the amino acid sequence represented by SEQ ID NO: 21, 26, 31, 36, 41, or 46, and in which the Fab binds directly or through a linker to the heavy chain N terminus of the IgG portion that binds to TfR.

As the bispecific antibody represented by the above (i) to (vi), a region that binds directly or through a linker to the heavy chain N terminus of the IgG portion that binds to TfR may be either VH-CH1 or VL-CL of the Fab, but is preferably VH-CH1.

As one embodiment of the present invention, a bispecific antibody, in which an N-terminal side polypeptide binds directly or through a linker to the heavy chain N terminus of an IgG portion that binds to TfR, and in which a constant region of the IgG portion that binds to TfR is IgG1, IgG4, or a modified form thereof is exemplified. As a more preferred embodiment of the present invention, a bispecific antibody, which includes IgG4PE or IgG4PE R409K in a heavy chain constant region of an IgG portion that binds to TfR, and in which an N-terminal side polypeptide binds directly or through a linker to the heavy chain N terminus of the IgG portion that binds to TfR is exemplified.

As one embodiment of the present invention, a bispecific antibody, which includes an IgG portion that binds to TfR and an N-terminal side polypeptide that binds to EGFR, and in which the N-terminal side polypeptide is Fab, and the Fab binds to the heavy chain N terminus of the IgG portion through a linker is exemplified. As a more preferred embodiment, a bispecific antibody, in which the amino acid sequence of the linker is one selected from ES (SEQ ID NO: 79), ESKYG (SEQ ID NO: 80), ESKYGPP (SEQ ID NO: 81), GGGGS (SEQ ID NO: 82), or a repetitive sequence of GGGGS (SEQ ID NO: 82) is exemplified.

As an example of the bispecific antibody of the present invention, E08-TfR1071 or E12-TfR1071 is exemplified.

The bispecific antibody or the antibody fragment thereof of the present invention also includes an antibody or an antibody fragment thereof having an effector activity.

The effector activity refers to an antibody-dependent cellular cytotoxicity activity that is caused via the Fc region of the antibody, and examples thereof include an antibody-dependent cellular cytotoxicity activity (ADCC activity), a complement-dependent cytotoxicity activity (CDC activity), an antibody-dependent cellular phagocytosis activity (ADCP activity) that is caused by phagocytes such as macrophages or dendritic cells, an opsonin effect, and the like.

In the present invention, the ADCC activity and the CDC activity can be measured using a known measurement method [Cancer Immunol. Immunother., 36, 373 (1993)].

The ADCC activity refers to an activity that activates an immune cell (a natural killer cell or the like) when an antibody having bound to an antigen on a target cell binds to an Fc receptor of the immune cell via the Fc region of the antibody so as to damage the target cell.

The Fc receptor (FcR) is a receptor that binds to the Fc region of the antibody, and induces various effector activities by binding of the antibody. Each FcR corresponds to the subclass of an antibody, and IgG, IgE, IgA, and IgM bind specifically to FcγR, FcεR, FcαR, and FcμR, respectively. Further, in the FcγR, there are subtypes of FcγRI (CD64), FcγRII (CD32), and FcγRIII (CD16), and the subtypes have isoforms of FcγRIA, FcγRIB, FcγRIC, FcγRIIA, FcγRIIB, FcγRIIC, FcγRIIIA, and FcγRIIIB, respectively. The different types of FcγRs are present on different cells [Annu. Rev. Immunol. 9: 457-492 (1991)]. In humans, FcγRIIIB is expressed specifically in neutrophils, and FcγRIIIA is expressed in monocytes, natural killer cells (NK cells), macrophages, and some T cells. An NK cell-dependent ADCC activity is induced through the binding of the antibody to FcγRIIIA.

The CDC activity refers to an activity that activates a series of cascades (complement activation pathways) composed of complement-related protein groups in the blood by an antibody having bound to an antigen on a target cell so as to damage the target cell. In addition, a protein fragment generated by the activation of the complement induces the migration and activation of an immune cell. The cascade of CDC activity starts when C1q first binds to the Fc region, and subsequently binds to C1r and C1s that are two serine proteases, whereby a C1 complex is formed.

The CDC activity or the ADCC activity of the bispecific antibody or the antibody fragment thereof of the present invention against an antigen-expressing cell can be evaluated by a known measurement method [Cancer Immunol. Immunother., 36, 373 (1993)].

As a method for controlling the effector activity of the bispecific antibody of the present invention, a method for controlling the amount of fucose (also referred to as core fucose) that is α-1,6-linked to N-acetylglucosamine (GlcNAc) present at the reducing end of an N-linked complex sugar chain that binds to asparagine (Asn) at position 297 of the Fc region (a constant region composed of CH2 and CH3 domains) of the antibody (WO 2005/035586, WO 2002/31140, and WO 00/61739), a method for controlling the effector activity by modifying an amino acid residue of the Fc region of the antibody (WO 00/42072), and the like are known.

The ADCC activity of the antibody can be increased or decreased by controlling the amount of fucose to be added to the bispecific antibody. For example, as a method for decreasing the content of fucose that binds to the N-linked complex sugar chain bound to Fc of the antibody, by expressing the bispecific antibody using an α1,6-fucosyltransferase gene-deficient host cell, the bispecific antibody having high ADCC can be obtained. On the other hand, as a method for increasing the content of fucose that binds to the N-linked complex sugar chain bound to Fc of the bispecific antibody, by expressing the antibody using a host cell transfected with an α1,6-fucosyltransferase gene, the bispecific antibody having a low ADCC activity can be obtained.

In addition, the ADCC activity or the CDC activity can be increased or decreased by modifying an amino acid residue in the Fc region of the bispecific antibody. For example, by using the amino acid sequence of the Fc region described in US Patent Application Publication No. 2007/0148165, the CDC activity of the bispecific antibody can be increased. Further, by performing an amino acid modification described in U.S. Pat. Nos. 6,737,056, 7,297,775, 7,317,091, or the like, the ADCC activity or the CDC activity can be increased or decreased.

Further, a bispecific antibody in which the effector activity is controlled may be obtained by combining the above-mentioned methods.

The stability of the bispecific antibody of the present invention can be evaluated by measuring the amount of an aggregate (oligomer) formed in a sample stored during a purification process or under certain conditions. That is, in the case where the aggregate amount decreases under the same conditions, it is evaluated that the stability of the antibody is improved. The aggregate amount can be measured by separating an aggregated antibody and a non-aggregated antibody using appropriate chromatography including gel filtration chromatography.

The productivity of the bispecific antibody of the present invention can be evaluated by measuring the amount of an antibody produced from an antibody-producing cell in a culture solution. More specifically, the productivity can be evaluated by measuring the amount of an antibody contained in a culture supernatant obtained by removing the producing cell from the culture solution using an appropriate method such as an HPLC method or an ELISA method.

In the present invention, the antibody fragment is a protein that includes an antigen-binding domain and has an antigen-binding activity to the antigen. For example, Fab, Fab', F(ab')$_2$, scFv, a diabody, dsFv, VHH, a peptide including CDR, or the like is exemplified.

The Fab is an antibody fragment, which has a molecular weight of about 50,000 and has an antigen-binding activity, and in which about a half of an H chain at the N-terminal side and the entire L chain are bound through a disulfide bond (S—S bond) among the fragments obtained by treating an IgG antibody with a protease papain (cleaved at an amino acid residue at position 224 in the H chain). The H chain of Fab including VH and CH1 is referred to as VH-CH1. Further, the L chain of Fab including VL and CL is referred to as VL-CL.

The F(ab')$_2$ is an antibody fragment, which has a molecular weight of about 100,000 and has an antigen-binding activity, and is slightly larger than a molecule obtained by binding Fabs through an S—S bond in the hinge region among the fragments obtained by treating IgG with a protease pepsin (cleaved at an amino acid residue at position 234 in the H chain).

The Fab' is an antibody fragment, which has a molecular weight of about 50,000 and has an antigen-binding activity, and in which an S—S bond in the hinge region of the above F(ab')$_2$ is cleaved.

The scFv is a VH-P-VL or VL-P-VH polypeptide in which one VH and one VL are linked using an appropriate peptide linker (P) of 12 or more residues, and is an antibody fragment having an antigen-binding activity.

The diabody is an antibody fragment in which scFvs having the same or different antigen-binding specificity form a dimer, and is an antibody fragment having a divalent antigen-binding activity to the same antigen or antigen-binding activities each specific for different antigens.

The dsFv refers to a molecule obtained by binding polypeptides in which one amino acid residue in each of VH and VL is substituted with a cysteine residue through an S—S bond between the cysteine residues.

The VHH refers to a heavy chain variable region in a VHH antibody, and can bind to an antigen without the presence of another polypeptide.

The VHH antibody is an antibody present in an animal of the family Camelidae such as an alpaca and an elasmobranch such as a shark, and does not include a light chain or CH1, and is composed only of a heavy chain.

The peptide including CDR is configured to include at least one region of CDRs of VH or VL. A peptide including a plurality of CDRs can be produced by binding CDRs directly or through an appropriate peptide linker. The peptide including CDR can be produced by constructing DNAs encoding CDRs of VH and VL of the bispecific antibody of the present invention, inserting the DNAs into an expression vector for a prokaryote or an expression vector for a eukaryote, and then introducing the expression vector into a prokaryote or a eukaryote to cause expression. In addition, the peptide including CDR can also be produced by a chemical synthesis method such as an Fmoc method or a tBoc method.

In the present invention, the bispecific antibody fragment is essentially composed of a partial structure of a bispecific antibody, and is a bispecific antibody fragment having an antigen-binding activity to two types of antigens.

A fusion protein in which Fc of the bispecific antibody of the present invention and an antibody fragment are bound, an Fc fusion protein (also referred to as immunoadhesin) in which the Fc and a naturally occurring ligand or receptor are bound, an Fc fusion protein in which a plurality of Fc regions are fused, and the like are also included in the present invention. In addition, an Fc region that includes an amino acid residue modification aiming at enhancing or eliminating the effector activity of the antibody, stabilizing the antibody, and controlling the blood half-life can also be used for the bispecific antibody of the present invention.

As the bispecific antibody or the bispecific antibody fragment thereof of the present invention, a derivative of the antibody in which a radioisotope, a low-molecular weight drug, a high-molecular weight drug, a protein, an antibody drug, or the like is bound chemically or in a genetic engineering manner to the bispecific antibody or the bispecific antibody fragment thereof of the present invention is included.

The derivative of the antibody in the present invention can be produced by binding a radioisotope, a low-molecular weight drug, a high-molecular weight drug, an immunostimulant, a protein, an antibody drug, or the like to the N-terminal side or the C-terminal side of an H chain or an L chain of the bispecific antibody or the bispecific antibody fragment thereof of the present invention, an appropriate substituent or side chain in the antibody or the antibody fragment thereof, further, a sugar chain or the like in the antibody or the antibody fragment thereof using a chemical method [Introduction to Antibody Engineering, Chijin Shokan Co., Ltd. (1994)].

Further, the derivative of the antibody in the present invention can be produced by a genetic engineering technique in which a DNA encoding the bispecific antibody or the bispecific antibody fragment thereof of the present invention is ligated to a DNA encoding a desired protein or antibody drug, the resultant is inserted into an expression vector, and the expression vector is introduced into an appropriate host cell to cause expression.

Examples of the radioisotope include $^{111}$In, $^{131}$I, $^{125}$I, $^{90}$Y, $^{64}$Cu, $^{99}$Tc, $^{77}$Lu, $^{211}$At, and the like. The radioisotope can be directly bound to the antibody by a chloramine T method or the like. In addition, a substance that chelates the radioisotope may be bound to the antibody. Examples of the chelating agent include 1-isothiocyanatobenzyl-3-methyldiethylenetriaminepentaacetic acid (MX-DTPA) and the like.

Examples of the low-molecular weight drug include anticancer agents such as an alkylating agent, a nitrosourea agent, an antimetabolite, an antibiotic, a plant alkaloid, a topoisomerase inhibitor, a hormonal therapy agent, a hormone antagonist, an aromatase inhibitor, a P-glycoprotein inhibitor, a platinum complex derivative, an M-phase inhibitor, or a kinase inhibitor [Clinical oncology, Japanese Journal of Cancer and Chemotherapy (1996)], anti-inflammatory agents such as a steroidal agent such as hydrocortisone or prednisone, a nonsteroidal agent such as aspirin or indomethacin, an immunomodulatory agent such as gold thiomalate or penicillamine, an immunosuppressive agent such as cyclophosphamide or azathioprine, an antihistamine agent such as chlorpheniramine maleate or clemastine [Inflammation and anti-inflammatory therapy, Ishiyaku Publishers, Inc. (1982)], and the like.

Examples of the anticancer agent include amifostine (ETHYOL®; trihydrate form of amifostine), cisplatin, dacarbazine (DTIC), dactinomycin, mechlorethamine (nitrogen mustard), streptozocin, cyclophosphamide, ifosfamide, carmustine (BCNU), lomustine (CCNU), doxorubicin (ADRIAMYCIN®; doxorubicin hydrochloride), epirubicin, gemcitabine (GEMZAR®; gemcitabine), daunorubicin, procarbazine, mitomycin, cytarabine, etoposide, 5-fluorouracil, fluorouracil, vinblastine, vincristine, bleomycin, daunomycin, peplomycin, estramustine, paclitaxel (TAXOL®; paclitaxel), docetaxel (TAXOTERE®; docetaxel), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegaspargase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacitidine, UFT, oxaloplatin, gefitinib (IRESSA®; gefitinib), imatinib (STI571), erlotinib, an FMS-like tyrosine kinase 3 (Flt3) inhibitor, a vascular endothelial growth factor receptor (VEGFR) inhibitor, a fibroblast growth factor receptor (FGFR) inhibitor, an epidermal growth factor receptor (EGFR) inhibitor such as TARCEVA® (erlotinib), radicicol, 17-allylamino-17-demethoxygeldanamycin, rapamycin, amsacrine, all-trans retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (TARGRETIN®; bexarotene), tamoxifen, dexamethasone, a progestin, an estrogen, anastrozole (ARIMIDEX®; anastrozole), Leuplin, aspirin, indomethacin, celecoxib, azathioprine, penicillamine, gold thiomalate, chlorpheniramine maleate, chlorpheniramine, clemastine, tretinoin, bexarotene, arsenic, bortezomib, allopurinol, calicheamicin, ibritumomab tiuxetan, targretin, ozogamine, clarithromycin, leucovorin, ketoconazole, aminoglutethimide, suramin, methotrexate, or maytansinoid, or a derivative thereof, and the like.

Examples of a method for binding a low-molecular weight drug to the bispecific antibody or the bispecific antibody fragment thereof of the present invention include a method for binding the drug to an amino group of the antibody through glutaraldehyde, a method for binding an amino group of the drug to a carboxyl group of the antibody through a water-soluble carbodiimide, and the like.

Examples of the high-molecular weight drug include polyethylene glycol (PEG), albumin, dextran, polyoxyethylene, a styrene-maleic acid copolymer, polyvinylpyrrolidone, a pyran copolymer, hydroxypropyl methacrylamide, and the like. By binding such a high-molecular weight compound to the bispecific antibody or the antibody fragment of the present invention, an effect such as (1) improvement of the stability against various chemical, physical, or biological factors, (2) significant extension of the blood half-life, or (3) elimination of immunogenicity or suppression of antibody production is expected [Bioconjugate pharmaceutical, Hirokawa-Shoten Ltd. (1993)].

Examples of a method for binding PEG to the bispecific antibody of the present invention include a method for reacting with a PEGylation reagent, and the like [Bioconjugate pharmaceutical, Hirokawa-Shoten Ltd. (1993)]. Examples of the PEGylation reagent include a modifying agent to an ε-amino group of lysine (JP-A-S61-178926), a modifying agent to a carboxyl group of aspartic acid and glutamic acid (JP-A-S56-23587), a modifying agent to a guanidino group of arginine (JP-A-H2-117920), and the like.

The immunostimulant may be a natural product known as an immunoadjuvant, and specific examples thereof include a drug that enhances immunity such as a β(1→3) glucan (for example, lentinan or schizophyllan) or α-galactosylceramide (KRN7000), and the like.

Examples of the protein include a cytokine or a growth factor that activates immunocompetent cells such as NK cells, macrophages, or neutrophils, or a toxic protein, and the like.

Examples of the cytokine or the growth factor include interferon (hereinafter referred to as IFN)-α, IFN-β, and IFN-γ, interleukin (hereinafter referred to as IL)-2, IL-12, IL-15, IL-18, IL-21, and IL-23, a granulocyte colony stimulating factor (G-CSF), a granulocyte-macrophage colony stimulating factor (GM-CSF), a macrophage colony stimulating factor (M-CSF), and the like.

Examples of the toxic protein include ricin, diphtheria toxin, ONTAK, and the like, and also include a toxic protein in which a mutation is introduced into a protein for regulating toxicity.

A fusion antibody with a protein or an antibody drug can be produced by ligating a cDNA encoding the protein to a cDNA encoding the bispecific antibody or the antibody fragment of the present invention to construct a DNA encoding the fusion antibody, inserting the DNA into an expression vector for a prokaryote or a eukaryote, and then introducing the expression vector into a prokaryote or a eukaryote to cause expression.

When the derivative of the antibody is used for a detection method or a quantitative determination method, or as a reagent for detection, a reagent for quantitative determination, or a diagnostic agent, examples of the drug to be bound to the bispecific antibody or the antibody fragment thereof of the present invention include a labeling substance to be used for a general immunological detection or measurement method. Examples of the labeling substance include an enzyme such as alkaline phosphatase, peroxidase, or luciferase, a luminescent substance such as acridinium ester or lophine, or a fluorescent substance such as fluorescein isothiocyanate (FITC) or tetramethylrhodamine isothiocyanate (RITC), Alexa (registered trademark) Fluor 488, or R-phycoerythrin (R-PE), and the like.

In the present invention, the bispecific antibody and the bispecific antibody fragment thereof having a cytotoxic activity such as a CDC activity or an ADCC activity are included. The CDC activity or the ADCC activity of the bispecific antibody or the bispecific antibody fragment thereof of the present invention against an antigen-expressing cell can be evaluated by a known measurement method [Cancer Immunol. Immunother., 36, 373 (1993)].

Further, the present invention relates to a composition containing the bispecific antibody or the bispecific antibody fragment thereof that specifically recognizes and binds to TfR and a cell surface antigen such as EGFR or a therapeutic agent for a disease associated with at least one of TfR and a cell surface antigen such as EGFR, preferably a disease involved in a cell that expresses TfR and a cell surface antigen such as EGFR, containing the bispecific antibody or the bispecific antibody fragment thereof as an active ingredient.

The disease associated with at least one of TfR and a cell surface antigen such as EGFR may be any as long as it is a disease associated with at least one of TfR and a cell surface antigen such as EGFR, and for example, a malignant tumor, cancer, and the like are exemplified.

In the present invention, examples of the malignant tumor and the cancer include, large intestine cancer, colorectal cancer, lung cancer, breast cancer, glioma, malignant melanoma (melanoma), thyroid cancer, renal cell carcinoma, leukemia, lymphoma, T cell lymphoma, stomach cancer, pancreatic cancer, cervical cancer, endometrial cancer, ovarian cancer, bile duct cancer, esophageal cancer, liver cancer, head and neck cancer, skin cancer, urinary tract cancer, bladder cancer, prostate cancer, choriocarcinoma, pharyngeal cancer, laryngeal cancer, mesothelioma, pleural tumor, arrhenoblastoma, endometrial hyperplasia, endometriosis, embryoma, fibrosarcoma, Kaposi's sarcoma, angioma, cavernous hemangioma, angioblastoma, retinoblastoma, astrocytoma, neurofibroma, oligodendroglioma, medulloblastoma, neuroblastoma, glioma, rhabdomyosarcoma, glioblastoma, osteogenic sarcoma, leiomyosarcoma, Wilm's tumor, and the like.

The therapeutic agent containing the bispecific antibody or the bispecific antibody fragment thereof of the present invention, or a derivative thereof may contain only the bispecific antibody or the bispecific antibody fragment thereof, or a derivative thereof as an active ingredient, however, in general, it is preferably provided as a pharmaceutical preparation produced using an arbitrary method known in the technical field of pharmaceutics by mixing it together with one or more pharmacologically acceptable carriers.

As the route of administration, it is preferred to use the most effective route for the treatment, and examples thereof include oral administration or parenteral administration such as intraoral, intra-airway, intrarectal, subcutaneous, intramuscular, and intravenous administration. Above all, intravenous administration is preferred.

Examples of a dosage form include a spray, a capsule, a tablet, a powder, a granule, a syrup, an emulsion, a suppository, an injection, an ointment, a tape, and the like.

A dose or administration frequency varies depending on a desired therapeutic effect, an administration method, a treatment duration, an age, a body weight, or the like, but is generally 10 µg/kg to 10 mg/kg per day for an adult.

Further, the present invention relates to a reagent for immunological detection or measurement of at least one of TfR and a cell surface antigen such as EGFR, or a diagnostic agent for a disease associated with at least one of TfR and a cell surface antigen such as EGFR, preferably a disease involved in a cell that expresses TfR and a cell surface antigen such as EGFR, each of which contains the bispecific antibody or the bispecific antibody fragment thereof of the present invention. In addition, the present invention relates to a method for immunological detection or measurement of at least one of TfR and a cell surface antigen such as EGFR, a therapeutic method for a disease associated with at least one of TfR and a cell surface antigen such as EGFR, preferably a disease involved in a cell that expresses TfR and a cell surface antigen such as EGFR, or a diagnostic method for a disease associated with at least one of TfR and a cell surface antigen such as EGFR, preferably a disease involved in a cell that expresses TfR and a cell surface antigen such as EGFR, each using the bispecific antibody or the bispecific antibody fragment thereof of the present invention.

As a method for detecting or measuring the amount of at least one of TfR and a cell surface antigen such as EGFR in the present invention, a known arbitrary method is exemplified. For example, an immunological detection or measurement method or the like is exemplified.

The immunological detection or measurement method is a method for detecting or measuring the amount of an antibody or the amount of an antigen using a labeled antigen or antibody. Examples of the immunological detection or measurement method include a radioimmunoassay method (RIA), an enzyme immunoassay method (EIA or ELISA), a fluorescence immunoassay method (FIA), a luminescent immunoassay method, a Western blotting method, a physicochemical method, and the like.

By detecting or measuring a cell that has expressed at least one of TfR and a cell surface antigen such as EGFR using the bispecific antibody or the bispecific antibody fragment thereof of the present invention, it is possible to diagnose a disease associated with at least one of TfR and a cell surface antigen such as EGFR, preferably a disease involved in a cell that expresses TfR and a cell surface antigen such as EGFR.

It is possible to use a known immunological detection method for detecting a cell that has expressed at least one of TfR and a cell surface antigen such as EGFR, however, for example, an immunoprecipitation method, an immunocytological staining method, an immunohistological staining method, a fluorescent antibody staining method, or the like is exemplified. In addition, for example, a fluorescent antibody staining method such as an FMAT 8100 HTS system (manufactured by Applied Biosystems, Inc.), or the like is also exemplified.

Examples of a biological sample to be subjected to detection or measurement of at least one of TfR and a cell surface antigen such as EGFR in the present invention include a tissue cell, blood, plasma, serum, pancreatic juice, urine, feces, a tissue fluid, a culture solution, and the like, and there is no particular limitation as long as the sample may contain a cell that has expressed at least one of TfR and a cell surface antigen such as EGFR.

The diagnostic agent containing the bispecific antibody or the bispecific antibody fragment thereof of the present invention, or a derivative thereof, may contain a reagent for performing an antigen-antibody reaction or a reagent for detecting the reaction in accordance with a desired diagnostic method. Examples of the reagent for performing an antigen-antibody reaction include a buffer, a salt, and the like.

Examples of the reagent for detection include a reagent, which is used for a general immunological detection or measurement method, such as a labeled secondary antibody that binds to the bispecific antibody or the bispecific antibody fragment thereof, or a derivative thereof, or a substrate corresponding to a label.

Hereinafter, a method for producing the bispecific antibody of the present invention, a method for evaluating the activity of the bispecific antibody or the bispecific antibody fragment thereof, and a therapeutic method and a diagnostic method for a disease using the bispecific antibody or the bispecific antibody fragment thereof will be specifically described.

1. Method for Producing Monoclonal Antibody

A method for producing a monoclonal antibody of the present invention includes the following operation steps. That is, (1) at least one of purifying an antigen to be used as an immunogen and producing a cell that has overexpressed the antigen on the cell surface, (2) a step of preparing an antibody-producing cell by immunizing an animal with the antigen, followed by collecting the blood, examining an antibody titer thereof to determine when to resect the spleen or the like, (3) preparing a myeloma cell (myeloma), (4) fusing the antibody-producing cell with the myeloma, (5) screening a hybridoma group that produces a target antibody, (6) separating (cloning) a monoclonal cell from the hybridoma group, (7) in some cases, culturing the hybridoma for producing a monoclonal antibody in a large amount, or breeding an animal implanted with the hybridoma, (8) investigating the bioactivity of the monoclonal antibody produced in this manner, and the antigen-binding specificity thereof, or examining the characteristic as a labeling reagent, and the like.

Hereinafter, a method for producing a monoclonal antibody that binds to TfR and a monoclonal antibody that binds to a cell surface antigen such as EGFR, which are used for producing the bispecific antibody that binds to TfR and a cell surface antigen such as EGFR of the present invention, will be described in detail according to the above-mentioned steps. The method for producing the antibody is not limited thereto, and for example, an antibody-producing cell other than a spleen cell, and a myeloma can also be used.

(1) Purification of Antigen

A cell allowed to express a cell surface antigen such as EGFR or TfR can be obtained by introducing an expression vector containing a cDNA encoding the full length of the cell surface antigen such as EGFR or TfR or a partial length thereof into E. coli, yeast, an insect cell, an animal cell, or the like. In addition, at least one of TfR and the cell surface antigen such as EGFR is purified from various cultured human tumor cells or human tissues or the like that have expressed at least one of TfR and the cell surface antigen such as EGFR in a large amount and can be used as an antigen. In addition, the cultured tumor cell or the tissue or the like can also be used as an antigen as it is. Further, a synthetic peptide having a partial sequence of the cell surface antigen such as EGFR or TfR is prepared by a chemical synthesis method such as an Fmoc method or a tBoc method and can also be used as an antigen.

The cell surface antigen such as EGFR or TfR used in the present invention can be produced using a method described in Molecular Cloning, A Laboratory Manual, Second Edition, Cold Spring Harbor Laboratory Press (1989), or Current Protocols In Molecular Biology, John Wiley & Sons (1987-1997), or the like, for example, by expressing a DNA encoding the cell surface antigen such as EGFR or TfR in a host cell using the following method.

A recombinant vector is produced by inserting a full-length cDNA containing a region encoding the cell surface antigen such as EGFR or TfR downstream of a promoter in an appropriate expression vector. A DNA fragment that has been prepared based on the full-length cDNA and has an appropriate length and contains a region encoding a polypeptide may be used in place of the full-length cDNA. Subsequently, by introducing the obtained recombinant vector into a host cell suitable for the expression vector, a transformant that produces the cell surface antigen such as EGFR or TfR can be obtained.

As the expression vector, any vector can be used as long as it can autonomously replicate in a host cell to be used or can be integrated into a chromosome, and contains an appropriate promoter at a position capable of transcribing a DNA encoding the cell surface antigen such as EGFR or TfR.

As the host cell, any cell, for example, a microorganism belonging to the genus Escherichia such as E. coli, yeast, an insect cell, an animal cell, or the like, can be used as long as it can express a target gene.

When a prokaryote such as E. coli is used as the host cell, the recombinant vector is preferably a vector that can replicate autonomously in the prokaryote, and also contains a promoter, a ribosomal binding sequence, a DNA containing a region encoding the cell surface antigen such as EGFR or TfR, and a transcription termination sequence. In addition, the transcription termination sequence is not necessarily needed for the recombinant vector, however, it is preferred that the transcription termination sequence is located immediately downstream of a structural gene. Further, the recombinant vector may contain a gene that controls the promoter.

As the recombinant vector, it is preferred to use a plasmid in which a distance between a Shine-Dalgarno sequence that is a ribosomal binding sequence and a start codon is appropriately adjusted (for example, 6 to 18 nucleotides).

In addition, in the nucleotide sequence of the DNA encoding the cell surface antigen such as EGFR or TfR, it is possible to substitute a nucleotide so that a codon becomes optimum for expression in a host, and as a result, the production rate of the target cell surface antigen such as EGFR or TfR can be improved.

As the expression vector, any vector can be used as long as it can exhibit its function in a host cell to be used, and examples thereof include pBTrp2, pBTac1, pBTac2 (manufactured by Roche Diagnostics K.K.), pKK233-2 (manufactured by Pharmacia Corporation), pSE280 (manufactured by Invitrogen, Inc.), pGEMEX-1 (manufactured by Promega Corporation), pQE-8 (manufactured by QIAGEN, Inc.), pKYP10 (JP-A-S58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (manufactured by Stratagene Corporation), pTrs30 [prepared from E. coli JM109/pTrS30 (FERM BP-5407)], pTrs32 [prepared from E. coli JM109/pTrS32 (FERM BP-5408)], pGHA2 [prepared from E. coli IGHA2 (FERM BP-400), JP-A-S60-221091], pGKA2 [prepared from E. coli IGKA2 (FERM BP-6798), JP-A-S60-221091], pTerm2 (U.S. Pat. Nos. 4,686,191, 4,939,094, or U.S. Pat. No. 5,160,735), pSupex, pUB110, pTP5, pC194, pEG400 [J. Bacteriol., 172, 2392 (1990)], pGEX (manufactured by Pharmacia Corporation), pET System (manufactured by Novagen, Inc.), pME18SFL3 (manufactured by Toyobo Co., Ltd.), and the like.

As the promoter, any promoter may be used as long as it functions in a host cell to be used. Examples thereof include promoters derived from E. coli, a phage, or the like such as a trp promoter (Ptrp), a lac promoter, a PL promoter, a PR promoter, or a T7 promoter. In addition, examples thereof also include artificially designed and modified promoters such as a tandem promoter in which two Ptrp promoters are linked in tandem, a tac promoter, a lacT7 promoter, or a let I promoter, and the like.

Examples of the host cell include E. coli XL1-Blue, E. coli XL2-Blue, E. coli DH1, E. coli MC1000, E. coli KY3276, E. coli W1485, E. coli JM109, E. coli HB101, E. coli No. 49, E. coli W3110, E. coli NY49, E. coli DH5α, and the like.

As a method for introducing a recombinant vector into a host cell, any method can be used as long as it is a method for introducing a DNA into a host cell to be used, and examples thereof include a method using calcium ions [Proc. Natl. Acad. Sci. USA, 69, 2110 (1972), Gene, 17, 107 (1982), Molecular & General Genetics, 168, 111 (1979)].

When an animal cell is used as a host, as the expression vector, any vector can be used as long as it functions in an animal cell, and examples thereof include pcDNAI (manufactured by Invitrogen, Inc.), pcDM8 (manufactured by Funakoshi Co., Ltd.), pAGE107 [JP-A-H3-22979; Cytotechnology, 3, 133 (1990)], pAS3-3 (JP-A-H2-227075), pCDM8 [Nature, 329, 840 (1987)], pcDNAI/Amp (manufactured by Invitrogen, Inc.), pcDNA3.1 (manufactured by Invitrogen, Inc.), pREP4 (manufactured by Invitrogen, Inc.), pAGE103 [J. Biochemistry, 101, 1307 (1987)], pAGE210, pME18SFL3, pKANTEX93 (WO 97/10354), and the like.

As the promoter, any promoter can be used as long as it can exhibit its functions in an animal cell, and examples thereof include a cytomegalovirus (CMV) immediate early (IE) gene promoter, an SV40 early promoter, a retrovirus promoter, a metallothionein promoter, a heat-shock promoter, an SRα promoter, or a Moloney murine leukemia virus promoter or enhancer. In addition, a human CMV IE gene enhancer may be used together with the promoter.

Examples of the host cell include a human Burkitt's lymphoma cell Namalwa, an African Green Monkey kidney-derived cell COS, a Chinese hamster ovary-derived cell CHO, a human leukemia cell HBT5637 (JP-A-S63-000299), and the like.

As a method for introducing a recombinant vector into a host cell, any method can be used as long as it is a method for introducing a DNA into an animal cell, and examples thereof include an electroporation method [Cytotechnology, 3, 133 (1990)], a calcium phosphate method (JP-A-H2-227075), a lipofection method [Proc. Natl. Acad. Sci. USA, 84, 7413 (1987)], and the like.

The cell surface antigen such as EGFR or TfR can be produced by culturing a microorganism having a recombinant vector incorporating a DNA encoding the cell surface antigen such as EGFR or TfR, or a transformant derived from an animal cell or the like obtained as described above in a culture medium, allowing the microorganism or the transformant to produce and accumulate at least one of the TfR and the cell surface antigen such as EGFR in the culture, and collecting it from the culture. A method for culturing the transformant in a culture medium can be carried out according to a usual method used for culturing a host.

In the case of being expressed in a cell derived from a eukaryote, it is possible to obtain the cell surface antigen such as EGFR or TfR to which a sugar or a sugar chain is added.

When culturing a microorganism transformed with a recombinant vector using an inducible promoter, an inducer may be added to a culture medium as needed. For example, when a microorganism transformed with a recombinant vector using a lac promoter is cultured, isopropyl-β-D-thiogalactopyranoside or the like may be added to a culture medium, and when a microorganism transformed with a recombinant vector using a trp promoter is cultured, indoleacrylic acid or the like may be added to a culture medium.

Examples of the culture medium in which the transformant obtained using an animal cell as a host is cultured include RPMI 1640 medium [The Journal of the American Medical Association, 199, 519 (1967)], Eagle's MEM medium [Science, 122, 501 (1952)], Dulbecco's modified MEM medium [Virology, 8, 396 (1959)], Medium 199 [Proc. Soc. Exp. Biol. Med., 73, 1 (1950)], Iscove's modified Dulbecco's medium (IMDM), which are generally used, or a culture medium in which fetal bovine serum (FBS) or the like is added to any of these culture media, and the like. The culture is usually carried out for 1 to 7 days under the conditions of pH 6 to 8 and 30 to 40° C. in the presence of 5% $CO_2$. In addition, during the culture, an antibiotic such as kanamycin or penicillin may be added to the culture medium as needed.

As a method for expressing a gene encoding the cell surface antigen such as EGFR or TfR, a method of secretory production, fused protein expression, or the like [Molecular Cloning, A Laboratory Manual, Second Edition, Cold Spring Harbor Laboratory Press (1989)] can be used in addition to direct expression. Examples of a method for producing the cell surface antigen such as EGFR or TfR include a method for producing it in a host cell, a method for secreting it out of a host cell, and a method for producing it on an outer membrane of a host cell, and an appropriate method can be selected by changing a host cell to be used or the structure of the cell surface antigen such as EGFR or TfR to be produced.

For example, an antigen-fusion protein can be produced by preparing a DNA in which a DNA encoding an Fc region of an antibody, a DNA encoding glutathione S-transferase (GST), a DNA encoding a FLAG tag or a DNA encoding a Histidine tag, or the like is ligated to a DNA encoding the amino acid sequence of an extracellular domain, followed by expression and purification. Specific examples thereof include an Fc-fusion protein in which an extracellular domain of the cell surface antigen such as EGFR or TfR is bound to an Fc region of human IgG, and a fusion protein of an extracellular domain of the cell surface antigen such as EGFR or TfR with glutathione S-transferase (GST).

When the cell surface antigen such as EGFR or TfR is produced in a host cell or on an outer membrane of a host cell, the cell surface antigen such as EGFR or TfR can be actively secreted outside the host cell using the method of Paulson et al. [J. Biol. Chem., 264, 17619 (1989)], the method of Lowe et al. [Proc. Natl. Acad. Sci., USA, 86, 8227 (1989), Genes Develop., 4, 1288 (1990)], or a method described in JP-A-H05-336963, WO 94/23021, or the like. In addition, the production amount of the cell surface antigen such as EGFR or TfR can also be increased by utilizing a gene amplification system using a dihydrofolate reductase gene or the like (JP-A-H2-227075).

The produced cell surface antigen such as EGFR or TfR can be isolated and purified, for example, as follows.

When the cell surface antigen such as EGFR or TfR is expressed in cells in a dissolved state, the cells are collected by centrifugation after completion of the culture, suspended in an aqueous buffer solution, followed by homogenization of the cells using an ultrasonic homogenizer, a French press, a Manton Gaulin homogenizer, a Dyno mill, or the like, whereby a cell-free extract solution is obtained. It is possible to obtain a purified protein from a supernatant obtained by centrifugation of the cell-free extract solution using methods such as general protein isolation and purification methods, that is, a solvent extraction method, a salting-out method using ammonium sulfate or the like, a desalting method, a precipitation method using an organic solvent, anion exchange chromatography using a resin such as diethylaminoethyl (DEAE)-Sepharose or DIAION HPA-75 (manufactured by Mitsubishi Chemical Corporation), cation exchange chromatography using a resin such as S-Sepharose FF (manufactured by Pharmacia Corporation), hydrophobic chromatography using a resin such as Butyl Sepharose or Phenyl Sepharose, a gel filtration method using a molecular sieve, affinity chromatography, a chromatofocusing method, an electrophoresis method such as isoelectric focusing electrophoresis, and the like alone or in combination.

When the cell surface antigen such as EGFR or TfR is expressed in cells by forming an insoluble body, the cells are collected and then homogenized in the same manner as described above, followed by centrifugation, whereby the insoluble body of the cell surface antigen such as EGFR or TfR is collected as a precipitated fraction. The collected insoluble body of the cell surface antigen such as EGFR or TfR is solubilized with a protein denaturing agent. The cell surface antigen such as EGFR or TfR is returned to a normal conformation by diluting or dialyzing the solubilized solution, and thereafter, a purified protein of a polypeptide can be obtained by the same isolation and purification methods as described above.

When the cell surface antigen such as EGFR or TfR, or a derivative thereof such as a sugar-modified form thereof is extracellularly secreted, the cell surface antigen such as EGFR or TfR, or the derivative thereof such as a sugar-modified form thereof can be collected in a culture supernatant. The culture supernatant is subjected to a treatment using a method such as centrifugation in the same manner as described above, thereby obtaining a soluble fraction, and then by using the same isolation and purification methods as described above, a purified protein can be obtained from the soluble fraction.

In addition, the cell surface antigen such as EGFR or TfR used in the present invention can also be produced using a chemical synthesis method such as an Fmoc method or a tBoc method. Specifically, for example, chemical synthesis can be carried out using a peptide synthesizer manufactured by Advanced Chemtech, Inc., PerkinElmer, Inc., Pharmacia Corporation, Protein Technology Instrument, Inc., Synthecell-Vega Biomolecules Corporation, Perceptive, Inc., Shimadzu Corporation, or the like.

(2) Step of Preparing Antibody-Producing Cell

By immunizing an animal such as a mouse, a rat, a hamster, a rabbit, cattle, or an alpaca with the antigen obtained in (1), and an antibody-producing cell in the spleen, the lymph node, or the peripheral blood of the animal is collected. In addition, as the animal, for example, a transgenic mouse that produces a human-derived antibody described in the document of Tomizuka. et al. [Tomizuka. et al., Proc Natl Acad Sci USA., 97, 722 (2000)], a conditional knockout mouse of TfR or the cell surface antigen such as EGFR for enhancing immunogenicity, or the like is exemplified as an immunized animal.

The immunization is carried out by administering an antigen together with an appropriate adjuvant such as a Freund's complete adjuvant, an aluminum hydroxide gel, *Bordetella pertussis* vaccine, or the like. As a method for administration of an immunogen when immunizing a mouse, any method of subcutaneous injection, intraperitoneal injection, intravenous injection, intradermal injection, intramuscular injection, footpad injection, and the like may be used, but intraperitoneal injection, footpad injection, or intravenous injection is preferred. When the antigen is a partial peptide, a conjugate of the antigen with a carrier protein such as BSA (bovine serum albumin) or KLH (Keyhole Limpet hemocyanin) is produced and used as an immunogen.

The administration of the antigen is carried out 5 to 10 times every 1 to 2 weeks after the first administration. On day 3 to 7 after each administration, the blood is collected from a venous plexus of the fundus, and the antibody titer of the serum thereof is measured using an enzyme immunoassay method [Antibodies—A Laboratory Manual, Cold Spring Harbor Laboratory (1988)] or the like. If an animal whose serum shows a sufficient antibody titer against the antigen used for the immunization is used as a supply source for the antibody-producing cell for fusion, the effect of the subsequent operation can be enhanced.

On day 3 to 7 after the final administration of the antigen, a tissue including the antibody-producing cell such as the spleen is extracted from the immunized animal, and the antibody-producing cell is collected. The antibody-producing cell is a lymphocyte that is a plasma cell and a progenitor cell thereof. The cell may be obtained from any site of an individual and can be generally obtained from the spleen, lymph node, bone marrow, tonsil, peripheral blood, or an appropriate combination thereof, or the like, but spleen cells are most generally used. When spleen cells are used, the spleen is shredded and loosened, followed by centrifugation, and then red blood cells are removed, whereby the antibody-producing cells for fusion are obtained.

(3) Step of Preparing Myeloma

As a myeloma, a cell that is derived from a mammal such as a mouse, a rat, a guinea pig, a hamster, a rabbit, or a human, and that has no autoantibody producing ability can be used, however, generally, an established cell line obtained from a mouse, for example, an 8-azaguanine resistant mouse (BALB/c derived) myeloma cell line P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], P3-X63-Ag8 (X63) [Nature, 256, 495 (1975)], or the like is used. The cell line is subcultured in a suitable culture medium, for example, an 8-azaguanine medium [RPMI 1640 medium supplemented with glutamine, 2-mercaptoethanol, gentamicin, FCS, and 8-azaguanine], Iscove's modified Dulbecco's medium (hereinafter referred to as "IMDM"), Dulbecco's modified Eagle medium (hereinafter referred to as "DMEM"), or the like. The above cell line is subcultured in a normal culture medium (for example, DMEM medium containing 10% FCS) 3 to 4 days before cell fusion, and $2 \times 10^7$ or more cells are ensured on the day of performing the fusion.

(4) Cell Fusion

The antibody-producing cells for fusion obtained in (2) and the myeloma cells obtained in (3) are well washed with Minimum Essential Medium (MEM) or PBS (1.83 g of disodium phosphate, 0.21 g of monopotassium phosphate, 7.65 g of sodium chloride, 1 L of distilled water, pH 7.2), and mixed to give the antibody-producing cells for fusion: the myeloma cells=5:1 to 10:1, followed by centrifugation, and then the supernatant is removed. After the precipitated cell clusters are well loosened, a mixed solution of polyethylene glycol 1000 (PEG-1000), MEM medium, and dimethylsulfoxide is added thereto while stirring at 37° C. Further, 1 to 2 mL of MEM medium is added thereto every 1 to 2 minutes several times, and then MEM medium is added thereto so that the total amount becomes 50 mL. After centrifugation, the supernatant is removed, the precipitated cell clusters are gently loosened, and then, the cells are gently suspended in HAT medium [a normal culture medium supplemented with hypoxanthine, thymidine, and aminopterin]. The resulting suspension is cultured in a 5% $CO_2$ incubator at 37° C. for 7 to 14 days.

In addition, the cell fusion can also be carried out by the following method. The spleen cells and the myeloma cells are well washed with a serum-free medium (for example, DMEM), or phosphate buffered saline (hereinafter referred to as "phosphate buffer solution"), and mixed so that the ratio of the spleen cells to the myeloma cells becomes about 5:1 to 10:1, followed by centrifugation. The supernatant is removed, and after the precipitated cell clusters are well loosened, 1 mL of a serum-free medium containing 50% (w/v) polyethylene glycol (molecular weight 1000 to 4000) is added dropwise thereto while stirring. Thereafter, 10 mL of the serum-free medium is slowly added thereto, followed by centrifugation. The supernatant is removed again, the precipitated cells are suspended in a normal culture medium containing an appropriate amount of a hypoxanthine-aminopterin-thymidine (HAT) solution and human interleukin 2 (IL-2) (hereinafter referred to as HAT medium), and the suspension is dispensed in each well of a culture plate (hereinafter referred to as plate), and then, the cells are cultured in the presence of 5% carbon dioxide gas at 37° C. for about 2 weeks. During the culture, the HAT medium is supplemented as appropriate.

(5) Selection of Hybridoma Group

When the myeloma cells used for the fusion are an 8-azaguanine resistant strain, that is, a hypoxanthine-guanine-phosphoribosyltransferase (HGPRT)-deficient strain, the unfused myeloma cells and the fused cells between the myeloma cells cannot survive in the HAT medium. On the other hand, the fused cells between the antibody-producing cells, and the hybridomas of the antibody-producing cell and the myeloma cell can survive in the HAT medium, however, the life span of the fused cells between the antibody-producing cells is reached shortly. Therefore, by continuing the culture in the HAT medium, only the hybridomas of the antibody-producing cell and the myeloma cell survive, and as a result, the hybridomas can be obtained.

For a hybridoma grown in the form of a colony, medium replacement with a culture medium obtained by removing aminopterin from the HAT medium (hereinafter referred to as HT medium) is carried out. Thereafter, a portion of the culture supernatant is collected, and a hybridoma that produces an antibody can be selected using the below-mentioned antibody titer measurement method. Examples of the antibody titer measurement method include various known techniques such as a radioisotopic immunoassay method (RIA method), a solid-phase enzyme immunoassay method (ELISA method), a fluorescent antibody method, and a passive hemagglutination reaction method, but an RIA method or an ELISA method is preferred from the viewpoint of detection sensitivity, rapidity, accuracy, a possibility of automation of an operation, and the like.

The hybridoma determined to produce a desired antibody by measuring the antibody titer is transferred to another plate, and cloning is carried out. Examples of the cloning method include a limiting dilution method in which culture is carried out by dilution so that one cell is contained in one well of a plate, a soft agar method in which culture is carried out in a soft agar medium to collect a colony, a method in which one cell is isolated using a micromanipulator, a method in which one cell is isolated using a cell sorter, and the like.

For a well in which the antibody titer is observed, cloning is repeated 2 to 4 times using, for example, a limiting dilution method, and the cell in which the antibody titer is stably observed is selected as a hybridoma strain that produces a monoclonal antibody against TfR or the cell surface antigen such as EGFR.

(6) Preparation of Monoclonal Antibody

The monoclonal antibody-producing hybridoma obtained in (5) is intraperitoneally injected into a mouse or a nude mouse at the age of 8 to 10 weeks having been subjected to a pristane treatment [0.5 mL of 2,6,10,14-tetramethylpentadecane (Pristane) is intraperitoneally administered, followed by breeding for 2 weeks]. In 10 to 21 days, the hybridoma is converted into an ascites tumor. The ascites is collected from this mouse, and then, solids are removed by centrifugation, followed by salting out with 40 to 50% ammonium sulfate, and thereafter, purification is carried out by a caprylic acid precipitation method, a DEAE-Sepharose column, a protein A column, or a gel filtration column, and then, an IgG or IgM fraction is collected and a purified monoclonal antibody is prepared. In addition, by growing the hybridoma in the peritoneal cavity of a mouse of the same strain (for example, BALB/c) or a Nu/Nu mouse, a rat, a guinea pig, a hamster, a rabbit, or the like, ascites containing a large amount of a monoclonal antibody that binds to TfR or the cell surface antigen such as EGFR can be obtained.

After culturing the monoclonal antibody-producing hybridoma obtained in (5) in RPMI 1640 medium supplemented with 10% FBS, or the like, the supernatant is removed by centrifugation, and the residue is suspended in GIT medium, Hybridoma SFM medium supplemented with 5% Daigo's GF21, or the like, and then cultured for 3 to 7 days by flask culture, spinner culture, bag culture, or the like. The obtained cell suspension is centrifuged, and purification from the obtained supernatant is carried out by a protein A column or a protein G column, and then an IgG fraction is collected, whereby a purified monoclonal antibody can also be obtained. As a simple method for the purification, it is also possible to use a commercially available monoclonal antibody purification kit (for example, MabTrap GII kit manufactured by Amersham Pharmacia Biotech, Inc.), and the like.

The determination of the subclass of the antibody is carried out by an enzyme immunoassay method using a subclass typing kit. The quantitative determination of a protein amount can be carried out by a Lowry method or a method of calculation from the absorbance at 280 nm [1.4 ($OD_{280}$)=1 mg/mL immunoglobulin].

(7) Binding Assay of Monoclonal Antibody to TfR or Cell Surface Antigen Such as EGFR The binding activity of the monoclonal antibody to TfR or the cell surface antigen such as EGFR can be measured by a binding assay system such as an Ouchterlony method, an ELISA method, an RIA method, a flow cytometry method (FCM), or a surface plasmon resonance method (SPR).

An Ouchterlony method is a simple method, but a concentration operation is needed when the concentration of the antibody is low. On the other hand, when an ELISA method or an RIA method is used, by allowing a culture supernatant to directly react with an antigen-adsorbed solid phase and further by using antibodies corresponding to various immunoglobulin isotypes and subclasses as secondary antibodies, it is possible to identify the isotype and subclass of the antibody and also to measure the binding activity of the antibody.

As a specific example of the procedure, the purified or partially purified recombinant cell surface antigen such as EGFR or TfR is adsorbed onto a solid phase surface of a 96-well plate for ELISA or the like, and then the solid phase surface on which the antigen is not adsorbed is blocked with a protein unrelated to the antigen, for example, bovine serum albumin (BSA). After an ELISA plate is washed with phosphate buffer saline (PBS) and PBS containing 0.05% TWEEN® 20 (polysorbate; Tween-PBS) or the like, a serially diluted first antibody (for example, mouse serum, a culture supernatant, or the like) is allowed to react therewith, and then the antibody is bound to the antigen immobilized on the plate. Subsequently, as a second antibody, an anti-immunoglobulin antibody labeled with biotin, an enzyme (horse radish peroxidase (HRP), alkaline phosphatase (ALP), or the like), a chemiluminescent substance, a radioactive compound, or the like, is dispensed to allow the second antibody to react with the first antibody bound to the plate. After well washing with Tween-PBS, a reaction according to the labeling substance of the second antibody is carried out, and then, a monoclonal antibody that specifically reacts with the target antigen is selected.

In an FCM method, the binding activity of an antibody to an antigen-expressing cell can be measured [Cancer Immunol. Immunother., 36, 373 (1993)]. Binding of an antibody to a membrane protein antigen expressed on a cell membrane means that the antibody recognizes the conformation of a naturally occurring antigen and binds thereto.

Examples of an SPR method include a kinetics analysis by Biacore. For example, by using Biacore T100, the kinetics in binding of an antigen and a test substance are measured, and the result is analyzed with an analysis software attached to an instrument. As a specific example of the procedure, after fixing an anti-mouse IgG antibody to a sensor chip CM5 by an amine coupling method, a test substance such as a hybridoma culture supernatant or a purified monoclonal antibody is allowed to flow to bind an appropriate amount, further the antigen at a plurality of known concentrations is allowed to flow, and then binding and dissociation are measured. Subsequently, a kinetics analysis by a 1:1 binding model is carried out with respect to the obtained data using the software attached to the instrument to obtain various parameters. Alternatively, after fixing the cell surface antigen such as EGFR or TfR onto the sensor chip by, for example, an amine coupling method, a purified monoclonal antibody at a plurality of known concentrations is allowed to flow, and then binding and dissociation are measured. A kinetics analysis by a bivalent binding model is carried out with respect to the obtained data using the software attached to the instrument to obtain various parameters.

In addition, in the present invention, it is possible to select an antibody that binds to TfR or the cell surface antigen such as EGFR competitively with the antibody against TfR or the cell surface antigen such as EGFR by allowing a test antibody to coexist in the above-mentioned binding assay system to cause a reaction. That is, by screening an antibody whose binding to the antigen is inhibited when the test antibody is added, it is possible to obtain an antibody that competes with the antibody obtained above for binding to TfR or the cell surface antigen such as EGFR.

(8) Identification of Epitope for Monoclonal Antibody Against TfR or Cell Surface Antigen Such as EGFR In the present invention, the identification of an epitope which the antibody recognizes and binds to can be carried out as follows.

For example, a partially deficient variant of an antigen, a mutant of an antigen in which an amino acid residue different among species is modified, or a mutant of an antigen in which a specific domain is modified is produced, and if the reactivity of the antibody against the deficient variant or the mutant is lowered, it becomes clear that the deficient site or the amino acid modified site is an epitope for the antibody. Such a partially deficient variant or a mutant of an antigen may be obtained as a secretory protein using a suitable host cell, for example, E. coli, yeast, a plant cell, a mammalian cell, or the like, or may be prepared as an antigen-expressing cell by expressing it on a cell membrane of a host cell. In the case of a membrane-associated antigen, in order to express it while maintaining the conformation of the antigen, it is preferred to express it on the membrane of a host cell. In addition, it is also possible to confirm the reactivity of the antibody by producing a synthetic peptide mimicking the primary structure or the conformation of the antigen. As for the synthetic peptide, a method for producing various partial peptides of the molecule thereof using a known peptide synthesis technique, and the like are exemplified.

For example, with respect to the extracellular domain of TfR or the cell surface antigen such as EGFR of a human or a mouse, it is possible to identify an epitope for an antibody by producing a chimeric protein in which domains constituting the respective regions are appropriately combined, and then confirming the reactivity of the antibody with the protein. Thereafter, it is possible to specify the epitope in more detail by variously synthesizing an oligopeptide of the corresponding region or a mutant or the like of the peptide using an oligopeptide synthesis technique well known to those skilled in the art, and then confirming the reactivity of the antibody with the peptide. As a simple method for obtaining various types of oligopeptides, a commercially available kit [for example, SPOTs Kit (manufactured by Genosys Biotechnologies, Inc.), a series of multipin-peptide synthesis kit (manufactured by Chiron Corporation) using a multipin synthesis method, or the like] can also be used.

An antibody that binds to the same epitope as an epitope to which an antibody that binds to TfR or the cell surface antigen such as EGFR binds can be obtained by identifying an epitope for an antibody obtained in the above-mentioned binding assay system, producing a partial synthetic peptide of the epitope, a synthetic peptide mimicking the conformation of the epitope, a recombinant of the epitope, or the like, and then performing immunization therewith.

For example, if the epitope is a membrane protein, an antibody specific to the epitope can be more efficiently produced by producing a recombinant fusion protein in which the entire extracellular domain or a part of the extracellular domain is linked to an appropriate tag, for example, a FLAG tag, a Histidine tag, a GST protein, an antibody Fc region, or the like, and performing immunization with the recombinant protein.

2. Production of Genetically Recombinant Antibody

Production examples of genetically recombinant antibodies are schematically described in P. J. Delves., ANTIBODY PRODUCTION ESSENTIAL TECHNIQUES., 1997 WILEY, P. Shepherd and C. Dean. Monoclonal Antibodies., 2000 OXFORD UNIVERSITY PRESS, and J. W. Goding., Monoclonal Antibodies: principles and practice., 1993 ACADEMIC PRESS, and the like, but methods for producing a chimeric antibody, a humanized antibody, and a human antibody will be described below. In addition, genetically recombinant mouse, rat, hamster, and rabbit antibodies can also be produced using the same method.

(1) Acquisition of cDNA Encoding V Region of Monoclonal Antibody from Hybridoma

Acquisition of cDNAs encoding VH and VL of a monoclonal antibody can be carried out, for example, as follows.

First, mRNA is extracted from a hybridoma that produces a monoclonal antibody, and cDNAs are synthesized. Subsequently, the synthesized cDNAs are each cloned into a vector such as a phage or a plasmid, thereby producing a cDNA library. A recombinant phage or a recombinant plasmid containing a cDNA encoding VH or VL is isolated from the library using a DNA encoding a C region part or a V region part of the antibody as a probe, respectively. The entire nucleotide sequence of VH or VL in the isolated recombinant phage or recombinant plasmid is determined, and then, the entire amino acid sequence of VH or VL is deduced from the nucleotide sequence.

As a non-human animal used for producing a hybridoma, a mouse, a rat, a hamster, a rabbit, or the like is used, but any animal can be used as long as a hybridoma can be produced.

In the preparation of the total RNA from a hybridoma, a guanidine thiocyanate-cesium trifluoroacetate method [Methods in Enzymol., 154, 3 (1987)], or a kit such as RNA easy Kit (manufactured by QIAGEN, Inc.), or the like is used.

In the preparation of mRNA from the total RNA, an oligo (dT)-immobilized cellulose column method [Molecular Cloning, A Laboratory Manual, Second Edition, Cold Spring Harbor Laboratory Press (1989)], or a kit such as Oligo-dT30<Super> mRNA Purification Kit (manufactured by Takara Bio, Inc.), or the like is used. Further, it is also possible to prepare mRNA using a kit such as Fast Track mRNA Isolation Kit (manufactured by Invitrogen, Inc.), or QuickPrep mRNA Purification Kit (manufactured by Pharmacia Corporation).

In the synthesis of cDNAs and the production of a cDNA library, a known method [Molecular Cloning, A Laboratory Manual, Second Edition, Cold Spring Harbor Laboratory Press (1989), Current Protocols in Molecular Biology, Supplement 1, John Wiley & Sons (1987-1997)], or a kit such as SuperScript Plasmid System for cDNA Synthesis and Plasmid Cloning (manufactured by Invitrogen, Inc.) or ZAP-cDNA Synthesis Kit (manufactured by Stratagene Corporation), or the like is used.

When the cDNA library is produced, as the vector into which a cDNA synthesized using mRNA extracted from a hybridoma as a template is incorporated, any vector can be used as long as it can incorporate the cDNA.

For example, ZAP Express [Strategies, 5, 58 (1992)], pBluescript II SK(+) [Nucleic Acids Research, 17, 9494 (1989)], λZAP II (manufactured by Stratagene Corporation), λgt 10, λgt 11 [DNA Cloning: A Practical Approach, I, 49 (1985)], Lambda BlueMid (manufactured by Clontech Laboratories, Inc.), λExCell, pT7T3-18U (manufactured by Pharmacia Corporation), pcD2 [Mol. Cell. Biol., 3, 280 (1983)], pUC18 [Gene, 33, 103 (1985)], or the like is used.

As E. coli into which a cDNA library constructed by a phage or plasmid vector is introduced, any E. coli can be used as long as it can introduce, express, and maintain the cDNA library. For example, XL1-Blue MRF' [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], JM105 [Gene, 38, 275 (1985)], or the like is used.

In the selection of a cDNA clone encoding VH or VL of a non-human antibody from the cDNA library, a colony hybridization method using an isotope or a fluorescently labeled probe, or a plaque hybridization method [Molecular Cloning, A Laboratory Manual, Second Edition, Cold Spring Harbor Laboratory Press (1989)], or the like is used.

In addition, it is possible to prepare a cDNA encoding VH or VL by preparing a primer and performing a polymerase chain reaction method [hereinafter referred to as PCR method, Molecular Cloning, A Laboratory Manual, Second Edition, Cold Spring Harbor Laboratory Press (1989), Current Protocols in Molecular Biology, Supplement 1, John Wiley & Sons (1987-1997)] using a cDNA synthesized from mRNA or a cDNA library as a template.

The selected cDNA is cleaved with an appropriate restriction enzyme or the like, and then cloned into a plasmid such as pBluescript SK(−) (manufactured by Stratagene Corporation), and the nucleotide sequence of the cDNA is determined by a commonly used nucleotide sequence analysis method or the like. For example, after performing a reaction of a dideoxy method [Proc. Natl. Acad. Sci. USA, 74, 5463 (1977)] or the like, an analysis is performed using an automatic nucleotide sequence analyzer such as A.L.F. DNA sequencer (manufactured by Pharmacia Corporation).

By deducing the entire amino acid sequence of each of VH and VL from the determined entire nucleotide sequence and comparing it with the entire amino acid sequence of each of VH and VL of a known antibody [Sequences of Proteins of Immunological Interest, US Dept. Health and Human Services (1991)], it is confirmed whether the obtained cDNA encodes the complete amino acid sequence of each of VH and VL of the antibody containing a secretion signal sequence.

With respect to the complete amino acid sequence of each of VH and VL of the antibody containing a secretion signal sequence, by comparison with the entire amino acid sequence of each of VH and VL of a known antibody [Sequences of Proteins of Immunological Interest, US Dept. Health and Human Services (1991)], the length of the secretion signal sequence and the N-terminal amino acid sequence can be deduced, and further the subgroup to which these belong can be identified.

In addition, the amino acid sequence of each of CDRs of VH and VL can be deduced by comparison with the amino acid sequence of each of VH and VL of a known antibody [Sequences of Proteins of Immunological Interest, US Dept. Health and Human Services (1991)].

Further, with respect to the obtained complete amino acid sequence of each of VH and VL, it is possible to confirm whether the complete amino acid sequence of each of VH and VL is new by, for example, performing a homology search by the BLAST method [J. Mol. Biol., 215, 403 (1990)] or the like using an arbitrary database such as SWISS-PROT or PIR-Protein.

(2) Construction of Expression Vector for Genetically Recombinant Antibody

An expression vector for a genetically recombinant antibody can be constructed by cloning a DNA encoding at least one of CH and CL of a human antibody into an expression vector for an animal cell.

As a C region of a human antibody, CH and CL of an arbitrary human antibody can be used, and for example, CH of γ1 subclass and CL of κ class of a human antibody, or the like can be used. As a DNA encoding CH or CL of a human antibody, a cDNA is used, but it is also possible to use a chromosomal DNA composed of an exon and an intron.

As the expression vector for an animal cell, any vector can be used as long as it can incorporate a gene encoding a C region of a human antibody and express the gene, and for example, pAGE107 [Cytotechnol., 3, 133 (1990)], pAGE103 [J. Biochem., 101, 1307 (1987)], pHSG274

[Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)], INPEP4 (manufactured by Biogen-IDEC, Inc.), N5KG1val (U.S. Pat. No. 6,001,358), N5KG4PE R409K (described in WO 2006/033386), an N5KG2 vector (described in WO 2003/033538), a transposon vector (WO 2010/143698), or the like can be used.

As a promoter and an enhancer of the expression vector for an animal cell, an SV40 early promoter [J. Biochem., 101, 1307 (1987)], Moloney murine leukemia virus LTR [Biochem. Biophys. Res. Commun., 149, 960 (1987)], a CMV promoter (U.S. Pat. No. 5,168,062), or a promoter [Cell, 41, 479 (1985)] and an enhancer [Cell, 33, 717 (1983)] of an immunoglobulin H chain, or the like can be used.

In the expression of a genetically recombinant antibody, a vector carrying both genes of the antibody H chain and L chain (tandem-type vector) [J. Immunol. Methods, 167, 271 (1994)] is used from the viewpoints of ease of construction of the vector, ease of introduction into an animal cell, balance of the expression levels of the antibody H chain and L chain in the cell, and the like, however, a plurality of vectors separately carrying each of the genes of the antibody H chain and L chain (separation-type vectors) can also be used in combination.

As the tandem-type expression vector for a genetically recombinant antibody, pKANTEX93 (WO 97/10354), pEE18 [Hybridoma, 17, 559 (1998)], N5KG1val (U.S. Pat. No. 6,001,358), N5KG4PE R409K (described in WO 2006/033386), an N5KG2 vector (described in WO 2003/033538), a Tol2 transposon vector (WO 2010/143698), or the like is used.

(3) Construction of Chimeric Antibody Expression Vector

By cloning the cDNA encoding VH or VL of a non-human antibody obtained in (1) upstream of each gene encoding CH or CL of a human antibody in the expression vector for a genetically recombinant antibody obtained in (2), a chimeric antibody expression vector can be constructed.

First, in order to ligate the cDNA encoding VH or VL of a non-human antibody at the 3' end side with CH or CL of a human antibody at the 5' end side, cDNAs of VH and VL designed so that the nucleotide sequence of a ligation region encodes an appropriate amino acid and to become an appropriate restriction enzyme recognition sequence are produced. Subsequently, the produced cDNAs of VH and VL are each cloned upstream of each gene encoding CH or CL of a human antibody in the expression vector for a genetically recombinant antibody obtained in (2) so that they are expressed in an appropriate form, whereby a chimeric antibody expression vector is constructed.

In addition, each cDNA encoding VH or VL of a non-human antibody is amplified by a PCR method using a synthetic DNA containing an appropriate restriction enzyme recognition sequence at both ends, and is cloned into the expression vector for a genetically recombinant antibody obtained in (2), whereby a chimeric antibody expression vector can also be constructed.

(4) Production of cDNA Encoding V Region of Humanized Antibody

A cDNA encoding VH or VL of a humanized antibody can be produced as follows. First, each amino acid sequence of a framework region (hereinafter referred to as FR) of VH or VL of a human antibody, to which the amino acid sequence of CDR of VH or VL of a non-human antibody obtained in (1) is to be grafted is selected.

As the amino acid sequence of FR to be selected, any amino acid sequence can be used as long as it is derived from a human antibody. For example, an amino acid sequence of FR of a human antibody registered in a database such as Protein Data Bank, or a common amino acid sequence in each subgroup of FR of a human antibody [Sequences of Proteins of Immunological Interest, US Dept. Health and Human Services (1991)], or the like is used. In order to suppress a decrease in the binding activity of an antibody, an amino acid sequence of human FR having a homology as high as possible (60% or more) with the amino acid sequence of FR of VH or VL of the original non-human antibody is selected.

Subsequently, each of the amino acid sequences of CDRs of the original non-human antibody is grafted to the selected amino acid sequence of FR of VH or VL of a human antibody, and each amino acid sequence of VH or VL of a humanized antibody is designed. By converting the designed amino acid sequence into a DNA sequence in consideration of the usage frequency of codons found in the nucleotide sequence of the antibody gene [Sequences of Proteins of Immunological Interest, US Dept. Health and Human Services (1991)], each cDNA sequence of VH or VL of a humanized antibody is designed.

Based on the designed cDNA sequence, several synthetic DNAs having a length of around 100 to 150 nucleotides are synthesized and a PCR reaction is carried out using them. In that case, from the viewpoint of the reaction efficiency in the PCR reaction and the length of a synthesizable DNA, preferably 4 to 6 synthetic DNAs are designed for each of the H chain and the L chain. In addition, it is also possible to synthesize and use a synthetic DNA having a full-length variable region.

Further, by introducing an appropriate restriction enzyme recognition sequence at the 5' end of the synthetic DNA located at both ends, a cDNA encoding VH or VL of a humanized antibody can be easily cloned into the expression vector for a genetically recombinant antibody obtained in (2). After the PCR reaction, each amplified product is cloned into a plasmid such as pBluescript SK(−) (manufactured by Stratagene Corporation), the nucleotide sequence is determined by the same method as described in (1), and thus a plasmid containing a DNA sequence encoding the amino acid sequence of VH or VL of a desired humanized antibody is obtained.

(5) Modification of Amino Acid Sequence of V Region of Humanized Antibody

The antigen-binding activity of a humanized antibody prepared merely by grafting only CDRs of VH and VL of a non-human antibody to FRs of VH and VL of a human antibody is lowered as compared with that of the original non-human antibody [BIO/TECHNOLOGY, 9, 266 (1991)]. For this reason, the lowered antigen-binding activity of a humanized antibody can be increased by identifying amino acid residues directly involved in the binding to an antigen, amino acid residues interacting with the amino acid residues of CDRs, and amino acid residues maintaining the conformation of the antibody and indirectly involved in the binding to an antigen among the amino acid sequences of FRs of VH and VL of a human antibody, and substituting the amino acid residues with amino acid residues of the original non-human antibody.

In order to identify the amino acid residues of FR involved in the antigen-binding activity, it is possible to construct and analyze the conformation of the antibody using X-ray crystallography [J. Mol. Biol., 112, 535 (1977)], or computer modeling [Protein Engineering, 7, 1501 (1994)], or the like. Further, it is possible to obtain a modified humanized antibody having a necessary antigen-binding activity by producing several types of modified antibodies for each antibody, and repeatedly examining the correlation with the antigen-binding activity thereof through trial and error.

The amino acid residues of FRs of VH and VL of a human antibody can be modified by performing a PCR reaction described in (4) using a synthetic DNA for modification. With respect to the amplification product after the PCR reaction, the nucleotide sequence is determined to confirm that the desired modification has been carried out by the method described in (1).

(6) Construction of Humanized Antibody Expression Vector

A humanized antibody expression vector can be constructed by cloning each cDNA encoding VH or VL of the constructed humanized antibody upstream of each gene encoding CH or CL of a human antibody of the expression vector for a genetically recombinant antibody obtained in (2).

For example, the cloning is carried out upstream of each gene encoding CH or CL of a human antibody in the expression vector for a genetically recombinant antibody obtained in (2) by introducing an appropriate restriction enzyme recognition sequence at the 5' end of the synthetic DNA located at both ends among the synthetic DNAs used when constructing VH or VL of the humanized antibody obtained in (4) and (5) so that they are expressed in an appropriate form.

(7) Construction of Human Antibody Expression Vector

When a hybridoma that produces a monoclonal antibody is established using an animal that produces a human antibody as an immunized animal, the amino acid sequences and the cDNA sequences of VH and VL of a human antibody can be obtained in (1). Therefore, by cloning each gene encoding VH or VL of a human antibody obtained in (1) upstream of each gene encoding CH or CL of a human antibody of the expression vector for a genetically recombinant antibody obtained in (2), a human antibody expression vector can be constructed.

(8) Transient Expression of Genetically Recombinant Antibody

By transiently expressing a genetically recombinant antibody using the expression vector for a genetically recombinant antibody obtained in (3), (6), and (7), or an expression vector obtained by modification thereof, the antigen-binding activities of many types of genetically recombinant antibodies obtained can be efficiently evaluated.

As a host cell into which the expression vector is introduced, any cell can be used as long as it is a host cell capable of expressing a genetically recombinant antibody, and for example, a COS-7 cell [American Type Culture Collection (ATCC) number: CRL1651] is used. In the introduction of the expression vector into a COS-7 cell, a DEAE-dextran method [Methods in Nucleic Acids Res., CRC press (1991)], a lipofection method [Proc. Natl. Acad. Sci. USA, 84, 7413 (1987)], or the like is used.

After the introduction of the expression vector, the expression level and the antigen-binding activity of the genetically recombinant antibody in a culture supernatant are measured using an enzyme immunoassay method [Monoclonal Antibodies-Principles and practice, Third Edition, Academic Press (1996), Antibodies-A Laboratory Manual, Cold Spring Harbor Laboratory (1988), Monoclonal Antibody Experimental Manual, Kodansha scientific books (1987)], or the like.

(9) Acquisition of Stable Expression Cell Line of Genetically Recombinant Antibody and Preparation of Genetically Recombinant Antibody A transformant that stably expresses a genetically recombinant antibody can be obtained by introducing the expression vector for a genetically recombinant antibody obtained in (3), (6), and (7) into an appropriate host cell.

As the introduction of the expression vector into a host cell, for example, an electroporation method [JP-A-H2-257891, Cytotechnology, 3, 133 (1990)], a calcium ion method, an electroporation method, a spheroplast method, a lithium acetate method, a calcium phosphate method, a lipofection method, and the like are exemplified. In addition, as a method for introducing a gene into an animal described below, for example, a microinjection method, a method for introducing a gene into an ES cell using an electroporation or lipofection method, a nuclear transfer method, and the like are exemplified.

As a host cell into which the expression vector for a genetically recombinant antibody is introduced, any cell can be used as long as it is a host cell capable of expressing a genetically recombinant antibody. For example, mouse SP2/0-Ag14 cells (ATCC CRL 1581), mouse P3X63-Ag8.653 cells (ATCC CRL 1580), Chinese hamster CHO-K1 cells (ATCC CCL-61), DUKXB11 (ATCC CCL-9096), Pro-5 cells (ATCC CCL-1781), CHO-S cells (Life Technologies, Cat No. 11619), dihydrofolate reductase gene (dhfr)-deficient CHO cells (CHO/DG44 cells) [Proc. Natl. Acad. Sci. USA, 77, 4216 (1980)], Lec13 cells having acquired lectin resistance [Somatic Cell and Molecular Genetics, 12, 55 (1986)], α1,6-fucosyltransferase gene-deficient CHO cells (WO 2005/035586 and WO 02/31140), Rat YB2/3HL.P2.G11.16Ag.20 cells (ATCC No.: CRL 1662), and the like are used.

In addition, it is also possible to use a host cell in which the activity of a protein such as an enzyme involved in the intracellular synthesis of sugar nucleotide GDP-fucose, a protein such as an enzyme involved in a sugar chain modification such that the 1-position of fucose is α-linked to the 6-position of N-acetylglucosamine at the reducing end of an N-glycoside-linked complex sugar chain, a protein involved in the intracellular transport of sugar nucleotide GDP-fucose to the Golgi body, or the like is decreased or lost, for example, α1,6-fucosyltransferase gene-deficient CHO cells (WO 2005/035586 and WO 02/31140), or the like.

After introduction of the expression vector, a transformant that stably expresses a genetically recombinant antibody is selected by culturing the transformant in a medium for animal cell culture containing a drug such as G418 sulfate (hereinafter referred to as G418) (JP-A-H2-257891).

As the medium for animal cell culture, RPMI 1640 medium (manufactured by Invitrogen, Inc.), GIT medium (manufactured by Nippon Pharmaceutical Co., Ltd.), EX-CELL 301 medium (manufactured by JRH Biosciences, Inc.), EX-CELL 302 medium (manufactured by JRH Bioscience, Inc.), EX-CELL 325 medium (manufactured by JRH Bioscience., Inc.), IMDM medium (manufactured by Invitrogen, Inc.) or Hybridoma-SFM medium (manufactured by Invitrogen, Inc.), or a medium in which any of various additives such as FBS is added to any of these media, or the like is used. By culturing the obtained transformant in the medium, a genetically recombinant antibody is expressed and accumulated in the culture supernatant. The expression level and the antigen-binding activity of the genetically recombinant antibody in the culture supernatant can be measured by an ELISA method or the like. In addition, the expression level of the genetically recombinant antibody produced by the transformant can be increased using a DHFR amplification system (JP-A-H2-257891) or the like.

The genetically recombinant antibody can be purified using a protein A column from the culture supernatant of the transformant [Monoclonal Antibodies—Principles and Practice, Third Edition, Academic Press (1996), Antibodies—A Laboratory Manual, Cold Spring Harbor Laboratory (1988)]. In addition, the purification can also be carried out by combining methods used for purifying a protein such as gel filtration, ion exchange chromatography, and ultrafiltration.

The molecular weights of an H chain, an L chain, or the entire antibody molecule of a purified genetically recombinant antibody can be measured using a polyacrylamide gel electrophoresis method [Nature, 227, 680 (1970)], or a Western blotting method [Monoclonal Antibodies—Principles and Practice, Third Edition, Academic Press (1996), Antibodies—A Laboratory Manual, Cold Spring Harbor Laboratory (1988)], or the like.

3. Designing of Bispecific Antibody

The bispecific antibody of the present invention can be produced by designing each of the N-terminal side polypeptide and the IgG portion, and designing the bispecific antibody in which these are linked.

3-1. Designing of IgG Portion

An IgG portion can be obtained by obtaining monoclonal antibodies using the method described in the above 1., determining the cDNA sequences of CDR and a variable region of each antibody using the method described in the above 2., and designing the IgG portion including the CDR or the variable region of the antibody.

3-2. Designing of N-Terminal Side Polypeptide

When CDR or a variable region of an antibody is included in an N-terminal side polypeptide, the N-terminal side polypeptide can be produced by determining the DNA sequence of the CDR or the variable region of the antibody using the method described in the above 1, and 2, and designing the N-terminal side polypeptide including them. As such an N-terminal side polypeptide, a single-stranded one obtained by binding VH and VL directly or through an appropriate linker as scFV or the like, one obtained by being expressed in the form of a double strand as Fab, dsFv, or the like, and being designed to form an S—S bond after expression, or VHH or the like can also be used. The antigen-binding activity of the N-terminal side polypeptide can be evaluated by the above-mentioned method, and one retaining the antigen-binding activity can be selected.

4. Production of Bispecific Antibody 4-1. Production of Light Chain Common-type Bispecific Antibody A bispecific antibody in which the N-terminal side polypeptide is Fab, and the light chain is common to the Fab and the IgG portion can be specifically produced as follows.

A DNA encoding a polypeptide in which VH-CH1 of the N-terminal side polypeptide and VH of the IgG portion are linked is synthesized, and also a DNA encoding VL of each antibody is synthesized, and these DNAs are integrated into the expression vector for a genetically recombinant antibody described in the above 2. (2) to express the bispecific antibody, whereby the bispecific antibody can be produced. When the IgG portion and the N-terminal side polypeptide are bound through a linker, the synthesis is carried out also including a DNA encoding the linker sequence.

4-2. Production of Light Chain Non-Common-type Bispecific Antibody Including CDR in N-Terminal Side Polypeptide (1) A light chain non-common-type bispecific antibody in which the N-terminal side polypeptide is Fab can be specifically produced as follows.

A DNA encoding a polypeptide in which VL-CL of the N-terminal side polypeptide and VH of the IgG portion are linked, a DNA encoding VH-CH1 of the N-terminal side polypeptide, and a DNA encoding VL of the IgG portion are synthesized, and these DNAs are integrated into the expression vector for a genetically recombinant antibody described in the above 2. (2) to express the bispecific antibody, whereby the bispecific antibody can be produced. When the IgG portion and the N-terminal side polypeptide are bound through a linker, the synthesis is carried out also including a DNA encoding the linker sequence.

(2) A bispecific antibody in which the N-terminal side polypeptide is VHH can be specifically produced as follows.

A DNA encoding a polypeptide in which VHH and VH of the IgG portion are linked, and a DNA encoding VL of the IgG portion are synthesized, and these DNAs are integrated into the expression vector for a genetically recombinant antibody described in the above 2. (2) to express the bispecific antibody, whereby the bispecific antibody can be produced. When the VHH and the IgG portion are bound through a linker, the synthesis is carried out also including a DNA encoding the linker sequence.

(3) A bispecific antibody in which the N-terminal side polypeptide is a polypeptide including scFv, dsFv, or CDR other than the above (1) and (2) can be specifically produced as follows.

When the N-terminal side polypeptide is a single strand, a DNA in which a DNA encoding the N-terminal side polypeptide and a DNA encoding VH of the IgG portion are linked is synthesized. When the N-terminal side polypeptide is an assembly composed of two single-stranded polypeptides, one of the single-stranded polypeptides constituting the N-terminal side polypeptide is linked to a DNA encoding VH of the IgG portion and synthesized, and also a DNA encoding the other single-stranded polypeptide constituting the N-terminal side polypeptide is synthesized. In addition, a DNA encoding VL of the IgG portion is also synthesized. When the IgG portion and the N-terminal side polypeptide are bound through a linker, the synthesis is carried out also including a DNA encoding the linker sequence. These DNAs are integrated into the expression vector for a genetically recombinant antibody described in the above 2. (2) to express the bispecific antibody, whereby the bispecific antibody can be produced.

4-3. Production of Bispecific Antibody Including N-Terminal Side Polypeptide Other than Above When the N-terminal side polypeptide is a polypeptide other than the above, the bispecific antibody of the present invention can be specifically produced as follows.

When the N-terminal side polypeptide is a single strand, a DNA in which a DNA encoding the N-terminal side polypeptide and a DNA encoding VH of the IgG portion are linked is synthesized. When the N-terminal side polypeptide is an assembly composed of two or more single-stranded polypeptides, one of the single-stranded polypeptides constituting the N-terminal side polypeptide is linked to a DNA encoding VH of the IgG portion and synthesized, and also a DNA encoding the rest of the single-stranded polypeptides constituting the N-terminal side polypeptide is synthesized. In addition, a DNA encoding VL of the IgG portion is also synthesized. When the IgG portion and the N-terminal side polypeptide are bound through a linker, the synthesis is carried out also including a DNA encoding the linker sequence. These DNAs are integrated into the expression vector for a genetically recombinant antibody described in the above 2. (2) to express the bispecific antibody, whereby the bispecific antibody can be produced.

These DNAs are integrated into the expression vector for a genetically recombinant antibody described in the above 2. (2) to express the bispecific antibody, whereby the bispecific antibody can be produced. When the IgG portion and the N-terminal side polypeptide are bound through a linker, the synthesis is carried out also including a DNA encoding the linker sequence.

The antigen-binding domain can be isolated and obtained by a technique such as a phage display method or a yeast display method other than the method using a hybridoma described in the above 1. [Emmanuelle Laffy et. al., Human Antibodies 14, 33-55, (2005)].

Further, when a bispecific antibody composed of a plurality of VHs and a single VL (hereinafter also referred to as light chain common-type bispecific antibody) is produced, a screening using a phage display method or the like is carried out and each VH most suitable for the single VL is selected so that each antigen-binding domain contained in the bispecific antibody reacts with each specific antigen.

Specifically, first, an animal is immunized with a first antigen using the method described in the above 1., and a hybridoma is produced from its spleen, and then, a DNA sequence encoding a first antigen-binding domain is cloned. Subsequently, an animal is immunized with a second antigen, and a cDNA library is prepared from its spleen, and then, a DNA encoding the amino acid sequence of VH is obtained from the library by PCR.

Subsequently, a phage library expressing scFv in which VH obtained by immunization with the second antigen and VL of the first antigen-binding domain are linked is produced, and a phage displaying scFv that specifically binds to the second antigen is selected by panning using the phage library. From the selected phage, a DNA sequence encoding the amino acid sequence of VH of a second antigen-binding domain is cloned.

Further, when the N-terminal side polypeptide is Fab, a DNA sequence encoding the amino acid sequence of a polypeptide in which VH of the first antigen-binding domain and VH of the second antigen-binding domain are linked through CH1 or CH1 and a linker is designed, and the DNA sequence and a DNA sequence encoding the amino acid sequence of the single VL are inserted into, for example, the expression vector for a genetically recombinant antibody described in the above 2. (2), whereby the expression vector for the bispecific antibody of the present invention can be constructed.

5. Evaluation of Activity of Bispecific Antibody or Antibody Fragment Thereof of the Present Invention The evaluation of the activity of the purified bispecific antibody or bispecific antibody fragment thereof can be carried out as follows.

The binding activity of the bispecific antibody of the present invention to a cell line that has expressed at least one of TfR and the cell surface antigen such as EGFR can be measured using the binding assay system described in the above 1. (7).

The CDC activity or the ADCC activity against a cell that has expressed at least one of TfR and the cell surface antigen such as EGFR can be measured by a known measurement method [Cancer Immunol. Immunother., 36, 373 (1993)].

The anticellular activity (also referred to as growth inhibitory activity) of the bispecific antibody of the present invention can be measured by the following method. For example, cells are seeded in a 96-well plate, and after adding an antibody and culturing the cells for a certain period of time, WST-8 reagent (manufactured by Dojindo Molecular Technologies, Inc.) is allowed to react, and then an absorbance at 450 nm is measured with a plate reader to measure the viability of the cells.

The signal transduction into a cell from TfR or the cell surface antigen such as EGFR can be evaluated by detecting phosphorylation of a protein in the cell through Western blotting or the like.

6. Therapeutic Method for Disease Using Bispecific Antibody or Antibody Fragment Thereof of the Present Invention The bispecific antibody or the bispecific antibody fragment thereof of the present invention can be used for a treatment of a disease associated with at least one of TfR and the cell surface antigen such as EGFR, preferably a disease involved in a cell that expresses TfR and the cell surface antigen such as EGFR. As the disease associated with at least one of TfR and the cell surface antigen such as EGFR, for example, a malignant tumor, cancer, and the like are exemplified.

Examples of the malignant tumor and cancer include, large intestine cancer, colorectal cancer, lung cancer, breast cancer, glioma, malignant melanoma (melanoma), thyroid cancer, renal cell carcinoma, leukemia, lymphoma, T cell lymphoma, stomach cancer, pancreatic cancer, cervical cancer, endometrial cancer, ovarian cancer, bile duct cancer, esophageal cancer, liver cancer, head and neck cancer, squamous cell cancer, skin cancer, urinary tract cancer, bladder cancer, prostate cancer, choriocarcinoma, pharyngeal cancer, laryngeal cancer, pleural tumor, arrhenoblastoma, endometrial hyperplasia, endometriosis, embryoma, fibrosarcoma, Kaposi's sarcoma, angioma, cavernous hemangioma, angioblastoma, retinoblastoma, astrocytoma, neurofibroma, oligodendroglioma, medulloblastoma, neuroblastoma, glioma, rhabdomyosarcoma, glioblastoma, osteogenic sarcoma, leiomyosarcoma, Wilm's tumor, and the like.

A therapeutic agent containing the bispecific antibody or the bispecific antibody fragment thereof of the present invention, or a derivative thereof may contain only the antibody or the antibody fragment thereof, or a derivative thereof as an active ingredient, however, in general, it is preferably provided as a pharmaceutical preparation produced using a method known in the technical field of pharmaceutics by mixing it together with one or more pharmacologically acceptable carriers.

Examples of a route of administration include oral administration or parenteral administration such as intraoral, intra-airway, intrarectal, subcutaneous, intramuscular, and intravenous administration. Examples of a dosage form include a spray, a capsule, a tablet, a powder, a granule, a syrup, an emulsion, a suppository, an injection, an ointment, a tape, and the like. Various pharmaceutical preparations can be produced by a conventional method using an excipient, a filler, a binder, a wetting agent, a disintegrating agent, a surfactant, a lubricant, a dispersant, a buffer, a preservative, a solubilizing agent, an antiseptic, a coloring agent, a flavoring agent, a stabilizer, and the like that are generally used.

Examples of the excipient include lactose, fructose, glucose, corn starch, sorbit, crystalline cellulose, sterile water, ethanol, glycerol, physiological saline, a buffer solution, and the like. Examples of the disintegrating agent include starch, sodium alginate, gelatin, calcium carbonate, calcium citrate, dextrin, magnesium carbonate, synthetic magnesium silicate, and the like. Examples of the binder include methyl cellulose or a salt thereof, ethyl cellulose, gum arabic, gelatin, hydroxypropyl cellulose, polyvinylpyrrolidone, and the like. Examples of the lubricant include talc, magnesium stearate, polyethylene glycol, hydrogenated vegetable oil, and the like.

Examples of the stabilizer include amino acids such as arginine, histidine, lysine and methionine, human serum albumin, gelatin, dextran 40, methyl cellulose, sodium sulfite, sodium metasulfite, and the like.

Examples of other additives include syrup, vaseline, glycerin, ethanol, propylene glycol, citric acid, sodium chloride, sodium nitrite, sodium phosphate, and the like.

Examples of the pharmaceutical preparation suitable for oral administration include an emulsion, a syrup, a capsule, a tablet, a powder, a granule, and the like.

A liquid preparation such as an emulsion or a syrup is produced using water, a saccharide such as sucrose, sorbitol, or fructose, a glycol such as polyethylene glycol or propylene glycol, an oil such as sesame oil, olive oil, or soybean oil, a preservative such as p-hydroxybenzoic acid ester, a flavor such as strawberry flavor or peppermint, or the like, as an additive.

A capsule, a tablet, a powder, a granule, or the like can be produced using an excipient such as lactose, glucose, sucrose, or mannitol, a disintegrating agent such as starch or sodium alginate, a lubricant such as magnesium stearate or talc, a binder such as polyvinyl alcohol, hydroxypropyl cellulose, or gelatin, a surfactant such as a fatty acid ester, a plasticizer such as glycerin, or the like as an additive.

Examples of the pharmaceutical preparation suitable for parenteral administration include an injection, a suppository, a spray, and the like. An injection is produced using a carrier composed of a salt solution, a glucose solution, or a mixture of both, or the like.

A suppository is produced using a carrier such as cacao butter, a hydrogenated fat, or carboxylic acid. A spray is produced using a carrier which does not stimulate the buccal or airway mucous membrane of a recipient and disperses the monoclonal antibody or the antibody fragment thereof of the present invention as fine particles so as to facilitate absorption thereof, or the like. Examples of the carrier include lactose, glycerin, and the like. In addition, it can also be produced as an aerosol or a dry powder. Further, a component exemplified as the additive for the pharmaceutical preparation suitable for oral administration can also be added in the above-mentioned parenteral preparation.

An effective amount to be administered as a combination of an effective amount of the bispecific antibody of the present invention and a suitable diluent and a pharmacologically usable carrier is 0.0001 mg to 100 mg per kg of the body weight at one time, and is administered at intervals of 2 days to 8 weeks.

7. Diagnostic Method for Disease Using Bispecific Antibody or Bispecific Antibody Fragment Thereof of the Present Invention By detecting or measuring a cell that has expressed at least one of TfR and the cell surface antigen such as EGFR using the bispecific antibody or the bispecific antibody fragment thereof of the present invention, it is possible to diagnose a disease associated with at least one of TfR and the cell surface antigen such as EGFR, preferably a disease involved in a cell that expresses TfR and the cell surface antigen such as EGFR.

The diagnosis of a malignant tumor or cancer that is a disease associated with at least one of TfR and the cell surface antigen such as EGFR can be carried out by, for example, detecting or measuring at least one of TfR and the cell surface antigen such as EGFR as follows.

First, with respect to biological samples collected from the bodies of a plurality of healthy subjects, at least one of TfR and the cell surface antigen such as EGFR is detected or measured by the following immunological method using the bispecific antibody or the bispecific antibody fragment thereof of the present invention, or a derivative thereof, and then the existing amount of at least one of TfR and the cell surface antigen such as EGFR in the biological samples of the healthy subjects is examined.

Subsequently, the existing amount of at least one of TfR and the cell surface antigen such as EGFR in a biological sample of a test subject is also examined in the same manner, and then the existing amount is compared with the existing amount of the healthy subjects. When the existing amount of at least one of TfR and the cell surface antigen such as EGFR of the test subject increases as compared with that of the healthy subjects, the test subject is diagnosed as having cancer. With respect also to the diagnosis of the other diseases associated with at least one of TfR and the cell surface antigen such as EGFR, the diagnosis can be carried out in the same manner.

The immunological method is a method for detecting or measuring the amount of an antibody or the amount of an antigen using a labeled antigen or antibody. Examples thereof include a radioactive material labeled immune antibody method, an enzyme immunoassay method, a fluorescence immunoassay method, a luminescence immunoassay method, a Western blotting method, a physicochemical method, and the like.

Examples of the radioactive material labeled immune antibody method include a method in which the bispecific antibody or the antibody fragment thereof of the present invention is allowed to react with an antigen or a cell or the like that has expressed an antigen, and further allowed to react with an anti-immunoglobulin antibody or a binding fragment subjected to radiolabeling, followed by measurement with a scintillation counter or the like.

Examples of the enzyme immunoassay method include a method in which the bispecific antibody or the bispecific antibody fragment thereof of the present invention is allowed to react with an antigen or a cell or the like that has expressed an antigen, and further allowed to react with an anti-immunoglobulin antibody or a binding fragment subjected to labeling, followed by measurement of a coloring dye with an absorptiometer. For example, a sandwich ELISA method and the like are exemplified.

As a labeling substance used in the enzyme immunoassay method, a known enzyme label [enzyme immunoassay method, IGAKU-SHOIN Ltd. (1987)] can be used. For example, an alkaline phosphatase label, a peroxidase label, a luciferase label, a biotin label, or the like is used.

The sandwich ELISA method is a method in which after binding an antibody to a solid phase, an antigen that is a detection or measurement target is trapped, and then a second antibody is allowed to react with the trapped antigen. In the ELISA method, two types of antibodies that are antibodies or antibody fragments binding to an antigen desired to be detected or measured and have different antigen-binding domains are prepared, and among them, a first antibody or antibody fragment is adsorbed onto a plate (for example, a 96-well plate) in advance, and subsequently, a second antibody or antibody fragment is labeled with a fluorescent substance such as FITC, an enzyme such as peroxidase, biotin, or the like beforehand. Cells separated from the inside of the living body or a homogenate liquid thereof, tissues or a homogenate liquid thereof, a cell culture supernatant, serum, pleural effusion, ascites, intraocular fluid, or the like is allowed to react with the plate on which the antibody is adsorbed, and thereafter to react with the labeled antibody or antibody fragment, and then, a detection reaction is carried out according to the labeling substance. From a calibration curve prepared by serially diluting an antigen at a known concentration, the antigen concentration in the test sample is calculated.

As the antibody used in the sandwich ELISA method, either a polyclonal antibody or a monoclonal antibody may be used, and an antibody fragment such as Fab, Fab', or F(ab)$_2$ may be used. The combination of the two types antibodies used in the sandwich ELISA method may be a combination of monoclonal antibodies or antibody fragments thereof that bind to different epitopes, or may be a combination of a polyclonal antibody and a monoclonal antibody or an antibody fragment thereof.

As the fluorescence immunoassay method, measurement is carried out by, for example, a method described in the document [Monoclonal Antibodies—Principles and Practice, Third Edition, Academic Press (1996), Monoclonal Antibody Experimental Manual, Kodansha scientific books (1987)], or the like. As a labeling substance used in the fluorescence immunoassay method, a known fluorescent label [Fluorescent Antibody Method, Soft Science, Inc. (1983)] can be used. For example, FITC, RITC, or the like is used.

As the luminescence immunoassay method, measurement is carried out by, for example, a method described in the document [Bioluminescence and Chemiluminescence Clinical Test 42, Hirokawa-Shoten Ltd. (1998)], or the like. As a labeling substance used in the luminescence immunoassay method, a known luminescent label is exemplified, and for example, an acridinium ester, lophine, or the like is used.

As the Western blotting method, measurement is carried out by fractionating an antigen or a cell or the like that has expressed an antigen by SDS (sodium dodecyl sulfate)—PAGE [Antibodies—A Laboratory Manual Cold Spring Harbor Laboratory (1988)], thereafter blotting the gel onto a polyvinylidene fluoride (PVDF) membrane or a nitrocellulose membrane, allowing an antibody or an antibody fragment that binds to the antigen to react with the membrane, and then further allowing an anti-IgG antibody or an antibody fragment thereof labeled with a fluorescent substance such as FITC, labeled with an enzyme such as peroxidase, or labeled with biotin, or the like to react therewith, followed by visualizing the label. One example is shown below.

First, cells or tissues that have expressed a polypeptide having a desired amino acid sequence are lysed, and 0.1 to 30 µg in terms of protein amount per lane is electrophoresed by an SDS-PAGE method under reducing conditions. Subsequently, the electrophoresed protein is transferred to a PVDF membrane and is allowed to react with PBS containing 1 to 10% BSA (hereinafter referred to as BSA-PBS) for 30 minutes at room temperature to perform a blocking operation. Then, the bispecific antibody of the present invention is allowed to react therewith, and the membrane is washed with PBS containing 0.05 to 0.1% Tween 20 (Tween-PBS), and then a goat anti-mouse IgG labeled with peroxidase is allowed to react therewith for 2 hours at room temperature. By washing with Tween-PBS, and detecting a band to which the antibody is bound using ECL Western Blotting Detection Reagents (manufactured by Amersham, Inc.) or the like, an antigen is detected. As the antibody used for detection by Western blotting, an antibody capable of binding to a polypeptide that does not retain a natural conformation is used.

As the physicochemical method, for example, by binding at least one of TfR and the cell surface antigen such as EGFR which are antigens and the bispecific antibody or the bispecific antibody fragment thereof of the present invention, an aggregate is formed, and the aggregate is detected. As another physicochemical method, a capillary tube method, a one-dimensional immunodiffusion method, an immunoturbidimetric method, a latex immunoturbidimetric method [Outline of Clinical Examination Method, KANEHARA & Co., LTD. (1998)], or the like can also be used.

In the latex immunoturbidimetric method, when a carrier such as a polystyrene latex having a particle diameter of about 0.1 to 1 µm sensitized with an antibody or an antigen is used to cause an antigen-antibody reaction with a corresponding antigen or antibody, the scattered light is increased in a reaction solution and the transmitted light is decreased. The antigen concentration or the like in a test sample is measured by detecting this change as an absorbance or an integrating sphere turbidity.

On the other hand, for the detection or measurement of a cell that has expressed at least one of TfR and the cell surface antigen such as EGFR, a known immunological detection method can be used, but it is preferred to use an immunoprecipitation method, an immunocytological staining method, an immunohistological staining method, a fluorescent antibody staining method, or the like.

As the immunoprecipitation method, a cell or the like that has expressed at least one of TfR and the cell surface antigen such as EGFR is allowed to react with the bispecific antibody or the antibody fragment thereof of the present invention, and then a carrier having a specific binding ability to an immunoglobulin such as Protein G Sepharose is added thereto, thereby precipitating an antigen-antibody complex.

Alternatively, it can also be carried out by the following method. First, the bispecific antibody or the bispecific antibody fragment thereof of the present invention is immobilized on a 96-well plate for ELISA, followed by blocking with BSA-PBS. Subsequently, BSA-PBS is discarded, and the plate is well washed with PBS, and then, a lysate solution of cells or tissues that have expressed at least one of TfR and the cell surface antigen such as EGFR is allowed to react therewith. From the plate after being well washed, an immunoprecipitated material is extracted with a sample buffer for SDS-PAGE, and then detected by the above-mentioned Western blotting.

The immunocytological staining method or the immunohistological staining method is a method in which a cell or a tissue that has expressed an antigen or the like is treated with a surfactant or methanol, or the like for enhancing the permeability of the antibody in some cases, and then allowed to react with the bispecific antibody of the present invention, and further react with an anti-immunoglobulin antibody or a binding fragment thereof fluorescently labeled with FITC or the like, labeled with an enzyme such as peroxidase, or labeled with biotin, or the like, and thereafter the label is visualized, and then observed with a microscope. In addition, detection can be carried out by a fluorescent antibody staining method in which a fluorescently labeled antibody is allowed to react with a cell and analyzed with a flow cytometer [Monoclonal Antibodies—Principles and Practice, Third edition, Academic Press (1996), Monoclonal Antibody Experimental Manual, Kodansha scientific books (1987)]. In particular, the bispecific antibody or the bispecific antibody fragment thereof of the present invention enables detection of at least one of TfR and the cell surface antigen such as EGFR expressed on a cell membrane by a fluorescent antibody staining method.

In addition, when the FMAT 8100 HTS system (manufactured by Applied Biosystems, Inc.) or the like is used among the fluorescent antibody staining methods, it is possible to measure the amount of an antigen or the amount of an antibody without separating the formed antibody-antigen complex from a free antibody or antigen not involved in the formation of the antibody-antigen complex.

EXAMPLES

Hereinafter, the present invention will be more specifically described by way of Examples, however, the present invention is not limited to the following Examples.

[Example 1] Preparation of Soluble Human and Monkey TfR Antigens and Soluble Human and Monkey EGFR Antigens 1. Preparation of Soluble Antigens of Human TfR and Monkey TfR Each of the extracellular domain proteins of human and monkey TfR in which FLAG-Fc was added to the N terminus was produced by the method described below. The nucleotide sequence encoding the extracellular domain of human TfR is represented by SEQ ID NO: 1, the amino acid sequence deduced from the nucleotide sequence is represented by SEQ ID NO: 2, the nucleotide sequence encoding the extracellular domain of monkey TfR is represented by SEQ ID NO: 3, and the amino acid sequence deduced from the nucleotide sequence is represented by SEQ ID NO: 4.
(1) Production of FLAG-Fc-Human TfR and FLAG-Fc-Monkey TfR Vectors A gene fragment of the extracellular domain of human TfR composed of the nucleotide sequence represented by SEQ ID NO: 1 was synthesized based on the gene sequence of human TfR (GenBank Accession Number: NM_003234.2, SEQ ID NO: 5, an amino acid sequence encoded by the gene is represented by SEQ ID NO: 6).

An INPEP4 vector (manufactured by Biogen-IDEC GmbH) containing a FLAG-tag and an Fc region of human IgG was digested with restriction enzymes BamHI and KpnI, and the nucleotide sequence represented by SEQ ID NO: 1 was inserted into the vector, whereby a FLAG-Fc-human TfR expression vector was produced.

In the same manner, a FLAG-Fc-monkey TfR expression vector containing a gene fragment of the extracellular domain of monkey TfR composed of the nucleotide sequence represented by SEQ ID NO: 3 was produced based on the gene sequence of monkey TfR (SEQ ID NO: 7, an amino acid sequence encoded by the gene is represented by SEQ ID NO: 8).
(2) Production of FLAG-Fc-Human TfR and FLAG-Fc-Monkey TfR Proteins The FLAG-Fc-human TfR expression vector produced in 1-(1) was introduced into HEK 293 cells using FreeStyle (trademark) 293 Expression System (manufactured by Thermo Fisher, Inc.) and the cells were cultured to express a protein in a transient expression system. The culture supernatant was collected 5 days after introduction of the vector, and filtered through a membrane filter (manufactured by Millipore Corporation) having a pore diameter of 0.22 μm.

The culture supernatant was subjected to affinity purification using a Protein A resin (MabSelect, manufactured by GE Healthcare, Inc.). The antibody adsorbed on the Protein A was washed with Dulbecco's phosphate buffered saline [D-PBS(-) without Ca and Mg, liquid; hereinafter referred to as D-PBS(-), manufactured by Nacalai Tesque, Inc.], eluted with a 100 mM sodium citrate buffer solution (pH 3.5) and collected in a tube containing 2 M Tris-HCl (pH 8.5).

Subsequently, the buffer solution was replaced with D-PBS(-) by ultrafiltration using VIVASPIN (manufactured by Sartrius stealin), followed by filter sterilization with a membrane filter Millex-Gv (manufactured by Millipore Corporation) having a pore diameter of 0.22 μm, whereby a FLAG-Fc-human TfR protein was produced. In the same manner, a FLAG-Fc-monkey TfR protein was produced using the FLAG-Fc-monkey TfR expression vector produced in 1-(1). The concentration of the obtained protein was determined by measuring an absorbance at a wavelength of 280 nm and calculating it using an extinction coefficient estimated from the amino acid sequence of each protein.
2. Preparation of Soluble Antigens of Human EGFR and Monkey EGFR Each of the extracellular domain proteins of human and monkey EGFR in which FLAG-Fc or GST was added to the C terminus was produced by the method described below. The nucleotide sequence encoding the signal sequence and the extracellular domain of human EGFR is represented by SEQ ID NO: 9, the amino acid sequence deduced from the nucleotide sequence is represented by SEQ ID NO: 10, the nucleotide sequence encoding the signal sequence and the extracellular domain of monkey EGFR is represented by SEQ ID NO: 11, and the amino acid sequence deduced from the nucleotide sequence is represented by SEQ ID NO: 12.

A gene fragment of the extracellular domain of human EGFR composed of the nucleotide sequence represented by SEQ ID NO: 9 was synthesized based on the gene sequence of human EGFR (GenBank Accession Number: NM_005228.4, SEQ ID NO: 13, an amino acid sequence encoded by the gene is represented by SEQ ID NO: 14). A gene fragment of the extracellular domain of monkey EGFR composed of the nucleotide sequence represented by SEQ ID NO: 11 was synthesized in the same manner. Each of human and monkey EGFR-FLAG-Fc proteins and human and monkey EGFR-GST proteins was obtained in the same manner as described in 1-(1) and (2).

The concentration of each of the obtained proteins was determined by measuring an absorbance at a wavelength of 280 nm and calculating it using an extinction coefficient estimated from the amino acid sequence of each protein.

[Example 2] Production of CHO Cells for Membrane Expression of Human or Monkey TfR The human TfR gene represented by SEQ ID NO: 5 was cloned into pKANTEX (described in U.S. Pat. No. 6,423,511), whereby a human TfR expression vector for membrane expression, pKANTEX-human TfR full was obtained.

The obtained expression vector pKANTEX-human TfR full was introduced into CHO cells, and the cells were cultured to express a protein in a transient expression system. After the introduction of the gene, the cells were subjected to single cell cloning, whereby human TfFR/CHO cells were obtained.

The monkey TfR gene represented by SEQ ID NO: 7 was cloned in the same manner, whereby monkey TfR/CHO cells were obtained.

The preparation of cells stained with Carblxyl fluorescein succininidyl ester (CFSE) was carried out by the following method. The human TfFR/CHO cells and the monkey TfR/CHO cells were detached with 0.02% EDTA-PBS (Nacalai Tesque, Inc.) and collected, and thereafter, CFSE (Sigma-Aldrich Co. LLC) was added thereto so as to give a final concentration of 0.2 μM, and allowed to react therewith at room temperature for 10 minutes, and then, D-PBS(−) containing 10% fetal bovine serum (Nacalai Tesque, Inc.) was added thereto, and the cells were incubated at 37° C. for 10 minutes. The cells after the reaction were centrifuged, and then, washed with 1% BSA-PBS (Nacalai Tesque, Inc.) containing 0.02% EDTA and 0.05% NaN$_3$. The obtained CFSE-stained cells were cryopreserved by CELLBANKER 1 (Nippon Zenyaku Kogyo Co., Ltd.).

[Example 3] Immunization of Human Antibody-Producing Animal

In order to obtain a monoclonal antibody against human TfR or human EGFR, a human antibody-producing animal was immunized with FLAG-Fc-human TfR or human EGFR-FLAG-Fc mixed with an adjuvant a total of 4 to 5 times. The serum was collected from the immunized animal, and the binding activity to human TfR or human EGFR was analyzed by ELISA to confirm that the antibody titer increased.

[Example 4] Acquisition of Anti-TfR Antibody

1. Production of TfR-Immunized Human Antibody M13 Phage Library in which Light Chain is A27

RNA was extracted from the spleen cells or the peripheral blood mononuclear cells (PBMCs) obtained from the immunized animal using RNeasy Mini kit (manufactured by QIAGEN, Inc.), cDNAs were amplified using SMARTer RACE cDNA amplification kit (manufactured by Clontech Laboratories, Inc.), and further, a VH gene fragment was amplified by PCR. The VH gene fragment and the A27 sequence that is a human antibody germ-line sequence and is composed of the nucleotide sequence represented by SEQ ID NO: 15 were inserted into a phagemid pCANTAB 5E (manufactured by Amersham Pharmacia, Inc.) so as to transform *E. coli* TG1 (manufactured by Lucigen Corporation), whereby plasmids were obtained.

Note that the A27 sequence encodes a light chain variable region (VL) of a human antibody composed of the amino acid sequence represented by SEQ ID NO: 16, and the amino acid sequences of CDRs 1, 2, and 3 of the VL (also represented by LCDRs 1, 2, and 3, respectively) are represented by SEQ ID NOS: 17, 18, and 19, respectively.

By infecting VCSM13 Interference Resistant Helper Phage (manufactured by Agilent Technologies, Inc.) with the obtained plasmids, a TfR-immunized human antibody M13 phage library that has a VL gene composed of the A27 sequence and includes a library of VH genes was obtained.

2. Acquisition of Anti-TfR Monoclonal Antibody in which Light Chain is A27

By using the TfR-immunized human antibody M13 phage library, an anti-TfR monoclonal antibody including the VL encoded by A27 was obtained by the following phage display method.

(1) Protein Panning Using Protein Immobilized Tube

MAXISORP STARTUBE (manufactured by NUNC, Inc.) in which human TfR (manufactured by BBI Solutions, Inc.) was immobilized and a portion to which the human TfR was not bound was blocked using SuperBlock Blocking Buffer (manufactured by Thermo Fisher, Inc.), and the human antibody M13 phage library were allowed to react at room temperature for 1 to 2 hours, and washing was performed 3 times each with D-PBS(−) and PBS containing 0.1% TWEEN® 20 (polysorbate) (hereinafter referred to as PBS-T, manufactured by Wako Pure Chemical Industries, Ltd.), and thereafter, the phage was eluted with 0.1 M Gly-HCl (pH 2.2), and the eluate was neutralized with 2 M Tris-HCl (pH 8.5).

(2) Panning using CHO Cells Expressing Human TfR or Monkey TfR on Membrane

The human antibody M13 phage library was allowed to react with CHO cells on ice for 30 minutes, the supernatant in which the cells were removed by centrifugation was collected, whereby a phage solution after reacting with the CHO cells was prepared. After the phage solution and the human TfR/CHO stained with CFSE obtained in Example 1 were allowed to react on ice for 30 minutes to 1 hour, the supernatant was removed by centrifugation. After washing with D-PBS(−) containing 5% fetal bovine serum, 1 mM EDTA, and 0.1% NaN$_3$ (hereinafter referred to as SM buffer) was repeated a plurality of times, as a primary antibody, an anti-M13 antibody (GE Healthcare, Inc.) was added thereto and allowed to react on ice for 30 minutes. The supernatant was removed by centrifugation, and washing with the SM buffer was repeated a plurality of times, and thereafter, as a secondary antibody, an APC-labeled goat anti-mouse IgG (H+L) antibody (Southern Biotech, Inc.) was added thereto and allowed to react on ice for 30 minutes. The supernatant was removed by centrifugation, and washing with the SM buffer was repeated a plurality of times, and thereafter, 7-aminoactinomycin D (AAD) (BD Biosciences, Inc.) was added thereto and allowed to react on ice for 10 minutes. Thereafter, sorting of a viable cell fraction negative for 7-AAD and an antigen-expressing cell fraction positive for CFSE was carried out using a flow cytometer (BD Biosciences, Inc., FACS Aria III). Note that in a round in which the condensation of the antigen-expressing cell binding phage could be confirmed, a phage binding fraction positive for APC was further sorted in addition to the above. The phage was eluted from the sorted cells with 0.1 M Gly-HCl (pH 2.2), and the eluate was neutralized with 2 M Tris-HCl (pH 8.5).

Cell panning using monkey/CHO cells was also carried out in the same manner. The eluted phage was used to infect TG1 competent cells to amplify the phage. The operation of the above (1) or (2) was repeated 2 or 3 times to concentrate the phage displaying scFv that specifically binds to human TfR. The concentrated phage was used to infect TG1, which was then inoculated in a SOBAG plate (2.0% tryptone, 0.5% Yeast extract, 0.05% NaCl, 2.0% glucose, 10 mM MgCl$_2$, 100 μg/mL ampicillin, and 1.5% agar) to form a colony.

The colony was inoculated and cultured, and then infected with VCSM13 Interference Resistant Helper Phage, and cultured again, whereby a monoclonal phage was obtained. By using the obtained monoclonal phage, a clone that binds to both human and monkey TfR was selected with a flow cytometer (Millipore Corporation, Guava easy Cyte HT).

The flow cytometry was carried out by adding the phage clone to the human or monkey TfR/CHO in Example 2. After the reaction was allowed to proceed under 4° C. for 30 minutes, each well was washed 3 times with PBS-T.

ELISA was carried out for confirming the TfR reactivity of the monoclonal phage. Specifically, it was carried out by adding a phage solution diluted with PBS-T containing 10% Block Ace (manufactured by Dainippon Pharmaceutical Co., Ltd.) to a 96-well immunoplate (NUNC, Inc.) on which an antigen protein was immobilized to allow a reaction to proceed at room temperature for 1 hour, followed by washing with PBS-T, and then, adding an anti-M13 antibody (manufactured by GE Healthcare, Inc.) labeled with horse-radish peroxidase diluted with 1% BSA-PBS thereto to allow a reaction to proceed at room temperature for 1 hour. After the plate was washed with PBS-T, a TMB chromogenic substrate solution (manufactured by DAKO, Inc.) was added thereto to allow a reaction to proceed at room temperature, and then, the coloring reaction was stopped by adding a 2 N HCl solution thereto, and an absorbance at a wavelength of 450 nm (reference wavelength: 570 nm) was measured using a plate reader (Emax, Molecular Devices, Inc.).

A sequence analysis was carried out for clones that bound to both human and monkey TfR, whereby anti-TfR antibodies having VL encoded by A27 were obtained. In Table 1, SEQ ID NOS of the entire nucleotide sequence encoding VH of each of the obtained anti-TfR antibodies and the amino acid sequence deduced from the nucleotide sequence, and the amino acid sequences of CDRs 1 to 3 of the VH (hereinafter sometimes referred to as HCDRs 1 to 3) are shown. Note that "-" in the table indicates that the sequence information is not described.

at 100 μL/well, and the cells were cultured for 8 to 10 days in a $CO_2$ incubator (5% $CO_2$ at 37° C.).

(2) Hybridoma Screening

The binding activity of the antibody contained in the hybridoma culture supernatant to TfR was evaluated by ELISA. The hybridoma culture supernatant was used as a test sample, and measurement was carried out in the same manner as in the above 2. (2).

(3) Hybridoma Subcloning

The cells in the wells that were positive in the screening were subcloned and cultured in the cloning medium for about 7 to 10 days.

(4) Cloning and Sequence Determination of Antibody Variable Region Gene

Total RNA was extracted from the cloned hybridoma using RNeasy Mini kit (QIAGEN, Inc.), and the antibody gene was amplified by a 5'-RACE method. In the synthesis of a cDNA for RACE, SMARTer RACE Kit (Clontech Laboratories, Inc.) was used. The amplified antibody vari-

TABLE 1

| | SEQ ID NO of VH of anti-TfR Antibody | | | | | | | | |
|---|---|---|---|---|---|---|---|---|---|
| Clone name | PSM4072 | R327 | TfR1071 | TfR4016 | Cyno186 | Cyno292 | TfR1007 | Cyno163 | T14 |
| Nucleotide sequence of VH | 20 | 25 | 30 | 35 | 40 | 45 | — | — | — |
| Amino acid sequence of VH | 21 | 26 | 31 | 36 | 41 | 46 | 50 | 51 | 52 |
| Amino acid sequence of HCDR1 | 22 | 27 | 32 | 37 | 42 | 47 | 107 | — | — |
| Amino acid sequence of HCDR2 | 23 | 28 | 33 | 38 | 43 | 48 | 108 | — | — |
| Amino acid sequence of HCDR3 | 24 | 29 | 34 | 39 | 44 | 49 | 109 | — | — |

3. Acquisition of Anti-TfR Antibody in which Light Chain is Other than A27

(1) Hybridoma Production by Cell Fusion

A mouse myeloma cell line P3-U1 (P3X63Ag8U.1, ATCC CRL-1597) was cultured in S-Clone cloning medium (EIDIA Co., Ltd.) and adapted to serum free conditions, and then used as a parent cell line for cell fusion. After the spleen of the immunized animal was aseptically collected and hemolyzed with RED BLOOD CELL LYSING BUFFER (Sigma-Aldrich Co. LLC), the cells were washed twice with PBS and mixed with P3-U1 so that the number of spleen cells and P3-U1 satisfied the following conditions: spleen cells: P3-U1=8:1, and then, the mixture was centrifuged (1200 rpm for 5 minutes).

After the cell clusters in the obtained precipitate fraction were well loosened, 0.5 mL of a mixed solution of 1 g of polyethylene glycol-1000 (PEG-1000, Junsei Chemical Co., Ltd.), 1 mL of MEM medium (Nacalai Tesque, Inc.), and 0.35 mL of dimethyl sulfoxide (Sigma-Aldrich Co. LLC) was added thereto at 37° C. while stirring, and 1 mL of MEM medium was added thereto 5 times every minute, and then, MEM medium was added thereto so that the total amount became 50 mL.

After the cell suspension was centrifuged (900 rpm for 5 minutes) and the cells in the obtained precipitate fraction were gently loosened, the spleen cells were suspended at a cell density of $1.5 \times 10^7$ cells/9 mL in S-Clone cloning medium supplemented with HAT SUPPLEMENT (Thermo Fisher Scientific, Inc.). In a 96-well culture plate, HAT-supplemented cloning medium was dispensed in advance at 100 μL/well, and the cell suspension was dispensed therein able region fragment was cloned using TOPO TA Cloning (Invitrogen, Inc.) to confirm the nucleotide sequence of the DNA fragment.

Among the obtained anti-TfR antibodies, the amino acid sequences deduced from the nucleotide sequences encoding the variable regions of the heavy chain and the light chain of clone 2230 are represented by SEQ ID NO: 53 and SEQ ID NO: 54, respectively.

4. Construction of Vector for Expressing Obtained Anti-TfR Antibody

Soluble IgG expression vectors into which genes of the obtained anti-TfR antibodies were integrated, respectively, were produced. First, the A27 gene encoding the common VL was subcloned into N5KG4PE (IDEC Pharmaceuticals) or N5KG4PE R409K (described in WO 2006/033386).

Thereafter, the VH gene was subcloned into N5KG4PE or N5KG4PE R409K, whereby expression vectors for the anti-TfR monoclonal antibodies having the constant region of human IgG4PE or the constant region of human IgG4PE R409K were obtained.

Further, in order to use anti-TfR monoclonal antibodies TfR434 and TfR435 that are TfR neutralizing antibodies described in WO 2012/153707 as positive control antibodies of the anti-TfR antibody, an expression vector was produced. The amino acid sequences of VH of TfR434 and TfR435 are represented by SEQ ID NOS: 55 and 56, respectively, and the amino acid sequence of VL thereof is represented by SEQ ID NO: 57.

Genes encoding VH and VL of TfR435 were synthesized and subcloned into an N5KG1 vector (described in WO 2003/033538), whereby an expression vector for the anti- TfR monoclonal antibody TfR435 having the constant region of human IgG1 was obtained.

Hereinafter, the monoclonal antibodies are denoted by the clone names.

[Example 5] Acquisition of Antibody Against Cell Surface Antigen (1) Production of EGFR Antibody
1. Production of EGFR-Immunized Human Antibody M13 Phage Library An EGFR-immunized human antibody M13 phage library that has a VL gene composed of the A27 sequence or the VL gene of the anti-TfR antibody 2230 and includes a library of VH genes was obtained in the same manner as in Example 4, 1.

2. Acquisition of Anti-EGFR Antibody

By using MAXISORP STARTUBE (manufactured by NUNC, Inc.) in which human EGFR-Fc or monkey EGFR-Fc obtained in Example 1 was immobilized and a portion to which the antigen was not bound was blocked using Super-Block Blocking Buffer (manufactured by Thermo Fisher, Inc.), and the EGFR-immunized human antibody M13 phage library, a phage displaying scFv that specifically binds to human EGFR and monkey EGFR was monocloned in the same manner as in Example 4, 2.

The operation was repeated 3 to 5 times to concentrate the phage displaying scFv that specifically binds to human and monkey EGFR-Fc.

The confirmation of a clone that specifically recognizes human and monkey EGFR-Fc was carried out by the ELISA method. ELISA was carried out in the same manner as in Example 4 by immobilizing human or monkey EGFR-Fc in Example 1.

From the clones that bound to both human and monkey EGFR, the following three clones having high affinity comparable to cetuximab were selected. A sequence analysis was carried out for the three clones, whereby anti-EGFR antibodies having VL encoded by A27 were obtained. By using the same representation method as in Table 1, the sequence information of VH of each of the anti-EGFR antibodies are shown in Table 2.

TABLE 2

Sequence Information of VH anti-EGFR Antibody

|  | E08 | E12 | E17 |
| --- | --- | --- | --- |
| Nucleotide sequence of VH | SEQ ID NO: 58 | SEQ ID NO: 63 | SEQ ID NO: 68 |
| Amino acid sequence of VH | SEQ ID NO: 59 | SEQ ID NO: 64 | SEQ ID NO: 69 |
| Amino acid sequence of HCDR1 | SEQ ID NO: 60 | SEQ ID NO: 65 | SEQ ID NO: 70 |
| Amino acid sequence of HCDR2 | SEQ ID NO: 61 | SEQ ID NO: 66 | SEQ ID NO: 71 |
| Amino acid sequence of HCDR3 | SEQ ID NO: 62 | SEQ ID NO: 67 | SEQ ID NO: 72 |

Similarly, anti-EGFR antibodies having the same VL as the anti-TfR antibody 2230 were obtained. Among the obtained anti-EGFR antibodies, the amino acid sequences deduced from the nucleotide sequences encoding the heavy chain variable regions of clones KME07, KME09, and KME11 are represented by SEQ ID NO: 73, SEQ ID NO: 74, and SEQ ID NO: 75, respectively.

Soluble IgG expression vectors into which genes of the obtained anti-EGFR antibodies were integrated, respectively, were produced in the same manner as in Example 4. As the constant region, the constant region of human IgG4PE or human IgG4PE R409K was used.

Further, as the positive control antibody of the anti-EGFR antibody, an antibody having the variable region of the anti-EGFR monoclonal antibody C225 described in WO 1996/040210 (hereinafter referred to as cetuximab) was produced. The amino acid sequence of VH of cetuximab is represented by SEQ ID NO: 76. Further, the amino acid sequence of VL of cetuximab is represented by SEQ ID NO: 77.

Genes encoding VH and VL of cetuximab were synthesized and subcloned into an N5KG1 vector in the same manner as in Example 4, whereby an expression vector for cetuximab having the constant region of human IgG1 was obtained.

(2) Production of Anti-Glypican-3 Antibody

An antibody having a variable region of an anti-glypican-3 monoclonal antibody HN3 described in WO 2012/145469 was produced. The amino acid sequence of VH of HN3 is represented by SEQ ID NO: 78. A gene encoding VH of HN3 was synthesized and subcloned into N5KG4PE R409K in the same manner as in Example 4, whereby an expression vector for the anti-glypican-3 monoclonal antibody HN3 having the constant region of human IgG4PE R409K was obtained.

[Example 6] Construction of Expression Vector for Bispecific Antibody that Binds to TfR and Cell Surface Antigen A bispecific antibody that has a structure shown in FIG. 1(A) and binds to human and monkey TfR as well as human and monkey EGFR was produced by the following method. In FIGS. 1(A) to 1(C), VH included in the N-terminal side polypeptide is referred to as VH1, and VH included in the C-terminal side IgG portion is referred to as VH2. As the form of the bispecific antibody, the form described in WO 2009/131239 was adopted.

VH1 and VH2 are either VH of the antibody obtained in Example 4 or Example 5, and VH1 and VH2 are VHs of the antibodies against different antigens.

In the following description, when the N-terminal side polypeptide and the IgG-type antibody are bound through a linker, a gene encoding the amino acid sequence of the linker is referred to as a linker gene.

As the linker sequence of the bispecific antibody produced by the following steps, a sequence in which a portion of the hinge region of IgG4 (ES (SEQ ID NO: 79), ESKYG (SEQ ID NO: 80), ESKYGPP (SEQ ID NO: 81), or the like) is linked, or a GS linker (GGGGS (SEQ ID NO: 82) or a repetitive sequence in which GGGGS (SEQ ID NO: 82) is repeated 3 times) was used. Further, as the heavy chain constant region of the IgG portion, the heavy chain constant region of IgG4PE or IgG4PE R409K (the nucleotide sequence is represented by SEQ ID NO: 83, and the amino acid sequence is represented by SEQ ID NO: 84) described in WO 2006/033386 was used.

Hereinafter, a bispecific antibody including the variable region of an anti-EGFR antibody in the N-terminal side polypeptide and including the variable region of an anti-TfR antibody in the IgG portion is referred to as an EGFR-TfR bispecific antibody. Further, for example, an EGFR-TfR bispecific antibody including the variable region of the anti-EGFR antibody E12 and the variable region of the anti-TfR antibody TfR1071 is referred to as E12-TfR1071. Similarly, a bispecific antibody including the variable region of an anti-TfR antibody in the N-terminal side polypeptide and the variable region of an anti-EGFR antibody in the IgG portion is referred to as a TfR-EGFR bispecific antibody.

In addition, for example, a TfR-EGFR bispecific antibody including the variable region of the anti-TfR antibody TfR1071 and the variable region of the anti-EGFR antibody E12 is referred to as TfR1071-E12. An antibody having a linker between the N-terminal side polypeptide and the IgG portion is referred to as an EGFR-linker-TfR bispecific antibody.

In addition, for example, an EGFR-linker-TfR bispecific antibody including the variable region of an anti-EGFR antibody E08, the variable region of the anti-TfR antibody TfR1071, and ES (SEQ ID NO: 79) as the linker is referred to as E08-ES-TfR1071. Note that in this notation method, the GS linker (SEQ ID NO: 82) is denoted by GS, and the sequence obtained by repeating the GS linker 3 times is denoted by GS3.

The name, structure, and linker of the bispecific antibody, the clone name of the anti-TfR antibody used in the production of the antibody, and the clone name of the antibody against the cell surface antigen are shown in Table 3. Note that "—" in the table indicates that the linker is not used and the sequence corresponding thereto is not present.

TABLE 3

| Name of bispecific antibody | Structure | VH1 | Linker | SEQ ID NO: | VH2 |
|---|---|---|---|---|---|
| E08-PSM4072 | FIG. 1(A) | E08 | — | | PSM4072 |
| E08-R327 | FIG. 1(A) | E08 | — | | R327 |
| E08-TfR1071 | FIG. 1(A) | E08 | — | | TfR1071 |
| E08-TfR4016 | FIG. 1(A) | E08 | — | | TfR4016 |
| E08-cyno186 | FIG. 1(A) | E08 | — | | cyno186 |
| E08-cyno292 | FIG. 1(A) | E08 | — | | cyno292 |
| E08-T14 | FIG. 1(A) | E08 | — | | T14 |
| E08-ES-TfR1071 | FIG. 1(A) | E08 | ES | 79 | TfR1071 |
| E08-ES-cyno186 | FIG. 1(A) | E08 | ES | 79 | cyno 186 |
| E08-ESKYG-TfR1071 | FIG. 1(A) | E08 | ESKYG | 80 | TfR1071 |
| E08-ESKYG-cyno186 | FIG. 1(A) | E08 | ESKYG | 80 | cyno186 |
| E08-ESKYGPP-TfR1071 | FIG. 1(A) | E08 | ESKYGPP | 81 | TfR1071 |
| E08-ESKYGPP-cyno186 | FIG. 1(A) | E08 | ESKYGPP | 81 | cyno186 |
| PSM4072-E08 | FIG. 1(A) | PSM4072 | — | | E08 |
| R327-E08 | FIG. 1(A) | R327 | — | | E08 |
| TfR1071-E08 | FIG. 1(A) | TfR1071 | — | | E08 |
| TfR4016-E08 | FIG. 1(A) | TfR4016 | — | | E08 |
| cyno186-E08 | FIG. 1(A) | cyno186 | — | | E08 |
| cyno292-E08 | FIG. 1(A) | cyno292 | — | | E08 |
| T14-E08 | FIG. 1(A) | T14 | — | | E08 |
| E12-PSM4072 | FIG. 1(A) | E12 | — | | PSM4072 |
| E12-TfR1007 | FIG. 1(A) | E12 | — | | TfR1007 |
| E12-cyno163 | FIG. 1(A) | E12 | — | | cyno 163 |
| E12-R327 | FIG. 1(A) | E12 | — | | R327 |
| E12-TfR1071 | FIG. 1(A) | E12 | — | | TfR1071 |
| E12-TfR4016 | FIG. 1(A) | E12 | — | | TfR4016 |
| E12-cyno186 | FIG. 1(A) | E12 | — | | cyno186 |
| E12-cyno292 | FIG. 1(A) | E12 | — | | cyno292 |
| E12-T14 | FIG. 1(A) | E12 | — | | T14 |
| KME07-2230 | FIG. 1(A) | KME07 | — | | 2230 |
| KME09-2230 | FIG. 1(A) | KME09 | — | | 2230 |
| KME11-2230 | FIG. 1(A) | KME11 | — | | 2230 |
| HN3-TfR1071 | FIG. 1(B) | HN3 | — | | TfR1071 |
| HN3-GS-TfR1071 | FIG. 1(B) | HN3 | GS | | TfR1071 |
| HN3-GS3-TfR1071 | FIG. 1(B) | HN3 | GS3 | | TfR1071 |

1. Production of Expression Vector for Light Chain Common-type Bispecific Antibody An expression vector for a light chain common-type bispecific antibody shown in FIG. 1(A) among the bispecific antibodies shown in Table 3 was produced by the method described below.

First, the A27 gene encoding the common VL was subcloned into N5KG4PE R409K (described in WO 2006/033386).

Thereafter, by using a gene (SEQ ID NO: 85), which encodes the same amino acid sequence as that of CH1 of human IgG4, and in which the used codon was changed, as a template, the gene fragment was amplified by PCR using KOD-Plus-Ver.2 (Toyobo Co., Ltd.). By using the VH gene of the antibody obtained in Example 4 or Example 5 as a template, a gene fragment of a VH2 portion was amplified in the same manner.

The two gene fragments were subcloned between the VH1 and the CH1 of the IgG portion of the expression vector of the antibody obtained in Example 4 or Example 5, whereby an expression vector for the bispecific antibody was obtained.

2. Production of Expression Vector for Light Chain Non-Common-type Bispecific Antibody An expression vector for a light chain non-common-type bispecific antibody among the bispecific antibodies shown in Table 3 was produced by the method described below.

An antibody shown in FIG. 1(B) is constituted by one type of vector. First, the A27 gene encoding VL was subcloned into a pCI-OtCAG-G4PE R409K vector containing a nucleotide sequence encoding the constant region of human IgG4PE R409K.

This vector is referred to as pCI-A27. The constant region sequence contained in the pCI-OtCAG_hG4PE R409K vector is a heavy chain constant region of an IgG4 mutant [hereinafter referred to as IgG4PE R409K (WO 2006/033386)] obtained by substituting a Ser residue at position 228 with Pro, a Leu residue at position 235 with Glu, and an Arg residue at position 409 with Lys in the EU index in the heavy chain constant region of human IgG4.

Note that such a vector is a vector produced through total synthesis by introducing a restriction enzyme site necessary for expressing a human antibody gene using a pCI vector of Promega Corporation as a common backbone.

Thereafter, when the VH gene and the linker of the antibody obtained in Example 5 are included, a totally synthesized nucleotide sequence of a polypeptide in which the gene of the linker and the VH gene of the anti-TfR antibody obtained in Example 4 were ligated was subcloned into pCI-A27, whereby the expression vector was obtained.

[Example 7] Preparation of Monoclonal Antibody that Binds to TfR, Monoclonal Antibody that Binds to Cell Surface Antigen, and Bispecific Antibody Each of the anti-TfR monoclonal antibody, the monoclonal antibody against a cell surface antigen, and the bispecific antibody having the binding domains for both antigens subcloned into the antibody expression vectors in Example 4 to Example 6 was expressed and purified by the following methods.

The antibody expression vector was co-transfected into Expi293 cells by Expi293 (trademark) Expression System (Thermo Fisher, Inc.), and after 12 to 16 hours, Transfection Enhancer was added thereto, whereby the antibody or the bispecific antibody was expressed in a transient expression system.

The culture supernatant was collected 4 to 7 days after introduction of the vector, and filtered through a membrane filter (manufactured by Millipore Corporation) having a pore diameter of 0.22 μm, and thereafter, the antibody was subjected to affinity purification using a Protein A resin (MabSelect SuRe, GE Healthcare, Inc.). As the washing solution, D-PBS(−) was used. The antibody or the bispecific antibody adsorbed on the Protein A was eluted with a 100 mM sodium citrate buffer solution (pH 3.5) and collected in a tube containing a 2 M Tris-HCl buffer solution (pH 8.5).

Subsequently, the solution was concentrated using VIVASPIN (manufactured by Sartrius stealin), and the buffer solution was replaced with D-PBS(−) using a Nap Column (manufactured by GE Healthcare, Inc.). Further, in the case where a monomer is purified, a monomer fraction was fractionated from the antibody or bispecific antibody solution using AKTA FPLC (manufactured by GE Healthcare, Inc.) and Superdex High-performance Columns (manufactured by GE Healthcare, Inc.). By performing filter sterilization with an AKTA system membrane filter (Millex-Gv, manufactured by Millipore Corporation) having a pore diameter of 0.22 μm, a purified antibody or a purified bispecific antibody was obtained.

An absorbance at a wavelength of 280 nm of the thus obtained antibody solution or bispecific antibody solution was measured, and the concentration of the purified antibody or the purified bispecific antibody was calculated using an extinction coefficient estimated from the amino acid sequence of each antibody or the bispecific antibody.

[Example 8] Evaluation of Binding Affinity of Bispecific Antibody to Antigen by Biacore For the purpose of confirming the binding activity and the species cross-reactivity of the EGFR-TfR bispecific antibodies obtained in Example 7 to each of human TfR, monkey TfR, human EGFR, and monkey EGFR, by using the FLAG-Fc-human TfR, FLAG-Fc-monkey TfR, human EGFR-GST, and monkey EGFR-GST produced in Example 1, a binding affinity test by a surface plasmon resonance method (SPR method) was carried out. As a measurement device, Biacore T100 (manufactured by GE Healthcare, Inc.) was used.

An anti-human IgG antibody was immobilized on a CM5 sensor chip (manufactured by GE Healthcare, Inc.) using Human Antibody Capture Kit (manufactured by GE Healthcare, Inc.) according to the package insert. A test bispecific antibody prepared at 1 to 3 μg/mL was added to a flow cell for 10 seconds at a flow rate of 10 μL/min.

Subsequently, each of antigen protein solutions (diluted with HBS-EP+ (manufactured by GE Healthcare, Inc.) containing 0.1% BSA) diluted by a factor of 3 in 5 steps from 1 or 9 nM as an analyte was added at a flow rate of 30 μL/min, and a binding reaction of each bispecific antibody and the analyte was measured for 2 minutes and a dissociation reaction was measured for 10 minutes.

The measurement was performed by a single cycle kinetics method. The obtained sensorgram was analyzed using Bia Evaluation Software (manufactured by GE Healthcare, Inc.), and the kinetic constant of each antibody was calculated.

The calculated dissociation constant [kd/ka=$K_D$] of each of the bispecific antibodies for human and monkey EGFR, and the value obtained by dividing the dissociation constant for the human antigen by the dissociation constant for the monkey antigen are shown in Table 4. N/A in the table indicates that the measurement was not performed.

TABLE 4

|  | Human EGFR [nM] | Monkey EGFR [nM] | Human EGFR [nM]/ Monkey EGFR [nM] | Human TfR [nM] | Monkey TfR [nM] | Human TfR [nM]/ Monkey TfR [nM] |
|---|---|---|---|---|---|---|
| E08-TfR1071 | 0.13 | 0.15 | 0.87 | 5.79 | 12.0 | 0.48 |
| E08-cyno186 | N/A | N/A | N/A | 1.56 | 1.97 | 0.79 |
| E12-TfR1071 | 0.21 | 0.25 | 0.84 | 2.42 | 22.2 | 0.11 |
| E12-cyno186 | N/A | N/A | N/A | 10.7 | 56.5 | 0.19 |
| E17-TfR1071 | 0.31 | 0.67 | 0.46 | 4.09 | 26.6 | 0.15 |
| E17-cyno186 | N/A | N/A | N/A | 4.02 | 5.39 | 0.75 |

As shown in Table 4, the $K_D$ values of the EGFR-TfR bispecific antibodies for human TfR and monkey TfR were in the order of $10^{-8}$ to $10^{-9}$ M. The $K_D$ values of the EGFR-TfR bispecific antibodies for monkey TfR are between 1/10 and 10 times the $K_D$ values for human TfR, and therefore, it was demonstrated that the antibodies have species cross-reactivity between human TfR and monkey TfR.

Similarly, the $K_D$ values of the EGFR-TfR bispecific antibodies for human EGFR and monkey EGFR are in the order of $10^{-9}$ to $10^{-10}$ M. The $K_D$ values for monkey EGFR are between 1/10 and 10 times the $K_D$ values for human EGFR, and therefore, it was demonstrated that the antibodies have species cross-reactivity between human EGFR and monkey EGFR.

[Example 9] Measurement of Antigen Expression Level of Cancer Cells Using Flow Cytometer and Evaluation of Binding Affinity of Obtained Antibodies The expression levels of various types of antigens in various types of cancer cell lines were evaluated by a fluorescence activated cell sorting (FACS) method according to the following procedure. In the evaluation, a PE-labeled anti-human CD71 antibody (BD Pharmingen, Inc.) and an Alexa Fluor 488-labeled anti-EGFR antibody (Santa Cruz Biotechnology, Inc.) were used.

The evaluation of the expression levels of TfR and EGFR in the various types of cancer cell lines was carried out as follows.

OE21 cells were suspended in Staining Buffer (SB) that is D-PBS(−) containing 0.1% $NaN_3$ and 1% FBS at a cell density of $1 \times 10^6$ cells/mL, and the suspension was dispensed in a 96-well round bottom plate (manufactured by Falcon, Inc.) at 100 μL/well. After centrifugation (2000 rpm, 4° C., 2 minutes), the supernatant was removed, and to the resulting pellet, the PE-labeled anti-human CD71 antibody or the Alexa Fluor 488-labeled anti-EGFR antibody was added, followed by incubation for 30 minutes at ice temperature. After washing twice with SB, the cells were suspended in SB, and the fluorescence intensity of each cell was measured using a flow cytometer FACSCANTO II (manufactured by BD Biosciences, Inc.). The TfR expression in each of T.Tn cells, U-937 cells, HepG2 cells, HuH-7 cells, and HLE cells was evaluated in the same manner.

Similarly, the expression level of GPC3 in HepG2 cells, HuH-7 cells, and HLE cells was also evaluated. Specifically, cells were prepared in the same manner as described above, and after the HN3 antibody was used as the primary antibody, Alexa Fluor (registered trademark) 488 goat anti-human IgG (H+L) (Molecular Probes, Inc.) was added thereto as the secondary antibody, followed by incubation for 30 minutes at ice temperature, and then, a fluorescence intensity was measured in the same manner.

As the negative control, an IgG4 antibody R409K mutant (hereinafter referred to as anti-DNP antibody) produced according to the method described in Example 5 of WO 2006/033386 using a vector encoding VL and VH (GenBank accession No. VL U16688, VH U116687) of the DNP-1 antibody described in Mol Immunol. 1996 June; 33 (9): 759-68, and PBS were used.

Figure 2:
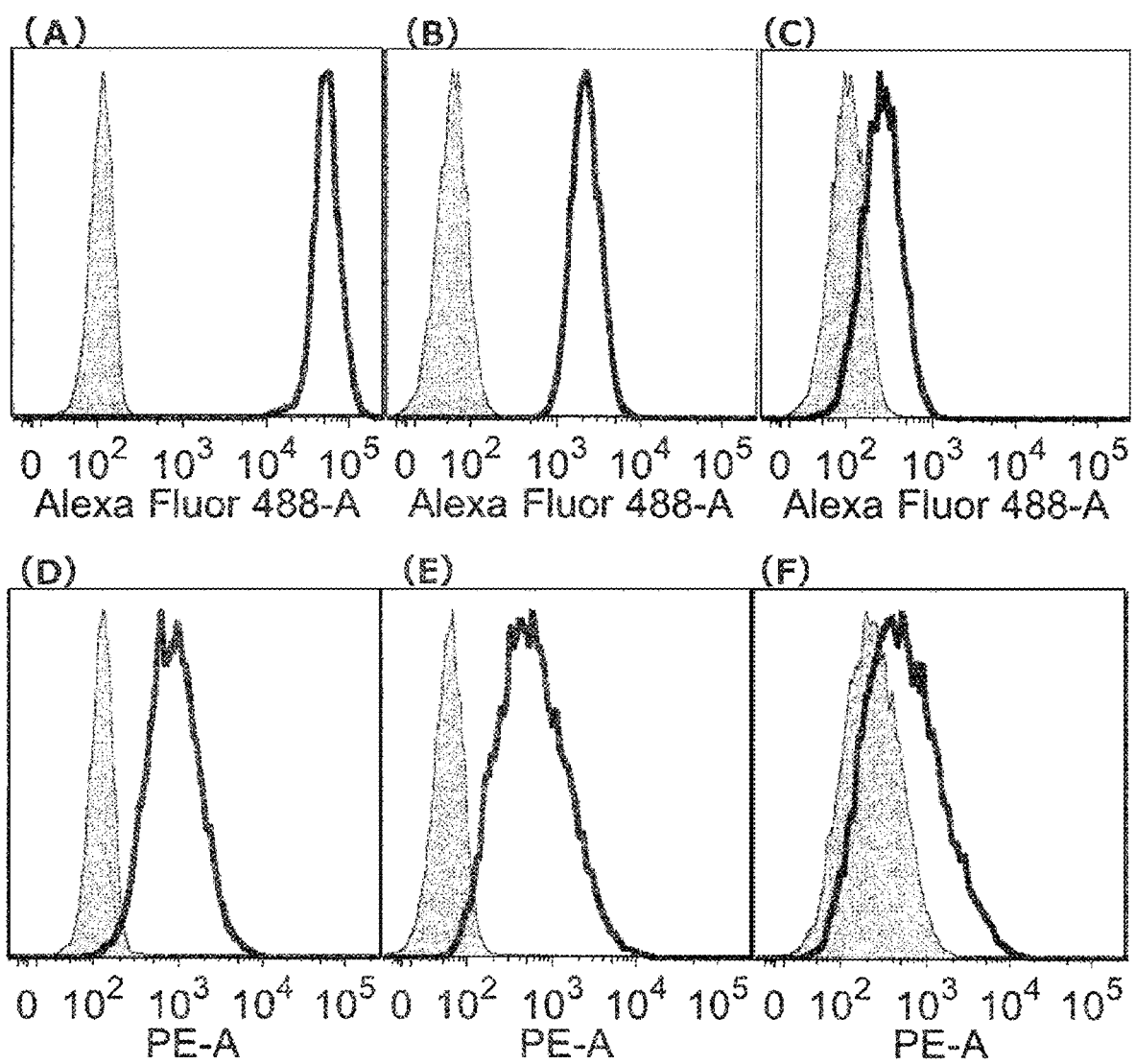
FIG. 2 shows the results of evaluating the expression level of an antigen in various types of cancer cell lines by flow cytometry.

FIGS. 2(A) to 2(C) show the results of evaluating the expression level of EGFR in OE21 cells, T.Tn cells, and U-937 cells, respectively, by a flow cytometer. Further, FIGS. 2(D) to 2(G) show the results of evaluating the expression level of TfR in OE21 cells, T.Tn cells, and U-937 cells, respectively, by a flow cytometer. As shown in FIG. 2, the OE21 cells expressed EGFR at a high level, the T.Tn cells expressed EGFR at a medium level, and the U-937 cells expressed EGFR at a low level.

Figure 3:
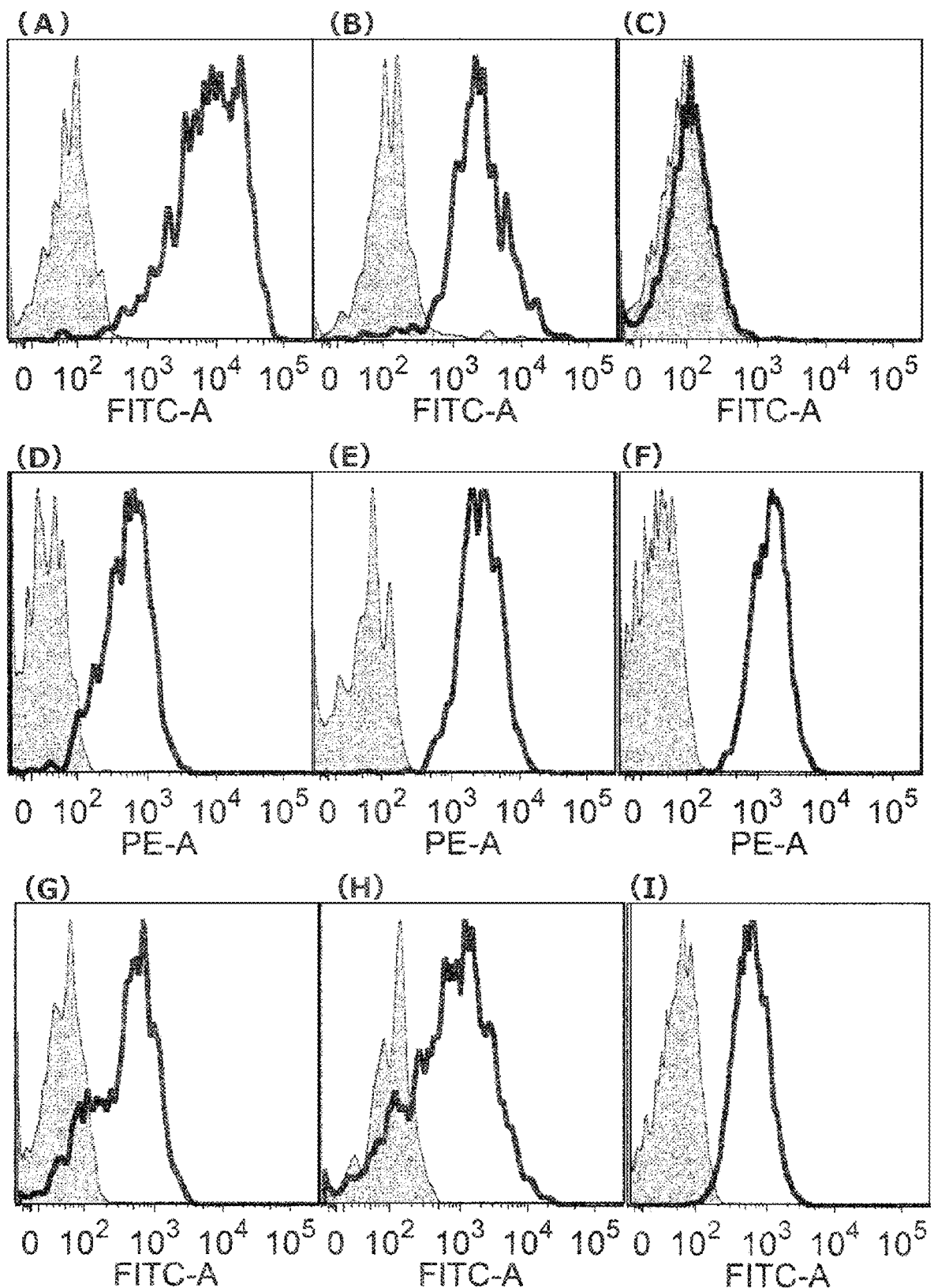
FIG. 3 shows the results of evaluating the expression level of an antigen in a liver cancer cell line by flow cytometry.
Figure 4:
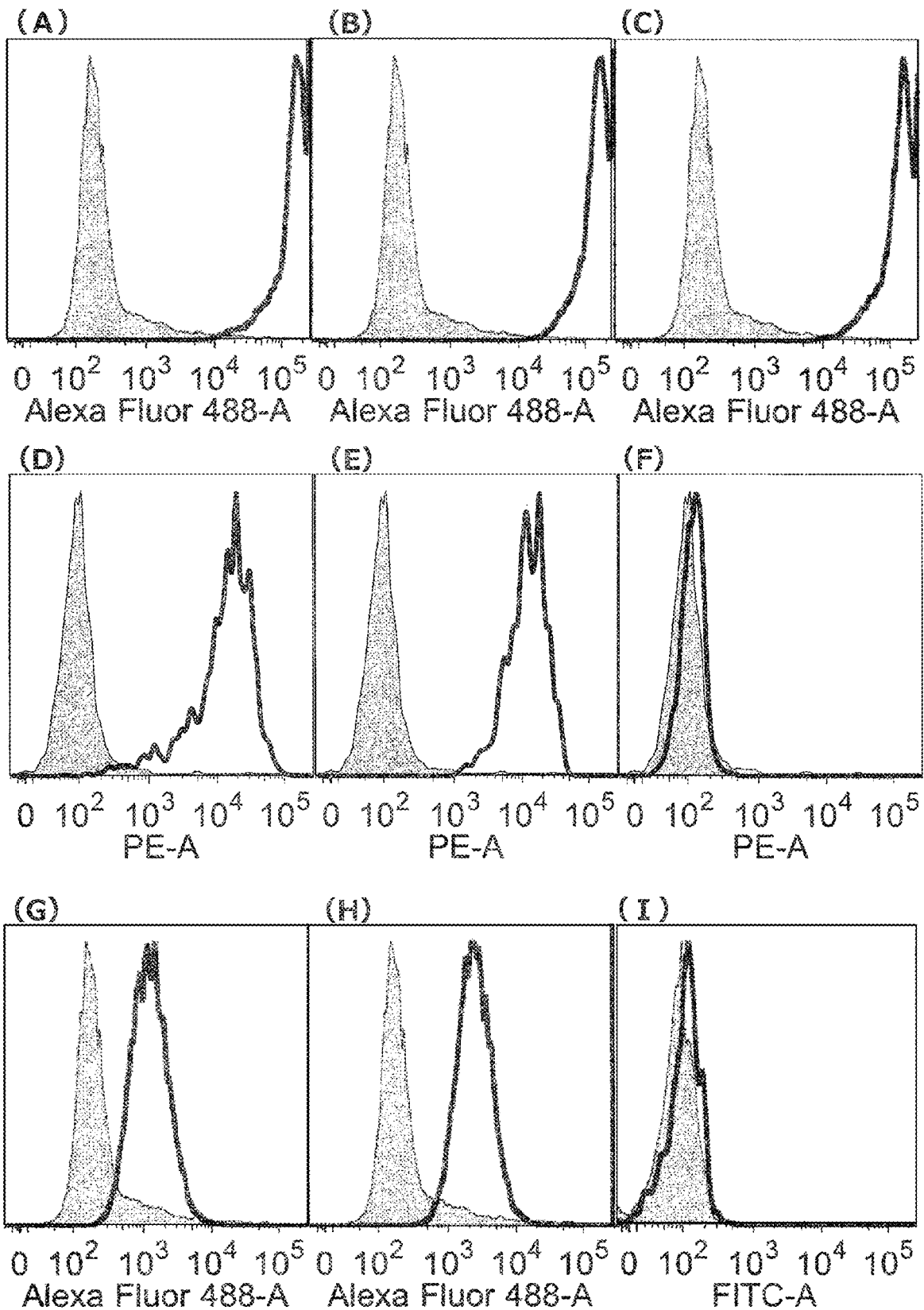
FIG. 4 shows the results of evaluating the binding affinity of each antibody to OE21 cells by a flow cytometer in panels (A) to (I). The vertical axis represents the cell count, and the horizontal axis represents the fluorescence intensity. The solid line indicates the binding affinity of an anti-EGFR antibody or an anti-TfR antibody, and the histogram filled with gray indicates the binding affinity of a secondary antibody that is a negative control.

FIGS. 3(A) to 3(C) show the results of evaluating the expression level of GPC3 in HepG2 cells, HuH-7 cells, and HLE cells, respectively, by a flow cytometer. Further, FIGS. 3(D) to 3(F) show the results of evaluating the expression level of TfR in HepG2 cells, HuH-7 cells, and HLE cells, respectively, by a flow cytometer. As shown in FIG. 3, the HepG2 cells expressed GPC3 at a high level, the HuH-7 cells expressed GPC3 at a medium level, and the HLE cells were negative for GPC3. Further, all the HepG2 cells, the HuH-7 cells, and the HLE cells expressed EGFR at a low level.

As shown in FIGS. 2 and 3, in cancer cell lines, the TfR expression was not much different among all cell lines, and TfR was expressed at a low to medium level.

Subsequently, the binding affinity of the anti-TfR antibodies and the anti-EGFR antibodies obtained in Example 4 and Example 5 to OE21 cells was confirmed by flow cytometry. FIGS. 4(A) to 4(I) show the results of E08, E12, E17, KME07, KME09, KME11, TfR1071, 2230, and T14, respectively.

As a result, binding to OE21 cells could not be confirmed only for KME11 among the anti-EGFR antibodies. KME11 was selected as the antibody that binds to the soluble EGFR protein as described in Example 5, however, from the results, it was demonstrated that KME11 does not bind to membrane-associated EGFR on a cell surface. Further, binding to OE21 cells could not be confirmed only for T14 among the anti-TfR antibodies. T14 was selected as the antibody that binds to the soluble TfR protein by ELISA as described in Example 4, however, from the results, it was demonstrated that T14 does not bind to membrane-associated TfR on a cell surface.

[Example 10] Evaluation of Growth Inhibitory Activity of Anti-TfR Antibody

The growth inhibitory activity of the TfR monoclonal antibodies obtained in Example 4 was evaluated as follows using the growth inhibitory activity against a cancer cell line as an index.

OE21 cells ($1 \times 10^3$ cells) were seeded in a flat-bottom 96-well plate (manufactured by Falcon, Inc.), and a test antibody diluted with RPMI 1640 medium (manufactured by Sigma-Aldrich Co. LLC) containing 10% FBS was added thereto to give a final concentration of 1 µg/mL, and the cells were cultured at 37° C. under 5.0% carbon dioxide gas for 4 to 6 days. Thereafter, CellTiter-Glo (registered trademark) Luminescent Cell Vialbility Assay (Promega Corporation) was added thereto, and a fluorescence intensity was measured using a microplate reader (1420 ARVO multi-label counter, manufactured by WALLAC, Inc.). Evaluation was carried out using 6 independent wells under each condition, and an average was calculated. The obtained value of the fluorescence intensity reflects the ATP level in viable cells in each well. As the negative control, the anti-DNP antibody was used.

Figure 5:
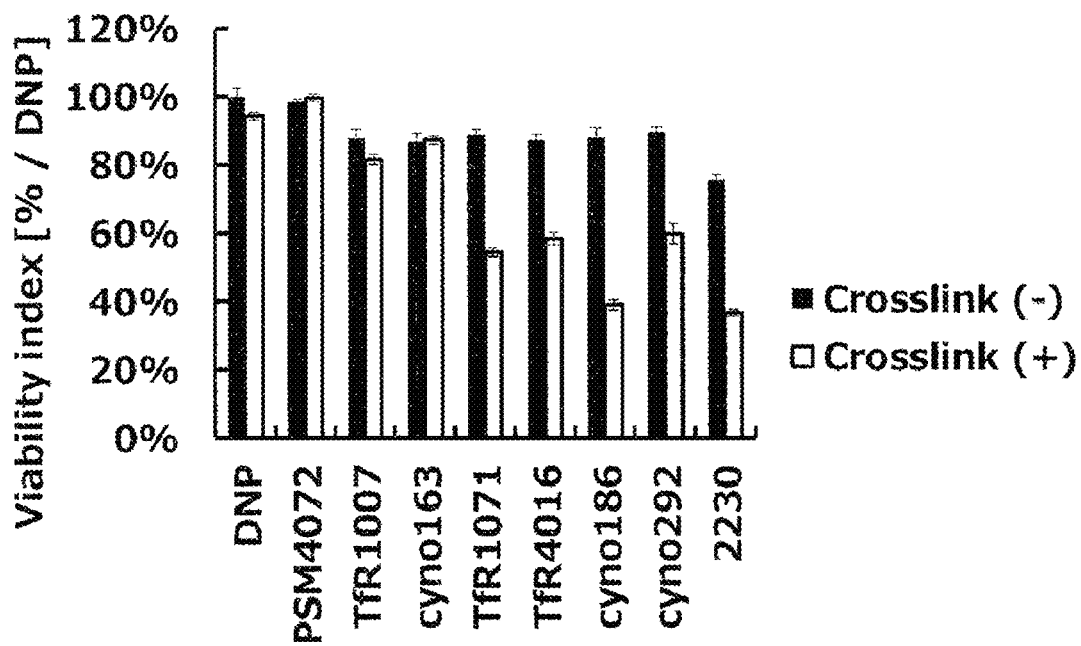
FIG. 5 shows the results of evaluating the growth inhibitory activity of each TfR antibody against OE21 cells. The vertical axis represents the cell viability expressed as a relative value of the ATP level in viable cells with respect to the negative control. The black bar graph indicates the results when only a monoclonal antibody was added, and the white bar graph indicates the results when a crosslinking antibody was added to crosslink the monoclonal antibody.

Further, together with the test antibody, an anti-human IgG polyclonal antibody (Sigma, Inc.) (hereinafter also referred to as crosslinking antibody) was added thereto at 10 g/mL, and evaluation was also carried out under the condition that the test antibody was crosslinked. The evaluation results for the respective antibodies are shown in FIG. 5. Among the test antibodies, an antibody that did not exhibit a growth inhibitory activity by the monoclonal antibody itself was selected as a TfR non-neutralizing antibody.

Further, when the crosslinking antibody was added to crosslink two molecules of test antibody, clones that exhibit a growth inhibitory activity (TfR1071, TfR4016, cyno186, cyno292, and 2230) and clones that do not exhibit a growth inhibitory activity (PSM4072, TfR1007, and cyno163) were confirmed.

[Example 11] Evaluation of Growth Inhibitory Activity of Antibody Against Cell Surface Antigen The growth inhibitory activity of the antibodies against a cell surface antigen obtained in Example 5 was evaluated as follows using the growth inhibitory activity against a cancer cell line as an index.

OE21 cells ($1 \times 10^3$ cells) were seeded in a flat-bottom 96-well plate (manufactured by Falcon, Inc.), and a test antibody diluted to various concentrations with RPMI 1640 medium (manufactured by Sigma-Aldrich Co. LLC) containing 10% FBS was added thereto, and the cells were cultured at 37° C. under 5.0% carbon dioxide gas for 4 to 6 days. Thereafter, CellTiter-Glo (registered trademark) Luminescent Cell Vialbility Assay (Promega Corporation) was added thereto, and a fluorescence intensity was measured using a microplate reader (1420 ARVO multi-label counter, manufactured by WALLAC, Inc.). Evaluation was carried out using 3 independent wells under each condition, and an average was calculated. The obtained value of the fluorescence intensity reflects the ATP level in viable cells in each well. As the negative control, the anti-DNP antibody was used.

Figure 6:
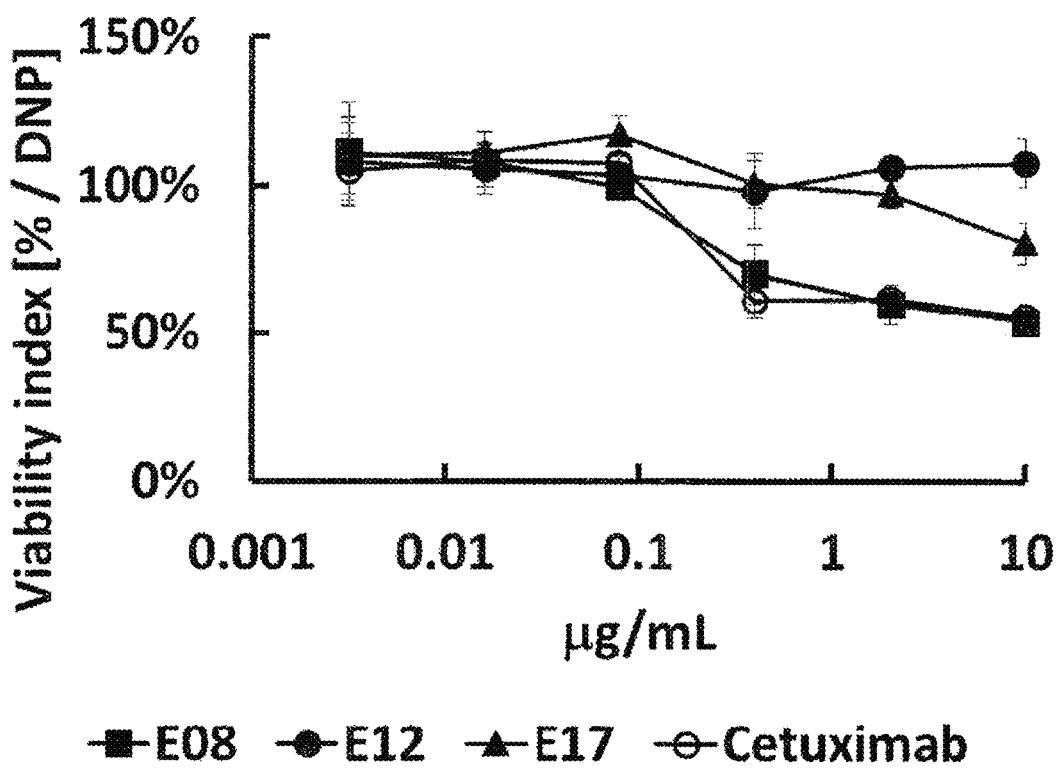
FIG. 6 shows the results of evaluating the growth inhibitory activity of each EGFR antibody against OE21 cells. The vertical axis represents the cell viability expressed as a relative value of the ATP level in viable cells with respect to the negative control.

In the evaluation of the growth inhibitory activity of the anti-EGFR antibody, OE21 cells were used. The results for the OE21 cells are shown in FIG. 6. As shown in FIG. 6, cetuximab and Clone E08 exhibited a strong growth inhibitory activity, E17 exhibited a weak growth inhibitory activity, and Clone E12 did not exhibit a growth inhibitory activity. The results are considered to reflect the EGF neutralizing activity of each antibody.

[Example 12] Evaluation of Growth Inhibitory Activity of Bispecific Antibody

The growth inhibitory activity of the bispecific antibodies obtained in Example 6 was evaluated as follows using the growth inhibitory activity against a cancer cell line as an index.

Cancer cells ($1 \times 10^3$ cells) were seeded in a flat-bottom 96-well plate (manufactured by Falcon, Inc.), and a test antibody diluted to various concentrations with RPMI 1640 medium (manufactured by Sigma-Aldrich Co. LLC) containing 10% FBS was added thereto, and the cells were cultured at 37° C. under 5.0% carbon dioxide gas for 4 to 6 days. Thereafter, CellTiter-Glo (registered trademark) Luminescent Cell Vialbility Assay (Promega Corporation) was added thereto, and a fluorescence intensity was measured using a microplate reader (1420 ARVO multi-label counter, manufactured by WALLAC, Inc.). Evaluation was carried out using 3 independent wells under each condition, and an average was calculated. The obtained value of the fluorescence intensity reflects the ATP level in viable cells in each well. As the negative control, the anti-DNP antibody was used.

In the evaluation of the growth inhibitory activity of the bispecific antibodies, OE21 cells were used. The evaluation results with respect to the bispecific antibodies having the variable region of the anti-EGFR antibody E08, the bispecific antibodies having the variable region of the anti-EGFR antibody E12, and the bispecific antibodies having the variable region of the anti-TfR antibody 2230 are shown in FIGS. 7A to 7C, respectively.

Figure 7A:
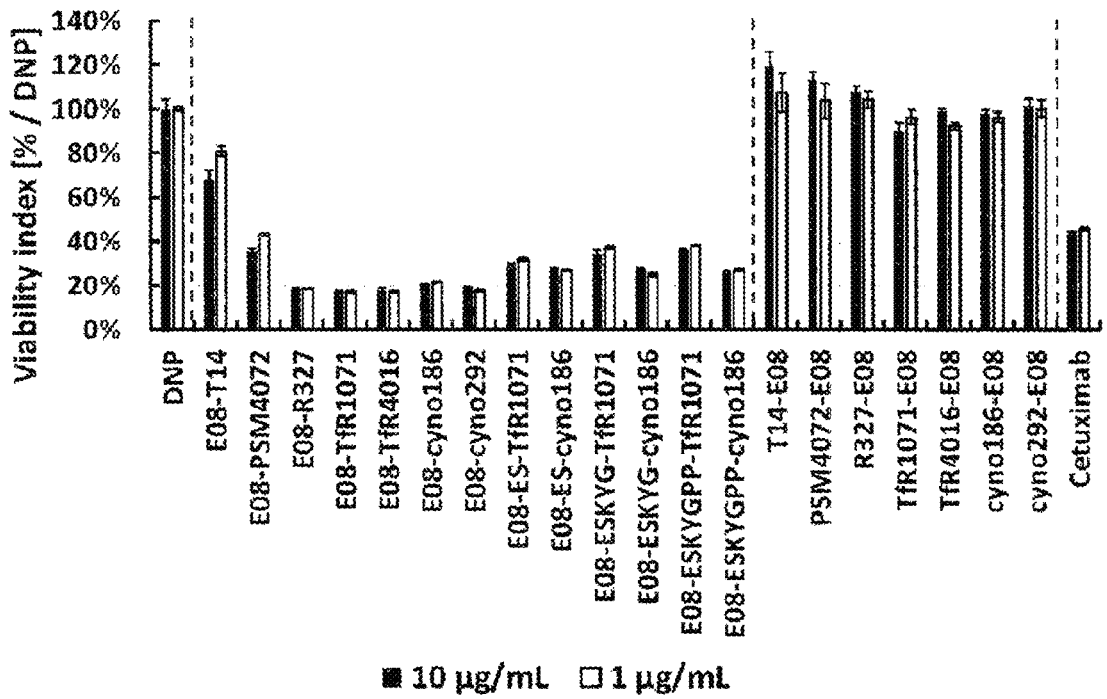
FIG. 7A shows the results of evaluating the growth inhibitory activity of various types of bispecific antibodies against OE21 cells. The vertical axis represents the cell viability expressed as a relative value of the ATP level in viable cells with respect to the negative control.

As shown in FIG. 7A, when the variable region of a clone (such as TfR1071) that exhibited a growth inhibitory activity in the case where the antibody molecules were crosslinked with the crosslinking antibody in Example 10 was disposed on the IgG portion side, and the variable region of the anti-EGFR antibody was disposed on the N-terminal side polypeptide side, a strong growth inhibitory activity was exhibited. At that time, also in the case where a part of the amino acid sequence of the hinge region (ES (SEQ ID NO: 79), ESKYG (SEQ ID NO: 80), or ESKYGPP (SEQ ID NO: 81)) of IgG4 was used as the linker, a growth inhibitory activity was exhibited in the same manner. On the other hand, a bispecific antibody including the variable region of the anti-TfR antibody in the N-terminal side polypeptide exhibited almost no growth inhibitory activity.

Note that as the results of Example 9, the anti-TfR antibody T14 does not react with TfR on a cell surface, and therefore, the growth inhibitory activity exhibited by E08-T14 and T14-E08 is considered to be attributed to the EGFR signaling inhibitory activity purely derived from E08 (Example 11).

Figure 7B:
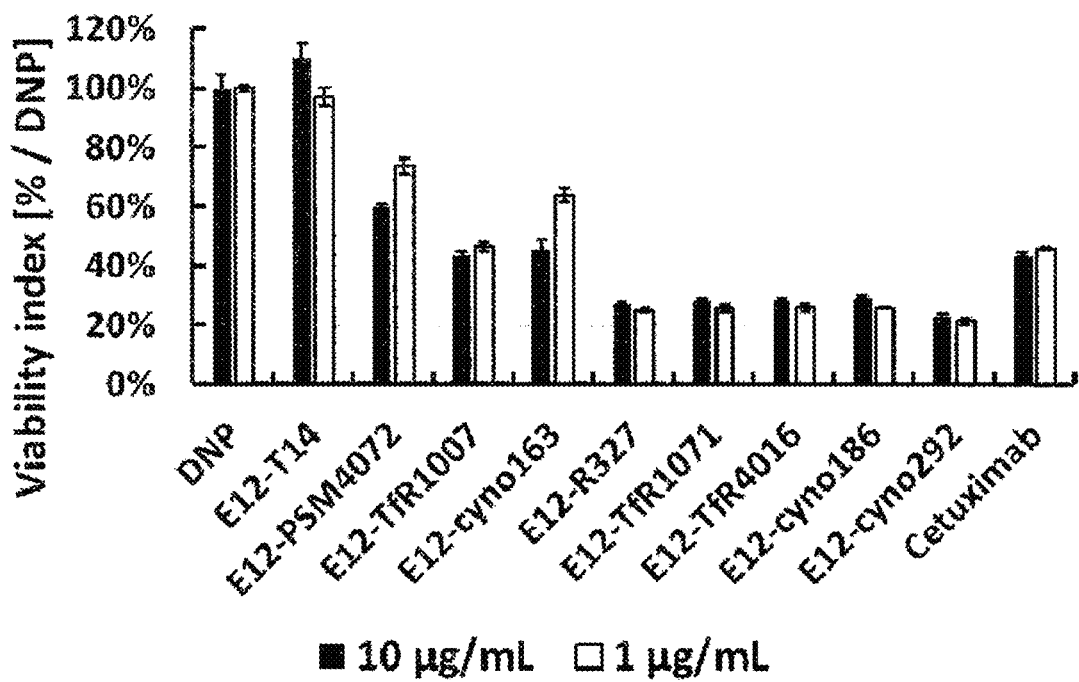
FIG. 7B shows the results of evaluating the growth inhibitory activity of various types of bispecific antibodies against OE21 cells. The vertical axis represents the cell viability expressed as a relative value of the ATP level in viable cells with respect to the negative control.
Figure 7C:
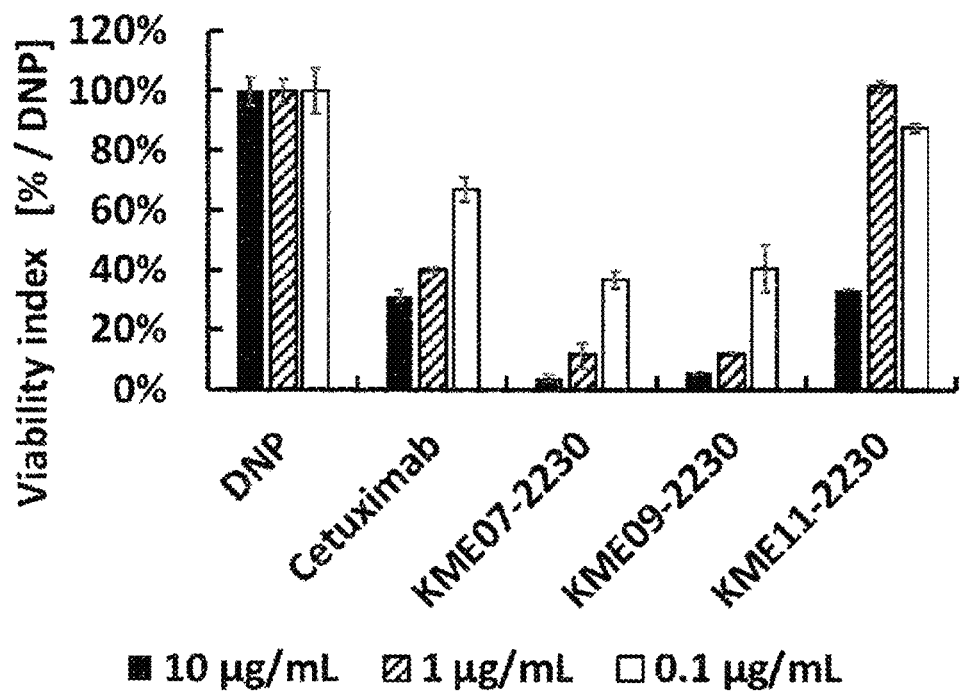
FIG. 7C shows the results of evaluating the growth inhibitory activity of various types of bispecific antibodies against OE21 cells. The vertical axis represents the cell viability expressed as a relative value of the ATP level in viable cells with respect to the negative control.

Further, as shown in FIG. 7B, the bispecific antibodies including the variable region of any of the clones (R327, TfR1071, TfR4016, cyno186, and cyno292) that exhibited a growth inhibitory activity in the case where the antibody molecules were crosslinked with the crosslinking antibody in Example 10 in the IgG portion exhibited a stronger growth inhibitory activity than the bispecific antibodies including the variable region of any of the clones (PSM4072, TfR1007, and cyno163) that did not exhibit a growth inhibitory activity even in the case where the antibody molecules were crosslinked with the crosslinking antibody in the IgG portion.

With respect to the bispecific antibodies including the variable region of the anti-TfR antibody 2230, as shown in FIG. 7C, KME07-2230, KME09-2230, and KME11-2230 exhibited a growth inhibitory activity. As shown in Example 9, KME11 does not bind to EGFR on cells, and therefore, it was revealed that the bispecific antibody KME11-2230 exhibits a cell growth inhibitory activity in a manner independent of EGFR. There is a concern that the clones having such a property may be toxic to normal cells that are negative for EGFR and positive for TfR such as bone marrow cells.

From the above results, it was demonstrated that a bispecific antibody including the variable region of an anti-TfR antibody that does not exhibit a growth inhibitory activity by itself but exhibits a growth inhibitory activity when being crosslinked such as R327, TfR1071, TfR4016, cyno186, or cyno292 in the IgG portion exhibits a strong growth inhibitory activity selectively for a cell surface antigen. In addition, it was demonstrated that the growth inhibitory activity of the bispecific antibody is not affected by the presence or absence of a linker.

Figure 8A:
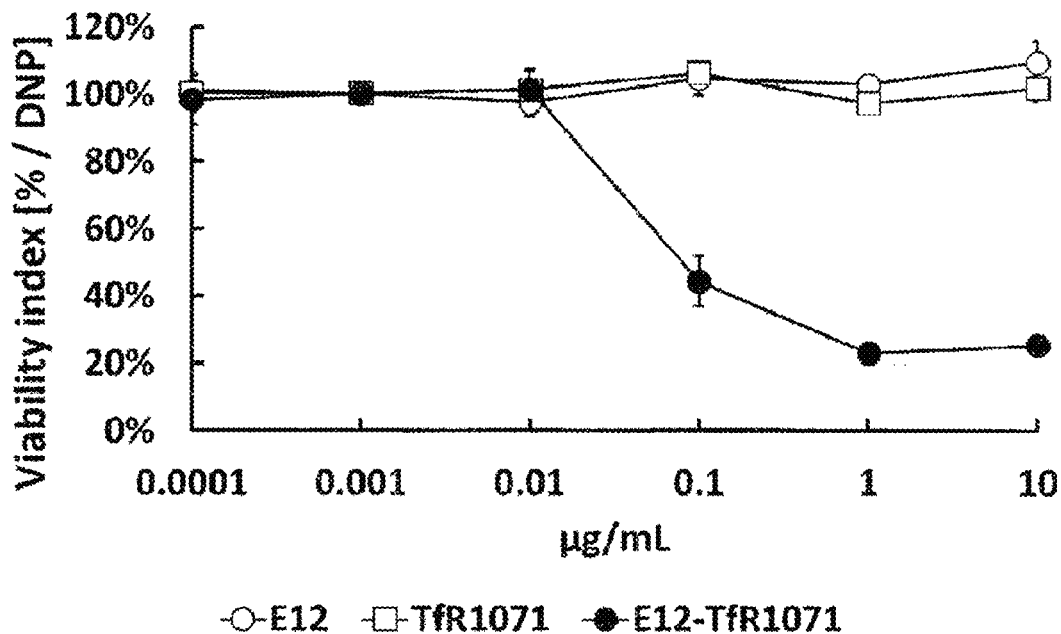
FIG. 8A shows the results of evaluating the growth inhibitory activity of an EGFR-TfR bispecific antibody against OE21 that is a cancer cell line expressing EGFR. The vertical axis represents the cell viability expressed as a relative value of the ATP level in viable cells with respect to the negative control.
Figure 8B:
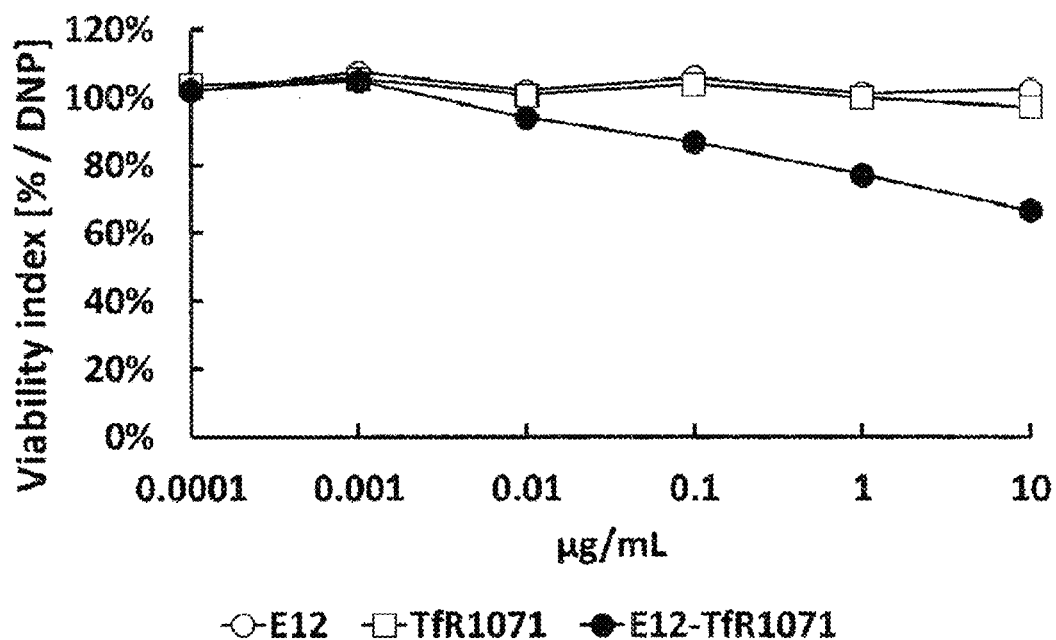
FIG. 8B shows the results of evaluating the growth inhibitory activity of an EGFR-TfR bispecific antibody against T.Tn that is a cancer cell line expressing EGFR. The vertical axis represents the cell viability expressed as a relative value of the ATP level in viable cells with respect to the negative control.
Figure 8C:
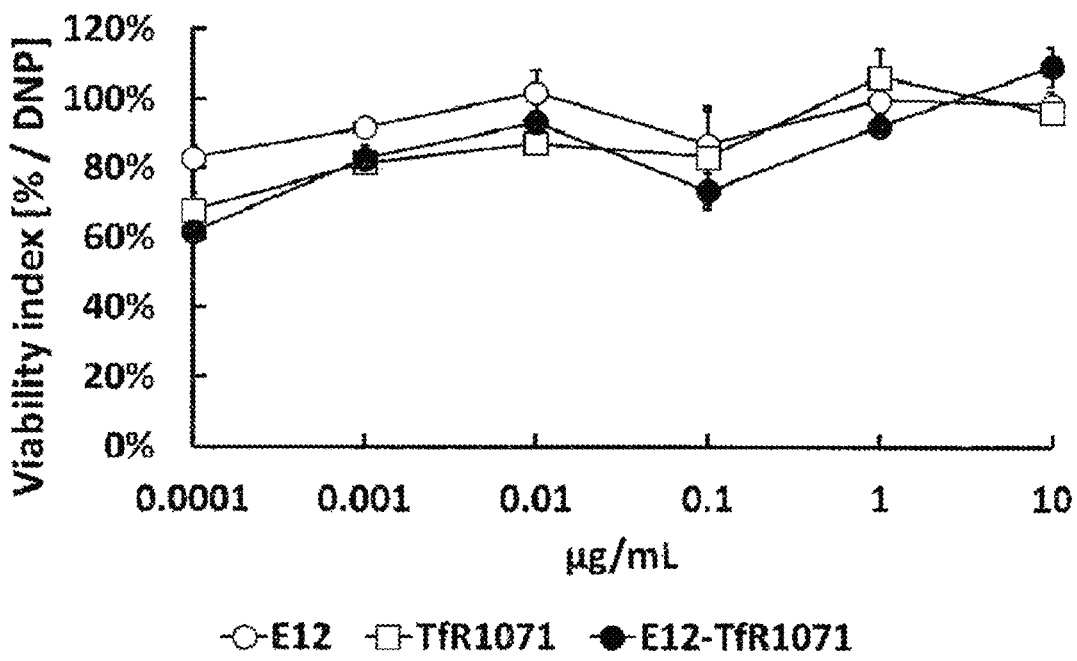
FIG. 8C shows the results of evaluating the growth inhibitory activity of an EGFR-TfR bispecific antibody against U-937 that is a cancer cell line expressing EGFR. The vertical axis represents the cell viability expressed as a relative value of the ATP level in viable cells with respect to the negative control.

Subsequently, in order to verify the relationship between the growth inhibitory activity of the EGFR-TfR bispecific antibody and the expression level of EGFR, by using cell lines, in which the expression levels of EGFR are different, the growth inhibitory activity of the bispecific antibody E12-TfR1071 obtained in Example 6 was evaluated. From the results of Example 9, as cells that express EGFR at a high level, OE21 cells, as cells that express EGFR at a medium level, T.Tn cells, and as cells that express EGFR at a low level, U-937 cells were used. As shown in FIGS. 8A to 8C, E12-TfR1071 exhibited a strong growth inhibitory activity against OE21 cells and exhibited a medium growth inhibitory activity against T.Tn cells, but did not exhibit a growth inhibitory activity against U-937 cells. From these results, it was found that E12-TfR1071 exhibits a growth inhibitory activity in a manner dependent on the expression level of EGFR.

Figure 9:
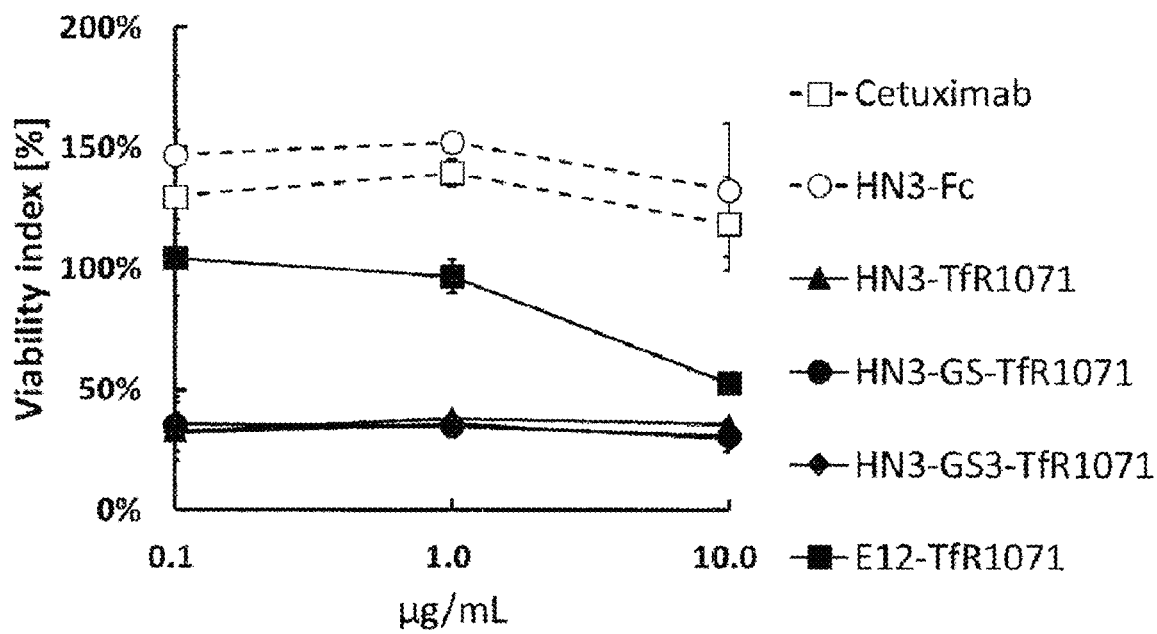
FIG. 9 shows the results of evaluating the growth inhibitory activity of a GPC3-TfR bispecific antibody against HepG2 cells. The vertical axis represents the cell viability expressed as a relative value of the ATP level in viable cells with respect to the negative control.

In the evaluation of the growth inhibitory activity of various types of GPC3-TfR bispecific antibodies, HepG2 cells were used. As shown in FIG. 9, HN3-TfR1071, HN3-GS-TfR1071, and HN3-GS3-TfR1071 exhibited a very strong growth inhibitory activity.

In order to verify the relationship between the growth inhibitory activity of the GPC3-TfR bispecific antibody and the expression level of GPC3, by using cell lines, in which the expression levels of GPC3 are different, the growth inhibitory activity of the bispecific antibody HN3-TfR1071 obtained in Example 6 was evaluated in the same manner as in Example 10.

Figure 10A:
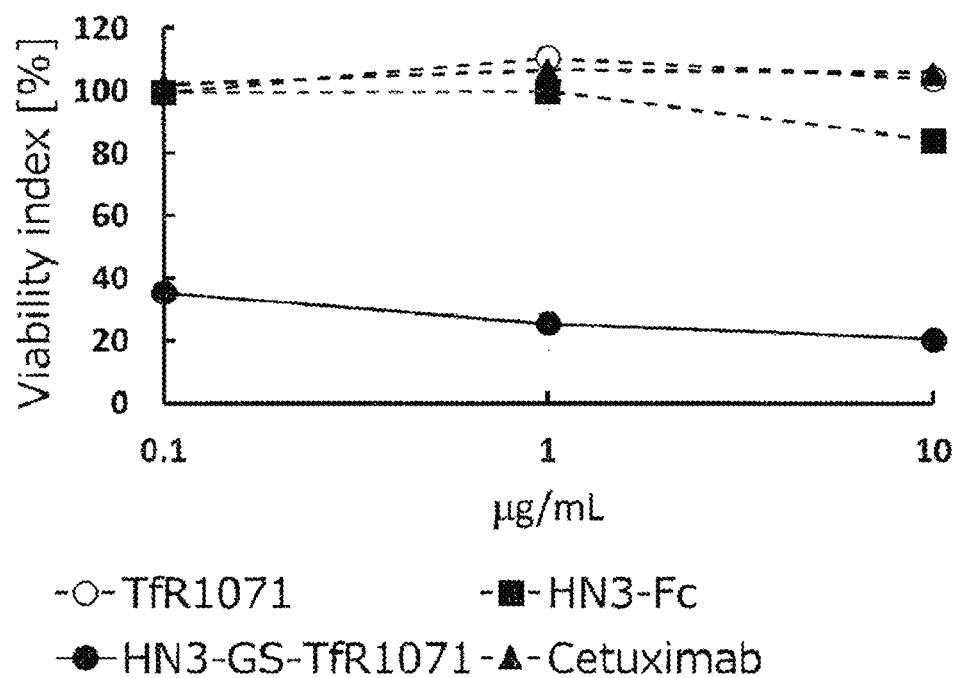
FIG. 10A shows the results of evaluating the growth inhibitory activity of a GPC3-TfR bispecific antibody against HepG2 that is a liver cancer cell line expressing GPC3. The vertical axis represents the cell viability expressed as a relative value of the ATP level in viable cells with respect to the negative control.
Figure 10B:
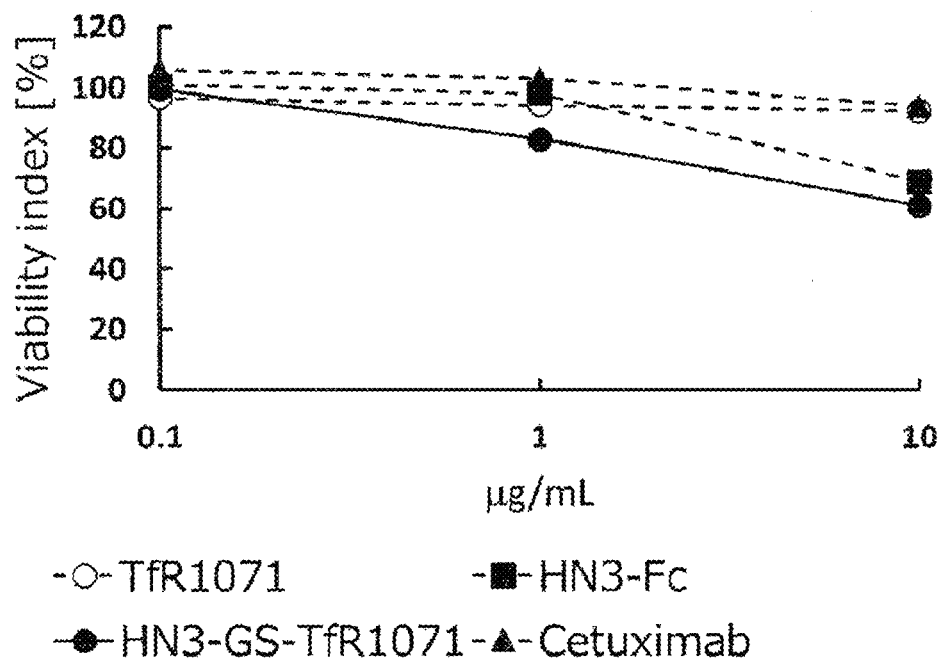
FIG. 10B shows the results of evaluating the growth inhibitory activity of a GPC3-TfR bispecific antibody against HuH-7 that is a liver cancer cell line expressing GPC3. The vertical axis represents the cell viability expressed as a relative value of the ATP level in viable cells with respect to the negative control.
Figure 10C:
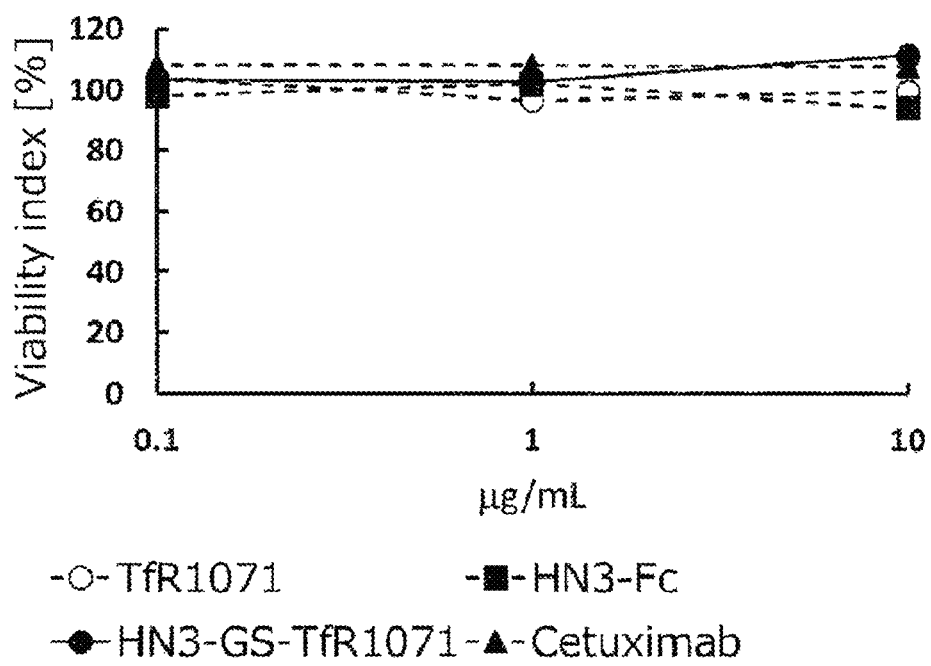
FIG. 10C shows the results of evaluating the growth inhibitory activity of a GPC3-TfR bispecific antibody against HLE that is a liver cancer cell line expressing GPC3. The vertical axis represents the cell viability expressed as a relative value of the ATP level in viable cells with respect to the negative control.
Figure 11:
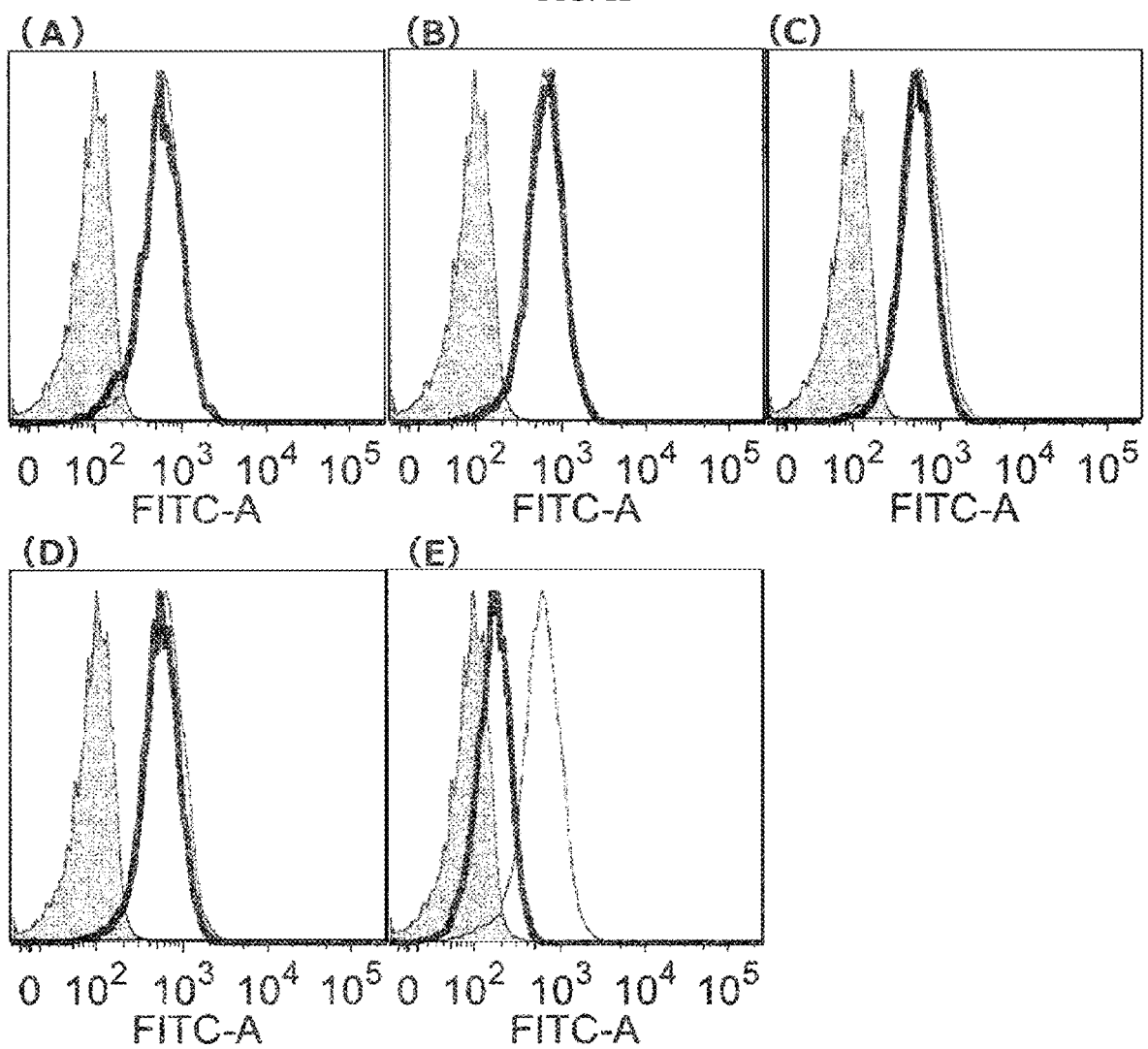
FIG. 11 shows the results of evaluating the inhibitory activity of each antibody or bispecific antibody against binding of TfR on OE21 cells to Tf in panels (A) to (E). The vertical axis represents the cell count, and the horizontal axis represents the fluorescence intensity. The thin solid line indicates the binding activity when fluorescently labeled transferrin was added after adding a negative control, the thick solid line indicates the binding activity when fluorescently labeled transferrin was added after adding an antibody or a bispecific antibody, and the histogram filled with gray indicates the negative control in which fluorescently labeled transferrin was not added.

As shown in Example 9, the results obtained using HepG2 cells as cells that express GPC3 at a high level are shown in FIG. 10A, the results obtained using HuH-7 cells as cells that express GPC3 at a medium level are shown in FIG. 10B, and the results obtained using HLE cells as negative cells are shown in FIG. 10C. As shown in FIGS. 10A to 10C, HN3-TfR1071 exhibited a strong growth inhibitory activity against HepG2 cells that express GPC3 at a high level and exhibited a medium growth inhibitory activity against HuH-7 cells that express GPC3 at a medium level, but did not exhibit a growth inhibitory activity against HLE cells that are negative for GPC3. From these results, it was found that HN3-TfR1071 exhibits a growth inhibitory activity in a manner dependent on the expression level of GPC3.

Further, it was revealed that the bispecific antibody including the variable region of an anti-TfR antibody in the IgG portion exhibits a strong cell growth inhibitory activity also against a cell surface antigen other than EGFR, in a manner dependent on the cell surface antigen.

[Example 13] Binding Inhibitory Activity of Anti-TfR Antibody and Bispecific Antibody Against TfR and Transferrin In order to clarify the mode of action of the growth inhibitory activity of the bispecific antibody against cancer cells, it was evaluated whether the EGFR-TfR bispecific antibody inhibits binding of TfR on a cancer cell to transferrin using a flow cytometer.

OE21 cells ($1 \times 10^6$ cells) were seeded in a U-bottom 96-well plate (manufactured by Falcon, Inc.) with RPMI 1640 medium (manufactured by Sigma-Aldrich Co. LLC) containing 10% FBS, and a test antibody at 10 µg/mL was added thereto, and the resulting mixture was left to stand on ice for 1 hour. Thereafter, Alexa Fluor 488-labeled mouse transferrin (Jackson ImmunoResearch, Inc.) was added thereto, and the resulting mixture was left to stand on ice for an additional 1 hour. After washing twice with SB, the cells were suspended in SB, and the fluorescence intensity of each cell was measured using a flow cytometer in the same manner as in Example 9.

In FIGS. 11(A) to 11(D), the results for cetuximab, TfR1071, E08-TfR1071, E12-TfR1071, and TfR435 are shown, respectively. As a result, the TfR neutralizing antibody TfR435 that is the positive control inhibited binding of transferrin to TfR, but the TfR antibody TfR1071 and the EGFR-TfR bispecific antibodies E08-TfR1071 and E12-TfR1071 all did not inhibit binding of transferrin to TfR in the same manner as cetuximab that is the negative control.

From the results, it was demonstrated that the EGFR-TfR bispecific antibody of the present invention does not have a TfR neutralizing activity and does not inhibit binding of TfR on a cell surface to transferrin.

[Example 14] Verification of Mechanism of Drug Efficacy Exhibition of EGFR-TfR Bispecific Antibody (EGFR Level, TFR Level, and EGFR Downstream Signaling in Cells)

In order to clarify the mode of action of the growth inhibitory activity of the bispecific antibody against cancer cells, the effect on the downstream signaling of EGFR and the TfR protein level when the EGFR-TfR bispecific antibody was added to cancer cells was evaluated by Western blotting as follows.

OE21 cells ($1 \times 10^6$ cells) were seeded in a flat-bottom 6-well plate (manufactured by Falcon, Inc.) with RPMI 1640 medium (manufactured by Sigma-Aldrich Co. LLC) containing 10% FBS, and a test antibody was added thereto, and the cells were cultured at 37° C. under 5.0% carbon dioxide gas for 24 hours. Thereafter, the cells were left to stand on ice, and washed once with PBS(−), and then, RIPA buffer (Thermo Fisher, Inc.) containing Protease/Phosphatase Inhibitor Cocktail (CST Japan, Co., Ltd.) was added thereto, and the resulting lysate was collected with a cell scraper (company).

After the collected lysate was centrifuged (15000 rpm, 4° C., 5 minutes), the supernatant was collected, and by using a portion of the supernatant, the protein level in the supernatant was determined with Pierce 660 nm Protein Assay Kit (Thermo Fisher, Inc.). To the supernatant, a sample buffer solution (for SDS-PAGE, 6 times concentrated, containing a reducing agent, Nacalai Tesque, Inc.) was added, and the resulting solution in an amount corresponding to 10 g of protein was loaded to a ready-made polyacrylamide gel (ATTO, Inc.) and electrophoresed for 25 to 80 minutes using an electrophoresis device (ATTO, Inc.).

As the standard for the electrophoresis, Prestained Protein Size Marker III (Wako Pure Chemical Corporation) was used. The electrophoresed gel was placed on Blotter (ATTO, Inc.) together with a filter paper (ATTO, Inc.) and a membrane (ATTO, Inc.), and blotting was carried out for 1 hour at 125 mA per gel. The membrane after the blotting was shaken at room temperature for 1 hour or overnight at 4° C. using a blocking buffer solution (Pierce, Inc.).

Each of primary antibodies against various types of proteins (a biotinylated anti-Akt antibody, a biotinylated anti-Phospho-Akt antibody, a biotinylated anti-EGFR antibody, a biotinylated anti-Phospho-EGFR antibody, and a rabbit anti-CD71 antibody; all Cell Signaling Trechnology, Inc.) were added to the membrane, followed by shaking at room temperature for 1 hour or overnight at 4° C.

After washing three times with TBS-T (Wako Pure Chemical Corporation), a secondary antibody (Streptoavidin antibody-HRP or anti-rabbit IgG antibody-HRP; Cell Signaling Trechnology, Inc.) against each of the primary antibodies was added thereto, followed by shaking at room temperature for 1 hour. After washing three times with TBS-T, ECL Prime Western Blotting Detection Regent (GE Healthcare, Inc.) was added thereto, and detection was carried out using Amersham Imager 600 (GE Healthcare, Inc.).

Figure 12:
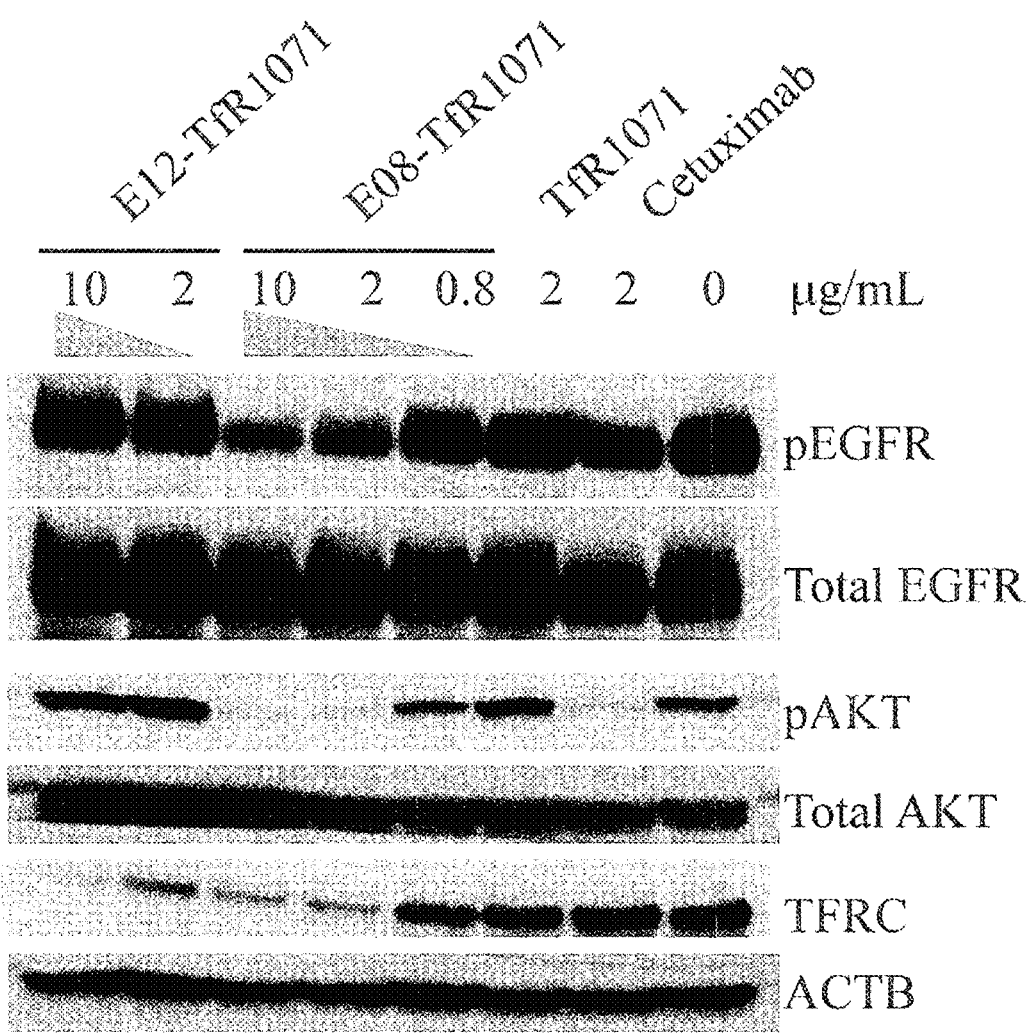
FIG. 12 shows the results of evaluating the effect on the EGFR downstream signaling and the expression level of TfR when adding an EGFR-TfR bispecific antibody to OE21 cells by Western blotting. Each band shows the expression level of each protein indicated on the right of the graph when adding each bispecific antibody or antibody at a concentration indicated above the graph. pEGFR denotes a phosphorylated EGFR protein, AKT denotes an EGFR downstream signaling protein, pAKT denotes a phosphorylated AKT protein, TFRC denotes a TfR protein, and ACTB denotes β-actin.
Figure 13:
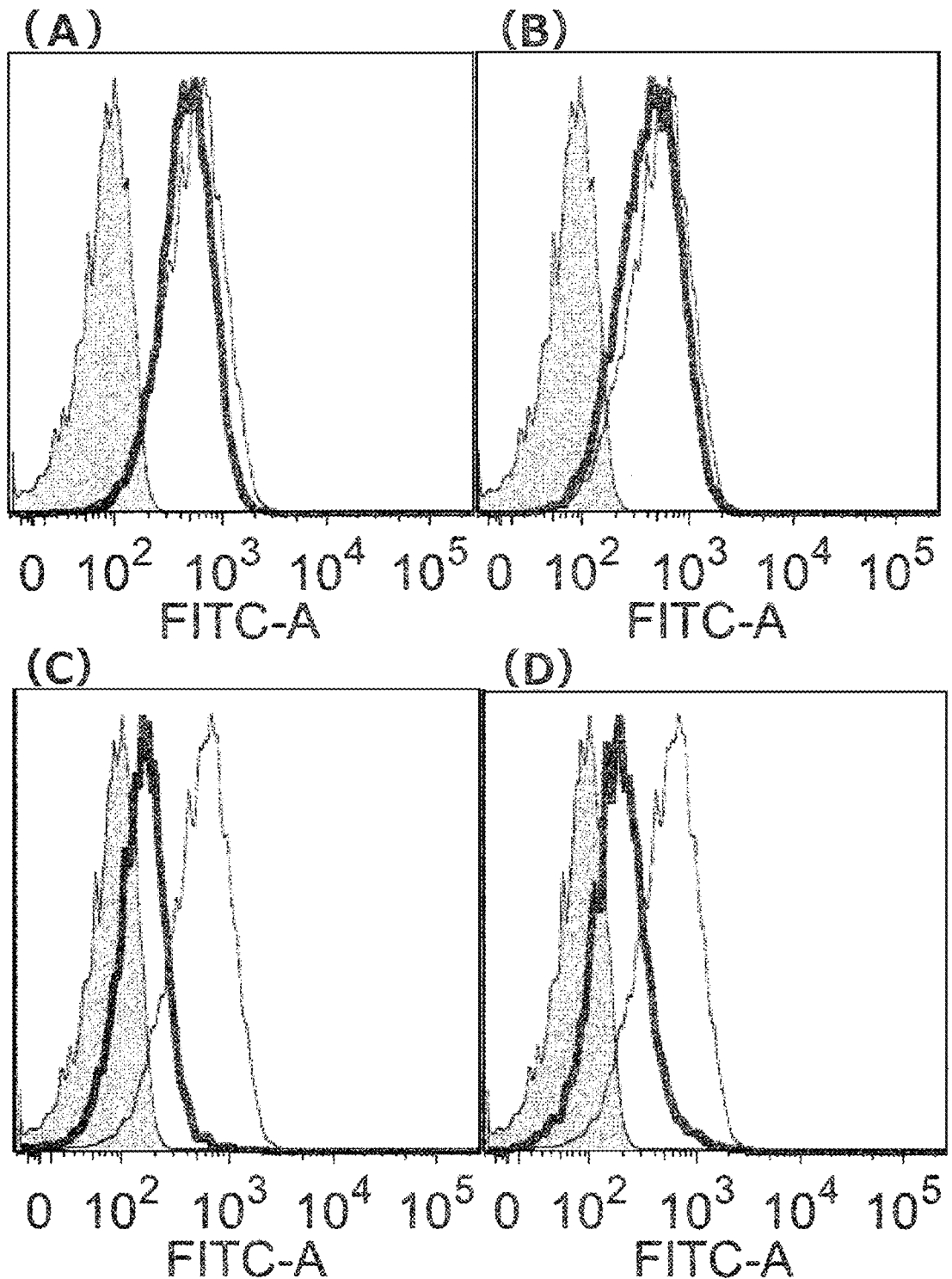
FIG. 13 shows the results of evaluating the expression level of TfR on a cell surface when adding an EGFR-TfR bispecific antibody to OE21 cells using a flow cytometer in panels (A) to (D). The vertical axis represents the cell count, and the horizontal axis represents the fluorescence intensity. The thin solid line indicates the binding activity when fluorescently labeled transferrin was added after adding a negative control and performing culture for 24 hours, the thick solid line indicates the binding activity when fluorescently labeled transferrin was added after adding an antibody or a bispecific antibody and performing culture for 24 hours, and the histogram filled with gray indicates the negative control in which fluorescently labeled transferrin was not added.

As shown in FIG. 12, by the addition of E08-TfR1071, phosphorylated EGFR and phosphorylated AKT decreased in the same manner as in the case of cetuximab that is the positive control, however, by the addition of E12-TfR1071, a decrease was not observed. On the other hand, the TfR protein level decreased by the addition of E08-TfR1071 and E12-TfR1071, but did not decrease in the case of cetuximab.

From the results, it was demonstrated that E08-TfR1071 has an EGFR signaling inhibitory activity and a TfR degradation activity, and E12-TfR1071 does not have an EGFR signaling inhibitory activity, but has only a TfR degradation activity.

[Example 15] Evaluation of Effect of EGFR-TfR Bispecific Antibody on TfR Expression In order to clarify the mode of action of the growth inhibitory activity of the bispecific antibody against cancer cells, it was evaluated whether the EGFR-TfR bispecific antibody affects the expression level of TfR on a cell membrane as follows.

OE21 cells ($1 \times 10^6$ cells) were seeded in a flat-bottom 6-well plate (manufactured by Falcon, Inc.) with RPMI 1640 medium (manufactured by Sigma-Aldrich Co. LLC) containing 10% FBS, and a test antibody at 10 µg/mL was added thereto, followed by incubation at 37° C. for 24 hours. Thereafter, the cells were detached in the same manner as in Example 9, and Transferrin from human serum, Alexa Fluor 488 conjugate (Molecular Probes, Inc.) was added thereto at 5 µg/mL, and the resulting mixture was left to stand at 4° C. for 30 minutes, and washing was performed in the same manner as in Example 9. Thereafter, the amount of transferrin bound onto the cell surface was measured using the fluorescence intensity of each cell as an index with a flow cytometer.

In FIGS. 13(A) to 13(D), the results for cetuximab, the TfR1071 antibody, the E08-TfR1071 bispecific antibody, and the E12-TfR1071 bispecific antibody are shown, respectively. As shown in FIG. 13, while the amount of transferrin bound onto the cell surface did not decrease when adding the TfR1071 antibody, the amount of transferrin bound onto the cell surface decreased when adding the EGFR-TfR bispecific antibodies.

From these results, it was demonstrated that the growth inhibitory activity of the EGFR-TfR bispecific antibody of the present invention through TfR is attributed to degradation of TfR protein of cancer cells so as to decrease TfR on the cell surface.

[Example 16] Evaluation of Effect of EGFR-TfR Bispecific Antibody on Iron Uptake In order to confirm whether iron is involved in the growth inhibitory activity of the EGFR-TfR bispecific antibody against cancer cells, evaluation was carried out as follows.

OE21 cells ($1 \times 10^3$ cells) were seeded in a flat-bottom 96-well plate (manufactured by Falcon, Inc.) with RPMI 1640 medium (manufactured by Sigma-Aldrich Co. LLC) containing 10% FBS, and ferric ammonium sulfate (Nacalai Tesque, Inc., hereinafter referred to as FAS) was added thereto to give a final concentration of 10 μM together with a test antibody, and the cells were cultured at 37° C. under 5.0% carbon dioxide gas for 4 to 6 days. Thereafter, the ATP level in viable cells was measured in the same manner as in Example 10.

Figure 14:
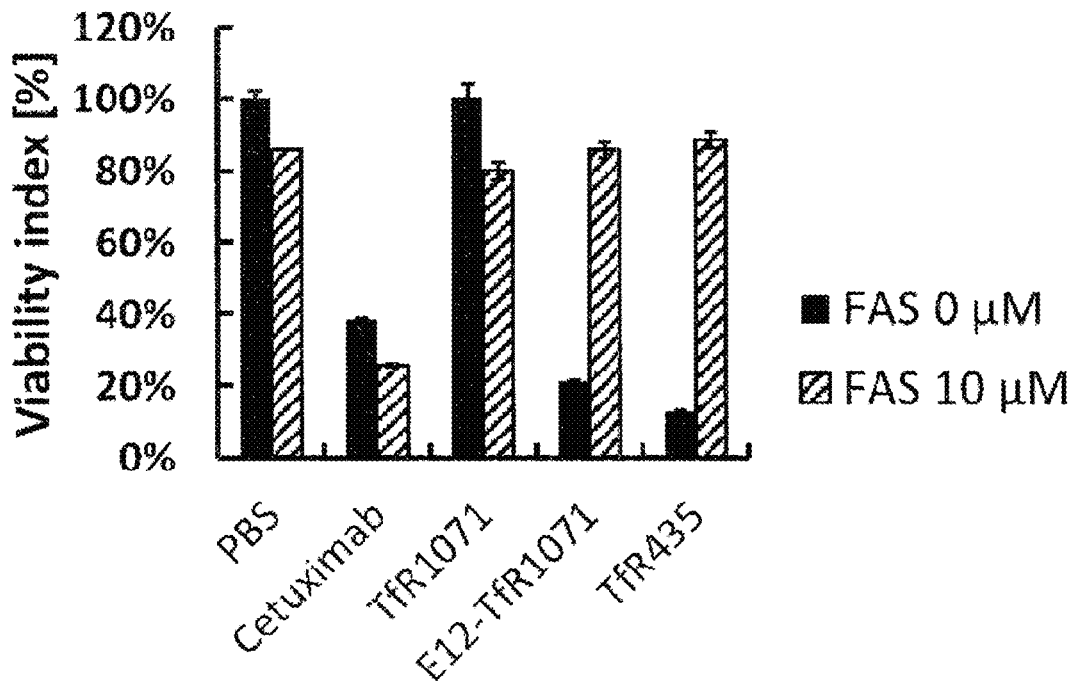
FIG. 14 shows the results of evaluating whether the growth inhibitory activity when adding an EGFR-TfR bispecific antibody to OE21 cells is attributed to iron depletion. The vertical axis represents the cell viability expressed as a relative value of the ATP level in viable cells with respect to the negative control under the condition that PBS was added and FAS was not added. The black bar graph indicates the viability when only an antibody or a bispecific antibody was added, and the shaded bar graph indicates the viability when FAS was added together with an antibody or a bispecific antibody.

As shown in FIG. 14, under the condition that FAS was not added, the growth of the cells was inhibited by the addition of cetuximab, the TfR neutralizing antibody TfR435, or the bispecific antibody E12-TfR1071. On the other hand, when FAS was added, there was no effect on the growth inhibitory activity of cetuximab, however, the growth inhibitory activity of the TfR neutralizing antibody TfR435 and the bispecific antibody E12-TfR1071 was lost.

By the addition of FAS, iron can be supplied into cells through a pathway not via TfR. Therefore, under the condition that FAS was added, an iron depletion state accompanying the inhibition of TfR by the TfR neutralizing antibody or the degradation of TfR by the EGFR-TfR bispecific antibody is canceled, and the growth inhibitory activity attributed to TfR is lost. On the other hand, the growth inhibitory activity attributed to EGFR signaling inhibition is not canceled even if iron is supplied by the addition of FAS. Accordingly, it was demonstrated that the growth inhibitory activity of E12-TfR1071 is caused not by EGFR signaling inhibition but by stop supplying iron into cells which is the same manner as the TfR neutralizing antibody.

[Example 17] Comparison of Drug Efficacy of EGFR-TfR Bispecific Antibody and EGFR Signaling Inhibitor In order to compare the activity between two growth inhibitory mechanisms of EGFR signaling inhibition and TfR inhibition, evaluation was carried out using IncuCyte (Sartorius AG).

OE21 cells ($1 \times 10^3$ cells) were seeded in a flat-bottom 96-well plate (manufactured by company) with RPMI 1640 medium (manufactured by Sigma-Aldrich Co. LLC) containing 10% FBS, and a test antibody diluted to 10 μg/mL with the same medium was added thereto, and the cells were incubated at 37° C. for 5 days in the setting that three visual fields per well were photographed every two hours using IncuCyte. Medium replacement was performed, and the test antibody at 10 μg/mL was added thereto, and the cells were incubated for 2 days in the same manner. Thereafter, medium replacement was further performed, and the cells were incubated for 7 days in the same manner without adding the test antibody. After completion of the measurement, the proportion of the cells in the well was analyzed with the software of IncuCyte at each photographed point.

Figure 15:
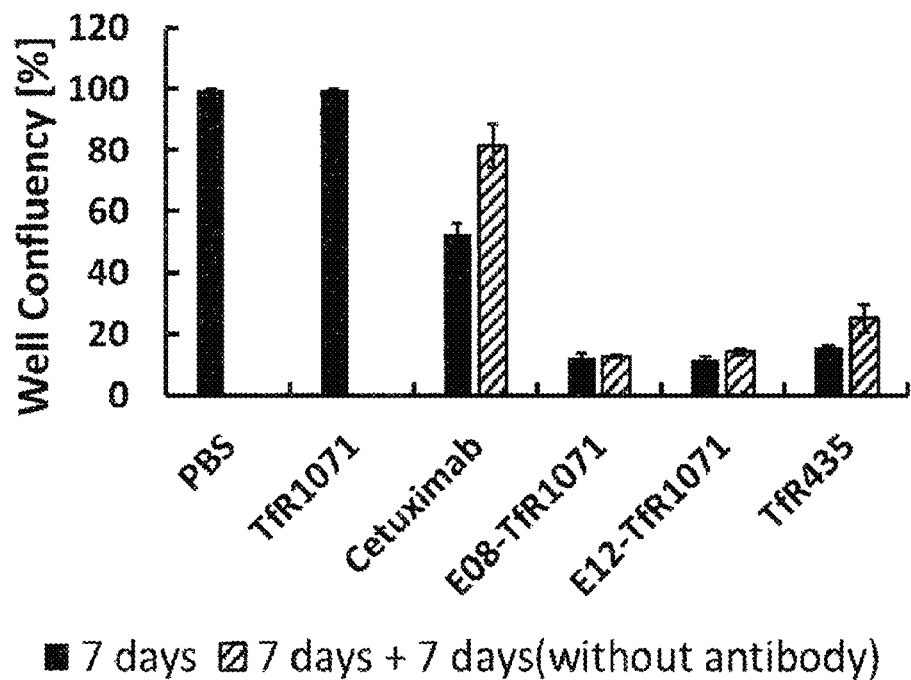
FIG. 15 shows the results of evaluating the growth inhibitory activity when adding an EGFR-TfR bispecific antibody to OE21 cells. The vertical axis represents the proportion (%) of the cells in a well. The black bar graph indicates the proportion (%) of the cells in a well when culturing the cells for 7 days in the presence of an antibody or a bispecific antibody, and the shaded bar graph indicates the proportion (%) of the cells in a well when culturing the cells for 7 days in the presence of an antibody or a bispecific antibody, and further culturing the cells for an additional 7 days after removing the antibody by medium replacement.

As shown in FIG. 15, under the condition that cetuximab was added, when the antibody was removed, the growth was resumed, however, under the condition that the bispecific antibody E08-TfR1071 or E12-TfR1071 was added, resumption of growth was not observed even after the antibody was removed. Under the condition that the TfR neutralizing antibody TfR435 was added, the cell growth inhibitory activity was also observed after the antibody was removed, however, a tendency of cell growth resumption was observed, and it was suggested that a stronger growth inhibitory activity is maintained even after the bispecific antibody is removed in the case of E08-TfR1071 or E12-TfR1071 that induces degradation of TfR.

From the results, it was demonstrated that TfR inhibition maintains the cell growth inhibitory activity even after the inhibitor is removed as compared with EGFR signaling inhibition.

[Example 18] Effect of EGFR-TfR Bispecific Antibody on Human Bone Marrow Cells

In order to confirm the effect of the bispecific antibodies E08-TfR1071 and E12-TfR1071 on normal human bone marrow cells (negative for EGFR and positive for TfR), evaluation was carried out as follows.

Human bone marrow cells (AllCells, Inc.) (7,500 cells) were seeded in a 96-well plate (manufactured by Falcon, Inc.) with StemSpan (trademark) SFEM II (STEMCELL Technologies, Inc.), and a test antibody was added thereto, and the cells were cultured at 37° C. under 5.0% carbon dioxide gas for 5 days. Thereafter, CellTiter-Glo (registered trademark) Luminescent Cell Vialbility Assay (Promega Corporation) was added thereto, and a fluorescence intensity was measured using a microplate reader (1420 ARVO multi-label counter, manufactured by WALLAC, Inc.). Evaluation was carried out using 2 independent wells under each condition, and an average was calculated. The obtained value of the fluorescence intensity reflects the ATP level in viable cells in each well.

Note that in order to induce the differentiation of human bone marrow cells into mature multipotential hematopoietic stem cells (hereinafter referred to as GEMMs), Recombinant Human SCF (PeproTech, Inc.) at a final concentration of 50 ng/mL, Human IL-3 (Miltenyi Biotec, Inc.) at a final concentration of 10 ng/mL, Human IL-6 (Sigma-Aldrich Co. LLC) at a final concentration of 20 ng/mL, Human GM-CSF (Miltenyi Biotec, Inc.) at a final concentration of 20 ng/mL, G-CSF (Miltenyi Biotec, Inc.) at a final concentration of 20 ng/mL, Human Flt3-Ligand (Miltenyi Biotec, Inc.) at a final concentration of 50 ng/mL, erythropoietin (Kyowa Hakko Kirin Co., Ltd.) at a final concentration of 3 U/mL, and Human TPO (Miltenyi Biotec, Inc.) at a final concentration of 30 ng/mL were added thereto during culture.

Figure 16:
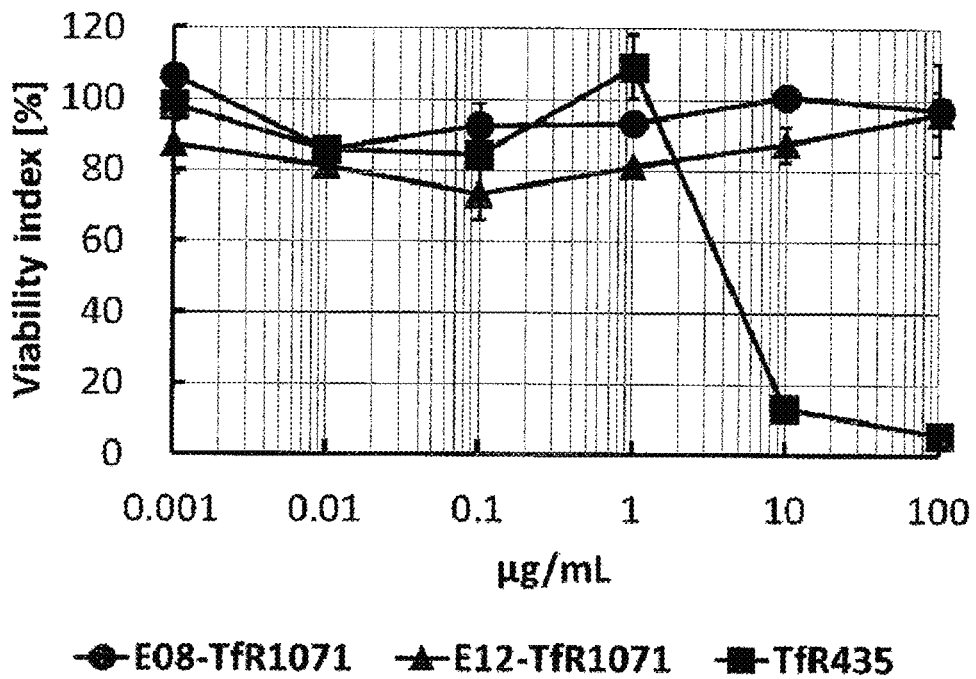
FIG. 16 shows the results of evaluating the growth inhibitory activity when adding an EGFR-TfR bispecific antibody to GEMM. The vertical axis represents the viability when the ATP level in viable cells in the case where PBS was added was assumed to be 100%.

As shown in FIG. 16, while the TfR neutralizing antibody TfR435 exhibited a growth inhibitory activity, both the bispecific antibodies E08-TfR1071 and E12-TfR1071 did not exhibit a growth inhibitory activity.

From the results, it was confirmed that the bispecific antibody of the present invention does not exhibit a growth inhibitory activity against normal bone marrow cells that express TfR. Therefore, the bispecific antibody of the present invention is expected to have lower bone marrow toxicity than the TfR neutralizing antibody.

[Example 19] Growth Inhibitory Activity of EGFR-TfR Bispecific Antibody Having Amino Acid Modification The growth inhibitory activity of an E12-TfR1071 bispecific antibody, in which an amino acid of TfR1071 VH was modified, was evaluated in the same manner as in Example 12 using OE21 cells. First, an amino acid modified EGFR-TfR bispecific antibody was produced as follows. As for an expression vector for the bispecific antibody having an amino acid modification (also referred to as amino acid substitution), the nucleotide sequence encoding the amino acid before the substitution was substituted with the nucleotide sequence encoding the amino acid after the substitution in the expression vector for E12-TfR1071 according to the method described in Example 6. The expression and preparation of the amino acid modified bispecific antibodies were carried out according to the method described in Example 7. As the amino acid modified bispecific antibody, the following antibodies were produced.

(TfR1071 Modified Antibodies)

Y32A, Y32F, T33A, T33G, L45A, V48A, V50A, I51A, I51L, N52A-A, N52A-D, V55E, D58A, D61P, Q97A, Q97D, P98A, W99A, W99F, W99H, W99Y, Y100A-A, Y100A-F, V102L, P98Y, P98S, P98D, P98Q, P98E, P98T, P98R, P98G, P98K, P98M, P98V, P98L, P98I, P98W, P98F, P98H

Each of the above symbols indicates an amino acid substitution included in each of the TfR modified antibodies and represents [one-letter notation of an amino acid residue before the substitution][the site of an amino acid residue in the VH (SEQ ID NO: 31) of TfR1071 indicated in the EU index][one-letter notation of an amino acid residue after the substitution]. Hereinafter, an amino acid substitution is denoted in the same manner.

For example, Y32A means that an amino acid residue Y (tyrosine) at position 32 in the EU index was substituted with A (alanine). Further, 52A and 100A are branch numbers that mean an amino acid residue "between positions 52 and 53" and an amino acid residue "between positions 100 and 101", respectively, in the EU index. For example, N52A-D means that an amino acid residue at position 52A in the EU index was changed from N to A, and Y100A-A means that an amino acid residue at position 100A in the EU index was changed from Y to A.

Cancer cells ($1 \times 10^3$ cells) were seeded in a flat-bottom 96-well plate (manufactured by Falcon, Inc.), and a test antibody diluted to various concentrations with RPMI 1640 medium (manufactured by Sigma-Aldrich Co. LLC) containing 10% FBS was added thereto, and the cells were cultured at 37° C. under 5.0% carbon dioxide gas for 4 to 6 days. Thereafter, Cell Counting Kit-8 (Dojindo, Inc.) was added thereto, and an absorbance was measured using a microplate reader (1420 ARVO multi-label counter, manufactured by WALLAC, Inc.). Evaluation was carried out using 3 independent wells under each condition, and an average was calculated. The obtained value of the fluorescence intensity reflects the viable cell count in each well. As the negative control, the anti-DNP antibody was used. The evaluation results with respect to the growth inhibitory activity of the above-mentioned bispecific antibodies are shown in FIGS. 17A and 17B.

Figure 17A:
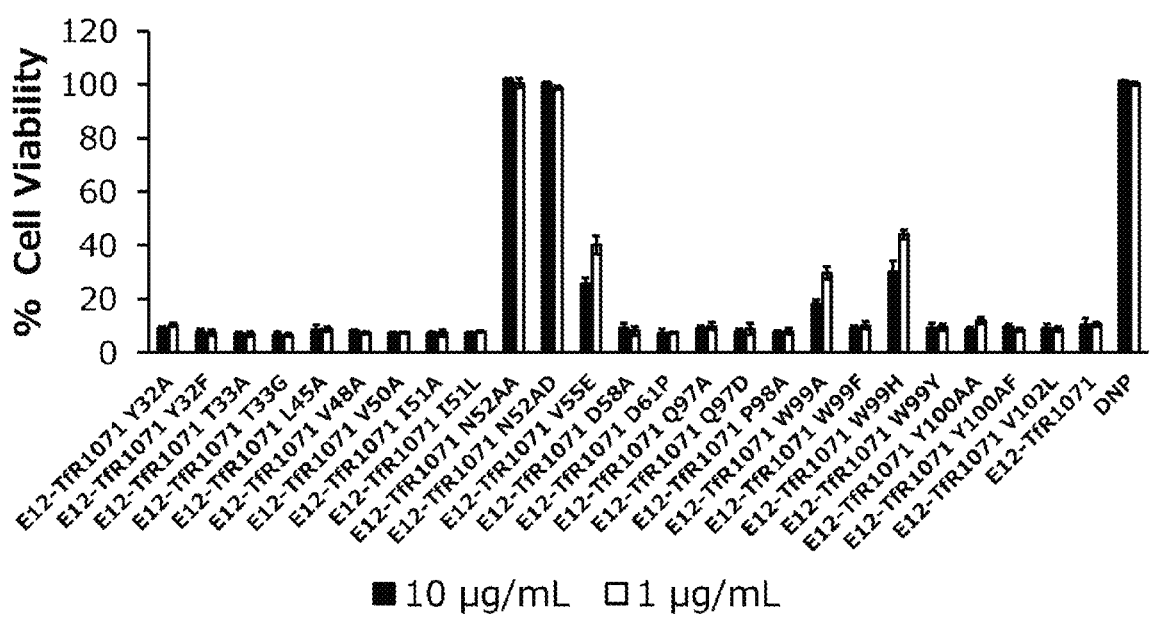
FIG. 17A shows the results of evaluating the growth inhibitory activity of EGFR-TfR bispecific antibodies.
Figure 17B:
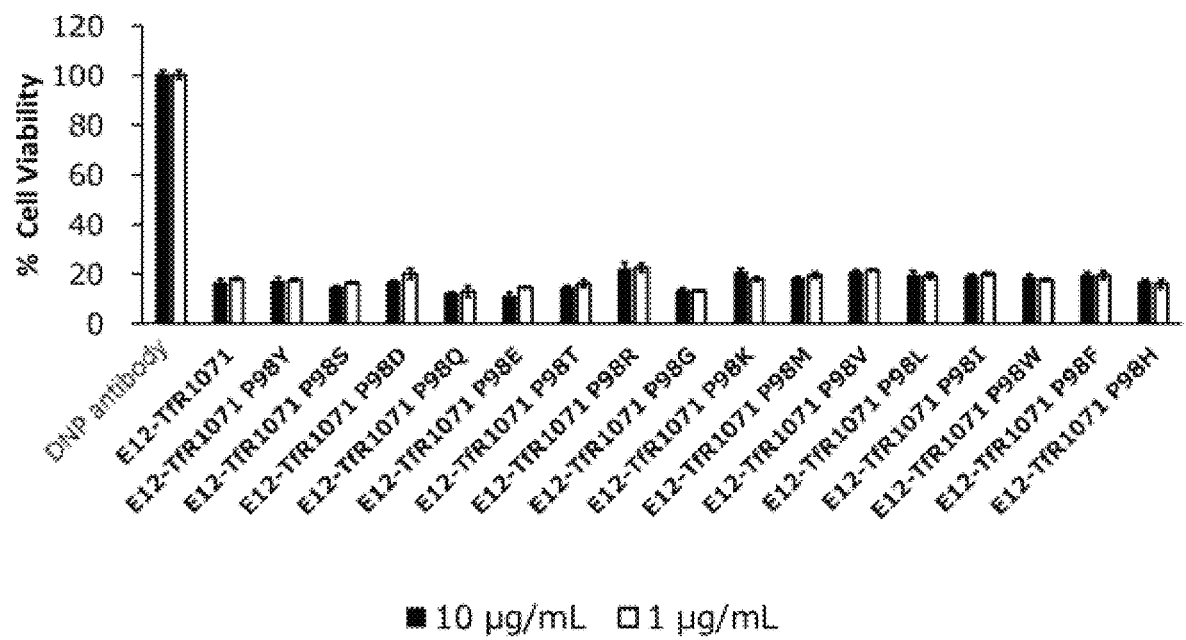
FIG. 17B shows the results of evaluating the growth inhibitory activity of EGFR-TfR bispecific antibodies.

As shown in FIGS. 17A and 17B, in the N52A-A and N52A-D modified antibodies of the clone TfR1071, the growth inhibitory activity was not observed, and in the V55E, W99A, and W99H modified antibodies, the growth inhibitory activity somewhat decreased, but the other modified antibodies exhibited a strong growth inhibitory activity comparable to that before the modification.

From the results, it was demonstrated that in the bispecific antibody E12-TfR1071 of the present invention, N52 is important for exhibiting a growth inhibitory activity. Further, even if P98 is substituted with any other various amino acids, an equivalent growth inhibitory activity is exhibited, and it was suggested that P98 can be substituted with any other natural amino acid.

[Example 20] Identification of Epitope for Anti-TfR Antibody

The epitope for the anti-TfR antibody 1071 was identified as follows.

From the sequence information described in WO 2014/189973, anti-TfR antibodies 15G11v5, 7A4v15, and 16F6v4, each of which binds to the apical domain of human TfR, and an anti-TfR antibody 7G7v1 which recognizes the protease-like domain were produced in the same manner as described in Example 7.

The extracellular domain protein of human TfR described in Example 1 was produced. Further, a chimeric protein in which the apical domain or the protease-like domain in the extracellular domain of human TfR was substituted with a corresponding domain of mouse TfR (containing the amino acid sequence represented by GenBank accession No. NP_001344227 or the amino acid represented by SEQ ID NO: 87) was produced. Specifically, the nucleotide sequence encoding such an amino acid sequence was subcloned into a pCI-OtCMV vector into which a His tag was introduced, whereby a protein expression vector was obtained. By using the protein expression vector, His-huTfR, huTfR with mouse apical domain (SEQ ID NO: 88), and huTfR with mouse protease-like domain (SEQ ID NO: 89), in each of which a His tag was added to each protein, were obtained in the same manner as described in Example 1.

The His-huTfR represents a human TfR extracellular domain with a His tag, the huTfR with mouse apical domain represents a human TfR extracellular domain with a His tag in which the apical domain was substituted with a corresponding mouse sequence, and the huTfR with mouse protease-like domain represents a human TfR extracellular domain with a His tag in which the protease-like domain was substituted with a corresponding mouse sequence.

Similarly, chimeric TfR A01 to A16 in which some amino acid residues of the apical domain of human TfR were substituted with corresponding amino acid residues of mouse TfR were produced. The produced chimeric TfR proteins are shown in Table 5, and the amino acid sequences thereof are represented by SEQ ID NOS: 90 to 105, respectively.

In Table 5, the amino acid substitution sites in each chimeric protein are shown. For example, Q285K-T286N-T362S of A01 means that in the amino acid sequence of human TfR represented by SEQ ID NO: 6, an amino acid at position 285 was changed from Q to K, an amino acid at position 286 was changed from T to N, and an amino acid at position 362 was changed from T to S. In the case where there is no corresponding mouse amino acid as V210 of A08, the amino acid was deleted.

TABLE 5

Chimeric TfR for Epitope Identification

| | |
|---|---|
| A01 | Q285K-T286N-T362S |
| A02 | D352S-S355A-D356R-K358N |
| A03 | D245E-K261E |
| A04 | D245E-K261E-D356R |
| A05 | P249S-L274F |
| A06 | E272Q |
| A07 | M365L-V366E-E369Q |
| A08 | N348K-K371Q-V210-Y211D-D204Q |
| A09 | NA225P-A226T-T227E-T229S |
| A10 | A225P-A226T-T227E |
| A11 | D194S-A1961G-S378K |
| A12 | G217E-S296A |
| A13 | D204Q-K205S |
| A14 | D204Q-K205S-E369Q |
| A15 | S199M-I201T-L212P-N215S |
| A16 | SI99M-T376I-T227E |

Subsequently, an epitope analysis for various types of TfR antibodies was carried out. First, the reactivity of the anti-TfR antibodies produced in the present invention with human TfR/CHO produced in Example 2 and mouse TfR/CHO produced in the same manner as in Example 2 was analyzed by flow cytometry in the same manner as in Example 9. As a result, R327, TfR1071, cyno186, cyno292, and 2230 all bound to human TfR, but did not bind to mouse TfR. Further, it is known that 15G11v5, 7A4v15, 16F6v4, and 7G7v1 do not cross-react with mouse (WO 2014/189973).

Further, the binding activity of the anti-TfR antibody to various types of chimeric TfR produced above was analyzed by ELISA, and the binding domain of the anti-TfR antibody and the recognition epitope therefor were identified. When the binding activity to the chimeric TfR was lost, the amino acid residue substituted in the chimeric TfR was identified as the epitope.

ELISA was carried out by the following method. To a 96-well immunoplate (NUNC, Inc.) on which an antigen protein was immobilized, 1% (w/v) BSA-PBS(−) pH 7.0 without KCl (hereinafter referred to as blocking solution, Nacalai Tesque, Inc.) was added to perform blocking at room temperature, and thereafter, the anti-TfR antibody diluted with the same solution was added thereto and a reaction was allowed to proceed at room temperature for 1 hour. Thereafter, washing was performed with 0.05% (w/v)-tPBS (1×) without KCl (pH 7.2) (hereinafter referred to as washing solution, Nacalai Tesque, Inc.), Anti-Human IgG (Fc) Goat IgG Fab"-HRP (IBL, Inc.) diluted with the blocking solution was added thereto, and a reaction was allowed to proceed at room temperature for 1 hour. Thereafter, washing was performed with the washing solution, and 1-Step (registered trademark) Ultra TMB-ELISA Substrate Solution (Thermo, Inc.) was added thereto, and a reaction was allowed to proceed at room temperature. The coloring reaction was stopped by adding a 5 N HCl solution, and an absorbance at a wavelength of 450 nm (reference wavelength: 570 nm) was measured using a plate reader (EPOCH 2: BioTek Instruments, Inc.).

The results are shown in Table 6. N/A in the table indicates that data were not obtained. Further, a value obtained by subtracting the absorbance at the reference wavelength of 570 nm from the absorbance at a wavelength of 450 nm was regarded as the binding activity to any of various types of antigen proteins, and a case where a value obtained by dividing the binding activity to any of various types of chimeric TfR by the binding activity to His-huTfR was 0.5 or more was denoted by ++, a case where the value was 0.2 or more and less than 0.5 was denoted by +, and a case where the value was less than 0.2 was denoted by −.

TABLE 6

Epitopes for Various Types of TfR Antibodies

| | ELISA binding | | | | | | | | | |
|---|---|---|---|---|---|---|---|---|---|---|
| Clone | huTfR with mouse apical domain | huTfR with mouse protease-like domain | Binding domain | ELISA binding to chimera TfR | | | | | | Binding site in apical domain |
| | | | | A02 | A03 | A04 | A05 | A07 | A14 | |
| T14 | − | ++ | Apical | ++ | ++ | + | − | ++ | ++ | A05 |
| R327 | − | ++ | Apical | − | ++ | + | ++ | − | ++ | A02, A07 |
| TfR1007 | − | ++ | Apical | − | ++ | + | ++ | − | ++ | A02, A07 |
| TfR1071 | − | ++ | Apical | − | ++ | + | ++ | − | ++ | A02, A07 |
| cyno186 | − | ++ | Apical | − | ++ | + | ++ | − | − | A02, A07, A14 |
| cyno292 | − | ++ | Apical | − | ++ | ++ | ++ | − | ++ | A02, A07 |
| 2230 | ++ | − | Protease-like | ++ | ++ | ++ | ++ | ++ | ++ | (Protease-like) |
| 15G11v5 | − | ++ | Apical | − | − | − | ++ | + | ++ | A02, A03, A04 |
| 7A4v15 | − | ++ | Apical | − | ++ | + | ++ | + | ++ | A02 |
| 16F6v4 | − | ++ | Apical | − | ++ | + | ++ | ++ | ++ | A02 |
| 7G7v1 | ++ | − | Protease-like | N/A | N/A | N/A | N/A | N/A | N/A | (Protease-like) |

From the results, it was demonstrated that T14, R327, TfR1071, cyno186, cyno292, 15G11v5, 7A4v15, and 16F6v4 recognize the apical domain, and 2230 and 7G7v1 recognize the protease-like domain. Further, it was demonstrated that among the antibodies that recognize the apical domain, T14 recognizes the amino acid substitution sites in A05, R327, TfR1007, TfR1071, and cyno292 recognize the amino acid substitution sites in A02 and A07, cyno186 recognizes the amino acid substitution sites in A02, A07, and A14, 15G11v5 recognizes the amino acid substitution sites in A02, A03, and A04, and 7A4v15 and 16F6v4 recognize the amino acid substitution sites in A02.

It was demonstrated that the amino acid residues recognized by TfR1071 are sites where the amino acids were substituted in A02 and A07. Therefore, it was suggested that the amino acid residues recognized by TfR1071 are seven amino acid residues of D352, S355, D356, K358, M365, V366, and E369. The same thing can be said of R327, TfR1007, and cyno292.

[Example 21] Epitope for Anti-TfR Antibody and Growth Inhibitory Activity of EGFR-TfR Bispecific Antibody In order to analyze the relationship between the growth inhibitory activity of the bispecific antibody of the present invention and the epitope in the variable region of the IgG portion that binds to TfR, E12-TfR bispecific antibodies were produced using various types of TfR antibodies for which epitopes are different, and the growth inhibitory activity was evaluated.

Figure 18:
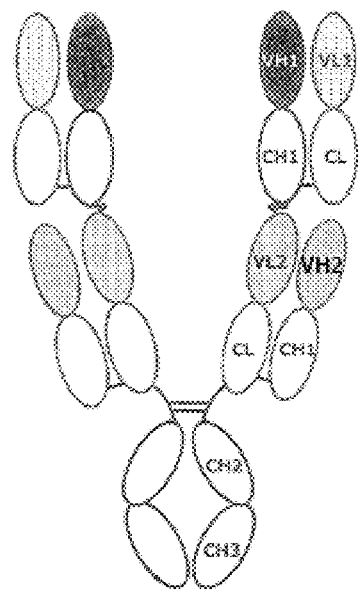
FIG. 18 is a schematic view showing a structure of an EGFR-TfR bispecific antibody produced in Example 6 (panel (A) and a schematic view showing a structure of a heterodimeric antibody produced in Example 23 (panel (B)).
Figure 18:
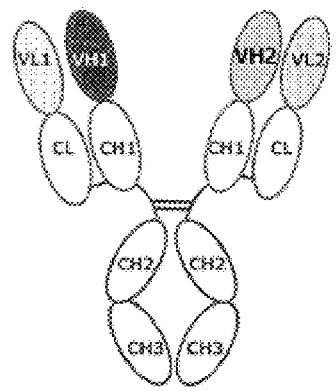

The light chain of each of the anti-TfR antibodies 15G11v5, 7A4v15, 16F6v4, and 7G7v1 and the light chain of the anti-EGFR antibody E12 are different, and therefore, a bispecific antibody having a structure as shown in FIG. 18(A) was produced in the same manner as described in Example 6. In the same manner as in Example 8, Penta-His Antibody (QIAGEN, Inc.) was immobilized on a CM5 sensor chip, and after His-huTfR was added thereto, the binding activity of each bispecific antibody as an analyte to TfR was measured, and a kinetic constant of each of the produced various types of bispecific antibodies was calculated. The results are shown in Table 7.

TABLE 7

Binding Activity of Bispecific Antibody to TfR

| | ka | kd | KD |
|---|---|---|---|
| E12-TfR1071 | 6.02E+05 | 9.73E−03 | 1.62E−08 |
| E12-15G11v5 | 1.68E+05 | 2.03E−04 | 1.21E−09 |
| E12-7A4v15 | 1.04E+05 | 8.75E−04 | 8.39E−09 |
| E12-16F6v4 | 2.86E+04 | 7.88E−04 | 2.76E−08 |
| E12-7G7v1 | 1.23E+05 | 1.07E−03 | 8.74E−09 |
| Centuximab-TfR1071 | 5.48E+05 | 1.05E−02 | 1.92E−08 |
| Panitumumab-TfR1071 | 4.84E+05 | 1.00E−02 | 2.07E−08 |
| Necitumumab-TfR1071 | 4.77E+05 | 9.19E−03 | 1.93E−08 |
| Nimotuzumab-TfR1071 | 5.17E+05 | 9.52E−03 | 1.84E−08 |

As shown in Table 7, it was found that all the produced bispecific antibodies strongly bind to TfR.

Figure 19A:
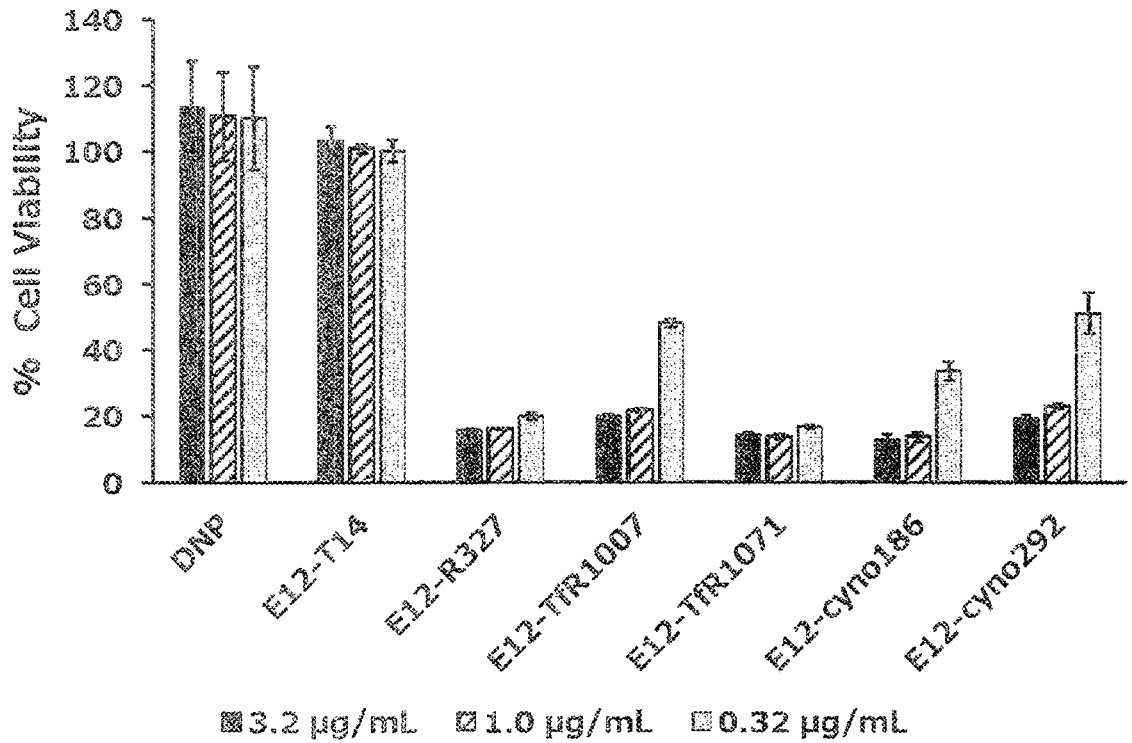
FIG. 19A shows the results of evaluating the growth inhibitory activity of EGFR-TfR bispecific antibodies.
Figure 19B:
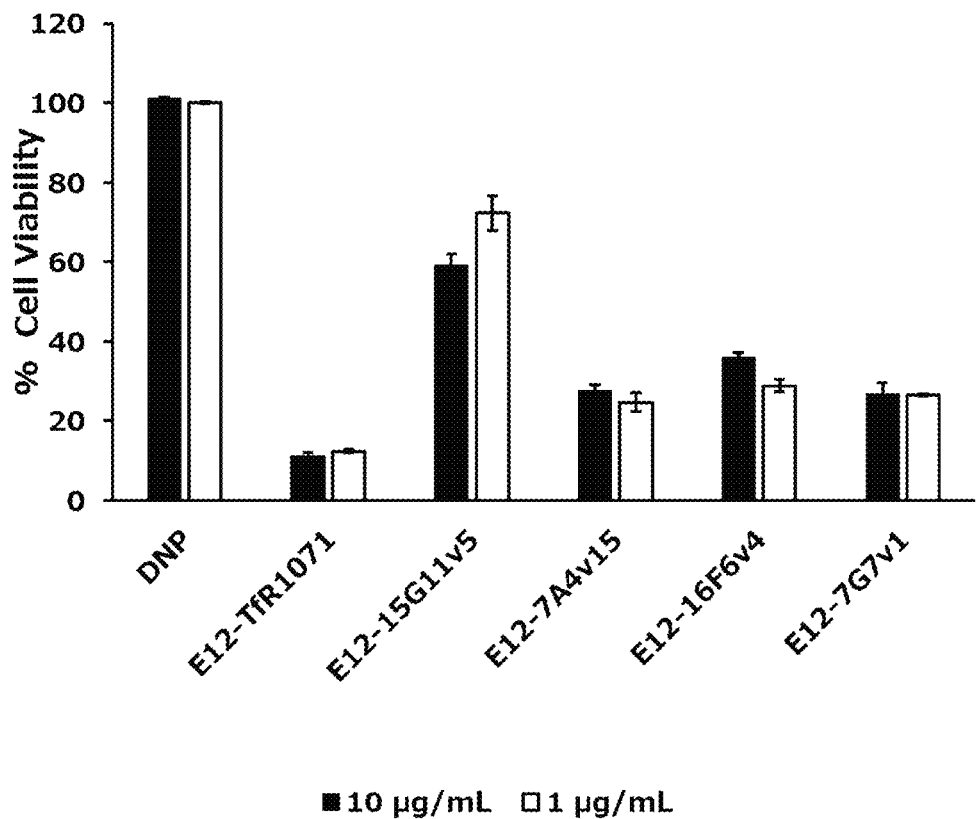
FIG. 19B shows the results of evaluating the growth inhibitory activity of EGFR-TfR bispecific antibodies.

The results of evaluating the growth inhibitory activity of each of the obtained bispecific antibodies to OE21 in the same manner as in Example 19 are shown in FIGS. 19A and 19B.

As shown in FIGS. 19A and 19B, the maximum activity of the EGFR-TfR bispecific antibodies using R327, TfR1007, TfR1071, cyno186, and cyno292 was higher than that of the other bispecific antibodies. From the results and the results of Example 20, it was found that the bispecific antibodies using R327, TfR1007, TfR1071, and cyno292 for which the epitopes are the amino acid substitution sites in A02 and A07, and using cyno186 for which the epitopes are the amino acid substitution sites in A02, A07, and A14 have a high growth inhibitory activity. Therefore, it was demonstrated that it is important for achieving a high growth inhibitory activity to include the amino acid substitution sites in A02 and A07 in the epitope.

Further, as shown in FIG. 19A, even among the bispecific antibodies for which the epitope includes the amino acid substitution sites in A02 and A07, the bispecific antibodies using TfR1071 and R327 exhibited a high activity from the lowest concentration, and it was demonstrated that TfR1071 and R327 are particularly excellent among the clones.

[Example 22] Growth Inhibitory Activity of EGFR-TfR Bispecific Antibodies Using Various Types of Anti-EGFR Antibodies and TfR1071

In order to confirm whether TfR1071 is important for the growth inhibitory activity of the bispecific antibody, EGFR-TfR bispecific antibodies were produced using anti-EGFR antibodies which are on the market and have an EGFR inhibitory activity, and the TfR antibody TfR1071, and the growth inhibitory activity was evaluated.

Bispecific antibodies of an anti-EGFR antibody (cetuximab, panitumumab, necitumumab, or nimotuzumab) and the TfR antibody TfR1071 were produced in the same manner as described in Example 6. As the sequences of the variable regions of cetuximab, panitumumab, necitumumab, and nimotuzumab, those described in WO 1996/040210, WO 1998/050433, WO 2011/116387, and US Patent Application Publication No. 2012/0308576, respectively, were used. A schematic view of the structure of each of the produced bispecific antibodies is shown in FIG. 1(C).

Figure 20:
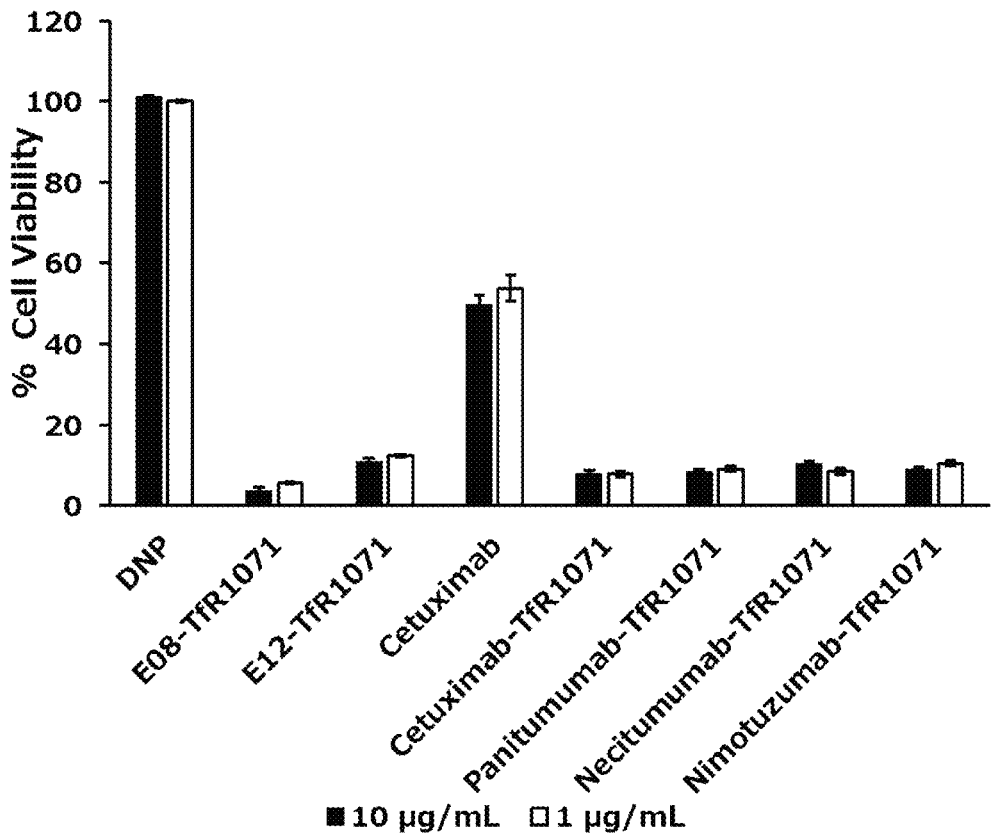
FIG. 20 shows the results of evaluating the growth inhibitory activity of EGFR-TfR bispecific antibodies using the growth inhibitory activity against a cancer cell line as an index.

The results of evaluating the growth inhibitory activity of each of the obtained bispecific antibodies in the same manner as in Example 20 using the growth inhibitory activity against a cancer cell line as an index are shown in FIG. 20.

As shown in FIG. 20, the EGFR-TfR bispecific antibodies having CDR of TfR1071 exhibited a strong growth inhibitory activity even including the variable region of any of the anti-EGFR antibodies.

From the results, it was suggested that it is important for achieving a high growth inhibitory activity of the bispecific antibody of the present invention to have CDR of TfR1071 in the IgG portion.

[Example 23] Comparison of Growth Inhibitory Activity of Heterodimeric Bispecific Antibody In order to analyze the effect of the valence for binding to TfR and EGFR on the growth inhibitory activity of the present bispecific antibody, a heterodimeric bispecific antibody having one antigen-binding domain of the anti-EGFR antibody E12 and one antigen-binding domain of the anti-TfR antibody TfR1071 (hereinafter referred to as heterodimeric antibody) was produced, and the growth inhibitory activity was evaluated. In FIG. 18(B), a schematic view of the structure of the produced heterodimeric antibody is shown.

A bispecific antibody Hetero E12-TfR1071 having one antigen-binding domain of E12 and one antigen-binding domain of TfR1071 was produced by the method described in the Patent Literature (US Patent Application Publication No. 2014/0348839), and the growth inhibitory activity was evaluated in the same manner as in Example 11. The results are shown in FIG. 21.

Figure 21:
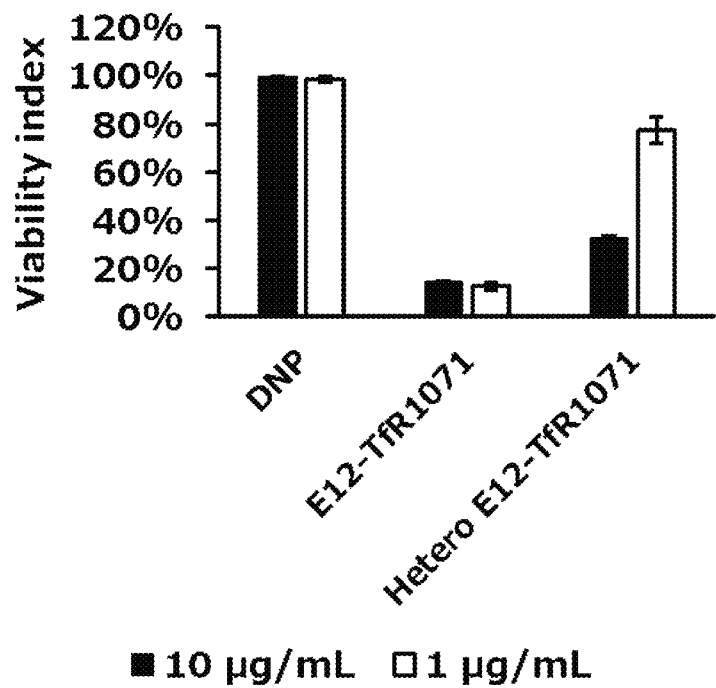
FIG. 21 shows the results of evaluating the growth inhibitory activity of EGFR-TfR bispecific antibodies.

As shown in FIG. 21, it was found that both the maximum activity and the specific activity of growth inhibition of Hetero E12-TfR1071 are weaker than those of E12-TfR1071. From the results, it was demonstrated that the bispecific antibody of the present invention in which the valence for each of TfR and EGFR is two has a stronger growth inhibitory activity than the heterodimeric antibody in which the valence for each of TfR and EGFR is one.

[Example 24] TfR Binding Activity of E12-TfR1071YE Bispecific Antibody

An E12-TfR1071YE bispecific antibody having a VH sequence (SEQ ID NO: 106) in which an amino acid at position 1 of the VH sequence (SEQ ID NO: 31) of TfR1071 was changed from Y (tyrosine) to E (glutamic acid) was produced according to a conventional method. The binding activity to human TfR protein was analyzed by ELISA in the same manner as described in Example 20. As a result, E12-TfR1071YE exhibited a binding activity comparable to that of E12-TfR1071.

The present invention has been explained in detail using the specific aspects, but it is obvious for those skilled in the art that various changes and modifications can be made without departing from the spirit and scope of the present invention. The present application is based on a Japanese patent application filed on Dec. 28, 2018 (Patent Application No. 2018-248334), which is incorporated by reference in its entirety.

SEQUENCE LISTING FREE TEXT

SEQ ID NO: 1: nucleotide sequence of extracellular domain of human TfR
SEQ ID NO: 2: amino acid sequence of extracellular domain of human TfR
SEQ ID NO: 3: nucleotide sequence of extracellular domain of monkey TfR
SEQ ID NO: 4: amino acid sequence of extracellular domain of monkey TfR
SEQ ID NO: 5: nucleotide sequence of human TfR
SEQ ID NO: 6: amino acid sequence of human TfR
SEQ ID NO: 7: nucleotide sequence of cynomolgus monkey TfR
SEQ ID NO: 8: amino acid sequence of cynomolgus monkey TfR
SEQ ID NO: 9: nucleotide sequence of extracellular domain of human EGFR (including signal sequence)
SEQ ID NO: 10: amino acid sequence of extracellular domain of human EGFR (including signal sequence)
SEQ ID NO: 11: nucleotide sequence of extracellular domain of monkey EGFR (including signal sequence)
SEQ ID NO: 12: amino acid sequence of extracellular domain of monkey EGFR (including signal sequence)
SEQ ID NO: 13: nucleotide sequence of human EGFR
SEQ ID NO: 14: amino acid sequence of human EGFR
SEQ ID NO: 15: nucleotide sequence of VL of A27
SEQ ID NO: 16: amino acid sequence of VL of A27
SEQ ID NO: 17: amino acid sequence of LCDR1 of A27
SEQ ID NO: 18: amino acid sequence of LCDR2 of A27
SEQ ID NO: 19: amino acid sequence of LCDR3 of A27
SEQ ID NO: 20: nucleotide sequence of VH of PSM4072
SEQ ID NO: 21: amino acid sequence of VH of PSM4072
SEQ ID NO: 22: amino acid sequence of HCDR1 of PSM4072
SEQ ID NO: 23: amino acid sequence of HCDR2 of PSM4072
SEQ ID NO: 24: amino acid sequence of HCDR3 of PSM4072
SEQ ID NO: 25: nucleotide sequence of VH of R327
SEQ ID NO: 26: amino acid sequence of VH of R327
SEQ ID NO: 27: amino acid sequence of HCDR1 of R327
SEQ ID NO: 28: amino acid sequence of HCDR2 of R327
SEQ ID NO: 29: amino acid sequence of HCDR3 of R327
SEQ ID NO: 30: nucleotide sequence of VH of TfR1071
SEQ ID NO: 31: amino acid sequence of VH of TfR1071
SEQ ID NO: 32: amino acid sequence of HCDR1 of TfR1071
SEQ ID NO: 33: amino acid sequence of HCDR2 of TfR1071
SEQ ID NO: 34: amino acid sequence of HCDR3 of TfR1071
SEQ ID NO: 35: nucleotide sequence of VH of TfR4016
SEQ ID NO: 36: amino acid sequence of VH of TfR4016
SEQ ID NO: 37: amino acid sequence of HCDR1 of TfR4016
SEQ ID NO: 38: amino acid sequence of HCDR2 of TfR4016
SEQ ID NO: 39: amino acid sequence of HCDR3 of TfR4016
SEQ ID NO: 40: nucleotide sequence of VH of cyno186
SEQ ID NO: 41: amino acid sequence of VH of cyno186
SEQ ID NO: 42: amino acid sequence of HCDR1 of cyno186
SEQ ID NO: 43: amino acid sequence of HCDR2 of cyno186
SEQ ID NO: 44: amino acid sequence of HCDR3 of cyno186
SEQ ID NO: 45: nucleotide sequence of VH of cyno292
SEQ ID NO: 46: amino acid sequence of VH of cyno292
SEQ ID NO: 47: amino acid sequence of HCDR1 of cyno292
SEQ ID NO: 48: amino acid sequence of HCDR2 of cyno292
SEQ ID NO: 49: amino acid sequence of HCDR3 of cyno292
SEQ ID NO: 50: amino acid sequence of VH of TfR1007
SEQ ID NO: 51: amino acid sequence of VH of cyno163
SEQ ID NO: 52: amino acid sequence of VH of 2230
SEQ ID NO: 53: amino acid sequence of VL of 2230
SEQ ID NO: 54: amino acid sequence of VH of T14
SEQ ID NO: 55: amino acid sequence of VH of TfR434
SEQ ID NO: 56: amino acid sequence of VH of TfR435
SEQ ID NO: 57: amino acid sequence of VL of TfR434 and 435
SEQ ID NO: 58: nucleotide sequence of VH of E08
SEQ ID NO: 59: amino acid sequence of VH of E08
SEQ ID NO: 60: amino acid sequence of HCDR1 of E08
SEQ ID NO: 61: amino acid sequence of HCDR2 of E08
SEQ ID NO: 62: amino acid sequence of HCDR3 of E08
SEQ ID NO: 63: nucleotide sequence of VH of E12
SEQ ID NO: 64: amino acid sequence of VH of E12
SEQ ID NO: 65: amino acid sequence of HCDR1 of E12
SEQ ID NO: 66: amino acid sequence of HCDR2 of E12
SEQ ID NO: 67: amino acid sequence of HCDR3 of E12
SEQ ID NO: 68: nucleotide sequence of VH of E17
SEQ ID NO: 69: amino acid sequence of VH of E17
SEQ ID NO: 70: amino acid sequence of HCDR1 of E17
SEQ ID NO: 71: amino acid sequence of HCDR2 of E17
SEQ ID NO: 72: amino acid sequence of HCDR3 of E17
SEQ ID NO: 73: amino acid sequence of VH of KME07
SEQ ID NO: 74: amino acid sequence of VH of KME09
SEQ ID NO: 75: amino acid sequence of VH of KME11
SEQ ID NO: 76: amino acid sequence of VH of cetuximab
SEQ ID NO: 77: amino acid sequence of VL of cetuximab
SEQ ID NO: 78: amino acid sequence of VH of HN3
SEQ ID NO: 79: amino acid sequence of linker
SEQ ID NO: 80: amino acid sequence of linker
SEQ ID NO: 81: amino acid sequence of linker SEQ ID NO: 82: amino acid sequence of linker
SEQ ID NO: 83: nucleotide sequence of constant region of IgG4PE R409K
SEQ ID NO: 84: amino acid sequence of constant region of IgG4PE R409K
SEQ ID NO: 85: nucleotide sequence of modified codon of CH1 of IgG4
SEQ ID NO: 86: amino acid sequence of constant region of IgG4PE
SEQ ID NO: 87: amino acid sequence of mouse TfR
SEQ ID NO: 88: amino acid sequence of chimeric protein of human TfR extracellular domain with mouse apical domain
SEQ ID NO: 89: amino acid sequence of chimeric protein of human TfR extracellular domain with mouse protease-like domain
SEQ ID NO: 90: amino acid sequence of A01
SEQ ID NO: 91: amino acid sequence of A02
SEQ ID NO: 92: amino acid sequence of A03
SEQ ID NO: 93: amino acid sequence of A04
SEQ ID NO: 94: amino acid sequence of A05
SEQ ID NO: 95: amino acid sequence of A06
SEQ ID NO: 96: amino acid sequence of A07
SEQ ID NO: 97: amino acid sequence of A08
SEQ ID NO: 98: amino acid sequence of A09
SEQ ID NO: 99: amino acid sequence of A10
SEQ ID NO: 100: amino acid sequence of A11
SEQ ID NO: 101: amino acid sequence of A12
SEQ ID NO: 102: amino acid sequence of A13
SEQ ID NO: 103: amino acid sequence of A14
SEQ ID NO: 104: amino acid sequence of A15
SEQ ID NO: 105: amino acid sequence of A16
SEQ ID NO: 106: amino acid sequence of VH of TfR1071 starting from EVQL
SEQ ID NO: 107: amino acid sequence of HCDR1 of TfR1007
SEQ ID NO: 108: amino acid sequence of HCDR2 of TfR1007
SEQ ID NO: 109: amino acid sequence of HCDR3 of TfR1007
SEQ ID NO: 110: amino acid sequence of VH of cetuximab
SEQ ID NO: 111: amino acid sequence of VL of cetuximab
SEQ ID NO: 112: amino acid sequence of VH of panitumumab
SEQ ID NO: 113: amino acid sequence of VL of panitumumab
SEQ ID NO: 114: amino acid sequence of VH of necitumumab
SEQ ID NO: 115: amino acid sequence of VL of necitumumab
SEQ ID NO: 116: amino acid sequence of VH of nimotuzumab
SEQ ID NO: 117: amino acid sequence of VL of nimotuzumab

The invention claimed is:

1. A bispecific antibody or a bispecific antibody fragment thereof, comprising:
   an IgG portion that binds to a transferrin receptor (TfR) and an N-terminal side polypeptide that binds to a cell surface antigen,
   wherein the IgG portion includes VH having CDRs 1 to 3 containing the amino acid sequences represented by SEQ ID NOs: 32 to 34, respectively, and VL having CDRs 1 to 3 containing the amino acid sequences represented by SEQ ID NOs: 17 to 19, respectively,
   wherein the N-terminal side polypeptide is Fab of an antibody against EGFR, and the antibody includes VH having CDRs 1 to 3 containing the amino acid sequences represented by SEQ ID NOs: 65 to 67, respectively, and VL having CDRs 1 to 3 containing the amino acid sequences represented by SEQ ID NOs: 17 to 19, respectively,
   wherein the bispecific antibody or the bispecific antibody fragment thereof binds to TfR and the cell surface antigen,
   wherein the N-terminal side polypeptide binds directly or through a linker to the N terminus of a heavy chain of the IgG portion.

2. The bispecific antibody or the bispecific antibody fragment thereof according to claim 1, wherein the IgG portion includes VH containing the amino acid sequence represented by SEQ ID NO: 31, and VL containing the amino acid sequence represented by SEQ ID NO: 16.

3. The bispecific antibody or the bispecific antibody fragment thereof according to claim 1, wherein a heavy chain constant region of the IgG portion contains the amino acid sequence represented by SEQ ID NO: 84 or SEQ ID NO: 86.

4. The bispecific antibody or the bispecific antibody fragment thereof according to claim 1, wherein the antibody against EGFR includes
   VH containing the amino acid sequence represented by SEQ ID NO: 64 and VL containing the amino acid sequence represented by SEQ ID NO: 16.

5. The bispecific antibody or the bispecific antibody fragment thereof according to claim 1, wherein the bispecific antibody divalently binds to each of TfR and the cell surface antigen.

6. The bispecific antibody or the bispecific antibody fragment thereof according to claim 1, wherein the heavy chain C terminus of the Fab directly binds to the heavy chain N terminus of the IgG portion.

7. The bispecific antibody or the bispecific antibody fragment thereof according to claim 1, wherein the heavy chain C terminus of the Fab binds to the heavy chain N terminus of the IgG portion through the linker.

8. The bispecific antibody or the bispecific antibody fragment thereof according to claim 7, wherein the amino acid sequence of the linker is composed of part or all of the amino acid sequence of a hinge region of IgG.

9. The bispecific antibody or the bispecific antibody fragment thereof according to claim 1, wherein the IgG portion includes VH containing the amino acid sequence represented by SEQ ID NO: 31 and VL containing the amino acid sequence represented by SEQ ID NO: 16, and the N-terminal side polypeptide includes VH containing the amino acid sequence represented by SEQ ID NO: 64 and VL containing the amino acid sequence represented by SEQ ID NO: 16, and
wherein the bispecific antibody divalently binds to each of TfR and the cell surface antigen.

10. The bispecific antibody or the bispecific antibody fragment thereof according to claim 9, wherein the heavy chain C terminus of the Fab directly binds to the heavy chain N terminus of the IgG portion.

* * * * *